(12) United States Patent
Heller

(10) Patent No.: US 10,300,033 B2
(45) Date of Patent: *May 28, 2019

(54) PHARMACEUTICAL SUSPENSIONS CONTAINING DRUG PARTICLES, DEVICES FOR THEIR ADMINISTRATION, AND METHODS OF THEIR USE

(71) Applicant: SynAgile Corporation, Wilson, WY (US)

(72) Inventor: Adam Heller, Austin, TX (US)

(73) Assignee: SynAgile Corporation, Wilson, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/887,243

(22) Filed: Feb. 2, 2018

(65) Prior Publication Data

US 2018/0177752 A1 Jun. 28, 2018

Related U.S. Application Data

(63) Continuation of application No. 15/448,208, filed on Mar. 2, 2017, now Pat. No. 9,901,561, which is a continuation of application No. PCT/US2016/031308, filed on May 6, 2016.

(60) Provisional application No. 62/292,072, filed on Feb. 5, 2016, provisional application No. 62/157,806, filed on May 6, 2015.

(51) Int. Cl.
| | |
|---|---|
| *A61K 31/195* | (2006.01) |
| *A61K 31/198* | (2006.01) |
| *A61J 7/00* | (2006.01) |
| *A61K 9/00* | (2006.01) |
| *A61K 9/06* | (2006.01) |
| *A61K 9/10* | (2006.01) |
| *A61M 31/00* | (2006.01) |
| *A61K 47/02* | (2006.01) |
| *A61K 47/12* | (2006.01) |
| *A61K 47/18* | (2017.01) |
| *A61K 47/34* | (2017.01) |
| *A61K 9/14* | (2006.01) |

(52) U.S. Cl.
CPC .......... *A61K 31/198* (2013.01); *A61J 7/0076* (2013.01); *A61K 9/0053* (2013.01); *A61K 9/06* (2013.01); *A61K 9/10* (2013.01); *A61K 9/14* (2013.01); *A61K 31/195* (2013.01); *A61K 47/02* (2013.01); *A61K 47/12* (2013.01); *A61K 47/183* (2013.01); *A61K 47/34* (2013.01); *A61M 31/002* (2013.01)

(58) Field of Classification Search
CPC .................................................. A61K 31/195
USPC ....................................................... 514/561
See application file for complete search history.

(56) References Cited

U.S. PATENT DOCUMENTS

| | | | |
|---|---|---|---|
| 2,524,590 | A | 10/1950 | Boe |
| 3,851,051 | A | 11/1974 | Miskel et al. |
| 3,939,253 | A | 2/1976 | Bodor et al. |
| 3,998,799 | A | 12/1976 | Bodor et al. |
| 4,035,507 | A | 7/1977 | Bodor et al. |
| 4,062,475 | A | 12/1977 | Harris et al. |
| 4,575,375 | A | 3/1986 | Kozam |
| 4,764,377 | A | 8/1988 | Goodson |
| 4,826,875 | A | 5/1989 | Chiesi |
| 4,861,268 | A | 8/1989 | Garay et al. |
| 5,017,607 | A | 5/1991 | Chiesi |
| 5,021,053 | A | 6/1991 | Barclay et al. |
| 5,090,903 | A | 2/1992 | Taylor et al. |
| 5,147,654 | A | 9/1992 | Place et al. |
| 5,354,885 | A | 10/1994 | Milman et al. |
| 5,525,631 | A | 6/1996 | Milman et al. |
| 5,607,969 | A | 3/1997 | Milman et al. |
| 5,635,213 | A | 6/1997 | Nystrom et al. |
| 5,651,990 | A | 7/1997 | Takada et al. |
| 5,711,316 | A | 1/1998 | Elsberry et al. |
| 5,735,814 | A | 4/1998 | Elsberry et al. |
| 5,766,150 | A | 6/1998 | Langkau |
| 5,769,823 | A | 6/1998 | Otto |
| 5,776,493 | A | 7/1998 | Barclay et al. |
| 5,836,915 | A | 11/1998 | Steinbach et al. |
| 5,840,756 | A | 11/1998 | Cohen et al. |
| 5,842,860 | A | 12/1998 | Funt |
| 6,166,081 | A | 12/2000 | Kushnir et al. |
| 6,200,593 | B1 | 3/2001 | Place |
| 6,218,566 | B1 | 4/2001 | Lidor et al. |
| 6,221,379 | B1 | 4/2001 | Place |
| 6,227,203 | B1 | 5/2001 | Rise et al. |
| 6,264,921 | B1 | 7/2001 | Johnson et al. |
| 6,284,262 | B1 | 9/2001 | Place |
| 6,284,263 | B1 | 9/2001 | Place |
| 6,376,545 | B1 | 4/2002 | Levin |
| 6,477,410 | B1 | 11/2002 | Henley et al. |
| 6,696,600 | B2 | 2/2004 | Frenkel et al. |

(Continued)

FOREIGN PATENT DOCUMENTS

| | | |
|---|---|---|
| CA | 2143070 A1 | 8/1995 |
| CN | 103622942 A | 3/2014 |

(Continued)

OTHER PUBLICATIONS

"Apomorphine 10mg/ml solution for injection," dated Sep. 26, 2007 (31 pages).
"Apomorphine hydrochloride 10 mg/ml solution for injection/infusion," last revised in Apr. 2015 (6 pages).
"Codman 3000 Pump," available <http://www.codmanpumps.com/Patient_pain_pump.asp>, accessed Feb. 27, 2014 (3 pages).
"How to set up a 10ml fill continuous infusion using APO-gO PFS," Britannia Pharmaceuticals (2008) (2 pages).
"Information for patients: Gastro-duodenal / Pyloric Stent," Chesterfield Royal Hospital (2012) (1 page).

(Continued)

*Primary Examiner* — Raymond J Henley, III
(74) *Attorney, Agent, or Firm* — Clark & Elbing LLP

(57) ABSTRACT

The invention features a pharmaceutical suspension containing drug particles, a drug delivery device anchored in the mouth for continuously administering the pharmaceutical suspension, and methods of their use.

56 Claims, 41 Drawing Sheets

(56) References Cited

U.S. PATENT DOCUMENTS

| | | |
|---|---|---|
| 6,703,424 B2 | 3/2004 | Levin et al. |
| 6,746,688 B1 | 6/2004 | Kushnir et al. |
| 7,089,934 B2 | 8/2006 | Staniforth et al. |
| 7,101,912 B2 | 9/2006 | Xiang et al. |
| 7,237,697 B2 | 7/2007 | Dunne |
| 7,328,706 B2 | 2/2008 | Bardach et al. |
| 7,534,813 B2 | 5/2009 | Xiang et al. |
| 7,637,892 B2 | 12/2009 | Steinbach et al. |
| 7,671,089 B2 | 3/2010 | Xiang et al. |
| 7,708,730 B2 | 5/2010 | Steinbach et al. |
| 7,829,592 B2 | 11/2010 | Xiang et al. |
| 7,863,336 B2 | 1/2011 | Yacoby-Zeevi et al. |
| 7,879,358 B2 | 2/2011 | Jackson et al. |
| 7,891,358 B2 | 2/2011 | Kolb et al. |
| 7,914,510 B2 | 3/2011 | Steinbach et al. |
| 8,048,926 B2 | 11/2011 | Atlas |
| 8,177,750 B2 | 5/2012 | Steinbach et al. |
| 8,181,655 B2 | 5/2012 | Bardach et al. |
| 8,193,243 B2 | 6/2012 | Yacoby-Zeevi et al. |
| 8,211,060 B2 | 7/2012 | Steinbach |
| 8,231,598 B2 | 7/2012 | Steinbach et al. |
| 8,439,674 B2 | 5/2013 | Li et al. |
| 8,568,360 B2 | 10/2013 | Steinbach |
| 8,591,456 B2 | 11/2013 | Steinbach |
| 8,636,693 B2 | 1/2014 | Schleicher |
| 8,715,269 B2 | 5/2014 | Wolff et al. |
| 8,753,308 B2 | 6/2014 | Palmer et al. |
| 8,753,311 B2 | 6/2014 | Steinbach et al. |
| 8,808,231 B2 | 8/2014 | Steinbach |
| 8,915,893 B2 | 12/2014 | Steinbach |
| 8,961,466 B2 | 2/2015 | Steinbach |
| 9,901,561 B2 | 2/2018 | Heller et al. |
| 2003/0152628 A1 | 8/2003 | Licht et al. |
| 2003/0229310 A1 | 12/2003 | Flaherty et al. |
| 2004/0028613 A1 | 2/2004 | Quay |
| 2004/0147906 A1 | 7/2004 | Voyiazis et al. |
| 2004/0158194 A1 | 8/2004 | Wolff et al. |
| 2004/0234456 A1 | 11/2004 | Slaughter |
| 2005/0070608 A1 | 3/2005 | Remenar et al. |
| 2005/0203185 A1 | 9/2005 | Remenar et al. |
| 2006/0024368 A1 | 2/2006 | Fassihi et al. |
| 2006/0115532 A1 | 6/2006 | Shankar et al. |
| 2006/0165803 A1 | 7/2006 | Palacin et al. |
| 2007/0005042 A1 | 1/2007 | Anderson |
| 2007/0015763 A1 | 1/2007 | Romano |
| 2007/0016163 A1 | 1/2007 | Santini et al. |
| 2007/0031385 A1 | 2/2007 | Dixon |
| 2007/0112328 A1 | 5/2007 | Steinbach et al. |
| 2007/0225366 A1 | 9/2007 | Xiang et al. |
| 2008/0051459 A1 | 2/2008 | Nyholm et al. |
| 2008/0132570 A1 | 6/2008 | Xiang et al. |
| 2008/0171789 A1 | 7/2008 | Xiang et al. |
| 2008/0214663 A1 | 9/2008 | Xiang et al. |
| 2008/0255235 A1 | 10/2008 | Segrell |
| 2009/0163859 A1 | 6/2009 | Lloyd et al. |
| 2009/0170937 A1 | 7/2009 | Hobbs |
| 2009/0239941 A1 | 9/2009 | Hobbs |
| 2009/0326067 A1 | 12/2009 | Xiang et al. |
| 2010/0003238 A1 | 1/2010 | Frost et al. |
| 2010/0004332 A1 | 1/2010 | Xiang et al. |
| 2010/0047371 A1 | 2/2010 | Mumper et al. |
| 2010/0069892 A1 | 3/2010 | Steinbach et al. |
| 2010/0179171 A1 | 7/2010 | Wolf et al. |
| 2010/0190725 A1 | 7/2010 | Hobbs |
| 2010/0273852 A1 | 10/2010 | Iinuma et al. |
| 2010/0298428 A1 | 11/2010 | Yacoby-Zeevi et al. |
| 2010/0298429 A1 | 11/2010 | Yacoby-Zeevi et al. |
| 2010/0316712 A1 | 12/2010 | Nangia et al. |
| 2011/0182988 A1 | 7/2011 | Pillay et al. |
| 2011/0208163 A1 | 8/2011 | Miesel |
| 2011/0269833 A1 | 11/2011 | Yacoby-Zeevi et al. |
| 2012/0064142 A1 | 3/2012 | Pillay et al. |
| 2012/0118428 A1 | 5/2012 | Steinbach |
| 2012/0191074 A1 | 7/2012 | Steinbach |
| 2012/0203180 A1 | 8/2012 | Steinbach et al. |
| 2012/0220986 A1 | 8/2012 | Wolff et al. |
| 2012/0282335 A1 | 11/2012 | Venkatesh et al. |
| 2013/0046239 A1 | 2/2013 | Gonnelli et al. |
| 2013/0071412 A1 | 3/2013 | Leighton et al. |
| 2013/0103006 A1 | 4/2013 | Schleicher |
| 2013/0178463 A1 | 7/2013 | Damaj et al. |
| 2013/0224244 A1 | 8/2013 | Brownlie et al. |
| 2013/0337022 A1 | 12/2013 | Pillay et al. |
| 2014/0005269 A1 | 1/2014 | Ngwuluka et al. |
| 2014/0039469 A1 | 2/2014 | Steinbach |
| 2014/0073694 A1 | 3/2014 | Cicchetti et al. |
| 2014/0088192 A1 | 3/2014 | Heller et al. |
| 2014/0154328 A1 | 6/2014 | Sovic Brkicic et al. |
| 2014/0245587 A1 | 9/2014 | Steinbach et al. |
| 2014/0271835 A1 | 9/2014 | Wengner |
| 2016/0278899 A1 | 9/2016 | Heller et al. |

FOREIGN PATENT DOCUMENTS

| | | |
|---|---|---|
| DE | 102009027938 A1 | 1/2011 |
| EP | 0230294 A2 | 7/1987 |
| EP | 0330827 A1 | 4/1989 |
| EP | 2526924 A1 | 11/2012 |
| JP | S62-228007 A | 10/1987 |
| JP | 2008-521514 A | 6/2008 |
| JP | 2011-510963 A | 4/2011 |
| JP | 2012-527447 A | 11/2012 |
| WO | WO-98/16208 A1 | 4/1998 |
| WO | WO-03/41646 A2 | 5/2003 |
| WO | WO-2004/069076 A2 | 8/2004 |
| WO | WO-2005/023185 A2 | 3/2005 |
| WO | WO-2006/060547 A2 | 6/2006 |
| WO | WO-2007/140784 A2 | 12/2007 |
| WO | WO-2008/053297 A2 | 5/2008 |
| WO | WO-2009/059242 A1 | 5/2009 |
| WO | WO-2009/095681 A2 | 8/2009 |
| WO | WO-2010/134074 A1 | 11/2010 |
| WO | WO-2011/112723 A2 | 9/2011 |
| WO | WO-2012/066537 A2 | 5/2012 |
| WO | WO-2012/066538 A1 | 5/2012 |
| WO | WO-2012/079072 A2 | 6/2012 |
| WO | WO-2013/184646 A2 | 12/2013 |
| WO | WO-2015/069773 A1 | 5/2015 |

OTHER PUBLICATIONS

"Letters to the Editor," Movement Disorders. 12(4):624-6 (1997).
"Sirius: Summary of Product Characteristics." SIRIO first authorized Jan. 16, 2004 (8 pages).
"Summary of product characteristics," APO-go product insert, first authorized Sep. 2004 (11 pages).
"The SenseCore Pump Technology for Advanced Drug Delivery" Sensile Medical (8 pages).
"VARTA Product Presentation: Mini-Actuator for energy-autarkic Dispensing & Dosing Applications," RawertConsult (2012) (17 pages).
"WPM Peristaltic Pump Selection Guide," WELCO (6 Pages).
Abbott Healthcare Products, Keeping the therapy window open in Parkinson's Disease. (56 pages) (2010).
Antonini et al., "Duodenal levodopa infusion for advanced Parkinson's disease: 12-month treatment outcome," Mov Disord. 22(8):1145-9 (2007).
Arzhavitina et al., "Foams for pharmaceutical and cosmetic application," Int J Pharm. 394(1-2):1-17 (2010).
Bend Research, "Osmotic controlled-release tablet technologies," (2 pages).
Bennett et al., "Continuous oral administration of L-dihydroxyphenylalanine (L-DOPA) solution to patients with advanced Parkinson's disease," Clinc Neuropharmacol. 12(4):285-292 (1989).
Bibbiani et al., "Continuous dopaminergic stimulation reduces risk of motor complications in parkinsonian primates," Exp Neurol. 192(1):73-8 (2005).
Blindauer et al., "A randomized controlled trial of etilevodopa in patients with Parkinson disease who have motor fluctuations," Arch Neurol. 63(2):210-6 (2006).

(56) References Cited

OTHER PUBLICATIONS

Bredberg et al., "Pharmacokinetics of levodopa and carbidopa in rats following different routes of administration," Pharm Res. 11(4):549-55 (1994).
Brunner-Guenat et al., "Esters of L-dopa: Structure-hydrolysis relationships and ability to induce circling behaviour in an experimental model of hemiparkinsonism," J Pharm Pharmacol. 47(10):861-9 (1995).
Bühler, Pharmaceutical technology of BASF excipients. BASF The Chemical Company, 1-162 (2008).
Csoti et al., "Investigation on the solubility of a levodopa/carbidopa tablet (isicom®)—overcome early morning akinesia more rapidly," Neuronews. 10:1-4 (2011).
D'Aurizio et al., "Preparation and characterization of poly(lactic-co-glycolic acid) microspheres loaded with a labile antiparkinson prodrug," Int J Pharm. 409(1-2):289-96 (2011).
Denora et al., "Novel L-Dopa and dopamine prodrugs containing a 2-phenyl-imidazopyridine moiety," Pharm Res. 24(7):1309-1324 (2007).
Denys et al., "Effect of magnesium on the crystal structure and thermodynamics of the La 3-x Mg x Ni 9 hydrides," J Alloys Compd. 509(2):5540-48 (2011).
Dewey et al., "A randomized, double-blind, placebo-controlled trial of subcutaneously injected apomorphine for parkinsonian off-state events," Arch Neurol. 58(9):1385-92 (2001).
Di Stefano et al., "L-Dopa prodrugs: an overview of trends for improving Parkinson's disease treatment," Curr Pharm Des. 17(32):3482-93 (2011).
Di Stefano et al., "L-dopa- and dopamine-(R)-alpha-lipoic acid conjugates as multifunctional codrugs with antioxidant properties," J Med Chem. 49(4):1486-93 (2006).
Di Stefano et al., "Maleic- and fumaric-diamides of (O,O-diacetyl)-L-Dopa-methylester as anti-Parkinson prodrugs in liposomal formulation," J Drug Target. 14(9):652-661 (2006).
Dixit, "Floating Drug Delivery System," Journal of Current Pharmaceutical Research. 7(1):6-20 (2011).
Djaldetti et al., "Effect of subcutaneous administration of levodopa ethyl ester, a soluble prodrug of levodopa, on dopamine metabolism in rodent striatum: implication for treatment of Parkinson's disease," Clin Neuropharmacol. 19(1):65-71 (1996).
Djaldetti et al., "Levodopa ethylester: a novel rescue therapy for response fluctuations in Parkinson's disease," Ann Neurol. 39(3):400-4 (1996).
Djaldetti et al., "Oral solution of levodopa ethylester for treatment of response fluctuations in patients with advanced Parkinson's disease," Mov Disord. 17(2):297-302 (2002).
Djaldetti et al., "Pharmacokinetics of etilevodopa compared to levodopa in patients with Parkinson's disease: an open-label, randomized, crossover study," Clin Neuropharmacol. 26(6):322-6 (2003).
Djaldetti et al., "Subcutaneous injections of levodopa ethylester: a potential novel rescue therapy for response fluctuations in patients with Parkinson's disease," Neurology. 45(Suppl 4):A276 (Abstract 415S) (1995).
Doi et al., "Nizatidine ameliorates gastroparesis in Parkinson's disease: a pilot study," Mov Disord 29(4):562-6 (2014) (4 pages).
Durso et al., "Variable absorption of carbidopa affects both peripheral and central levodopa metabolism," J Clin Pharmacol. 40(8):854-60 (2000).
Ettmayer et al., "Lessons learned from marketed and investigational prodrugs," J Med Chem. 47(10):2393-204 (2004).
European Pharmocopoeia 5.0, "Apomorphine hydrochloride," <http://lib.njutcm.edu.cn/yaodian/ep/EP5.0/16_monographs/monographs_a-c/Apomorphine%20hydrochloride.pdf>. Retrieved on Jun. 26, 2013 (2 pages).
Extended European Search Report for European Application No. 11847546.6, dated Apr. 22, 2015 (15 pages).
Fix et al., "Short-chain alkyl esters of L-dopa as prodrugs for rectal absorption," Pharm Res. 6(6):501-505 (1989).

Fuchs et al., "Solubility of amino acids: influence of the pH value and the addition of alcoholic cosolvents on aqueous solubility," Ind Eng Chem Res. 45(19):6578-84 (2006).
Furukawa et al., "L-DOPA cyclohexyl ester is a novel potent and relatively stable competitive antagonist against L-DOPA among several L-DOPA ester compounds," Jpn J Pharmacol. 82(1):40-7 (2000).
Gancher et al., "Peripheral pharmacokinetics of apomorphine in humans," Ann Neurol. 26(2):232-8 (1989).
Ganesalingam et al., "Apomorphine-induced necrotic ulcers," Mov Disord. 26(12):2182 (2011).
Goole et al., "Development and evaluation of new multiple-unit levodopa sustained-release floating dosage forms," Int J Pharm. 334(1-2):35-41 (2007).
Goole et al., "Levodopa delivery systems for the treatment of Parkinson's disease: An overview," Int J Pharm. 380(1-2):1-15 (2009).
Gray, "Initial test of viscous fluid with SS Piezo pump," Dolomite—US Office, Quote No. 977795, dated Jul. 14, 2014 (5 pages).
Göttsche et al., "IntelliDrug—an integrated intelligent oral drug delivery system," Integrated Microsystems for Biomedicine (2 pages).
Hamada et al., "Interaction of L-3,4-dihydroxyphenylalanin (L-DOPA) as a coordinating ligand with a series of metal ions; reaction of L-DOPA," J Coord Chem. 60(20):2149-63 (2007).
Hamedi et al., "Solubility diagrams in solvent-antisolvent systems by titration calorimetry," J Therm Anal Calorim. 89(1):87-92 (2007).
Hardie et al., "On-off fluctuations in Parkinson's disease. A clinical and neuropharmacological study," Brain. 107(Pt 2):487-506 (1984).
Hardie et al., "The pharmacokinetics of intravenous and oral levodopa in patients with Parkinson's disease who exhibit on-off fluctuations," Br J Clin Pharmacol. 22(4):429-36 (1986).
Hargraves et al., "Chronic intrastriatal dopamine infusions in rats with unilateral lesions of the substantia nigra," Life Sci. 40(10):959-66 (1987).
Haznar-Garbacz et al., "A novel liquefied gas based oral controlled release drug delivery system for liquid drug formulations," Eur J Pharm Biopharm. 81(2):334-8 (2012).
Haznar-Garbacz et al., "An oral-controlled release drug delivery system for liquid and semisolid drug formulations," AAPS PharmSciTech. 12(4):1183-1185 (2011).
Herken et al., "Die erzeugung von natrium- und wasserretentionen zur prüfung der diuretica," Arch. exper. Path. u. Pharmakol. 229:123-38 (1956). English summary included.
Herrlich et al., "Miniaturized osmotic pump for oromucosal drug delivery with external readout station." 33rd Annual International Conference of the IEEE EMBS. Boston, MA, 8380-3. Aug. 30-Sep. 3, 2011 (4 pages).
Herrlich et al., "Osmotic micropumps for drug delivery." Adv Drug Deliv Rev. 64(14):1617-27 (2012).
Hood et al., "Possible treatment of Parkinson's disease with intrathecal medication in the MPTP model," Ann NY Acad Sci. 531:200-5 (1988).
International Preliminary Report on Patentability and Written Opinion for International Patent Application No. PCT/US2013/044049, dated Dec. 9, 2014 (9 pages).
International Preliminary Report on Patentability and Written Opinion for International Patent Application No. PCT/US2014/064137, dated May 10, 2016 (8 pages).
International Preliminary Report on Patentability for International Patent Application No. PCT/US2011/064398, dated Jan. 14, 2014 (11 pages).
International Search Report and Written Opinion for International Application No. PCT/US16/31308, dated Aug. 16, 2016 (12 pages).
International Search Report and Written Opinion for International Patent Application No. PCT/US13/44049, dated Jan. 2, 2014 (12 pages).
International Search Report and Written Opinion for International Patent Application No. PCT/US14/64137, dated Mar. 11, 2015 (17 pages).
International Search Report for International Patent Application No. PCT/US2011/064398, dated Jun. 22, 2012 (6 pages).

(56) References Cited

OTHER PUBLICATIONS

Itoh et al., "A feasibility study of differential delivery of levodopa ester and benserazide using site-specific intestinal loops in rats," J Pharm Sci. 99(1):227-33 (2010).
Juncos et al., "Levodopa methyl ester treatment of Parkinson's disease," Neurology. 37(7):1242-5 (1987).
Jung et al.,"Efficient synthesis of selectively protected L-dopa derivatives from L-tyrosine via reimer-tiemann and dakin reactions," J Org Chem. 62(5):1553-55 (1997).
Kao et al., "Enhancement of the systemic and CNS specific delivery of L-dopa by the nasal administration of its water soluble prodrugs," Pharm Res. 17(8):978-84 (2000).
Kleedorfer et al., "Subcutaneous and sublingual levodopa methyl ester in parkinson's disease," J Neurol Neurosurg Psychiatry. 54(4):373 (1991).
Kralova et al., "Surfactants used in food industry: a review," J Dispers Sci Technol. 30(9):1363-83 (2009).
Kurlan et al., "Duodenal and gastric delivery of levodopa in parkinsonism." Ann Neurol. 23(6):589-95 (1988).
Kurth et al., "Oral levodopa/carbidopa solution versus tablets in Parkinson's patients with severe fluctuations: a pilot study," Neurology. 43(5):1036-9 (1993) (6 pages).
Lees et al., "Apomorphine for parkinson's disease," Prac Neurol. 2(5):280-6 (2002).
LeWitt, "Subcutaneously administered apomorphine: Pharmacokinetics and metabolism," Neurology. 62(6 Suppl 4):S8-S11 (2004).
Liu et al., "Mosapride citrate, a novel 5-HT4 agonist and partial 5-HT3 antagonist, ameliorates constipation in parkinsonian patients," Mov Disord 20(6):680-6 (2005).
Lundqvist, "Continuous levodopa for advanced parkinson's disease," Neuropsychiatr Dis Treat. 3(3):335-48 (2007).
Marriott et al., "Pharmacokinetic and clinical evaluation of liquid L-dopa/carbidopa in Parkinson's disease," J Clin Neurosci. 5(2):178-81 (1998).
Moonan et al., "Effect of pressure on the mechanical properties of polymers. 2. Expansivity and compressibility measurements," Macromolecules 16(1):55-9 (1983).
Muchmore et al., "Review of the mechanism of action and clinical efficacy of recombinant human hyaluronidase coadministration with current prandial insulin formulations," J Diabetes Sci Technol. 4(2):419-28 (2010).
Ngwuluka et al., "A novel pH-responsive interpolyelectrolyte hydrogel complex for the oral delivery of levodopa. Part I. IPEC modeling and synthesis," J Biomed Mater Res A. 103(3):1077-84 (2015).
Nicolle et al., "Pharmacokinetics of apomorphine in parkinsonian patients," Fundam Clin Pharmacol. 7(5):245-52 (1993).
Nord et al., "The effect of peripheral enzyme inhibitors on levodopa concentrations in blood and CSF," Mov Disord. 25(3):363-7 (2010).
Nutt et al., "Levodopa pharmacokinetics and pharmacodynamics in fluctuating parkinsonian patients," Neurology. 36(6):739-44 (1986).
Nyholm et al., "Frequent administration of levodopa/carbidopa microtablets vs levodopa/carbidopa/entacapone in healthy volunteers," Acta Neurol Scand. 127(2):124-32 (2013).
Nyholm et al., "Levodopa fractionation in Parkinson's disease," J Parkinsons Dis. 4(1):89-96 (2014).
Nyholm et al., "Pharmacokinetics of levodopa, carbidopa, and 3-O-methyldopa following 16-hour jejunal infusion of levodopa-carbidopa intestinal gel in advanced Parkinson's disease patients," AAPS J. 15(2):316-23 (2013).
Nyholm et al., "Pharmacokinetics of levodopa/carbidopa microtablets versus levodopa/benserazide and levodopa/carbidopa in healthy volunteers," Clin Neurophamacol. 35(3):111-7 (2012).
Nyholm, "Infusing levodopa to stabilise blood levels," EPNN Journal. 5:10-1 (2005).
Olanow et al., "The scientific and clinical basis for the treatment of Parkinson disease (2009)," Neurology. 72(21 Suppl 4):S1-S136 (2009).
Palin et al., "Determination of gastric-emptying profiles in the rat: influence of oil structure and volume," Int J Pharm. 12(4):315-322 (1982).
Pappert et al., "Levodopa stability in solution: time course, environmental effects, and practical recommendations for clinical use," Mov Disord. 11(1):24-6 (1996).
Pappert et al., "Liquid levodopa/carbidopa produces significant improvement in motor function without dyskinesia exacerbation," Neurology. 47(6):1493-5 (1996).
Park et al., "Malignant obstruction of gastric outlet and duodenum: palliation with flexible covered metallic stents," Radiology. 219(3) (5 pages) (2001).
PCT: Nursing Policy and Procedure, "Standard operating procedure for: administration of apomorphine via the apo-go pump," (2010) (12 pages).
Pinnen et al., "Codrugs linking L-dopa and sulfur-containing antioxidants: new pharmacological tools against Parkinson's disease," J Med Chem. 52(2):559-63 (2009).
Principles and Practice. Burger's Medicinal Chemistry and Drug Discovery. Wolff, 975-977 (1997).
Public Assessment Report: Scientific discussion for Flexilev (levodopa/carbidopa), Mar. 20, 2014 (10 pages).
Quinn et al., "Complicated response fluctuations in Parkinson's disease: response to intravenous infusion of levodopa," Lancet. 2(8295):412-5 (1982).
Quinn et al., "Control of on/off phenomenon by continuous intravenous infusion of levodopa," Neurology. 34(9):1131-6 (1984).
Rayner et al., "New management approaches for gastroparesis," Nat Clin Pract Gastroenterol Hepatol. 2(10):454-62 (2005) (13 pages).
Reuter et al., "Nocturnal subcutaneous apomorphine infusion in Parkinson's disease and restless legs syndrome," Acta Neurol Scand. 100(3):163-7 (1999).
Rodríguez-Molinero et al., "Treatment of Parkinson's disease could be regulated by movement sensors: subcutaneous infusion of varying apomorphine doses according to the intensity of motor activity," Med Hypotheses. 72(4):430-3 (2009).
Rosin et al., "Parkinsonism with 'on-off' phenomena. Intravenous treatment with levodopa after major abdominal surgery," Arch Neurol. 36(1):32-4 (1979).
Sabel et al., "Extended levodopa release from a subcutaneously implanted polymer matrix in rats," Ann Neurol. 28(5):714-7 (1990).
Saghir et al., "Rapid in vivo hydrolysis of fatty acid ethyl esters, toxic nonoxidative ethanol metabolites," Am J Physiol. 273(1 Pt 1):G184-90 (1997).
Scientific Discussion of IONSYS (fentanyl HCl), EMEA (2005) (42 pages).
Sensidose, "Press Release," <http://sensidose.se/press-release/>, Mar. 26, 2014 (5 pages).
Shoulson et al., "On-off response. Clinical and biochemical correlations during oral and intravenous levodopa administration in parkinsonian patients," Neurology. 25(12):1144-8 (1975).
Solvay Pharmaceuticals, "Duodopa's guide for health care givers," <http://www.asociatia-antiparkinson.ro/Doc/CDS/Carbiodopa-levodopa/Duodopa-Users_Guide-060818.pdf>. Retrieved on Jun. 26, 2013 (64 pages).
Solvay Pharmaceuticals, "Duodopa® Intestinal Gel: Product information," <http://www.mims.com.au/emims/errata/20080701/duodopa.pdf>. Retrieved on Jun. 26, 2013 (17 pages).
Soykan et al., "Effect of chronic oral domperidone therapy on gastrointestinal symptoms and gastric emptying in patients with Parkinson's disease," Mov Disord. 12(6):952-7 (1997).
Stella, "Prodrugs as therapeutics," Expert Opin Ther Patents. 14(3):277-80 (2004).
Stennett et al., "Stability of levodopa in 5% dextrose injection at pH 5 or 6," Am J Hosp Pharm. 43(7):1726-8 (1986).
Stocchi et al., "Fluctuating parkinsonism: a pilot study of single afternoon dose of levodopa methyl ester," J Neurol. 243(5):377-80 (1996).
Stocchi et al., "Intermittent vs continuous levodopa administration in patients with advanced Parkinson disease: a clinical and pharmacokinetic study," Arch Neurol. 62(6):905-10 (2005).
Stocchi et al., "Intravenous boluses and continuous infusions of L-dopa methyl ester in fluctuating patients with Parkinson's disease," Mov Disord. 7(3):249-56 (1992).

(56) References Cited

OTHER PUBLICATIONS

Stocchi et al., "Melevodopa/carbidopa effervescent formulation in the treatment of motor fluctuations in advanced Parkinson's disease," Mov Disord. 25(12):1881-7 (2010).

Stocchi et al., "Prospective randomized trial of lisuride infusion versus oral levodopa in patients with Parkinson's disease," Brain. 125(Pt 9):2058-66 (2002).

Sun et al., "Preparation of levodopa-2, 6-dimethyl-beta-cyclodextrin inclusion by saturation solution process," Artif Cells Blood Substit Immobil Biotechnol. 36(4):352-9 (2008).

Swope, "Rapid treatment of "wearing off" in Parkinson's disease," Neurology. 62(6 Suppl 4):S27-S31 (2004).

Syed et al., "Ten years' experience with enteral levodopa infusions for motor fluctuations in Parkinson's disease," Mov Disord. 13(2):336-8 (1998).

Tang et al., "Synthesis and characterization of water-soluble and photostable L-DOPA dendrimers," Org Lett. 8(20):4421-4 (2006).

Testa, "Prodrug research: futile or fertile?" Biochem Pharmacol. 68(11):2097-106 (2004).

The Merck Index: An Encyclopedia of Chemicals, Drugs, and Biologicals, Twelfth Edition. Budavari, O'Neil, Smith, Heckelman, Kinneary, 578 (1996).

Todd et al., "Apomorphine nodules in Parkinson's disease: best practice considerations," Br J Community Nurs. 13(10):457-63 (2008).

Varma et al., "pH-Dependent solubility and permeability criteria for provisional biopharmaceutics classification (BCS and BDDCS) in early drug discovery," Mol Pharm. 9(5):1199-212 (2012).

Wang et al., "Ghrelin prevents levodopa-induced inhibition of gastric emptying and increases circulating levodopa in fasted rats," Neurogastroenterol Motil. 24(5):e235-45 (2012).

Westin et al., "A pharmacokinetic-pharmacodynamic model for duodenal levodopa infusion," Clin Neuropharmacol. 34(2):61-5 (2011).

Wilson, Modern Delivery Strategies: Physiological Considerations for Orally Administered Medications. *Drug Bioavailability: Estimation of Solubility, Permeability, Absorption and Bioavailability.* ed. van de Waterbeemd et al., WILEY-VCH Verlag GmbH & Co., 547-568 (2003).

Yang et al., "Solubility of form alpha and form gamma of glycine in aqueous solutions," J Chem Eng Data. 53(5):1133-7 (2008).

Cobo et al., "MEMS: Enabled Drug Delivery Systems," Adv Healthc Mater. 4(7):969-82 (2015).

Goettsche et al., "Highly integrated oral drug delivery system with valve based on electro-active-polymer," IEEE 20th International Conference on Micro Electro Mechanical Systems. 461-4 (2007).

Meng et al., "Micro- and nano-fabricated implantable drug-delivery systems," available in PMC Oct. 1, 2013, published in final edited form as: Ther Deliv. 3(12):1457-67 (2012) (18 pages).

Velten et al., "Intelligent intraoral drug delivery microsystem," Proceedings of the Institution of Mechanical Engineers, Part C: Journal of Mechanical Engineering Science. 220(11):1609-1617 (2006).

after jet milling (5,000x mag)

PHARMACEUTICAL SUSPENSIONS CONTAINING DRUG PARTICLES, DEVICES FOR THEIR ADMINISTRATION, AND METHODS OF THEIR USE

FIELD OF THE INVENTION

The invention features a pharmaceutical suspension containing drug particles, a drug delivery device anchored in the mouth for continuously administering the pharmaceutical suspension, and methods of their use.

BACKGROUND

This invention relates to devices and methods for continuous or semi-continuous drug administration via the oral route. It is an aim of this invention to solve several problems related to drugs with short physiological half-lives of drugs (e.g., shorter than 8 hours, 6 hours, 4 hours, 2 hours, 1 hour, 30 min, 20 min or 10 min) and/or narrow therapeutic windows of drugs that are currently dosed multiple times per day: it is inconvenient to take a drug that must be dosed multiple times per day or at night, the drug's pharmacokinetics and efficacy may be sub-optimal, and side effects may increase in frequency and/or severity. Continuous or semi-continuous administration can be particularly beneficial for drugs with a short half-life (e.g., in the plasma), and/or short persistence of the drug's physiological effect, and/or a narrow therapeutic window, such as levodopa (LD), muscle relaxants (e.g., baclofen for managing spasticity), anti-epileptics (e.g., oxcarbazepine, topiramate, lamotrigine, gabapentin, carbamazepine, valproic acid, levetiracetam, pregabalin), parasympathomimetics (e.g., pyridostigmine) and sleep medications (e.g., zaleplon). Continuous or semi-continuous infusion in the mouth can provide for lesser fluctuation in the concentration of a drug in an organ or fluid, for example in the blood or plasma. Convenient, automatic administration of a drug can also increase patient compliance with their drug regimen, particularly for patients who must take medications at night and for patients with dementia.

Medical conditions managed by continuously orally administered drugs include Parkinson's disease, spasticity, muscular weakness, bacterial infections, cancer, pain, organ transplantation, disordered sleep, epilepsy and seizures, anxiety, mood disorders, post-traumatic stress disorder, arrhythmia, hypertension, heart failure, dementia, allergies, and diabetic nephropathy.

A challenge with most drug delivery devices in the prior art can be that they are not designed for placement and operation in the mouth. Devices must be designed to be small, comfortable, and non-irritating, and to not interfere with speech, swallowing, drinking and/or eating. In the mouth saliva, food or drink may penetrate into the drug reservoir and/or the pump, thereby potentially unpredictably extracting and delivering the drug, reacting with the drug, or clogging the delivery device. Pumps that have been suggested for operation in the mouth, such as osmotic tablets and mucoadhesive patches, often do not reliably provide constant rate drug delivery for extended periods of time under the conditions in the mouth. Drinking of hot or cold beverages may cause undesirable changes in drug delivery, e.g., delivery of a drug bolus. Likewise, sucking on the device may cause delivery of an unwanted bolus. Exposure to foods and liquids such as oils, alcohols, and acids may temporarily or permanently increase or decrease the drug delivery rate from the device. Intra-oral drug delivery devices must also administer the drug into a suitable location in the mouth, e.g., to a location where it can be immediately swallowed or to a location where the drug does not accumulate in an unwanted manner. There is, therefore, a need for improved drug delivery devices that can operate comfortably, safely, and reliably in the mouth over extended periods of time.

Intra-oral pumps have previously been proposed in inconvenient formats, e.g., wherein the device can be located within a replacement tooth. There is a need for improved intra-oral drug delivery devices that can conveniently be inserted and removed by the patient, without requiring the insertion or removal of a replacement tooth, dental bridge, or denture. A problem with these and other pumps that reside in the mouth and that can continuously deliver drug in the mouth, such as controlled release osmotic tablets and mucoadhesive drug delivery patches, can be that once drug delivery has begun it cannot be temporarily stopped. Temporarily stopping the drug delivery can be desirable so that drug is not wasted and, more importantly, so that dispensed drug does not accumulate on the surface of the device while the device is removed from the mouth. Such an unquantified accumulation of drug on the surface of the device might lead to the undesired delivery of a bolus of an unknown quantity of drug to the patient when the device is placed back into the mouth. Maintenance of accurate rate of drug delivery when the ambient atmospheric pressure changes, e.g., during air-travel or at elevated locations, can also be challenging.

The pumps of the invention can provide constant rate, continuous administration of drugs in the mouth, and in some embodiments can be temporarily stopped when the devices are removed from the mouth.

Most drugs intended for oral administration have been formulated as solids (e.g., pills, tablets), solutions, or suspensions that are administered once or several times per day. Such drugs are not formulated to meet the requirements of continuous or semi-continuous, constant-rate, intra-oral administration. For example, many suspensions and solutions have been formulated in relatively large daily volumes that don't fit in the mouth without interfering with its functions, particularly with speech, and/or in formulations that are physically or chemically unstable over the course of a day at body temperature; and pills and tablets have rarely been formulated in units and dosage amounts appropriate for dosing frequently throughout the day.

Large quantities of drug must be administered to treat some diseases. For example, 1,000 mg of levodopa is a typical daily dose administered to patients with advanced Parkinson's disease. In order to continuously administer such large quantities of drug into the mouth in a fluid volume that will fit comfortably in the mouth (typically less than 5 mL) for many hours, it is sometimes necessary to employ concentrated, often viscous, fluid formulations of the drug. Use of viscous fluids can provide the small volumes, high concentrations, uniform drug dispersion, storage stability, and operational stability desired for the drugs and methods of the invention. Consequently, it is often necessary to employ miniaturized pumps tailored to provide the pressures required to pump the viscous fluids. The drug devices and formulations of the invention address these unmet needs.

As a specific example, Parkinson's disease (PD) is characterized by the inability of the dopaminergic neurons in the substantia nigra to produce the neurotransmitter dopamine. PD impairs motor skills, cognitive processes, autonomic functions, and sleep. Motor symptoms include tremor, rigidity, slow movement (bradykinesia), and loss of the ability to initiate movement (akinesia) (collectively, the "off" state).

Non-motor symptoms of PD include dementia, dysphagia (difficulty swallowing), slurred speech, orthostatic hypotension, seborrheic dermatitis, urinary incontinence, constipation, mood alterations, sexual dysfunction, and sleep issues (e.g., daytime somnolence, insomnia).

After more than 40 years of clinical use levodopa (LD) therapy remains the most effective method for managing PD and provides the greatest improvement in motor function. Consequently, LD administration is the primary treatment for PD. LD is usually orally administered. The orally administered LD enters the blood and part of the LD in the blood crosses the blood brain barrier. It is metabolized, in part, in the brain to dopamine which temporarily diminishes the motor symptoms of PD. As the neurodegeneration underlying PD progresses, the patients require increasing doses of LD and the fluctuations of brain dopamine levels increase. When too much LD is transported to the brain, dyskinesia sets in (uncontrolled movements such as writhing, twitching and shaking); when too little is transported, the patient re-enters the off state. Furthermore, as PD progresses, the therapeutic window for oral formulations of LD narrows, and it becomes increasingly difficult to control PD motor symptoms without inducing motor complications. In addition, most PD patients develop response fluctuations to intermittent oral LD therapy, such as end of dose wearing off, sudden on/offs, delayed time to on, and response failures.

The devices, formulations and methods of the invention provide improved therapies for patients with PD.

SUMMARY OF THE INVENTION

The present invention features a pharmaceutical suspension containing drug particles, a drug delivery device for continuously administering the pharmaceutical suspension to the oral cavity, and methods of using the same.

In a first aspect, the invention features a pharmaceutical composition including a suspension, the suspension including (i) from about 35% to about 75% (w/w) (e.g., from about 35% to about 70%, from about 35% to about 65%, from about 35% to about 60%, from about 35% to about 55%, from about 35% to about 50%, from about 35% to about 45%, from about 35% to about 40%, from about 40% to about 45%, from about 40% to about 45%, from about 40% to about 50%, from about 40% to about 55%, from about 40% to about 60%, from about 40% to about 65%, from about 40% to about 65%, from about 40% to about 70%, from about 40% to about 75%, from about 45% to about 75%, from about 50% to about 75%, from about 55% to about 75%, from about 60% to about 75%, from about 65% to about 75%, from about 70% to about 75%, or from about 50% to about 65%) drug particles including levodopa and/or carbidopa, or salts thereof, (ii) from about 19% to about 30% (w/w) (e.g., from about 19% to about 28%, from about 19% to about 26%, from about 19% to about 24%, from about 19% to about 22%, from about 19% to about 21%, from about 21% to about 24%, from about 21% to about 30%, from about 24% to about 30%, from about 26% to about 30%, or from about 28% to about 30%) of one or more water-immiscible compounds, (iii) from about 2% to about 16% (w/w) (e.g., from about 2% to about 15%, from about 2% to about 13%, from about 2% to about 12%, from about 2% to about 10%, from about 2% to about 8%, from about 2% to about 6%, from about 2% to about 4%, from about 4% to about 13%, from about 6% to about 13%, from about 8% to about 13%, from about 6% to about 10%, from about 10% to about 13%, or from about 13% to about 16%) water, and (iv) from about 1% to about 8% (w/w) (e.g., from about 1% to about 7%, from about 1% to about 5%, from about 1% to about 3%, from about 3% to about 8%, or from about 5% to about 8%) surfactant, wherein the pharmaceutical composition is physically stable and suitable for continuous or frequent intermittent intra-oral delivery. In some embodiments, the pharmaceutical composition includes a drug particle-containing emulsion.

In a second aspect, the invention features a pharmaceutical composition including a suspension including (i) from about 35% to about 75% (w/w) (e.g., as described herein) drug particles, (ii) from about 19% to about 30% (w/w) (e.g., as described herein) of one or more water-immiscible compounds, (iii) from about 2% to about 16% (w/w) (e.g., as described herein) water, and (iv) from about 1% to about 8% (w/w) surfactant, wherein the pharmaceutical composition is physically stable and suitable for continuous or frequent intermittent intra-oral delivery. In some embodiments, the pharmaceutical composition includes a drug particle-containing emulsion. In other embodiments, the pharmaceutical composition is macroscopically substantially homogeneous.

In a third aspect, the invention features a pharmaceutical composition including a suspension including (i) an excess of one or more water-immiscible compounds over water, and (ii) from about 35% to about 75% (w/w) (e.g., as described herein) drug particles, wherein the pharmaceutical composition is physically stable (e.g., for 6 months, 8 months, 10 months, 12 months, or more) at about 5° C. and/or about 25° C. In some embodiments, the pharmaceutical composition includes an emulsion (e.g., a drug particle-containing emulsion). In other embodiments, the pharmaceutical composition is macroscopically substantially homogeneous. In some embodiments, the pharmaceutical composition is suitable for continuous or frequent intermittent intra-oral delivery.

In any of the preceding aspects, the suspension may be an extrudable, non-pourable emulsion. In some embodiments, the suspension is physically stable for about 12 months at about 5° C. In other embodiments, the suspension is physically stable for about 12 months at about 25° C. In certain embodiments, after 12 months (e.g., after 13 months, after 14 months, after 15 months, or more) the suspension is physically stable for about 48 hours at about 37° C.

In any of the preceding aspects, the pharmaceutical composition may include a continuous hydrophilic phase. The continuous hydrophilic phase can provide for rapid dispersion of solid drug particle containing suspensions in saliva and the well dispersed solid drug particles can dissolve rapidly in saliva.

In any of the preceding aspects, the concentration of drug in a pharmaceutical composition may be at least 1.75 M (e.g, more than 1.80 M, 1.85 M, 1.90 M, 1.95 M, 2.0 M, 2.5 M, 3.0 M, or even 3.5 M). In some embodiments, the pharmaceutical composition includes from about 50% to about 70% (w/w) (e.g., from about 50% to about 65%, from about 50% to about 60%, from about 50% to about 55%, from about 55% to about 70%, from about 60% to about 70%, or from about 65% to about 70%) solid drug particles, wherein the concentration of drug in the pharmaceutical composition is at least 3.0 M (e.g., 3.1 M, 3.2 M, 3.5 M, or more).

In some embodiments, the suspension of any of the preceding aspects includes one or more water-immiscible compounds that melts or softens below 45° C. (e.g., at 40° C., 37° C., 35° C., or less). In some embodiments, the weight ratio of the one or more water-immiscible compounds to water is greater than 1.0 (e.g., greater than 1.5, greater than 2.0, greater than 3.0, or greater than 5.0).

In some embodiments, the one or more water-immiscible compounds of any of the preceding aspects includes an oil. In some embodiments, the suspension includes a continuous hydrophilic phase including greater than 50% (w/w) (e.g., 55%, 60%, 65%, 70%, or 75%) drug particles. In certain embodiments, the suspension includes an oil in water emulsion. In some embodiments, the suspension is free of polymers of a molecular mass greater than 1,000 Daltons (e.g., greater than about 1,100 Daltons, greater than about 1,200 Daltons, greater than about 1,500 Daltons, greater than about 1,700 Daltons, or greater than about 2,000 Daltons). In some embodiments, the suspension has a dynamic viscosity of at least 100 cP (e.g., greater than 500 cP, 1,000 cP, 5,000 cP, 10,000 cP, 50,000 cP, or 100,000 cP) at 37° C.

In any of the preceding aspects, the suspension may include greater than 50% (w/w) (e.g., greater than 55%, greater than 60%, greater than 65%, or greater than 70%) drug particles. In some embodiments, the $D_{50}$ of the drug particles can be less than or equal to about 500 μm, about 250 μm, about 200 μm, about 150 μm, about 125 μm, or about 100 μm. In some embodiments, the $D_{50}$ of the drug particles can be greater than or equal to about 1 μm, about 3 μm, about 5 μm, about 10 μm, or about 25 μm, or the $D_{50}$ of the drug particles can be less than or equal to 50 μm such as less than or equal to 25 μm. In typical embodiments, the $D_{50}$ of the drug particles can be 25±24 μm; 1-10 μm; 11-20 μm; 21-30 μm; 31-40 μm; or 41-50 μm. In other embodiments, the $D_{50}$ of the drug particles can be 75±25 μm; 51-75 μm; or 76-100 μm. In certain embodiments, the $D_{50}$ of the drug particles can be 125±25 μm. In further embodiments, the $D_{50}$ of the drug particles can be 175±25 μm.

In any of the preceding aspects, the suspension may include less than or equal to about 16% (w/w), about 13% (w/w), about 12% (w/w), about 11% (w/w), or about 9% (w/w) water. In some embodiments, the suspension can include greater than or equal to about 1% (w/w), about 2% (w/w), or about 3% (w/w) water. In certain embodiments, the suspension can include 4±2% (w/w) water. In particular embodiments, the suspension can include 8±2% (w/w) water. In other embodiments, the suspension can include 13±3% (w/w) water.

In any of the preceding aspects, the one or more water-immiscible compounds may include an oil selected from a saturated fatty acid triglyceride, an unsaturated fatty acid triglyceride, a mixed saturated and unsaturated fatty acid tryglyceride, a medium-chain fatty acid triglyceride, canola oil, coconut oil, palm oil, olive oil, soybean oil, sesame oil, corn oil, or mineral oil. In some embodiments, the oil comprises a saturated fatty acid triglyceride or a mixture of saturated fatty acid triglycerides. In other embodiments, the oil can be a medium-chain fatty acid triglyceride or a mixture of medium-chain fatty acid triglycerides. For example, the oil can be a Miglyol® or chemical equivalent. In certain embodiments, the oil can be a canola oil. In particular embodiments, the oil can be a coconut oil. In some embodiments, the oil can be a triglyceride or one or more $C_6$-$C_{24}$ fatty acids, such as a triglyceride of one or more $C_8$-$C_{16}$ fatty acids. For example, the oil can be a triglyceride of $C_8$-$C_{12}$ fatty acids, $C_{14}$-$C_{18}$ fatty acids, or $C_{20}$-$C_{24}$ fatty acids, or a mixture thereof. In some embodiments, at least 50% (w/w) of the one or more water-immiscible compounds can be a triglyceride of one or more $C_8$-$C_{12}$ fatty acids. In certain embodiments, the suspension can include less than or equal to about 30% (w/w) (e.g., about 29% (w/w), about 27% (w/w), or about 25% (w/w)) of the oil. In particular embodiments, the suspension can include greater than or equal to about 19% (w/w) (e.g., about 21% (w/w), or about 23% (w/w)) of the oil. In certain embodiments, the suspension can include 20±2% (w/w) of the oil. In typical embodiments, the suspension can include 24±2% (w/w) of the oil. In some embodiments, the suspension can include 28±2% (w/w) of the oil.

In any of the preceding aspects, the pharmaceutical composition may include a surfactant. A surfactant of a pharmaceutical composition may be a non-ionic surfactant. In some embodiments, the non-ionic surfactant can include a polyglycolized glyceride, a poloxamer, an alkyl saccharide, an ester saccharide, or a polysorbate surfactant. In certain embodiments, the non-ionic surfactant can include a poloxamer. In other embodiments, the non-ionic surfactant can include a polyglycolized glyceride such as a polyethoxylated castor oil. In particular embodiments, the non-ionic surfactant can include a polysorbate surfactant that can be Polysorbate 60. In some embodiments, the suspension can include less than or equal to about 8% (w/w) (e.g., about 7% (w/w), about 6% (w/w), or about 5% (w/w)) of the surfactant. In some embodiments, the suspension can include greater than or equal to about 2% (w/w) (e.g., about 3% (w/w) or about 4% (w/w)) of the surfactant. In certain embodiments, the suspension can include about 5±2% (w/w) of the surfactant.

In some embodiments, a pharmaceutical composition of any of the preceding aspects can further include an antioxidant such as Vitamin E, TPGS, ascorbylpalmitate, a tocopherol, thioglycerol, thioglycolic acid, cysteine, N-acetyl cysteine, vitamin A, propyl gallate, octyl gallate, butylhydroxyanisole, or butylhydroxytoluene. In some embodiments, the antioxidant can be oil soluble. In other embodiments, the apparent pH of the suspension of any of the preceding aspects can be less than or equal to about 7.0, about 5.0, or about 4.0, the apparent pH being the pH measured by inserting an aqueous solution calibrated glass walled pH electrode into the formulation at 23±3° C. In certain embodiments, the apparent pH can be greater than or equal to about 2.5, such as greater than or equal to 3.0 or 3.5. In some embodiments, the shelf life of the pharmaceutical composition can be 1 year or longer at 5±3° C. In particular embodiments, the shelf life of the pharmaceutical composition can be 1 year or longer at 25±3° C. For example, the apparent pH of the pharmaceutical composition can be less than pH 5 and can remain less than pH 5 after 3 months storage at about 25° C., can remain less than pH 4 after 3 months storage at 25° C., or the apparent pH can equal or be less than pH 3 after 3 months storage at about 25° C. The pharmaceutical compositions can optionally include a bacteriostatic or a fungistatic agent, such as benzoic acid or a benzoate salt. In particular embodiments, the combined concentrations of benzoic acid and benzoate salt in the pharmaceutical composition can be between 0.1 percent by weight and 1 percent by weight. The pharmaceutical compositions can optionally include a transition metal ion complexing agent or a salt thereof, such as EDTA. In particular embodiments, the combined concentrations of EDTA and its salt or salts can be between 0.05 weight % and 0.25 weight %. The pharmaceutical compositions can optionally include a sulfur containing compound such as cysteine and N-acetylcysteine capable of reacting at 25±3° C. with dopaquinone or with quinone formed by oxidation of carbidopa.

In any of the preceding aspects, the suspension of the drug particles of a pharmaceutical composition may include levodopa or a levodopa prodrug, or carbidopa or a carbidopa prodrug, benserazide, or any mixture thereof. In particular embodiments, the suspension of the drug particles can include levodopa and/or carbidopa. In some embodiments that include carbidopa, the pharmaceutical composition can include less than about 2 µg (e.g., less than 1.5 µg, 1.2 µg, 1.0 µg, 0.8 µg, or even less) of hydrazine per mg of the one or more drugs after 1 week storage under ambient air at about 60° C. In certain embodiments, the suspension of the drug particles can include carbidopa and the pharmaceutical composition can further include less than about 8 µg (e.g., 7 µg, 6 µg, 5 µg, 4 µg, 3 µg, 2 µg, or 1 µg) of hydrazine per mg of carbidopa after 6 or 12 months storage at 5±3° C. or at 25±3° C.

In other embodiments, the drug particles can include one or more allergens, allergen extracts, or allergen derivatives. For example, the one or more allergens can be pollen, a part of a mite, or a component of the feline or canine skin, or an extract or a conversion product thereof.

In any of the preceding aspects, the suspension may not cream or sediment when centrifuged for 1 hour at an acceleration of about 5,000 G or greater (e.g., about 7,000 G, about 9,000 G, about 10,000 G, or about 16,000 G) at 25±3° C. In some embodiments, the pharmaceutical composition may not cream or sediment when stored for 12 months at 5±3° C. or 25±3° C. In some embodiments, after the centrifugation or storage, the concentrations of drug in the layer containing the top 20 volume % and the layer containing the bottom 20 volume % of the composition can differ by less than 10%. In particular embodiments, after the centrifugation or storage the concentrations of drug in the layer containing the top 20 volume % and the layer containing the bottom 20 volume % of the composition can differ by less than 6% (e.g., 5%, 4%, 3%, 2%, 1%, or less). In any of these embodiments, after the centrifugation or storage a pharmaceutical composition may exhibit no visible creaming or sedimentation.

In any of the preceding aspects, the pharmaceutical composition may have substantially no taste.

The invention features a pharmaceutical composition including a suspension including (i) from about 20% to about 80% (w/w) solid excipients; (ii) from about 5% to 60% (w/w) drug particles, (iii) from 19% to 30% (w/w) of one or more water-immiscible compounds, (iv) from 2% to 25% (w/w) water, and (v) from 1% to 10% (w/w) surfactant, wherein the pharmaceutical composition can be physically stable and suitable for continuous or frequent intermittent intra-oral delivery. The pharmaceutical composition can include a paste or an emulsion. In particular embodiments, the suspension can be physically stable for 12 months at 5° C., or can be physically stable for 12 months at 25° C., or after the 12 months the suspension can be physically stable for 48 hours at 37° C. The concentration of solid and/or dissolved drug in the pharmaceutical composition can be between about 50 mg/mL and about 1,000 mg/mL (e.g., 50-500, 70±20, 150±60, or 350±150 mg/mL, 500±200 mg/mL, 700±200 mg/mL, 800±200 mg/mL). In particular embodiments the pharmaceutical composition can include a solid excipient. The density of the solid excipient can be at about 25° C. between about 1.2 g/mL and 3.5 g/mL such as between 1.2 g/mL and 1.8 g/mL. The concentration of solid excipient in the pharmaceutical composition can be between 200 mg/mL and 1,500 mg/mL, such as between 200 and 800 mg/mL, or between 400 and 800 mg/mL. In some embodiments, the excipient particles may not substantially swell in water and/or in the oil of the suspension. In some embodiments, the $D_{50}$ of the excipient particles can be greater than or equal to about 1 µm, about 3 µm, about 5 µm, about 10 µm, or about 25 µm, or the $D_{50}$ of the excipient particles can be less than or equal to 50 µm such as less than or equal to 25 µm. In typical embodiments, the $D_{50}$ of the excipient particles can be 25±24 µm; 1-10 µm; 11-20 µm; 21-30 µm; 31-40 µm; or 41-50 µm. In other embodiments, the $D_{50}$ of the excipient particles can be 75±25 µm; 51-75 µm; or 76-100 µm. In certain embodiments, the $D_{50}$ of the excipient particles can be 125±25 µm. In further embodiments, the $D_{50}$ of the excipient particles can be 175±25 µm. In some embodiments, the solid excipient can include cellulose or cellulose derivatives that do not substantially swell in water or in oils, amino acids (such as tyrosine, phenyl alanine or cysteine), titanium dioxide, calcium silicate, or calcium phosphate.

In some embodiments, the drug in the pharmaceutical composition can include Baclofen, Tizanidine, Midodrine, Metoclopramide, Captopril, Treprostinil, Bitolterol, Oxybutinin, Darifenacin, pyridostigmine or a pharmaceutically acceptable salt thereof. In a typical embodiment, the pharmaceutical composition can have a viscosity greater than 10,000 cP at 37° C. In one particular embodiment of any of the pharmaceutical compositions described herein, the drug is baclofen or a salt thereof, or the pharmaceutical composition includes baclofen or a salt thereof. In another embodiment of any of the pharmaceutical compositions described herein, the drug is pyridostigmine or a salt thereof, or the pharmaceutical composition includes pyridostigmine or a salt thereof.

The invention also features a pharmaceutical composition suitable for continuous infusion in the mouth including: a solution, an oil-in-water emulsion, a water-in-oil emulsion, or a solid particle including a suspension of between 20 mg/mL and 150 mg/mL (e.g., 40±20, 75±25, or 125±75 mg/mL) of a drug selected from Baclofen, Tizanidine, Midodrine, Metoclopramide, Captopril, Treprostinil, Bitolterol, Oxybutinin, Darifenacin. The pharmaceutical composition can further include a thickener. In certain embodiments, the viscosity of the pharmaceutical composition can be greater than 100 cP, 1,000 cP, or 10,000 cP at about 37° C. In particular embodiments, the pharmaceutical composition can further include a surfactant.

The invention further features an extrudable pharmaceutical composition suitable for continuous infusion in the mouth having a pH of from 3 to 10 (e.g., 5±2, 7±2, or 8±2) including a magnesium compound, a zinc compound, or an iron compound at a concentration between 60 mg/mL to 1,600 mg/mL (e.g, 100±40, 600±200, or 1,300±300 mg/mL). The pharmaceutical composition can further include a gelling agent or a thickener. In particular embodiments, the viscosity of the pharmaceutical composition is greater than 1,000 cP, 10,000 cP, or 100,000 cP at about 37° C.

In still other embodiments, the pharmaceutical composition can include a magnesium compound and the $Mg^{2+}$ concentration in the pharmaceutical composition can be greater than 200 mg/mL (e.g., 300±100, 500±150, or 750±200 mg/mL).

The invention further features a pharmaceutical composition suitable for continuous infusion in the mouth including a solution, suspension or gel including between 0.1 mg/mL and 20 mg/mL of a drug selected from Tizanidine, Iloprost, Beraprost, Ciclesonide, Flunisolide, Budesonide, Beclomethasone, Mometasone, Vilanterol, Levosalbutamol sulfate, Salbutamol, Salmeterol, Glycopyrronium bromide, Ipatropium bromide, Aclidinium bromide, Hexoprenaline sulfate, Pirbuterol, Fenoterol, Terbutaline, Metaproterenol, Tolterodine tartarate. The pharmaceutical composition can further include a gelling agent or a thickener. In particular embodiments, the viscosity of the pharmaceutical composition can be greater than 100 cP, 1,000 cP, or 10,000 cP at about 37° C. In particular embodiments, the pharmaceutical composition can further include a surfactant.

The invention features a drug delivery device configured to be removably inserted in a patient's mouth and for continuous or semi-continuous intraoral administration of a drug, the device including a propellant-driven pump including a rigid housing, the rigid housing including a wall of a first chamber containing a drug-including fluid and a wall of a second chamber containing a propellant. The device can include a flexible and/or deformable propellant-impermeable diaphragm separating the first chamber from the second chamber. The diaphragm can include a wall of the first chamber and a wall of the second chamber. In particular embodiments, the density of the propellant-impermeable diaphragm can be greater than 2.0 g per cm$^3$ at 25° C. The diaphragm can be metallic (e.g., tin or silver or aluminum or copper or an alloy of tin or of silver or of aluminum or of copper). Optionally, the metallic diaphragm can comprise silver or an alloy of silver, or tin or an alloy of tin. The diaphragm can be shaped to substantially conform to the interior housing wall of the first chamber and/or the interior housing wall of the second chamber. The diaphragm can be between 10 µm and 250 µm thick, e.g., between 20 µm and 125 µm thick, such as between 25 µm and 75 µm thick. In particular embodiments, the thickness of the diaphragm can vary across the interior of the housing by less than ±25%, or by less than ±10%. In other embodiments, the diaphragm includes a rim that is thicker than the center of the diaphragm (e.g., the thickness of the rim can be at least 1.5 times greater than the thickness of the center of the diaphragm, the thickness of the rim can be between 1.5 times and 2 times the thickness of the center of the diaphragm, the thickness of the rim can be between 2 times and 3 times the thickness of the center of the diaphragm, or the thickness of the rim can be 3 times or more the thickness of the center of the diaphragm). The diaphragm can be folded, pleated, or scored. The device can be hermetically sealed except for one or more orifices for drug filling or drug delivery. Optionally, the one or more orifices for drug filling or drug delivery can be hermetically or non-hermetically sealed. Optionally, the one or more orifices for drug filling or delivery are hermetically sealed. In particular embodiments, the propellant chamber can be hermetically sealed and can include a hermetically sealed orifice for filling with propellant. In certain embodiments, the drug chamber can include two, three, or more hermetically sealable or sealed orifices for filling with drug or for drug delivery. In still other embodiments, the rigid housing and the diaphragm can be joined by a hermetically sealing weld. For example, the hermetically sealing weld can prevent the influx of air and water vapor or the outflux of water vapor, drug or propellant, or prevent the influx of air or oxygen, or prevent the influx or the outflux of helium. In particular embodiments, the rigid housing of the device can include a metal, a ceramic, or a composite of a polymer reinforced by fibers (e.g., carbon fibers, glass fibers, or metal fibers). The rigid housing can include a material having at 25±3° C. a yield strength greater than 100 MPa, and/or having at 25±3° C. a tensile yield strength greater than 100 MPa, and/or having at 25±3° C. a modulus of elasticity greater than 30 GPa, and/or having at 25±3° C. a Brinell hardness greater than 200 MPa, and/or having a density greater than 2.5 g/cm$^3$ at 25±3° C., e.g., greater than 3.5 g/cm$^3$ such as greater than 4.5 g/cm$^3$, or having a density equal to or greater than 5.5 g/cm$^3$. The rigid housing can include a metal selected from the group titanium or iron or aluminum or molybdenum or tungsten or an alloy of titanium or iron or aluminum or molybdenum or tungsten. In particular embodiments, the rigid housing can include titanium or an alloy of titanium and a metallic diaphragm (that can separate chambers within the housing) can be welded to the rigid housing including titanium or an alloy of titanium. In certain embodiments, the diaphragm can include silver or an alloy of silver or it can optionally include tin or an alloy of tin. In some embodiments, the diaphragm can include tin or an alloy of tin, or silver or an alloy of silver. In one embodiment, neither the metal of the rigid housing nor the metal of the metallic diaphragm can corrode visibly after 3 months when the housing metal and the diaphragm metal are electrically contacted and are immersed in an air exposed 0.1 M citrate buffer solution of pH 4.0 at 23±3° C.; or neither the metal of the rigid housing nor the metal of the metallic diaphragm can corrode visibly after 3 months when the housing metal and the diaphragm metal are electrically contacted and are immersed in a substantially de-oxygenated 0.1 M citrate buffer solution of pH 4.0 at 23±3° C. The density of the corrosion current flowing between two electrically shorted electrodes of about equal area, one of the metal of the rigid housing and the other of the metal of the diaphragm, can be less than 2 µA cm$^{-2}$, less than 0.5 µA cm$^{-2}$, or less than 0.1 µA cm$^{-2}$ after about 24 hour immersion of the electrodes in a substantially de-oxygenated 0.1 M citrate buffer solution of pH 4.0 at 23±3° C.

In one particular embodiment, the shapes of the interior housing wall of the first chamber and the interior housing wall of the second chamber can be substantially mirror images of each other excepting for grooves or ports for flow of drug-including fluid to the drug exit orifice. The first chamber can include one or more interior channels, grooves, or tubes for flow of drug-including fluid to the drug exit orifice. In one embodiment, at least one channel, groove, or tube is not blocked by the diaphragm after more than 60 weight %, more than 75 weight %, more than 85 weight %, or more than 95 weight % of the drug is depleted. In another embodiment, at least one channel, groove, or tube is not blocked by the diaphragm when the diaphragm has been fully extended into the drug chamber and drug flow has substantially stopped. Optionally, a housing wall can include the at least one channel, groove, or tube. Optionally, an insert can include the at least one channel, groove, or tube. In certain embodiments, the at least one channel, groove, or tube can include one or more flow restrictors that substantially control the rate of drug delivery. In certain embodiments, the diaphragm can be shaped and sized so that it contacts 0%-10%, 11%-20%, 21%-30%, 31%-40%, or 41%-50% of the interior surface area of the drug chamber (excluding the surface area of the diaphragm itself) after delivery of 85%, 90%, or 95% of the starting pharmaceutical composition in the drug chamber. In certain embodiments, the diaphragm can be shaped and sized so that it does not substantially block the flow of the pharmaceutical composition from the exit orifice after 85%, 90%, or 95% of the starting pharmaceutical composition in the drug chamber has been delivered.

In a related aspect, the invention features a method of forming the diaphragm for a delivery device of the invention, the method including stamping, hot-stamping, electroplating, electroless plating, or hydroforming. The method can include welding the rigid housing and the diaphragm to form a hermetic seal by, e.g., resistance welding, laser welding or electron beam welding. In particular embodiments, the method can also include preheating the housing and the diaphragm. The method can further include annealing at a temperature between 400° C. and 700° C. for 15 minutes or more.

In a related aspect, the invention features a drug delivery device configured to be removably inserted in a patient's mouth and for continuous or semi-continuous intraoral administration of a drug, the device including: a first chamber containing a drug-including fluid; a second chamber containing a propellant; and a flexible and/or deformable diaphragm separating the first chamber from the second chamber, wherein 75%-85%, 86%-95%, or >95% of the drug-including fluid can be dispensed while the delivery rate can vary by less than ±20%, ±15%, ±10%, or ±5%, over a period of at least 4, 8, 16, or 24 hours. The pump can include a liquid propellant, the liquid propellant having a boiling point of less than 37° C. at sea level atmospheric pressure. In particular embodiments, the liquid propellant can be a hydrocarbon, a halocarbon, a hydrofluoralkane, an ester, or an ether (e.g., the liquid propellant can be isopentane, trifluorochloromethane, dichlorofluoromethane, 1-fluorobutane, 2-fluorobutane, 1,2-difluoroethane, methyl ethyl ether, 2-butene, butane, 1-fluoropropane, 1-butene, 2-fluoropropane, 1,1-difluoroethane, cyclopropene, propane, propene, or diethyl ether). In certain embodiments, the liquid propellant is 1,1,1,2-tetrafluoroethane, 1,1,1,2,3,3,3-heptafluoropropane, 1,1,1,3,3,3-hexafluoropropane, octafluorocyclobutane or isopentane. The propellant can have a vapor pressure of greater than 1.5 bar and less than 20 bar at 37° C., such as a vapor pressure of greater than 2.0 bar and less than 15 bar at 37° C., or a vapor pressure of greater than 3.0 bar and less than 10 bar at 37° C. In some embodiments, (i) the propellant can have a vapor pressure of greater than 2.1 bar at 37° C., and (ii) the average rate of drug delivery can increase or decrease by less than ±20% across the atmospheric pressure range between 0.782 bar and 1.013 bar. In other embodiments, (i) the propellant can have a vapor pressure of greater than 3.2 bar at 37° C., and (ii) the average rate of drug delivery can increase or decrease by less than ±10% across the atmospheric pressure range between 0.782 bar and 1.013 bar. In certain embodiments, (i) the propellant can have a vapor pressure of greater than 4.7 bar at 37° C., and (ii) the average rate of drug delivery can increase or decreases by less than ±6% across the atmospheric pressure range between 0.782 bar and 1.013 bar. The drug delivery device can include a reservoir containing any pharmaceutical composition described herein.

In another aspect, the invention features a drug delivery device configured to be removably inserted in a patient's mouth and for continuous or semi-continuous intraoral administration of a drug, the device including: (i) a fastener to removably secure the drug delivery device to a surface of the patient's mouth; (ii) an electrical or mechanical pump; and (iii) an oral liquid impermeable drug reservoir containing any of the pharmaceutical compositions of the invention, the volume of the drug reservoir being from 0.1 mL to 5 mL (e.g., from 0.1 mL to 4 mL, from 0.1 mL to 3 mL, from 0.1 mL to 2 mL, from 0.1 mL to 1 mL, from 0.1 mL to 0.5 mL, from 0.1 mL to 0.25 mL, from 0.2 mL to 5 mL, from 0.3 mL to 5 mL, from 0.5 mL to 5 mL, from 1 mL to 5 mL, from 2 mL to 5 mL, from 4 mL to 5 mL, from 0.5 mL to 1 mL, from 0.5 mL to 2 mL, from 1 mL to 2 mL, from 2 mL to 3 mL).

In a further aspect, the invention features a drug delivery device configured to be removably inserted in a patient's mouth and for continuous or semi-continuous intraoral administration of a drug, the device including: (i) a fastener to removably secure the drug delivery device to a surface of the patient's mouth; (ii) an electrical or mechanical pump; (iii) an oral liquid impermeable drug reservoir containing any of the pharmaceutical compositions of the invention, the volume of the drug reservoir being from 0.1 mL to 5 mL (e.g., as described herein); and (iv) an automatic stop/start.

In some embodiments, the drug delivery device can be configured to be automatically stopped upon one or more of the following: (a) the drug delivery device, the pump, and/or the oral liquid impermeable reservoir are removed from the mouth; (b) the drug delivery device, the pump, and/or the oral liquid impermeable reservoir are disconnected from the fastener; or (c) the oral liquid impermeable reservoir is disconnected from the pump. In particular embodiments, the drug delivery device can be configured to be automatically started upon one or more of the following: (a) the drug delivery device, the pump, and/or the oral liquid impermeable reservoir are inserted into the mouth; (b) the drug delivery device, the pump, and/or the oral liquid impermeable reservoir are connected to the fastener; or (c) the oral liquid impermeable reservoir is connected to the pump. In certain embodiments, the automatic stop/start is selected from: a pressure sensitive switch, a clip, a fluidic channel that kinks, a clutch, a sensor, or a cap. In some embodiments, the drug delivery device can further include a suction-induced flow limiter, a temperature-induced flow limiter, bite-resistant structural supports, or a pressure-invariant mechanical pump.

In yet another aspect, the invention features a drug delivery device configured to be removably inserted in a patient's mouth and for continuous or semi-continuous intraoral administration of a drug, the device including: (i) a fastener to removably secure the drug delivery device to a surface of the patient's mouth; (ii) a mechanical pump; (iii) an oral liquid impermeable drug reservoir containing any of the pharmaceutical compositions of the invention, the volume of the drug reservoir being from 0.1 mL to 5 mL (e.g., as described herein); and (iv) a suction-induced flow limiter.

In some embodiments, the suction-induced flow limiter includes pressurized surfaces that are in fluidic (gas and/or liquid) contact with the ambient atmosphere via one or more ports or openings in the housing of the drug delivery device. In other embodiments, the suction-induced flow limiter is selected from the group consisting of a deformable channel, a deflectable diaphragm, a compliant accumulator, an inline vacuum-relief valve, and a float valve. In certain embodiments, the suction-induced flow limiter can be configured to prevent the delivery of a bolus greater than about 1% (e.g., 2%, 3%, 4%, 5%, or more) of the contents of a fresh reservoir, when the ambient pressure drops by 0.14 bar for a period of one minute. In some embodiments, the drug delivery device further includes an automatic stop/start, a temperature-induced flow limiter, bite-resistant structural supports, or a pressure-invariant mechanical pump.

In another aspect, the invention features a drug delivery device configured to be removably inserted in a patient's mouth and for continuous or semi-continuous intraoral administration of a drug, the device including: (i) a fastener to removably secure the drug delivery device to a surface of the patient's mouth; (ii) an electrical or mechanical pump; (iii) an oral liquid impermeable drug reservoir containing any of the pharmaceutical compositions of the invention, the volume of the drug reservoir being from 0.1 mL to 5 mL (e.g., as described herein); and (iv) a temperature-induced flow limiter.

In some embodiments, the temperature-induced flow limiter can include insulation with a material of low thermal conductivity proximate the drug reservoir and/or the pump. In certain embodiments, the temperature-induced flow limiter can include an elastomer whose force in a fresh reservoir increases by less than 30% when the oral temperature is raised from about 37° C. to about 55° C. for a period of one minute. In some embodiments, the pump can include a spring and the temperature-induced flow limiter can include a spring configured to produce a force in a fresh reservoir that increases by less than 30% (e.g., 25%, 20%, 15%, or less) when the oral temperature is raised from about 37° C. to about 55° C. for a period of one minute. In particular embodiments, the temperature-induced flow limiter can include a spring including a 300 series stainless steel, titanium, Inconel, or austenitic Nitinol. In certain embodiments, the pump can be gas-driven. It can comprise an actuator actuated by the temperature decrease upon removal from the mouth, i.e., a temperature change actuated flow limiter. Its liquefied or compressed gas can have a volume of less than about 40% (e.g., 35%, 30%, 25%, 20%, 10% or less) of the volume of the pharmaceutical composition in a fresh reservoir at 37° C. and about 1.013 bar.

In some embodiments of any of the above drug delivery devices, the device includes a rigid metal housing containing the pharmaceutical composition and the propellant. The rigid metal housing material can include titanium or a titanium alloy. In particular embodiments, the pharmaceutical composition and the propellant are separated by a flexible and/or deformable diaphragm comprising a metal. The flexible and/or deformable diaphragm can include tin or silver. In other embodiments, the pump can be propellant-driven and the temperature-induced flow limiter can include a propellant having a vapor pressure that increases by less than about 80% (e.g., 70%, 60%, 50%, 40%, 30%, 20%, or less) when the oral temperature is raised from about 37° C. to about 55° C. for a period of about one minute. In some embodiments, the drug delivery device further includes a suction-induced flow limiter, an automatic stop/start, bite-resistant structural supports, or a pressure-invariant mechanical pump.

In yet another aspect, the invention features a drug delivery device configured to be removably inserted in a patient's mouth and for continuous or semi-continuous intraoral administration of a drug, the device including: (i) a fastener to removably secure the drug delivery device to a surface of the patient's mouth; (ii) an electrical or mechanical pump; (iii) an oral liquid impermeable drug reservoir containing any of the pharmaceutical compositions of the invention, the volume of the drug reservoir being from 0.1 mL to 5 mL (e.g., as described herein); and (iv) bite-resistant structural supports.

In some embodiments, the bite-resistant structural supports are selected from: a housing that encapsulates the entire drug reservoir and pump components; posts; ribs; or a potting material. In particular embodiments, the drug delivery device further includes a suction-induced flow limiter, an automatic stop/start, a temperature-induced flow limiter, or a pressure-invariant mechanical pump.

In a further aspect, the invention features a drug delivery device configured to be removably inserted in a patient's mouth and for continuous or semi-continuous intraoral administration of a drug, the device including: (i) a fastener to removably secure the drug delivery device to a surface of the patient's mouth; (ii) a pressure-invariant mechanical pump; and (iii) an oral liquid impermeable drug reservoir containing any of the pharmaceutical compositions of the invention, the volume of the drug reservoir being from 0.1 mL to 5 mL (e.g., as described herein).

In some embodiments, the pressure-invariant mechanical pump includes pressurized surfaces that are in fluidic (gas and/or liquid) contact with the ambient atmosphere, optionally via one or more ports or openings in the housing of the drug delivery device. In certain embodiments, the pressure-invariant mechanical pump is configured to maintain an internal pressure of greater than or equal to about 2 bar, about 3 bar, about 4 bar, about 6 bar, or about 8 bar. In some embodiments, the pressure-invariant mechanical pump is configured such that the average rate of drug delivery increases by less than about 20% (e.g., 15%, 10%, 5%, 2% or less) when the atmospheric pressure decreases from about 0.898 bar to about 0.782 or from 1.013 bar to 0.898 bar; and/or decreases by less than about 20% (e.g., less than 15%, 10%, 5%, 2%) when the atmospheric pressure increases from about 0.782 bar to about 0.898 bar; and/or such that the average rate of drug delivery decreases by less than about 20% (e.g., 15%, 10%, 5%, 2% or less) when the atmospheric pressure increases from about 0.898 bar to about 1.013 bar. In particular embodiments, the drug delivery device further includes a suction-induced flow limiter, an automatic stop/start, a temperature-induced flow limiter, or bite-resistant structural supports.

In another aspect, the invention features a drug delivery device configured to be removably inserted in a patient's mouth and for continuous or semi-continuous intraoral administration of a drug, the device including: (i) a fastener to removably secure the drug delivery device to a surface of the patient's mouth; (ii) a mechanical pump; and (iii) an oral liquid impermeable drug reservoir containing any of the pharmaceutical compositions of the invention, the volume of the drug reservoir being from 0.1 mL to 5 mL (e.g., as described herein).

In some embodiments, the mechanical pump is pressure-invariant. In certain embodiments, the mechanical pump is driven by a spring, an elastomer, a compressed gas, or a propellant. In some embodiments, the oral liquid impermeable reservoir includes one or more of: metal reservoirs, plastic reservoirs, elastomeric reservoirs, metallic barrier layers, valves, squeegees, baffles, rotating augers, rotating drums, propellants, pneumatic pumps, diaphragm pumps, hydrophobic materials, and hydrophobic fluids. In particular embodiments, the drug delivery device can be configured such that 4 hours after inserting a drug delivery device including a fresh reservoir in a patient's mouth and initiating the administration, less than 5%, 3%, or 1% by weight of an originally contained pharmaceutical composition in the reservoir includes an oral liquid. In certain embodiments, the oral liquid impermeable drug reservoir includes a fluidic channel in a spiral configuration. In some embodiments, the drug delivery device further includes a suction-induced flow limiter, an automatic stop/start, a temperature-induced flow limiter, a pressure-invariant mechanical pump, or bite-resistant structural supports.

Certain drug delivery devices of the invention may feature an electrical pump. In some embodiments, an electrical pump is a piezoelectric pump or an electroosmotic pump. In particular embodiments, the electrical pump is a piezoelectric pump that is configured to operate at a frequency of less than about 20,000 Hz (e.g., 15,000 Hz, 10,000 Hz, 5,000 Hz, or less). In certain embodiments, the electrical pump includes a motor.

Any of the drug delivery devices of the preceding aspects may include a mechanical pump. In some embodiments, the mechanical pump is an elastomeric drug pump. In particular embodiments, the elastomeric drug pump includes an elastomeric balloon, an elastomeric band, or a compressed elastomer. In other embodiments, the mechanical pump is a spring-driven pump. In particular embodiments, the spring-driven pump includes a constant force spring. In certain embodiments, the spring-driven pump includes a spring that retracts upon relaxation. In some embodiments, the spring-driven pump includes two coaxial compression springs wherein, upon compression, a first spring with a first diameter is wholly or partially nested within a second spring with a second, larger diameter. In other embodiments, the mechanical pump is a negative pressure pump, a pneumatic pump, or a gas-driven pump. In certain embodiments, the mechanical pump is a gas-driven pump including a gas in a first compartment and drug in a second compartment, the gas providing a pressure exceeding about 1 bar. In some embodiments, the gas-driven pump includes a compressed gas cartridge. In particular embodiments, the gas-driven pump includes a compressed or liquefied gas, the volume of the compressed or liquefied gas being less than 35% (e.g., less than 30%, 25%, 20% or 10%) of the volume of the pharmaceutical composition. In some embodiments, a gas-driven pump includes a gas generator.

In any of the preceding aspects, a drug delivery device may include a mechanical pump that is a propellant-driven pump. In some embodiments, the pump includes a liquid propellant, the liquid propellant having a boiling point of less than 37° C. (e.g., less than or equal to 35° C., 33° C., 30° C., or 25° C.) at sea level atmospheric pressure. In certain embodiments, the liquid propellant is a hydrocarbon, a halocarbon, a hydrofluoralkane, an ester, or an ether. For example, the liquid propellant can be selected from the group consisting of isopentane, trifluorochloromethane, dichlorofluoromethane, 1-fluorobutane, 2-fluorobutane, 1,2-difluoroethane, methyl ethyl ether, 2-butene, butane, 1-fluoropropane, 1-butene, 2-fluoropropane, 1,1-difluoroethane, cyclopropene, propane, propene, or diethyl ether. In particular embodiments, the liquid propellant is 1,1,1,2-tetrafluoroethane, 1,1,1,2,3,3,3-heptafluoropropane, 1,1,1,3,3,3-hexafluoropropane, octafluorocyclobutane, or isopentane. In certain embodiments, the liquid propellant is isopentane, trifluorochloromethane, dichlorofluoromethane, or 1,1,1,2-tetrafluoroethane. In some embodiments, the liquid propellant has a vapor pressure of greater than 1.5 bar (e.g., 2.0 bar, 2.5 bar, 3 bar, or greater) and less than 20 bar (e.g., 15 bar, 12 bar, 10 bar, 9 bar, 8 bar, 7.0 bar, 6.0 bar, or less) at about 37° C. In other embodiments, (i) the liquid propellant has a vapor pressure of greater than 2.1 bar (e.g., greater than 2.2 bar, 2.5 bar, or 3.0 bar) at 37° C., and (ii) the average rate of drug delivery increases or decreases by less than ±20% across the atmospheric pressure range between about 0.782 bar and about 1.013 bar. In particular embodiments, (i) the liquid propellant has a vapor pressure of greater than 3.2 bar (e.g., greater than 3.3 bar, 3.4 bar, or 3.5 bar) at 37° C., and (ii) the average rate of drug delivery increases or decreases by less than ±10% across the atmospheric pressure range between about 0.782 bar and about 1.013 bar. In further embodiments, (i) the propellant has a vapor pressure of greater than 4.7 bar (e.g., 4.8 bar, 5.0 bar, or greater) at 37° C., and (ii) the average rate of drug delivery increases or decreases by less than ±6% across the atmospheric pressure range between about 0.782 bar and about 1.013 bar.

In any of the preceding aspects of the invention, a drug delivery device may include two or more drug pumps. A drug delivery device may also include two or more drug reservoirs.

In any of the preceding aspects of the invention, a drug reservoir may be substantially impermeable to oxygen gas. In certain embodiments, the drug reservoir includes a pharmaceutical composition comprising greater than 33% (e.g., greater than 35%, greater than 37%, greater than 39%, greater than 40%, greater than 50%, greater than 60%, or more) of the total volume of the drug reservoir and pump. In some embodiments, the total volume of the one or more drug reservoirs and the one or more drug pumps is less than 5 mL (e.g., less than 4 mL, less than 3 mL, less than 2 mL, or less than 1 mL).

In some embodiments, the drug reservoir of a drug delivery device of the invention is a syringe assembly including a plunger and a barrel, the plunger being in slidable arrangement with the barrel. In certain embodiments, the syringe assembly further includes a seal (e.g., an O-ring) fitted over the plunger, the seal being in contact with the barrel. In some embodiments, the barrel, plunger, and/or seal is not wetted by water and/or oil. In particular embodiments, the barrel, plunger, and/or seal is non-wettable by a pharmaceutical composition of the invention. In some embodiments, a barrel, plunger, and/or seal is formed from or coated with a fluoropolymer or fluoroelastomer. In certain embodiments, a barrel, plunger, and/or seal is coated with a lubricant. The solubility of the lubricant in the one or more water-immiscible compounds of the pharmaceutical composition may be less than 3% (w/w) (e.g., less than 2% (w/w) or less than 1% (w/w)) at, for example, 25° C. In some embodiments, the lubricant can be a halogenated oil or grease, such as a perfluorinated polymer, a chlorofluorinated polymer, or a fluorinated polyether. In certain embodiments, the lubricant can be a halogenated oil or grease having an average molecular mass equal to or greater than about 1,000 Daltons (e.g., greater than about 1,100 Daltons, greater than about 1,200 Daltons, greater than about 1,500 Daltons, greater than about 1,700 Daltons, or greater than about 2,000 Daltons). In some embodiments, the drug reservoir of a drug delivery device can be a syringe barrel and the drug delivery device can further include a deformable and/or mobile plug separating two compartments of the syringe barrel. In certain embodiments, the deformable and/or mobile plug includes a perfluorinated, fluorinated, or chlorofluorinated oil or grease. Such a drug delivery device may further include a propellant in one of the compartments and the pharmaceutical composition in the other of the compartments.

A drug delivery device of the invention may removably secure to one or more teeth of the patient. In some embodiments, the fastener that removably secures the drug delivery device to one or more teeth includes a band, a bracket, a clasp, a splint, or a retainer. For example, the fastener may include a transparent retainer or a partial retainer attachable to fewer than 5 teeth.

A drug delivery device of the invention may include one or more drug reservoirs and one or more pumps configured to be worn in the buccal vestibule, on the lingual side of the teeth, or simultaneously in the buccal vestibule and on the lingual side of the teeth. In some embodiments, one or more drug reservoirs and one or more pumps are configured bilaterally. In certain embodiments, the one or more drug reservoirs and/or pumps are configured to administer the pharmaceutical composition into the mouth of the patient on the lingual side of the teeth. A fluidic channel from the buccal side to the lingual side of the patient's teeth may be included for dispensing the pharmaceutical composition. In one particular embodiment of any of the above drug delivery devices, the device includes one or more drug reservoirs and one or more pumps, wherein the drug reservoirs or the pumps are configured to administer the pharmaceutical composition onto the buccal or sublingual mucosa of the patient. For example, the drug delivery device can include a tube, channel, or orifice having a distal end positioned proximal to the buccal or sublingual mucosa within a zone bounded in part by a water vapor and gas permeable membrane that is saliva-repelling. In some embodiments, the drug delivery device can include a fluidic channel in the fastener through which the pharmaceutical composition is administered into the mouth of the patient. In certain embodiments, the device may include a leak-free fluidic connector for direct or indirect fluidic connection of the fastener to the one or more drug reservoirs, and/or a flow restrictor in the fastener for controlling the flow of the pharmaceutical composition. In some embodiments, the fastener includes a pump or a power source.

In particular embodiments, the drug delivery device includes one or more drug metal wall including reservoirs and one or more pumps, wherein the drug reservoirs or the pumps are configured to administer the pharmaceutical composition onto the buccal or sublingual mucosa of the patient. The drug delivery device can include a tube, channel, or orifice having a distal end positioned proximal to the buccal or sublingual mucosa within a zone bounded in part by a water vapor and gas permeable membrane that is saliva-repelling.

In some embodiments, the drug reservoir of a drug delivery device of the invention is in fluid communication with a tube, channel, or orifice of less than 4 cm (e.g., less than 3 cm, less than 2 cm, less than 1 cm, less than 0.5 cm, or less than 0.2 cm) in length and the dynamic viscosity of the pharmaceutical composition can be greater than about 1,000 cP (e.g., greater than about 5,000 cP, greater than about 10,000 cP, greater than about 50,000 cP, or greater than about 100,000 cP), and the device is configured to administer drug via the tube, channel, or orifice. In certain embodiments, the tube, channel, or orifice has a minimum internal diameter of greater than about 0.2 mm, e.g., greater than about 0.3 mm, greater than about 0.4 mm, greater than about 0.5mm, greater than about 0.6 mm, greater than about 0.7 mm, greater than about 1 mm, greater than about 2 mm, greater than about 3 mm, greater than about 4 mm, greater than about 5 mm, or greater than about 6 mm. In certain embodiments, the internal diameter is greater than about 0.1 mm and less than 1 mm, 0.8 mm, 0.6 mm, 0.5 mm, 0.4 mm, 0.3 mm or 0.2 mm. Preferred minimum internal diameters are 0.1-2 mm (0.1-0.7 mm, 0.2-0.5 mm, 0.5-0.75 mm, 0.75-1.0 mm, 1.0-1.5 mm, or 1.5-2.0 mm) and preferred lengths are 0.25-5 cm (such as 1-2.5 cm, 1-5 cm, 0.25-0.5 cm, 0.5-0.75 cm, 0.75-1 cm, 1-2 cm, 2-3 cm, 3-4 cm, or 4-5 cm).

In some embodiments, a drug delivery device of the invention further includes a flow restrictor (e.g., a flared flow restrictor). The flow restrictor can have an internal diameter smaller than 1 mm and larger than 0.05 mm and a length between 0.5 cm and 10 cm. In particular embodiments, the flow restrictor can have an internal diameter smaller than 0.7 mm and larger than 0.2 mm. Preferred minimum internal diameters are 0.1-2 mm (0.1-0.7 mm, 0.2-0.5 mm, 0.5-0.75 mm, 0.75-1.0 mm, 1.0-1.5 mm, or 1.5-2.0 mm) and preferred lengths are 0.25-5 cm (such as 1-2.5 cm, 1-5 cm, 0.25-0.5 cm, 0.5-0.75 cm, 0.75-1 cm, 1-2 cm, 2-3 cm, 3-4 cm, or 4-5 cm).The flow restrictor can be made of a plastic, such as an engineering plastic. In particular embodiments, the engineering plastic includes a polyamide or a polyester, or a polycarbonate, or a polyetheretherketone, or a polyetherketone, or a polyimide, or a polyoxymethylene, or a polyphenylene sulfide, or a polyphenylene oxide, or a polysulphone, or polytetrafluoroethylene, or polyvinylidene difluoride, or ultra-high-molecular-weight polyethylene, or a strong elastomer.

In certain embodiments, the flow restrictor controls the flow of the pharmaceutical composition. In some embodiments, the length of the flow restrictor sets the administration rate of the pharmaceutical composition. In particular embodiments, the flow restrictor may be adjusted by a physician or the patient to set the rate of flow. In certain embodiments, a drug delivery device can include a tapered flow path for the drug with a taper less than or equal to about 60 degrees, about 45 degrees, or about 30 degrees. Optionally, the device can include one or more flow-controlling nozzles, channels or tubes which can be plastic, e.g. made of or including an engineering plastic. The optionally plastic nozzles, channels or tubes can have an internal diameter less than 1 mm, 0.6 mm, 0.3 mm or 0.1 mm and they can be shorter than 10 cm, 5 cm, 2 cm or 1 cm such as 0.5 cm. Preferred minimum internal diameters are 0.1-2 mm (0.1-0.7 mm, 0.2-0.5 mm, 0.5-0.75 mm, 0.75-1.0 mm, 1.0-1.5 mm, or 1.5-2.0 mm) and preferred lengths are 0.25-5 cm (such as 1-2.5 cm, 1-5 cm, 0.25-0.5 cm, 0.5-0.75 cm, 0.75-1 cm, 1-2 cm, 2-3 cm, 3-4 cm, or 4-5 cm).

Any of the drug delivery devices of the invention may be configured to to deliver an average hourly rate of volume of from about 0.015 mL/hour to about 1.25 mL/hour (e.g., from about 0.015 mL/hour to about 1.20 mL/hour, from about 0.015 mL/hour to about 1.15 mL/hour, from about 0.015 mL/hour to about 1.10 mL/hour, from about 0.015 mL/hour to about 1.05 mL/hour, from about 0.015 mL/hour to about 1.00 mL/hour, from about 0.015 mL/hour to about 0.90 mL/hour, from about 0.015 mL/hour to about 0.80 mL/hour, from about 0.015 mL/hour to about 0.70 mL/hour, from about 0.015 mL/hour to about 0.60 mL/hour, from about 0.015 mL/hour to about 0.50 mL/hour, from about 0.015 mL/hour to about 0.25 mL/hour, from about 0.015 mL/hour to about 0.10 mL/hour, from about 0.015 mL/hour to about 0.05 mL/hour, from about 0.015 mL/hour to about 0.025 mL/hour, from about 0.015 mL/hour to about 0.020 mL/hour, from about 0.020 mL/hour to about 1.25 mL/hour, from about 0.025 mL/hour to about 1.25 mL/hour, from about 0.050 mL/hour to about 1.25 mL/hour, from about 0.075 mL/hour to about 1.25 mL/hour, from about 0.10 mL/hour to about 1.25 mL/hour, from about 0.20 mL/hour to about 1.25 mL/hour, from about 0.50 mL/hour to about 1.25 mL/hour, from about 0.75 mL/hour to about 1.25 mL/hour, from about 1.00 mL/hour to about 1.25 mL/hour, from about 1.10 mL/hour to about 1.25 mL/hour, from about 1.15 mL/hour to about 1.25 mL/hour, from about 0.25 mL/hour to about 0.50 mL/hour, from about 0.5 mL/hour to about 0.75 mL/hour, or from about 0.75 mL/hour to about 1.0 mL/hour) over a period of from about 4 hours to about 168 hours (e.g., from about 4 hours to about 120 hours, from about 4 hours to about 100 hours, from about 4 hours to about 80 hours, from about 4 hours to about 72 hours, from about 4 hours to about 60 hours, from about 4 hours to about 48 hours, from about 4 hours to about 36 hours, from about 4 hours to about 24 hours, from about 4 hours to about 12 hours from about 4 hours to about 8 hours, from about 4 hours to about 6 hours, from about 6 hours to about 168 hours, from about 8 hours to about 168 hours, from about 12 hours to about 168 hours, from about 24 hours to about 168 hours, from about 36 hours to about 168 hours, from about 48 hours to about 168 hours, from about 60 hours to about 168 hours, or from about 72 hours to about 168 hours) at about 37° C. and a constant pressure of about 1.013 bar, wherein the average hourly rate varies by less than ±20% or ±10% per hour over a period of 4 or more hours (e.g., 6 hours, 8 hours, 10 hours, 12 hours, 18 hours, 24 hours, 36 hours, 48 hours, 60 hours, 72 hours, 168 hours, or more). In some embodiments, the drug delivery device can include oral fluid contacting surfaces that are compatible with the oral fluids, such that the average rate of delivery of the drug increases or decreases by less than ±20% or ±10% per hour after the drug delivery device is immersed for five minutes in a stirred physiological saline solution at 37° C. including any one of the following conditions: (a) pH of about 2.5; (b) pH of about 9.0; (c) 5% by weight olive oil; and (d) 5% by weight ethanol.

The invention also features a method of of treating Parkinson's disease (including patients with scores of 4 and 5 on the Hoehn and Yahr scale) including administering a pharmaceutical composition of the invention to a patient using a drug delivery device of the invention.

In another aspect, the invention features a method of administering a pharmaceutical composition to a patient, the method including removably attaching a drug delivery device of the invention to an intraoral surface of the patient. In certain embodiments, the method further includes detaching the device from the intraoral surface and/or administering drug to the patient for a delivery period of not less than about 4 hours and not more than about 7 days. In some embodiments, the drug delivery device includes a drug reservoir including a volume of a drug, and the method further includes oral administration at a rate in the range of from 15 μL per hour to about 1.25 mL per hour (e.g., as described herein) during the delivery period. In particular embodiments, the fluctuation index of the drug is less than or equal to 2.0, 1.5, 1.0, 0.75, 0.50, 0.25, or 0.15 during the delivery period. In some embodiments, the drug delivery device can include a drug reservoir including a pharmaceutical composition including a drug and the drug is administered to the patient at an average rate of not less than 0.01 mg per hour and not more than 125 mg per hour (e.g., from about 0.01 mg/hour to about 125 mg/hour, from about 0.05 mg/hour to about 125 mg/hour, from about 0.10 mg/hour to about 125 mg/hour, from about 0.50 mg/hour to about 125 mg/hour, from about 1.0 mg/hour to about 125 mg/hour from about 5.0 mg/hour to about 125 mg/hour, from about 10 mg/hour to about 125 mg/hour, from about 25 mg/hour to about 125 mg/hour, from about 50 mg/hour to about 125 mg/hour, from about 100 mg/hour to about 125 mg/hour, from about 0.01 mg/hour to about 100 mg/hour, from about 0.01 mg/hour to about 50 mg/hour, from about 0.01 mg/hour to about 25 mg/hour, from about 0.01 mg/hour to about 10 mg/hour, from about 0.01 mg/hour to about 5.0 mg/hour, from about 0.01 mg/hour to about 1.0 mg/hour, from about 0.01 mg/hour to about 0.5 mg/hour, from about 0.01 mg/hour to about 0.25 mg/hour, from about 0.01 mg/hour to about 0.1 mg/hour, from about 0.01 mg/hour to about 0.05 mg/hour, or from about 1 mg/hour to about 10 mg/hour, from about 10 mg/hour to about 100 mg/hour). In some embodiments, the pharmaceutical composition can be administered to the patient at least once every 60 minutes, at least once every 30 minutes, or at least once every 15 minutes. In other embodiments, the pharmaceutical composition is administered to the patient continuously. In certain embodiments, the pharmaceutical composition can be administered to the patient over a delivery period of about 8 or more hours (e.g., more than 10, 12, 14, 16, 18, 20, or 24 hours).

In certain embodiments, a method of administering a pharmaceutical composition of the invention further includes treating a disease in the patient, wherein the disease is spasticity, muscle weakness, mucositis, allergy, immune disease, anesthesia, bacterial infections, cancer, pain, organ transplantation, disordered sleep, epilepsy and seizures, anxiety, mood disorders, post-traumatic stress disorder, arrhythmia, hypertension, heart failure, or diabetic nephropathy.

In one particular embodiment of any of the above methods, the method further includes treating a disease in the patient, wherein the disease is multiple sclerosis, cerebral palsy, spasticity, neurogenic orthostatic hypotension, Wilson's disease, cystinuria, rheumatoid arthritis, Alzheimer's disease, myasthenia gravis, Type-1 Gaucher disease, Type C Niemann-Pick disease, eosinophilic gastroenteritis, chronic mastocytosis, ulcerative colitis, gastro-oesophageal reflux, gastroenteritis, hyperemesis gravidarum, glioblastoma multiformae, anaplastic astrocytoma, pulmonary hypertension, coronary heart disease congestive heart failure, angina, Type 2 diabetes, COPD, asthma, irritable bowel syndrome, overactive bladder, and urinary urge incontinence. In one particular embodiment, the method includes treating myasthenia gravis and the pharmaceutical composition includes pyridostigmine, or a pharmaceutically acceptable salt thereof.

In one particular embodiment, the pharmaceutical composition includes one or more drugs selected from methylphenidate, prostaglandins, prostacyclin, treprostinil, beraprost, nimodipine, and testosterone. In still other embodiments, the pharmaceutical composition includes a mucoadhesive polymer. The pharmaceutical composition can further include a permeation enhancer. In particular embodiments of any of the above methods, the pharmaceutical composition can include drug dissolved in an aqueous solution. The aqueous solution can optionally further include glycerol, ethanol, propylene glycol, polyethylene glycol (PEO, PEG) or DMSO. In still other embodiments, the pharmaceutical composition further includes a thickening agent (e.g., a sugar, a sugar alcohol, or a polymer, such as cellulose or a cellulose derivative). In particular embodiments, the thickening agent is selected from carboxymethyl cellulose, microcrystalline cellulose, hyaluronic acid, polyacrylic acid, polymethacrylic acid, alginic acid, or salts thereof. In still other embodiments, the thickening agent is selected from sucrose, glucose, fructose, sorbitol, and mannitol.

In any of the methods of the invention, the pharmaceutical composition may include one or more of methylphenidate, prostaglandins, prostacyclin, treprostinil, beraprost, nimodipine, and testosterone.

In any of the preceding embodiments of the above compositions and methods, the pharmaceutical composition may include a mucoadhesive polymer and, optionally, a permeation enhancer (e.g., to aid transport across the sublingual or buccal mucosa).

In any of the preceding embodiments of the above compositions and methods, the pharmaceutical composition may include drug dissolved in an aqueous solution. The aqueous solution can further include glycerol, ethanol, propylene glycol, polyethylene glycol (PEO, PEG) or DMSO (e.g., from 0.5% (w/w) to 20% (w/w)).

In any of the preceding embodiments of the above compositions and methods, the pharmaceutical composition may further include a viscosity-increasing agent (e.g., a dissolved sugar or sugar alcohol such as one selected from sucrose, glucose, fructose, sorbitol, and mannitol., or a dissolved polymer, or water-swollen polymer, or a gel forming polymer, such one selected from carboxymethyl cellulose, hyaluronic acid, polyacrylic acid, polymethacrylic acid, alginic acid, or salts thereof. Alternatively, it can be an undissolved viscosity increasing thickening agent. In particular embodiments, the thickening agent is a cellulose, such as a non-swelling cellulose derivative; or a cellulose derivative, or an undissolved polymer selected from carboxymethyl cellulose, hyaluronic acid, polyacrylic acid, polymethacrylic acid, alginic acid, or salts thereof, or a solid amino acid, like tyrosine or phenylalanine.

In any of the methods of the invention, the method may further include treating Parkinson's disease (including patients with scores of 4 and 5 on the Hoehn and Yahr scale), wherein the pharmaceutical composition includes levodopa or a levodopa prodrug.

The invention also features a method for treating Parkinson's disease in a patient (including patients with scores of 4 and 5 on the Hoehn and Yahr scale), the method including: (a) inserting a drug delivery device of the invention into the patient's mouth, the device having a drug reservoir including levodopa or a levodopa prodrug; (b) administering into the patient's mouth the levodopa or a levodopa prodrug for a period of at least 4, 6, or 8 hours (e.g., as described herein) at an hourly rate in the range of 30 mg/hour to 150 mg/hour (e.g., as described herein, such as 50 mg/hour to 125 mg/hour), such that a circulating plasma levodopa concentration greater than 1,200 ng/mL (e.g., greater than 1,400 ng/mL, 1,500 ng/mL, 1,600 ng/mL, 1,800 ng/mL, 2,000 ng/mL, or 2,200 ng, mL) and less than 2,500 ng/mL (e.g., less than 2,200 ng/mL, 2,000 ng/mL, 1,800 ng/mL, 1,600 ng/mL, or 1,400 ng/mL) is continuously maintained for a period of at least 4, 6, or 8 hours (e.g., as described herein) during the administration; and (c) removing the drug delivery device from the mouth.

In another aspect, the invention features a method for treating Parkinson's disease in a patient (including patients with scores of 4 and 5 on the Hoehn and Yahr scale), the method including: (a) inserting a drug delivery device including a pharmaceutical composition of the invention into the patient's mouth, the pharmaceutical composition including levodopa or levodopa prodrug; (b) administering into the patient's mouth the levodopa or levodopa prodrug for a period of at least 4, 6, or 8 hours (e.g., as described herein) at an hourly rate in the range of 30 mg/hour to 150 mg/hour (e.g., as described herein, such as 50 mg/hour to 125 mg/hour), such that a circulating plasma levodopa concentration greater than 1,200 ng/mL (e.g., as described herein) and less than 2,500 ng/mL (e.g., as described herein) is continuously maintained for a period of at least 4, 6, or 8 hours (e.g., as described herein) during the administration; and (c) removing the drug delivery device from the mouth.

In a method for treating Parkinson's disease in a patient (including patients with scores of 4 and 5 on the Hoehn and Yahr scale), the fluctuation index of levodopa may be less than or equal to 2.0, 1.5, 1.0, 0.75, 0.50, 0.25, or 0.15 for a period of at least 4 hours (e.g., at least 6 hours, at least 8 hours, or longer) during the administration. In some embodiments, during administration the circulating levodopa plasma concentration varies by less than +/−20% or +/−10% from its mean for a period of at least 1 hour (e.g., 2 hours, 3 hours, 4 hours, or more hours).

In a further aspect, the invention features a method for treating Parkinson's disease in a patient (including patients with scores of 4 and 5 on the Hoehn and Yahr scale), the method including continuous or semi-continuous administration of a pharmaceutical composition of the invention into the patient at a rate of 10 mg/hour to 200 mg/hour (e.g., as described herein, such as 30 mg/hour to 150 mg/hour or 50 mg/hour to 125 mg/hour) for a period of about 4 hours to about 168 hours (e.g., as described herein).

In some embodiments of methods of treating Parkinson's disease, the patient has a motor or non-motor complication of Parkinson's disease such as a complication including tremor, akinesia, bradykinesia, dyskinesia, dystonia, cognitive impairment, or disordered sleep. In particular embodiments, the method of treating Parkinson's disease includes treating a motor or non-motor complication of Parkinson's disease.

The invention also features a method of treating Parkinson's disease (including patients with scores of 4 and 5 on the Hoehn and Yahr scale) in a patient including administering a pharmaceutical composition of the invention to a patient using the methods described herein.

In a further aspect, the invention features a method of preparing a pharmaceutical composition including from about 35% (w/w) to about 70% (w/w) of a drug including levodopa and/or carbidopa; the pharmaceutical composition including a surfactant, an oil, and water; the pharmaceutical composition, when at 37° C., including solid particles of drug; the drug having a partition coefficient in favor of water; the surfactant being present in an amount sufficient to render the composition physically stable; and the method including contacting an aqueous solution including the surfactant and water with solid particles of the drug, to produce a mixture of solid particles in aqueous solution. The method may further include contacting the mixture with the oil.

In embodiments featuring delivery across the buccal mucosa, the invention further includes delivering the drug-containing composition into a location in the mouth such that the drug has a residence time at or near the mucosa of greater than 2 minutes, 5 minutes, 10 minutes, 30 minutes, or 60 minutes before being removed from contact with the oral mucosa (e.g., by saliva-dilution and/or swallowing). Several techniques and device configurations may be used to obtain the desired residence time, optionally in combination with each other. In one embodiment, the drug-containing composition is delivered into a portion of the mouth where the flux of saliva is slow, e.g., into the cheek pocket between the bottom teeth/gums and the cheek, and preferably not proximate a salivary gland. In a related embodiment, the composition may be mucoadhesive or include a mucoadhesive to retain the drug proximate the mucosa. In yet another related embodiment, the drug-containing composition may be delivered into a material that retains the drug proximate the mucosa, such as a sorbent.

In a related aspect, the invention features a method for treating Parkinson's disease in a subject, the method including: (a) inserting a drug delivery device into the subject's mouth, the device having (i) a fastener to removably secure the drug delivery device to a surface of the patient's mouth; (ii) an electrical or mechanical pump; and (iii) an oral liquid impermeable drug reservoir having a volume of from 0.1 ml to 5 ml including a suspension or solid containing levodopa or a levodopa prodrug; (b) administering into the patient's mouth the levodopa or a levodopa prodrug continuously or semi-continuously; and (c) removing the drug delivery device from the mouth of the subject, wherein the subject has a score of 4 and 5 on the Hoehn and Yahr scale. In some embodiments, step (b) includes administering into the subject's mouth the levodopa or a levodopa prodrug semi-continuously at a frequency of at least once every 30 minutes. In certain embodiments, the suspension or solid is administered to the subject for a period of at least 8 hours at an hourly rate in the range of 10-125 mg/hour, such that a circulating plasma levodopa concentration greater than 1,200 ng/m L and less than 2,500 ng/mL is continuously maintained for a period of at least 8 hours during the administration.

In one particular embodiment, the subject can have delayed gastric emptying or retarded gastrointestinal transit, e.g., induced by LD-derived dopamine, the dopamine being formed by decarboxylation of LD (e.g., in the mesentery of the gastrointestinal tract).

In still other embodiments, the drug reservoir includes a composition including a suspension that is a drug particle-containing emulsion including (i) from 35% to 70% (w/w) drug particles including levodopa and/or carbidopa, or salts thereof, (ii) from 19% to 30% (w/w) of one or more water-immiscible compounds, (iii) from 2% to 16% (w/w) water, and (iv) from 1% to 8% (w/w) surfactant. The suspension can include a continuous hydrophilic phase including greater than 50% (w/w) drug particles. Optionally, the drug delivery device includes an automatic stop/start, a suction-induced flow limiter, a temperature-induced flow limiter, and/or bite-resistant structural supports.

In a related aspect, the invention features a method for treating spasticity in a subject, the method including: (a) inserting a drug delivery device into the subject's mouth, the device having (i) a fastener to removably secure the drug delivery device to a surface of the patient's mouth; (ii) an electrical or mechanical pump; and (iii) an oral liquid impermeable drug reservoir having a volume of from 0.1 ml to 5 ml including a suspension or solid containing baclofen or a pharmaceutically acceptable salt thereof; (b) administering into the patients mouth the baclofen continuously or semi-continuously; and (c) removing the drug delivery device from the mouth of the subject.

In a related aspect, the invention features a method for treating myasthenia gravis in a subject, the method including: (a) inserting a drug delivery device into the subjects mouth, the device having (i) a fastener to removably secure the drug delivery device to a surface of the patient's mouth; (ii) an electrical or mechanical pump; and (iii) an oral liquid impermeable drug reservoir having a volume of from 0.1 ml to 5 ml including a solution or suspension of pyridostigmine or a pharmaceutically acceptable salt thereof; (b) administering into the patient's mouth the pyridostigmine continuously or semi-continuously; and (c) removing the drug delivery device from the mouth of the subject.

In an embodiment of any of the above devices, methods, and pharmaceutical compositions, the drug can be an analgesic (e.g., lidocaine, bupivacaine, mepivacaine, ropivacaine, tetracaine, etidocaine, chloroprocaine, prilocaine, procaine, benzocaine, dibucaine, dyclonine hydrochloride, pramoxine hydrochloride, benzocaine, proparacaine, and their pharmaceutically acceptable salts) or an opioid (e.g., buprenorphine, nor-buprenorphine, fentanyl, methadone, levorphanol, morphine, hydromorphone, oxymorphone codeine, oxycodone, hydrocodone, and their pharmaceutically acceptable salts) administered for the treatment of pain.

The invention features a method for treating disease in a subject suffering from delayed gastric emptying or retarded gastrointestinal transit, the method including: (a) inserting a drug delivery device into the subject's mouth, the device having (i) a fastener to removably secure the drug delivery device to a surface of the patients mouth; (ii) an electrical or mechanical pump; and (iii) an oral liquid impermeable drug reservoir having a volume of from 0.1 ml to 5 ml including a suspension or solid containing a drug useful for treating the disease; (b) administering into the patients mouth the drug continuously or semi-continuously at a frequency of at least once every 30 minutes; and (c) removing the drug delivery device from the mouth of the subject. In particular embodiments, an efficacious circulating plasma concentration of the drug is continuously maintained for a period of at least 8 hours during the administration. The drug delivery device can include an automatic stop/start, a suction-induced flow limiter, a temperature-induced flow limiter, and/or bite-resistant structural supports.

The invention features a drug delivery device configured for continuously or semi-continuously administering a drug into the mouth of a patient, the drug delivery device including: a pharmaceutical composition including a paste, solution or suspension having a viscosity greater than 100 poise and less than 500,000 poise at 37° C. and including the drug; and a mechanical pump including a flow restrictor, the flow restrictor including an internal diameter between 0.05 mm and 3.00 mm and a length between 0.25 cm and 20 cm, configured and arranged to administer the pharmaceutical composition at a rate between 0.001 mL/hour and 1.25 mL/hour. The mechanical pump can include a propellant. In particular embodiments, the propellant has a vapor pressure at about 37° C. greater than 1.2 bar and less than 50 bar. The pharmaceutical composition includes solid drug particles and/or excipient particles can have a $D_{90}$ between 0.1 μm and 200 μm and a $D_{50}$ between 0.1 μm and 50 μm when measured by light scattering with the particles dispersed in a non-solvent. The drug delivery device of can be configured such that: (i) the administration rate is greater than 0.03 mL/hour and less than 0.5 mL/hour; (ii) the viscosity greater than 200 poise and less than 100,000 poise; (iii) the flow restrictor has an internal diameter between 0.1 mm and 0.7 mm and a length between 1 cm and 5 cm; and (iv) the propellant has a vapor pressure at about 37° C. greater than 2.5 bar and less than 15 bar. In particular embodiments, the solid drug particles and/or excipient particles having a $D_{90}$ between 1 μm and 50 μm and a $D_{50}$ between 0.5 μm and 30 μm when measured by light scattering with the particles dispersed in a non-solvent. The drug delivery device of can be configured such that: (i) the administration rate is greater than 0.05 mL/hour and less than 0.2 mL/hour; (ii) the viscosity is greater than 500 poise and less than 75,000 poise; (iii) the flow restrictor has an internal diameter between 0.2 mm and 0.5 mm and a length between 1 cm and 2.5 cm; and (iv) the propellant has a vapor pressure at about 37° C. greater than 4 bar and less than 10 bar. In particular embodiments, the solid drug particles and/or excipient particles having a $D_{90}$ between 3 μm and 30 μm and a $D_{50}$ between 2 μm and 20 μm when measured by light scattering with the particles dispersed in a non-solvent.

The invention further features a method of administering a pharmaceutical composition to a patient, the method including: (i) inserting the drug delivery device into the mouth of the patient; (ii) continuously or semicontinuously administering the pharmaceutical composition into the mouth of a patient using at a rate between 0.001 mL/hour and 1.25 mL/hour; (iii) wherein the pharmaceutical composition includes a paste, solution or suspension having a viscosity greater than 100 poise and less than 500,000 poise at 37° C.; and (iv) the drug delivery device includes a mechanical pump including a flow restrictor including an internal diameter between 0.05 mm and 3.00 mm and a length between 0.25 cm and 20 cm. In certain embodiments, the mechanical pump includes a propellant, the propellant having a vapor pressure at about 37° C. greater than 1.2 bar and less than 50 bar. The solid drug particles and/or excipient particles can have a $D_{90}$ between 0.1 μm and 200 μm and a $D_{50}$ between 0.1 μm and 50 μm when measured by light scattering with the particles dispersed in a non-solvent. In certain embodiments, the administration rate is greater than 0.03 mL/hour and less than 0.5 mL/hour; the viscosity greater than 200 poise and less than 100,000 poise; the flow restrictor having an internal diameter between 0.1 mm and 0.7 mm and a length between 1 cm and 5 cm; and the propellant has a vapor pressure at about 37° C. greater than 2.5 bar and less than 15 bar. The solid drug particles and/or excipient particles can have a $D_{90}$ between 0.1 μm and 50 μm and a $D_{50}$ between 0.5 μm and 30 μm when measured by light scattering with the particles dispersed in a non-solvent. In particular embodiments, the administration rate is greater than 0.05 mL/hour and less than 0.2 mL/hour; the viscosity is greater than 500 poise and less than 75,000 poise; the flow restrictor has an internal diameter between 0.2 mm and 0.5 mm and a length between 1 cm and 2.5 cm; and the propellant has a vapor pressure at about 37° C. greater than 4 bar and less than 10 bar. The solid drug particles and/or excipient particles can have a $D_{90}$ between 3 μm and 30 μm and a $D_{50}$ between 2 μm and 20 μm when measured by light scattering with the particles dispersed in a non-solvent.

Abbreviations and Definitions

The term "about," as used herein, refers to a number that is±10% of a value that this term precedes except when the value is that of a temperature. For temperatures "about" means ±3° C.

The term "administration" or "administering" refers to a method of giving a dosage of a therapeutic drug, such as LD and/or carbidopa (CD), to a patient. The drug may be formulated as a fluid, such as a viscous suspension. Fluids may be infused. The dosage form of the invention is preferably administered into the mouth or nasal cavity, optionally using a drug delivery device such as an infusion pump, and the drug can be swallowed and/or absorbed anywhere within the mouth or alimentary canal, e.g., buccally, sublingually, or via the stomach, small intestine, or large intestine. Typical durations of administration from a single device or drug reservoir are greater than 4, 8, 12, or 16 hours per day, up to and including 24 hours per day. Administration can also take place over multiple days from a single device or drug reservoir, e.g., administration of a drug for 2 or more days, 4 or more days, or 7 or more days.

As used herein, "aqueous" refers to formulations of the invention including greater than 10% or 20% (w/w) water and, optionally, a cosolvent (e.g., propylene glycol, glycerol or ethanol) or solute (e.g., a sugar).

By "alkyl saccharide" is meant a sugar ether of a hydrophobic alkyl group (e.g., typically from 9 to 24 carbon atoms in length). Alkyl saccharides include alkyl glycosides and alkyl glucosides. Alkyl glycosides that can be used in the pharmaceutical compositions of the invention include, without limitation, $C_{08-14}$ alkyl (e.g., octyl-, nonyl-, decyl-, undecyl-, dodecyl-, tridecyl-, or tetradecyl-) ethers of a or β-D-maltoside, -glucoside or -sucroside, alkyl thiomaltosides, such as heptyl, octyl, dodecyl-, tridecyl-, and tetradecyl-β-D-thiomaltoside; alkyl thioglucosides, such as heptyl- or octyl 1-thio α- or β-D-glucopyranoside; alkyl thiosucroses; and alkyl maltotriosides. For example, the pharmaceutical composition can include a surfactant selected from octyl maltoside, dodecyl maltoside, tridecyl maltoside, and tetradecyl maltoside. Alkyl glucosides that can be used in the pharmaceutical compositions of the invention include, without limitation, $C_{8-14}$ alkyl (e.g., octyl-, nonyl-, decyl-, undecyl-, dodecyl-, tridecyl-, or tetradecyl-) ethers of glucoside, such as dodecyl glucoside or decyl glucoside.

The term "automatic stop/start," as used herein, refers to an element switching automatically between drug administering mode and non-administering mode upon actuation by an external stimulus (e.g., detachment of the device of the invention from an intraoral surface). Automatic stop/start encompasses automatically stopping delivery, automatically starting delivery, or both. For example, the automatic stop/start can be a pressure sensitive switch, a clip, a fluidic channel that kinks, a clutch (see FIGS. 7E and 7F).

The term "bite-resistant structural supports," as used herein, refers to structural elements in the drug delivery device that enable them to withstand a patient's bite with a force of at least 200 Newtons, without rupturing and without infusing a bolus of greater than 5% of the drug contents, when a fresh reservoir is newly inserted into the mouth.

The term "CD" refers to Carbidopa.

As used herein, "co-administered" or "co-infused" refers to two or more pharmaceutically active agents, formulated together or separately, and administered or infused into the mouth simultaneously or within less than 60, 30, 15, or 5 minutes of each other.

The term "COMT" refers to catechol-O-methyl transferase.

As used herein "continuous administration" or "continuous infusion" refers to uninterrupted administration or infusion of a drug in solid or fluid form.

As used herein the term "$D_{50}$" is defined as the median for a volume distribution (as opposed to a mass, number, or surface distribution) of the particles. The particle size can be measured by conventional particle size measuring techniques well known to those skilled in the art. Such techniques include, for example, optical microscopy, electron microscopy, sedimentation, field flow fractionation, photon correlation spectroscopy, light scattering (e.g., with a Microtrac UPA 150, Malvern Mastersizer), laser diffraction, and centrifugation. $D_{50}$ values are commonly derived of particle size distributions of particles suspended in a non-solvent, the distributions measured by light scattering.

The term "DDC" refers to DOPA decarboxylase.

As used herein, the term "drug particle" refers to solid particles including a drug. The drug particles can be included in the pharmaceutical compositions of the invention. For example, the pharmaceutical composition can contain particulates containing or formed from LD, LD salts, CD, or CD salts.

As used herein the term "emulsion" refers to a macroscopically substantially homogeneous system typically including solid drug particles, water, and a water-immiscible phase (e.g., oil). An emulsion may remain substantially homogeneous, e.g., it may not substantially cream or phase separate in 3 months at 25° C. and/or in 1 day at 37° C. The term encompasses oil in water emulsions and water in oil emulsions.

As used herein the term "engineering plastic" is synonomous with the terms "engineered plastic", "engineered polymer" and "engineering polymer". The term means a polymer differing from the most widely used polymers in its superior mechanical properties, or in its superior resistance to chemicals or its lesser wetting by water or by oils, or its lesser swelling in water or in oils. Exemplary engineering plastics include polyamides such as Nylon 6, Nylon 6-6 and other Nylons; polyesters like polybutylene terephthalate or polyethylene terephthalate; polycarbonates; polyetheretherketones; polyetherketones; polyimides; polyoxymethylenes such as polyacetals or polyformaldehydes; polyphenylene sulfide; polyphenylene oxide; polysulphone; polytetrafluoroethylene; polyvinylidene difluoride; ultra-high-molecular-weight polyethylene; and strong elastomers such as highly crosslinked acrylonitrile butadiene styrene, and their co-polymers.

By "ester saccharide" is meant a sugar ester of a hydrophobic alkyl group (e.g., typically from 8 to 24 carbon atoms in length). Ester saccharides include ester glycosides and ester glucosides. Ester glycosides that can be used in the pharmaceutical compositions of the invention include, without limitation, $C_{8-14}$ alkyl (e.g., octyl-, nonyl-, decyl-, undecyl-, dodecyl-, tridecyl-, or tetradecyl-) esters of α or β-D-maltoside, -glucoside or -sucroside. For example, the pharmaceutical compositions can include a surfactant selected from sucrose mono-dodecanoate, sucrose mono-tridecanoate, or sucrose mono-tetradecanoate.

As used herein, the term "fastener" refers to an element for attaching the device of the invention, or its components, to a surface of the mouth (e.g., to the teeth). Exemplary methods of attachment are fasteners banded, adhered, cemented or glued to one, two or more teeth; dental appliances; splints; transparent retainers; metal wire Hawley retainers; partial retainers on one side of the mouth (e.g., attached to 3, 4, or 5 teeth); thermo or vacuum-formed Essix retainers typically including a polypropylene or polyvinylchloride material, typically 0.020" or 0.030" thick; thermo-formed Zendura retainers including polyurethane; bonded (fixed) retainers including a passive wire bonded to the tongue-side of lower or upper teeth; muco-adhesives that adhere to the oral mucosal tissue and slowly erode; and fasteners that conform or are molded to fit a patient's teeth or soft tissue, similar to dental splints used to treat bruxism and sleep apnea. Similarly, the drug delivery devices, drug pumps, drug reservoirs and other devices of the invention may be directly or indirectly attached to a removable denture, a prosthetic tooth crown, a dental bridge, a moral band, a bracket, a mouth guard, or a dental implant.

As used herein the term "fluctuation index" refers to the magnitude of the rise and fall of drug level in plasma relative to the average plasma concentration, and is defined as $[C_{max}-C_{min}]/C_{avg}$. The fluctuation index is measured over a specified period of time. The time period can begin, for example, after the drug's plasma concentration: has reached the steady-state concentration; or has reached 90% of the steady-state concentration; or 30, 60, or 120 minutes after any of the drug delivery devices of the invention has been inserted into the mouth and begun to deliver drug. The time period can end, for example: at the end of the use period specified in the instructions for use of the drug delivery device; when the drug reservoir is 90% depleted or substantially depeleted; or about 4, 8, 16, 24, 72, or 168 hours after the start of the time period.

As used herein, the term "fluid" encompasses any drug-including liquid, gel, or non-pourable suspension that can be pumped or extruded. The fluid can be a Newtonian or a non-Newtonian fluid; it can be an easy to deform solid or a soft paste, which may move as a plug via slip flow. It can be, for example, a viscous Newtonian or non-Newtonian suspension. The term encompasses, for example, true solutions, colloidal solutions, emulsions, pastes, suspensions, and dense semi-solid toothpaste-like suspensions deforming under pressure sufficiently to be extruded into the mouth. The fluid infused can be aqueous, non-aqueous, single phase, two-phase, three-phase or multiphase. The emulsions can be, for example, oil-in-water or water-in-oil, and can include micelles and/or liposomes.

As used herein, "infused" or "infusion" includes infusion into any part of the body, preferably infusion into the mouth or nasal cavity. It is exemplified by extrusion into the mouth.

The term "LD" refers to levodopa, also known as L-DOPA, or a salt thereof.

As used herein the term "lubricant" means an oil, grease or lamellar solid that reduces the friction between two parts of a system having a moving component.

The term "MAO-B" refers to monoamine oxidase-B.

As used herein, "mechanical pump" means any drug delivery device whose motive force is not electricity, magnetism, or gravity. Examples of mechanical pumps include drug delivery devices wherein the drug is delivered by the force or pressure of a spring, an elastomer, a compressed gas, or a propellant.

As used herein, "mouth" includes the areas of the oral cavity, including those areas of the oral cavity adjacent the lips, cheeks, gums, teeth, tongue, roof of the mouth, hard palate, soft palate, tonsils, uvula, and glands.

The term "non-aqueous" can refer to the liquid carrier in a formulation or to the typically water insoluble liquid component in a formulation. The non-aqueous liquid component typically melts or softens below 37° C. and contains less than 20% (w/w) water (e.g., less than 10%, 5%, 3%, 2%, 1.5%, 1%, 0.5%, or less than 0.1% (w/w). Exemplary liquid components include lipids, edible oils, non-toxic esters of mid-range fatty acids, such as triglyceride esters of mid range fatty acids, butters, and paraffin oils melting or softening below 37° C.

As used herein, the term "operational life" means the time period during which the infused formulation containing the drug (e.g., LD or CD) is suitable for delivery into a patient, under actual delivery conditions. The operational life of the drugs (e.g., LD or CD) delivered by the devices of the invention can be greater than 12 hours, 24 hours, 48 hours, 72 hours, 96 hours (4 days), or 7 days. It typically requires that the product is not frozen or refrigerated. The product is typically infused at or near body temperature (about 37° C.) and typically remains substantially homogeneous during its infusion.

As used herein, an "oral liquid impermeable reservoir" means a reservoir including one or more drugs to be administered into the patient's mouth, wherein, for example, 1, 4, 8, 16, 24, 48 or 72 hours after placing a drug delivery device including a fresh reservoir in a patient's mouth and initiating the administration, less than 5% (e.g., 3% or 1%) by weight of the drug-including pharmaceutical composition in the reservoir includes an oral liquid. The one or more drugs may be in solid form or in fluid form. Oral liquids include any fluid originating from the mouth, including saliva (or its water component) and other fluids commonly found in the mouth or that are commonly drunk or consumed by the patient, including diluted oils and alcohols. Exemplary oral liquid impermeable reservoirs can be made of a metal, or a plastic that can optionally be elastomeric. Metallic reservoirs can include, for example aluminum, magnesium, titanium, iron, or alloys of these metals. When made of a plastic it can have a metallic barrier layer; or include plastics or elastomers that do not substantially swell in water, used for example for packaging of food, or for drink-containing bottles, or in a fabric of washable clothing (e.g., polyamides like Nylon or polyesters like Dacron), or in stoppers or seals of drink containing bottles, or in septums of vials containing solutions of drugs. Examples include perfluoropolymers like PTFE or FPE or fluorinated polyethers, polyolefins like polyethylene and polypropylene; other vinylic polymers like polystyrene and polyvinylchloride; polyvinylidene chloride, polyacrylates and polymethacrylates, e.g., polymethyl methacrylate and polymethyl acrylate; and polycarbonates; and polysilicones or their copolymers. The polymers can have glass transition temperatures greater than 37° C. Ingress of oral liquids into openings in the reservoir can be prevented or minimized by the use of one or more valves, squeegees, baffles, rotating augers, rotating drums, propellants, pneumatic pumps, diaphragm pumps, hydrophobic materials, and/or hydrophobic fluids. In some embodiments, the invention features multiple doses of solid drug within multiple, impermeable reservoirs or compartments. The plastic of the reservoir can be fiber reinforced, e.g., with carbon, glass, metal or strong polymer fibers.

The abbreviation "M" means moles per liter. Usage of the term does not imply, as it often does in chemistry, that the drug is dissolved. As used herein 1 M means that a 1 liter volume contains 1 mole of the combination of the undissolved (often solid) and/or the dissolved drug. For example, 1 M LD means that there is 197 mg of solid (undissolved) and dissolved LD in one mL.

The term "PD" refers to Parkinson's disease, including patients with scores of 4 and 5 on the Hoehn and Yahr scale.

The term "PEG" refers to polyethylene glycol.

As used herein, the term "pH" refers to the pH measured using a pH meter having a glass pH electrode connected to an electronic meter.

As used herein, the term "physically stable" refers to a macroscopically substantially homogenous composition including a suspension of drug particles, wherein the suspension does not exhibit substantial sedimentation upon (a) storage at about 5° C. under at about 1 G gravity for a period of at least 3, 6, 12, or 18 months; (b) storage at about 25° C. at about 1 G gravity for a period of at least 3, 6, 12, 18, or more months; or (c) centrifugation at about 5,000 G, 10,000 G, or 16,000 G gravity for at least 30 minutes (e.g., for 60 minutes or longer) at about 25° C. For compositions that include an emulsion including suspended drug particles, physically stable compositions also do not exhibit substantial creaming upon (a) storage at about 5° C. under ambient conditions for a period of at least 3, 6, 12, or 18 months; (b) storage at 25° C. under ambient conditions for a period of at least 3, 6, 12, or 18 months; or (c) centrifugation at about 5,000 G, 10,000 G, or 16,000 G gravity for at least 30 minutes (e.g., 60 minutes or longer) at about 25° C. Physically stable suspensions may also remain macroscopically substantially homogeneous when stored for about 8, 24, or 48 hours at about 37° C. without agitation, such as shaking, subsequent to the storage or centrifugation described above.

By "polyglycolized glyceride" is meant a polyethylene glycol glyceride monoester, a polyethylene glycol glyceride diester, a polyethylene glycol glyceride triester, or a mixture thereof containing a variable amount of free polyethylene glycol, such as a polyethylene glycol-oil transesterification product. The polyglycolized glyceride can include either monodisperse (i.e., single molecular weight) or polydisperse polyethylene glycol moieties of a predetermined size or size range (e.g., PEG2 to PEG 40). Polyethylene glycol glycerides include, for example: PEG glyceryl caprate, PEG glyceryl caprylate, PEG-20 glyceryl laurate (Tagat® L, Goldschmidt), PEG-30 glyceryl laurate (Tagat® L2, Goldschmidt), PEG-15 glyceryl laurate (Glycerox L series, Croda), PEG-40 glyceryl laurate (Glycerox L series, Croda), PEG-20 glyceryl stearate (Capmul® EMG, ABITEC), and Aldo® MS-20 KFG, Lonza), PEG-20 glyceryl oleate (Tagat® 0, Goldschmidt), and PEG-30 glyceryl oleate (Tagat® 02, Goldschmidt). Caprylocapryl PEG glycerides include, for example, caprylic/capric PEG-8 glyceride (Labrasol®, Gattefosse), caprylic/capric PEG-4 glyceride (Labrafac® Hydro, Gattefosse), and caprylic/capric PEG-6 glyceride (SOFTIGEN®767, Huls). Oleoyl PEG glyceride include, for example oleoyl PEG-6 glyceride, (Labrafil M1944 CS, Gattefosee). Lauroyl PEG glycerides includes, for example, lauroyl PEG-32 glyceride (Gelucire® ELUCIRE 44/14, Gattefosse). Stearoyl PEG glycerides include, for example stearoyl PEG-32 glyceride (Gelucrire 50/13, Gelucire 53/10, Gattefosse). PEG castor oils include PEG-3 castor oil (Nikkol CO-3, Nikko), PEG-5, 9, and 16 castor oil (ACCONON CA series, ABITEC), PEG-20 castor oil, (Emalex C-20, Nihon Emulsion), PEG-23 castor oil (Emulgante EL23), PEG-30 castor oil (Incrocas 30, Croda), PEG-35 castor oil (Incrocas-35, Croda), PEG-38 castor oil (Emulgante EL 65, Condea), PEG-40 castor oil (Emalex C-40, Nihon Emulsion), PEG-50 castor oil (Emalex C-50, Nihon Emulsion), PEG-56 castor oil (Eumulgin® PRT 56, Pulcra SA), PEG-60 castor oil (Nikkol CO-60TX, Nikko), PEG-100 castor oil, PEG-200 castor oil (Eumulgin® PRT 200, Pulcra SA), PEG-5 hydrogenated castor oil (Nikkol HCO-5, Nikko), PEG-7 hydrogenated castor oil (Cremophor W07, BASF), PEG-10 hydrogenated castor oil (Nikkol HCO-10, Nikko), PEG-20 hydrogenated castor oil (Nikkol HCO-20, Nikko), PEG-25 hydrogenated castor oil (Simulsol® 1292, Seppic), PEG-30 hydrogenated castor oil (Nikkol HCO-30, Nikko), PEG-40 hydrogenated castor oil (Cremophor RH 40, BASF), PEG-45 hydrogenated castor oil (Cerex ELS 450, Auschem Spa), PEG-50 hydrogenated castor oil (Emalex HC-50, Nihon Emulsion), PEG-60 hydrogenated castor oil (Nikkol HCO-60, Nikko), PEG-80 hydrogenated castor oil (Nikkol HCO-80, Nikko), and PEG-100 hydrogenated castor oil (Nikkol HCO-100, Nikko). Additional polyethylene glycol-oil transesterification products include, for example, stearoyl PEG glyceride (Gelucire® 50/13, Gattefosse). The polyglycolized glycerides useful in the pharmaceutical compositions of the invention can include polyethylene glycol glyceride monoesters, diesters, and/or triesters of hexanoic, heptanoic, caprylic, nonanoic, capric, lauric, myristic, palmitic, heptadecanoic, stearic, arachidic, behenic, lignoceric, α-linolenic, stearidonic, eicosapentaenoic, docosahexaenoic, linoleic, γ-linolenic, dihomo-γ-linolenic, arachidonic, oleic, elaidic, eicosenoic, erucic, or nervonic acid, or mixtures thereof. The polyglycol moiety in a polyglycolized glyceride can be polydisperse; that is, they can have a variety of molecular weights.

By "polysorbate surfactant" is meant an oily liquid derived from pegylated sorbitan esterified with fatty acids. Common brand names for polysorbate surfactant include Alkest™, Canarcel™ and TweenT™. Polysorbate surfactants include, without limitation, polyoxyethylene 20 sorbitan monolaurate (TWEEN™ 20), polyoxyethylene (4) sorbitan monolaurate (TWEEN™ 21), polyoxyethylene 20 sorbitan monopalmitate (TWEEN™ 40), polyoxyethylene 20 sorbitan monostearate (TWEEN™ 60); and polyoxyethylene 20 sorbitan monooleate (TWEEN™ 80).

The term "pressure-invariant pump," as used herein, refers to a pump whose average rate of drug delivery decreases by less than about 10% (e.g., less than about 7%, 5%, or 3%) at an ambient pressure of about 1.013 bar versus its average rate of delivery at an ambient pressure of about 0.898 bar and/or increases by less than about 10% (e.g., as described herein) at an ambient pressure of about 0.898 bar versus its average rate of delivery at an ambient pressure of about 1.013 bar.

As used herein, "pump" refers to any mechanism capable of administering a fluid formulated drug product over a period of 4 or more hours. Examples of pumps include battery-powered pumps (e.g., syringe pumps, piezoelectric, peristaltic pumps, or diaphragm pumps), mechanical devices with or without moving parts that are not battery-powered (e.g., gas-driven pumps, spring-driven pumps, shape memory alloy driven pumps, and elastomeric pumps), and battery operated electroosmotic pumps (with or without moving parts).

The terms "semi-continuous administration" and "frequent administration," as used interchangeably herein, refer to an administration (e.g., infusion) of a drug in solid or fluid form at a frequency of at least once every 120 minutes, and preferably at least every 90, 60, 30, 15, or 5 minutes.

As used herein, the term "shelf life" means the shelf life of the drug delivered by the inventive device (e.g., LD or CD), in its form as a product sold for use by consumers, during which period the product is suitable for use by a patient. The shelf life of the drugs (e.g., LD or CD) administered by the devices of the invention can be greater than 3, 6, 12, 18, or preferably 24 months. The shelf life may be achieved when the product is stored frozen (e.g., at about -18° C.), stored refrigerated (at 5±3° C., for example at 4±2° C.), or stored at room temperature (e.g., at about 25° C.). The drug (e.g., LD or CD) product sold to consumers may be the drug-containing suspension, e.g., suspension ready for infusion, or it may be its components.

As used herein, "stable" refers to stable formulations of any of the drugs administered by the devices of the invention. Stable formulations exhibit physical stability (as defined above) and a reduced susceptibility to chemical transformation (e.g., oxidation) prior to administration into a patient. Stable drug formulations have a shelf life at about 5° C. and/or at about 25° C. of equal to or greater than 3, 6, 12, 18, or 24 months, and an operational life of greater than or equal to 8 hours, 12 hours, 16 hours, 24 hours, 48 hours, 72 hours, 96 hours, or 7 days. In the context of LD and/or CD containing formulations, "stable" refers to formulations which are chemically stable and physically stable. Chemically stable formulations are those having a shelf life during which less than 20% (e.g., 10%, 5%, 4%, 3%, 2% or less than 1%) of the LD and/or CD is chemically transformed (e.g., oxidized) when stored for a period of 3, 6, 12, 18, or 24 months. For formulations such as suspensions and drug particle-containing emulsions, the term "stable" also refers to formulations that are physically stable. In the context of LD and CD, "stable" refers to formulations that are "oxidatively stable." Stable formulations of LD and CD are those having a shelf life during which less than 10% (e.g., 5%, 4%, 3%, 2% or less than 1%) of the LD and CD is oxidized when stored for a period of 3, 6, 12, 18, or 24 months. Stable formulations of LD and CD have an operational life during which less than 10% (e.g., as described herein) of the LD and CD is oxidized over a period of 8 hours, 12 hours, 16 hours, 24 hours, 48 hours, 72 hours, 96 hours, or 7 days. The chemically stable formulations may contain less than 1.6 µg of hydrazine per mg of LD and CD when stored for a period of 3, 6, 12, 18, or 24 months at about 5° C. and/or at about 25° C.

As used herein, "substantially free of oxygen" refers to compositions packaged in a container for storage or for use wherein the packaged compositions are largely free of oxygen gas (e.g., less than 10%, or less than 5%, of the gas that is in contact with the composition is oxygen gas) or wherein the partial pressure of the oxygen is less than 15 torr, 10 torr, or 5 torr. This can be accomplished, for example, by replacing a part or all of the ambient air in the container with an inert gas, such as nitrogen, carbon dioxide, argon, or neon, or by packaging the composition in a container under a vacuum.

The term "suction-induced flow limiter," as used herein, refers to one or more elements preventing the delivery of a bolus greater than about 5%, 3%, or 1% of the contents of a fresh drug reservoir, when the ambient pressure drops by 0.14 bar for a period of one minute. The suction-induced flow limiter can include pressurized surfaces that are in fluidic (gas and/or liquid) contact with the ambient atmosphere via one or more ports or openings in the housing of the drug delivery device. Alternatively, the suction-induced flow limiter can be selected from a deformable channel, a deflectable diaphragm, a compliant accumulator, an inline vacuum-relief valve, and a float valve.

As used herein, the term "suitable for continuous or frequent intermittent intra-oral delivery" refers to drug particle suspensions of the invention that are efficacious and safe upon intra-oral delivery. For example, local adverse events in or near the mouth (if any) produced by continuous or frequent intermittent intra-oral administration of the suspension are tolerable or mild.

As used herein the term "suspension" refers to a mixture including a liquid and particles of at least one solid. The liquid can be aqueous or non-aqueous or an emulsion. The non-aqueous liquid can be an edible oil and the emulsion can include an edible oil. Suspensions may be, for example, flowing suspensions or suspensions that are extruded, i.e., slipping as a plug (e.g., through a flow-controlling orifice, nozzle, or tubing).

The term "suspension flow-enhancement element," as used herein, refers to one or more elements that substantially prevent pressure-induced separation of pumped, viscous suspensions, e.g., formulations with particular multimodal particle size distributions, packing densities, and flow-enhancing excipients; flaring of the orifice, tube, or flow restrictor; orifice, tube or flow restrictor inner diameters substantially larger than the maximum particle size (e.g., the $D_{90}$, $D_{95}$, or $D_{98}$); and selection of specific combinations of viscosity, orifice/tube inner diameter, particle size, and pressure.

The term "temperature-induced flow limiter," as used herein, refers to one or more elements preventing the delivery of a bolus greater than about 5% of the contents of a fresh drug reservoir, when immersed for five minutes or for one minute in a stirred physiological saline solution at about 55° C. The temperature-induced flow limiter can include insulation with a material of low thermal conductivity proximate the drug reservoir and/or the pump. Optionally, the temperature-induced flow limiter includes an elastomer, a spring, or a gas.

As used herein, the term "treating" refers to administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to ameliorate the disease and improve the patient's condition. The term "treating" also includes treating a patient to delay progression of a disease or its symptoms. Thus, in the claims and embodiments, treating is the administration to a patient either for therapeutic or prophylactic purposes.

As used herein "viscosity" means dynamic viscosity also known as shear viscosity.

Other features and advantages of the invention will be apparent from the following Detailed Description, the drawings, and the claims.

BRIEF DESCRIPTION OF THE DRAWINGS

FIG. 5A is a representation of an empty elastomeric drug delivery device, while FIG. 5B represents a fresh, pressurized, drug-filled elastomeric drug delivery device.

FIG. 10 illustrates a disk 54 which contains compartments filled with drug suspension 55 that are injected by an air pressure bolus at a pre-determined rate through an orifice 56 that is fixed in place with respect to the rotating disk. The rotation of the disk, via a spring mechanism 37, exposes a single compartment and the bolus of air delivers the drug from that compartment to the mouth.

In FIG. 11A, the drug delivery device includes a housing containing a first, full elastomeric drug reservoir 3; a second elastomeric reservoir 7 substantially empty of gas and optionally containing liquid propellant; and an optional gas pump 11 and electronics. In one embodiment air is pumped by the electronic (e.g., piezoelectric) pump 11 into the second elastomeric reservoir 7. The pressure from the second elastomeric reservoir 7 compresses the first elastomeric drug reservoir 3 containing the drug, forcing the drug out of the reservoir through a flow restrictor 58 at a constant rate. FIG. 11B illustrates the system with a first, half-full drug reservoir 3 and a second, elastomeric reservoir 7 half-filled with pressurized air or propellant. FIG. 11C illustrates the system when the drug reservoir 3 is close to empty. In another embodiment, saliva can be pumped by the electronic pump 11 into the second elastomeric reservoir 7.

FIG. 13A shows the compressed expandable plastic compartment 61 containing propellant within the full drug reservoir 3. FIG. 13B shows the nearly empty drug reservoir 3 and the expanded expandable plastic compartment 61 containing propellant.

DETAILED DESCRIPTION

Figure 1A:
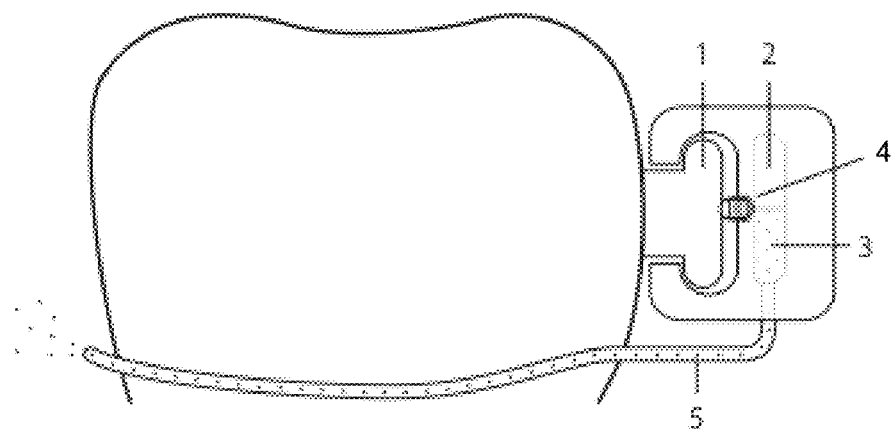
FIG. 1A depicts a drug delivery device that is removably attached to a tooth using a fastener 1. The pump 2 and drug reservoir 3 are contained within a housing 4 and are disposable.

The devices, compositions, and methods of the invention are useful for continuous or semi-continuous oral delivery of medicaments.

While syringes, drug reservoirs and pumps outside the mouth can be large because space is typically available, space in the mouth for a drug delivery device is limited and is particularly limited when a drug delivery device is so small that it does not interfere with speaking, swallowing, drinking, or eating. Consequently, the delivered drug, its reservoir and its delivery device must occupy a small volume. In the exemplary management of Parkinson's disease the concentration of the orally infused LD and/or CD including fluid of the invention can be typically greater than 1 M, such as greater than 1.5 M, 2 M, 2.5 M, 3 M, 3.5 M, 4 M or 4.5 M. These are substantially higher concentrations than the 0.1 M LD concentration of the Duodopa (also known as Duopa™) gels that are commercially available for jejunal, gastric or nasogastric infusions. The concentrated drug suspension can be viscous, for example its dynamic viscosity at 37° C. can be much greater than 100 cP, such as greater than 10,000 cP, 100,000 cP, or 1,000,000 cP. The suspension can have, for example, viscosity equal to or greater than that of toothpaste, the viscosity being greater than about 20,000 cP, for example greater than 50,000 cP, such as greater than 500,000 cP. The earlier practice of infusion of viscous fluids through long tubings, typically longer than 50 cm, such as those used for nasogastric, gastric or jejunal infusions, required that their internal diameter be large and/or that the pumping pressure be high. Furthermore, when the earlier suspensions were infused through the longer tubings, the likelihood of blockage of the flow because of clustering of the suspended LD particles increased and translucent, very fine particle colloids were used to reduce blockage. In contrast, the herein disclosed orally infused, more much concentrated suspensions of the invention are typically opaque because they can contain large solid particles scattering visible-wavelength light. The much more concentrated and much more viscous orally infused suspensions can be rich in particle sizes greater than 1 µm, 5 µm, 10 µm, or even 50 µm. The suspensions can be orally infused, for example, using orifices in reservoirs that are narrower than 2 mm or 1 mm, and/or through optionally plastic tubings or nozzles that can be shorter than 5 cm, e.g., shorter than 4 cm, 3 cm, 2 cm or 1 cm.

The invention addresses the problem of formulating a pharmaceutical suspension that is sufficiently concentrated to be useful for oral infusion as described above and that is sufficiently physically and chemically stable for long-term storage at room temperature and for infusion over a prolonged period of time. Thus, the invention features a pharmaceutical composition suitable for continuous or frequent intermittent intra-oral delivery. The composition can be a suspension of solid drug particles in a carrier that is physically stable at about 25° C. and/or at a physiological temperature, such as 37° C. The suspension can contain from about 35% (w/w) to about 70% (w/w) of the drug, this weight percentage including the solid drug particles and the drug dissolved in the carrier. The carrier can include a continuous hydrophilic phase, e.g., it can be an oil-in-water emulsion. It can contain more oil than water by weight, even when the continuous phase is hydrophilic or when it is an oil-in-water system. Alternatively, it can include a continuous hydrophobic (i.e., water-immiscible) phase including an oil or a water-in-oil emulsion.

Physical stability of the solid drug particle containing suspension can be enhanced by the combined presence of an oil, water and a surfactant, each in an amount sufficient to inhibit or retard sedimentation and/or phase separation.

The invention also features levodopa and carbidopa formulations that are chemically stable, with chemical degradation products of the levodopa and carbidopa (e.g., oxidation product and hydrolysis products) of less than 5%, 2%, or 1% of the starting amount of the drugs. In particular, the invention features CD and LD/CD formulations with low hydrazine concentrations, even after prolonged storage or exposure to elevated temperatures under air.

Administration in the Mouth

The drugs may be administered intraorally (i.e., onto or near any intraoral surface, e.g., the lips, cheeks, gums, teeth, tongue, roof of the mouth, hard palate, soft palate, tonsils, uvula, and glands). The drugs administered intraorally are typically swallowed by the patient, together with the patient's saliva. The drugs can be diluted by the patient's saliva and can optionally be partly or fully dissolved in the saliva. The drugs can be absorbed in the patient's gastrointestinal tract, e.g., in the small intestines or large intestines. In some cases, absorption of drugs delivered by the drug delivery devices of the invention may take place partially or even primarily through the mucous membranes in the mouth, e.g., buccal or sublingual absorption.

Medications and Diseases

The devices and methods of the invention are suitable for the administration of a variety of drugs that have a short half-life and/or a narrow therapeutic range. Complementary drugs may be co-administered or co-infused with these drugs. Such complementary drugs may improve the pharmacokinetics, improve the efficacy, and/or reduce the side effects of the primary drugs.

Exemplary diseases/medical conditions that may be treated with the devices and methods of the invention, and corresponding drugs and exemplary ranges of daily doses and of average administration rates, are listed below:

Parkinson's disease: levodopa, levodopa prodrugs, and dopamine agonists (such as Pramipexole (0.1-10 mg per day, 0.004-0.42 mg/hr), Bromocriptine, Ropinirole (0.25-10 mg per day, 0.01-0.42 mg/hr), Lisuride, Rotigotine). Examples of complementary drugs for Parkinson's disease, which may optionally be co-infused, are DDC inhibitors (such as carbidopa and benserazide (50-600 mg per day, 2.1-25 mg/hr)), COMT inhibitors (such as entacapone, tolcapone and opicapone), MAO-B inhibitors (such as Rasagiline and Selegiline), adenosine A2 receptor antagonists (such as Istradefylline), and gastroparesis drugs (such as Domperidone, Nizatidine, Relamorelin, Monapride and Cisapride).

Allergies: antigens or allergens (e.g., pollen, a part of a mite, or a component of the feline or canine skin, or an extract or a conversion product thereof)

Anesthesia: bupivacaine, lidocaine.

Anxiety: oxcarbazepine (300-3,000 mg per day, 12.5-125 mg/hr), prazosin (0.2-5 mg per day, 0.01-0.21 mg/hr).

Arrhythmia: quinidine (300-2,000 mg per day, 12.5-83 mg/hr)

Bacterial infections: beta-lactam antibiotics (e.g., cephalosporins).

Cancer: capecitabine (1,000-10,000 mg per day, 42-417 mg/hr) and other 5-fluorouracil prodrugs.

Dementia: Rivastigmine.

Diabetes: oral insulins

Diabetic nephropathy: angiotensin receptor blockers.

Disordered sleep: Zaleplon (3-20 mg per day, 0.38-0.83 mg/hr for 8 hours at night), gamma hydroxy butyrate (10-200 mg per day, 1.3-25 mg/hr for 8 hours at night), Zolpidem (3-20 mg per day 0.38-0.83 mg/hr for 8 hours at night), triazolam.

Epilepsy and seizures: Oxcarbazepine (300-3,000 mg per day, 12.5-125 mg/hr), topiramate (200-500 mg per day, 8.3-20.8 mg/hr), lamotrigine (100-700 mg per day, 4.2-29.2 mg/hr), gabapentin (600-3,600 mg per day, 25-150 mg/hr), carbamazepine (400-1,600 mg per day, 16.7-66.7 mg/hr), valproic acid (500-5,000 mg per day, 20.1-208 mg/hr), levetiracetam (1,000-3,000 mg per day, 41.7-125 mg/hr), pregabalin (150-600 mg per day, 6.25-25 mg/hr).

Heart failure: ACE inhibitors, angiotensin receptor blockers.

Hypertension: Prazosin (0.2-5 mg per day, 0.01-0.21 mg/hr), ACE inhibitors, angiotensin receptor blockers.

Orthostatic hypotension: droxidopa, fludrocortisone, midodrine.

Mood disorders: Oxcarbazepine (300-3,000 mg per day, 12.5-125 mg/hr), lithium.

Mucositis: pilocarpine, topical anesthetics or analgesics (e.g., lidocaine), mucosal coating agents (e.g., benzydamine HCl), and sialagogues.

Organ transplantation: Cyclosporine (150-1,500 mg per day, 6.3-62.5 mg/hr), Tacrolimus (3-25 mg per day, 0.13-1.04 mg/hr).

Pain: Fentanyl (0.05-2.0 mg per day, 0.002-0.083 mg/hr), Dilaudid (2-50 mg per day, 0.83-2.1 mg/hr).

Post-traumatic stress disorder: Prazosin (0.25-5 mg per day, 0.01-0.21 mg/hr).

Spasticity: Baclofen.

Hyperammonaemia associated with N-acetylglutamate synthase deficiency, isovaleric acidaemia, methymalonic acidaemia, propionic acidaemia: carglumic acid.

Lambert-Eaton disease: Amifampridine (15-60 mg per day, 0.625-2.5 mg/hour).

Myasthenia gravis: pyridostigmine (60-1,500 mg per day, 2.5-62.5 mg/hour. A typical dose is about 600 mg per day or about 25 mg/hour.)

Exemplary diseases/medical conditions that may be treated with the devices and methods of the invention, and corresponding drugs and exemplary ranges of daily doses and of average administration rates include those that are listed below in Tables A-C.

TABLE A

| Drug | Indication | Delivery Route | Formulation | Daily Hours | Daily Dose Range (mg) | | |
|------|------------|----------------|-------------|-------------|-----|------|---------|
| | | | | | Low | High | Typical |
| Baclofen | Multiple sclerosis, cerebral palsy, spastic conditions | GI | B, C | 16 | 30 | 100 | 50 |
| Tizanidine | Multiple sclerosis, cerebral palsy, spastic conditions | GI, Buccal | C, F | 16 | 12 | 36 | 18 |

TABLE A-continued

| Drug | Indication | Delivery Route | Formulation | Daily Hours | Daily Dose Range (mg) Low | High | Typical |
|---|---|---|---|---|---|---|---|
| Dantrolene | Multiple sclerosis, cerebral palsy, spastic conditions | GI | A | 16 | 25 | 400 | 100 |
| DroxiDOPA | Neurogenic orthostatic hypotension | GI | A | 16 | 300 | 1800 | 1,000 |
| Midodrine | Neurogenic orthostatic hypotension | GI | B, C | 16 | 25 | 35 | 30 |
| Penicillamine | Wilson's disease | GI | A | 16 | 250 | 2000 | 500 |
| Penicillamine | Cystinuria | GI | A | 24 | 2000 | 4000 | 3,000 |
| Penicillamine | Refractory rheumatoid arthritis | GI | A | 24 | 250 | 750 | 500 |
| Zinc acetate | Wilson's disease | GI | A, D | 24 | 100 | 200 | 150 |
| Zinc compounds water or stomach acid soluble, dose representing the $Zn^{2+}$ content only | Wilson's disease | GI | A, D | 24 | 30 | 80 | 50 |
| Magnesium compounds, water or stomach acid soluble, dose representing the $Mg^{2+}$ content only | Parkinson's disease; Alzheimer disease; cognitive diseases; learning disabilities | GI | A, D | 24 | 500 | 5000 | 3,000 |
| L-DOPA | Parkinson's disease | GI | A | 16 | 300 | 3000 | 1,200 |
| Pyridostigmine | Myasthenia gravis | GI | A | 16 | 60 | 1500 | 600 |
| Neostigmine | Myasthenia gravis | Buccal | B | 16 | 50 | 70 | 60 |
| Miglustat | Type-1 Gaucher disease, Type C Niemann-Pick disease | GI | A | 24 | 200 | 400 | 300 |
| Cromoglicic acid (cromolyn) | Eosinophilic gastroenteritis, chronic mastocytosis, ulcerative colitis | GI | A | 24 | 40 | 1000 | 800 |
| Metoclopramide | Gastroparesis, nausea, gastro-oesophageal reflux, gastroenteritis, hyperemesis gravidarum | GI | B, C | 24 |  | 40 | 30 |
| Trientine | Wilson's disease | GI | A | 16 | 1200 | 2400 | 1,800 |
| Temozolomide | Glioblastoma multiformae, anaplastic astrocytoma | GI | A | 24 | 300 | 400 | 350 |
| Captopril | Primary hypertension, coronary heart disease, congestive heart failure, angina | GI | B, C | 16 | 40 | 60 | 50 |
| Acarbose | Type 2 diabetes | GI | A | 24 | 250 | 350 | 300 |
| Iloprost | PH | Buccal | F | 16 | 0.02 | 0.1 | 0.048 |
| Beraprost | PH | Buccal | F | 16 | 0.2 | 0.5 | 0.36 |
| Treprostinil | PH | GI | B, C | 16 | 4 | 20 | 12 |
| Ciclesonide | COPD, PH | Buccal | F | 16 | 0.1 | 0.5 | 0.24 |
| Flunisolide | COPD, PH | Buccal | F | 16 | 0.5 | 2.5 | 1.2 |
| Budesonide | COPD, PH | Buccal | F | 16 | 0.6 | 3 | 1.5 |
| Beclomethason | COPD, PH | Buccal | F | 16 | 0.6 | 3 | 1.5 |
| Bosentan | COPD, PH | GI | A | 16 | 100 | 500 | 250 |
| Mometasone | COPD, PH | Buccal | F | 16 | 0.2 | 1 | 0.48 |
| Vilanterol | COPD | Buccal | F | 24 | 0.1 | 0.5 | 0.24 |
| Bitolterol | COPD; Asthma | GI | C | 24 | 2 | 10 | 4.8 |
| Levosalbutamol sulfate | COPD; Asthma | Buccal | F | 24 | 0.5 | 5 | 2.4 |
| Salbutamol | COPD; Asthma | Buccal | F | 24 | 0.5 | 5 | 2.4 |
| Salmeterol | COPD; Asthma | Buccal | F | 24 | 0.05 | 0.25 | 0.1 |
| Glycopyrronium bromide | COPD | GI | F | 24 | 0.02 | 0.1 | 0.048 |
| Ipatropium bromide | COPD | GI | F | 24 | 0.3 | 1.5 | 0.72 |
| Aclidinium bromide | COPD | GI | F | 24 | 0.3 | 1.5 | 0.72 |
| Carbocisteine | COPD | GI | A | 24 | 1 | 3 | 1500 |
| Erdosteine | COPD | GI | A | 24 | 0.3 | 1 | 600 |

TABLE A-continued

| Drug | Indication | Delivery Route | Formulation | Daily Hours | Daily Dose Range (mg) Low | Daily Dose Range (mg) High | Daily Dose Range (mg) Typical |
|---|---|---|---|---|---|---|---|
| Ambroxol | COPD | GI | A | 24 | 0.08 | 0.24 | 120 |
| Acetylcysteine | COPD | GI | A | 24 | 0.5 | 1.5 | 840 |
| Erythromycin | Gastroparesis | GI | A | 24 | 50 | 500 | 250 |
| Erythromycin | Bacterial infection control in COPD | GI | A | 24 | 500 | 1500 | 1000 |
| Clarithromycin | Bacterial infection control in COPD | GI | A | 24 | 300 | 900 | 500 |
| Hexoprenaline sulfate | Asthma | Buccal | F | 24 | 0.5 | 2.5 | 1.2 |
| Pirbuterol | Asthma | Buccal | F | 24 | 0.5 | 2.5 | 1.2 |
| Fenoterol | Asthma | Buccal | F | 24 | 2 | 10 | 4.8 |
| Terbutaline | Asthma | Buccal | F | 24 | 1.6 | 8 | 4 |
| Metaproterenol | Asthma | Buccal | F | 24 | 2 | 10 | 4.8 |
| Trimebutine | IBS | GI | A | 24 | 200 | 1000 | 630 |
| Mebeverine | IBS | GI | A | 24 | 100 | 500 | 300 |
| Dicycloverine | IBS | GI | A | 24 | 40 | 200 | 80 |
| Flavoxate | Overactive bladder; urinary urge incontinence | GI | A | 24 | 200 | 1000 | 720 |
| Oxybutinin | | GI | B, C | 24 | 20 | 100 | 14.4 |
| Tolterodine tartarate | | GI | F | 24 | 5 | 25 | 3.6 |
| Darifenacin | | GI | C | 24 | 10 | 50 | 7.2 |
| Curcumin | Cancer, e.g. colon, breast, ovarian | GI | A | 24 | 2000 | 5000 | 4000 |
| Curcumin analogs EF24, EF31, UBS109 or FLLL12 | Cancer, e.g. colon, breast, ovarian | GI | A | 24 | 2000 | 5000 | 4000 |

TABLE B

| Drug | Dose Rate (mg/hr) Low | Dose Rate (mg/hr) High | Dose Rate (mg/hr) Typical | Exemplary Concentrations (mg/mL) Low | Exemplary Concentrations (mg/mL) Middle | Exemplary Concentrations (mg/mL) High |
|---|---|---|---|---|---|---|
| Baclofen | 1.875 | 6.25 | 3.125 | 20 | 85 | 150 |
| Tizanidine | 0.75 | 2.25 | 1.125 | 10 | 30 | 50 |
| Dantrolene | 1.563 | 25 | 6.25 | 600 | 725 | 850 |
| DroxiDOPA | 18.75 | 112.5 | 62.5 | 600 | 725 | 850 |
| Midodrine | 1.563 | 2.188 | 1.875 | 20 | 85 | 150 |
| Penicillamine | 15.625 | 125 | 31.25 | 600 | 725 | 850 |
| Penicillamine | 83.333 | 166.667 | 125 | 600 | 725 | 850 |
| Penicillamine | 10.417 | 31.25 | 20.833 | 600 | 725 | 850 |
| Zinc acetate | 4.167 | 8.333 | 6.25 | 100 | 300 | 500 |
| Zinc compounds water or stomach acid soluble, dose representing the $Zn^{2+}$ content only | 1.25 | 3.333 | 2.083 | 30 | 90 | 150 |
| Magnesium compounds, water or stomach acid soluble, dose representing the $Mg^{2+}$ content only | 20.833 | 208.333 | 125 | 200 | 400 | 600 |
| L-DOPA | 18.75 | 187.5 | 75 | 600 | 725 | 850 |
| Pyridostigmine | 3.75 | 93.75 | 37.5 | 600 | 725 | 850 |
| Neostigmine | 3.125 | 4.375 | 3.75 | 20 | 85 | 150 |
| Miglustat | 8.333 | 16.667 | 12.5 | 600 | 725 | 850 |
| Cromoglicic acid (cromolyn) | 1.667 | 41.667 | 33.333 | 600 | 725 | 850 |
| Metoclopramide | 0 | 1.667 | 1.25 | 20 | 85 | 150 |
| Trientine | 75 | 150 | 112.5 | 600 | 725 | 850 |
| Temozolomide | 12.5 | 16.667 | 14.583 | 600 | 725 | 850 |
| Captopril | 2.5 | 3.75 | 3.125 | 20 | 85 | 150 |
| Acarbose | 10.417 | 14.583 | 12.5 | 600 | 725 | 850 |
| Iloprost | 0.001 | 0.006 | 0.003 | 0.1 | 0.3 | 0.5 |
| Beraprost | 0.013 | 0.031 | 0.023 | 0.5 | 1.75 | 3 |
| Treprostinil | 0.25 | 1.25 | 0.75 | 20 | 60 | 100 |
| Ciclesonide | 0.006 | 0.031 | 0.015 | 0.4 | 1.2 | 2 |
| Flunisolide | 0.031 | 0.156 | 0.075 | 2 | 6 | 10 |
| Budesonide | 0.038 | 0.188 | 0.094 | 3 | 9 | 15 |
| Beclomethasone | 0.038 | 0.188 | 0.094 | 3 | 9 | 15 |
| Bosentan | 6.25 | 31.25 | 15.625 | 500 | 675 | 850 |
| Mometasone | 0.013 | 0.063 | 0.03 | 0.8 | 2.4 | 4 |

TABLE B-continued

| Drug | Dose Rate (mg/hr) | | | Exemplary Concentrations (mg/mL) | | |
|---|---|---|---|---|---|---|
| | Low | High | Typical | Low | Middle | High |
| Vilanterol | 0.004 | 0.021 | 0.01 | 0.5 | 1.5 | 2.5 |
| Bitolterol | 0.083 | 0.417 | 0.2 | 10 | 30 | 50 |
| Levosalbutamol sulfate | 0.021 | 0.208 | 0.1 | 2.5 | 13.75 | 25 |
| Salbutamol | 0.021 | 0.208 | 0.1 | 2.5 | 13.75 | 25 |
| Salmeterol | 0.002 | 0.01 | 0.004 | 0.1 | 1.3 | 2.5 |
| Glycopyrronium bromide | 0.001 | 0.004 | 0.002 | 0.1 | 0.3 | 0.5 |
| Ipatropium bromide | 0.013 | 0.063 | 0.03 | 1 | 3 | 5 |
| Aclidinium bromide | 0.013 | 0.063 | 0.03 | 1 | 3 | 5 |
| Carbocisteine | 0.042 | 0.125 | 62.5 | 600 | 725 | 850 |
| Erdosteine | 0.013 | 0.042 | 25 | 600 | 725 | 850 |
| Ambroxol | 0.003 | 0.01 | 5 | 500 | 650 | 800 |
| Acetylcysteine | 0.021 | 0.063 | 35 | 600 | 725 | 850 |
| Erythromycin | 2.083 | 20.833 | 10.417 | 400 | 600 | 800 |
| Erythromycin | 20.833 | 62.5 | 41.667 | 700 | 775 | 850 |
| Clarithromycin | 12.5 | 37.5 | 20.833 | 600 | 700 | 800 |
| Hexoprenaline sulfate | 0.021 | 0.104 | 0.05 | 2 | 6 | 10 |
| Pirbuterol | 0.021 | 0.104 | 0.05 | 2 | 6 | 10 |
| Fenoterol | 0.083 | 0.417 | 0.2 | 8 | 24 | 40 |
| Terbutaline | 0.067 | 0.333 | 0.167 | 4 | 12 | 20 |
| Metaproterenol | 0.083 | 0.417 | 0.2 | 8 | 24 | 40 |
| Trimebutine | 8.333 | 41.667 | 26.25 | 600 | 725 | 850 |
| Mebeverine | 4.167 | 20.833 | 12.5 | 600 | 725 | 850 |
| Dicycloverine | 1.667 | 8.333 | 3.333 | 500 | 650 | 800 |
| Flavoxate | 8.333 | 41.667 | 30 | 600 | 725 | 850 |
| Oxybutinin | 0.833 | 4.167 | 0.6 | 40 | 95 | 150 |
| Tolterodine tartarate | 0.208 | 1.042 | 0.15 | 10 | 20 | 30 |
| Darifenacin | 0.417 | 2.083 | 0.3 | 20 | 35 | 50 |
| Curcumin | 83.333 | 208.333 | 166.667 | 600 | 725 | 850 |
| Curcumin analogs EF24, EF31, UBS109 or FLLL12 | 83.333 | 208.333 | 166.667 | 600 | 725 | 850 |

TABLE C

| Drug | Exemplary Delivery Rates (µL/hr) | | | Exemplary Daily Volume (mL) | |
|---|---|---|---|---|---|
| | Low | Middle | High | Low | High |
| Baclofen | 12.5 | 36.8 | 312.5 | 0.3 | 0.7 |
| Tizanidine | 15 | 37.5 | 225 | 0.4 | 0.7 |
| Dantrolene | 1.8 | 8.6 | 41.7 | 0.04 | 0.7 |
| DroxiDOPA | 22.1 | 86.2 | 187.5 | 0.3 | 2.5 |
| Midodrine | 10.4 | 22.1 | 109.4 | 0.2 | 0.7 |
| Penicillamine | 18.4 | 43.1 | 208.3 | 0.3 | 3 |
| Penicillamine | 98 | 172.4 | 277.8 | 2.5 | 4 |
| Penicillamine | 12.3 | 28.7 | 52.1 | 0.3 | 0.9 |
| Zinc acetate | 8.3 | 20.8 | 83.3 | 0.2 | 0.8 |
| Zinc compounds water or stomach acid soluble, dose representing the $Zn^{2+}$ content only | 8.3 | 23.1 | 111.1 | 0.2 | 0.8 |
| Magnesium compounds, water or stomach acid soluble, dose representing the $Mg^{2+}$ content only | 34.7 | 312.5 | 1,041.70 | 1 | 8 |
| L-DOPA | 22.1 | 103.4 | 312.5 | 0.4 | 4 |
| Pyridostigmine | 4.4 | 51.7 | 156.3 | 0.5 | 2 |
| Neostigmine | 20.8 | 44.1 | 218.8 | 0.3 | 0.5 |
| Miglustat | 9.8 | 17.2 | 27.8 | 0.25 | 0.8 |
| Cromoglicic acid (cromolyn) | 2 | 46 | 69.4 | 0.5 | 1.5 |
| Metoclopramide | 0 | 14.7 | 83.3 | 0.3 | 0.7 |
| Trientine | 88.2 | 155.2 | 250 | 1.5 | 3 |
| Temozolomide | 14.7 | 20.1 | 27.8 | 0.4 | 0.6 |
| Captopril | 16.7 | 36.8 | 187.5 | 0.3 | 0.7 |
| Acarbose | 12.3 | 17.2 | 24.3 | 0.3 | 0.5 |
| Iloprost | 2.5 | 10 | 62.5 | 0.04 | 0.2 |
| Beraprost | 4.2 | 12.9 | 62.5 | 0.07 | 0.7 |
| Treprostinil | 2.5 | 12.5 | 62.5 | 0.1 | 0.5 |
| Ciclesonide | 3.1 | 12.5 | 78.1 | 0.1 | 0.5 |
| Flunisolide | 3.1 | 12.5 | 78.1 | 0.1 | 0.5 |
| Budesonide | 2.5 | 10.4 | 62.5 | 0.1 | 0.5 |
| Beclomethasone | 2.5 | 10.4 | 62.5 | 0.1 | 0.5 |
| Bosentan | 7.4 | 23.1 | 62.5 | 0.2 | 0.7 |
| Mometasone | 3.1 | 12.5 | 78.1 | 0.1 | 0.5 |
| Vilanterol | 1.7 | 6.7 | 41.7 | 0.1 | 0.5 |
| Bitolterol | 1.7 | 6.7 | 41.7 | 0.1 | 0.5 |
| Levosalbutamol | 0.8 | 7.3 | 83.3 | 0.1 | 0.5 |
| Salbutamol | 0.8 | 7.3 | 83.3 | 0.1 | 0.5 |
| Salmeterol | 0.8 | 3.2 | 104.2 | 0.1 | 0.5 |
| Glycopyrronium bromide | 1.7 | 6.7 | 41.7 | 0.1 | 0.5 |
| Ipatropium bromide | 2.5 | 10 | 62.5 | 0.1 | 0.5 |
| Aclidinium bromide | 2.5 | 10 | 62.5 | 0.1 | 0.5 |
| Carbocisteine | 0 | 86.2 | 0.2 | 1 | 3 |
| Erdosteine | 0 | 34.5 | 0.1 | 0.6 | 1.5 |
| Ambroxol | 0 | 7.7 | 0 | 0.1 | 0.3 |
| Acetylcysteine | 0 | 48.3 | 0.1 | 0.5 | 1.5 |
| Erythromycin | 2.6 | 17.4 | 52.1 | 0.1 | 0.8 |
| Erythromycin | 24.5 | 53.8 | 89.3 | 0.6 | 2 |
| Clarithromycin | 15.6 | 29.8 | 62.5 | 0.4 | 1 |
| Hexoprenaline sulfate | 2.1 | 8.3 | 52.1 | 0.1 | 0.5 |
| Pirbuterol | 2.1 | 8.3 | 52.1 | 0.1 | 0.5 |
| Fenoterol | 2.1 | 8.3 | 52.1 | 0.1 | 0.5 |
| Terbutaline | 3.3 | 13.9 | 83.3 | 0.1 | 0.5 |
| Metaproterenol | 2.1 | 8.3 | 52.1 | 0.1 | 0.5 |

TABLE C-continued

| Drug | Exemplary Delivery Rates (µL/hr) | | | Exemplary Daily Volume (mL) | |
|---|---|---|---|---|---|
| | Low | Middle | High | Low | High |
| Trimebutine | 9.8 | 36.2 | 69.4 | 0.3 | 1 |
| Mebeverine | 4.9 | 17.2 | 34.7 | 0.2 | 0.8 |
| Dicycloverine | 2.1 | 5.1 | 16.7 | 0.08 | 0.3 |
| Flavoxate | 9.8 | 41.4 | 69.4 | 0.6 | 1.2 |
| Oxybutinin | 5.6 | 6.3 | 104.2 | 0.2 | 0.4 |
| Tolterodine tartarate | 6.9 | 7.5 | 104.2 | 0.2 | 0.4 |
| Darifenacin | 8.3 | 8.6 | 104.2 | 0.2 | 0.4 |
| Curcumin | 98 | 229.9 | 347.2 | 3 | 7 |
| Curcumin analogs EF24, EF31, UBS109 or FLLL12 | 98 | 229.9 | 347.2 | 3 | 7 |

Abbreviations for Tables A-C:

PH: pulmonary hypertension, including pulmonary arterial hypertension

IBS: irritable bowel syndrome

COPD: chronic occlusive pulmonary disease

The drugs and methods of the invention may be used for treating dental and maxillofacial conditions, such as xerostomia, dental caries, local infections (e.g., fluconazole, diflucan, nystatin, or clotrimazole for thrush) in the mouth or throat, and local pain in the mouth or throat (e.g., lidocaine).

Dry mouth (xerostomia) and hyposalivation are more prevalent in older patients and are a common side effect of medications, including medications for the treatment of PD. Patients with PD also commonly experience difficulty swallowing (dysphagia), which often results in drooling (sialorrhea). Drugs for the treatment of xerostomia, hyposalivation, dysphagia and/or sialorrhea may be delivered using the devices and methods of the invention. Examples of drugs for xerostomia and hyposalivation are saliva stimulants such as organic acids (e.g., citric acid, ascorbic acid, malic acid) or their acidic salts and parasympathomimetic drugs (e.g., choline esters such as pilocarpine hydrochloride, and cholinesterase inhibitors). Examples of drugs for dysphagia are Scopolamine, Tropicamide, Glyccopyrolate, and Botulinum Toxin. Examples of drugs for excess salivation are anticholinergics such as glycopyrrolate. In a preferred embodiment, drugs for the treatment of xerostomia, hyposalivation, and/or dysphagia are co-administered with the LD or CD, using the drug delivery devices and methods of the invention. In another preferred embodiment, intra-oral administration of an anti-Parkinson's medication itself stimulates increased salivation and/or more frequent or improved swallowing.

Gastroparesis, or delayed gastric emptying, is common in people with PD, especially in patients with scores of 4 and 5 on the Hoehn and Yahr scale. Drugs for the treatment of gastroparesis may be delivered using the devices and methods of the invention. In one embodiment, drugs for the treatment of gastroparesis are co-administered with the LD or CD, using the drug delivery devices and methods of the invention. In another embodiment, drugs for the treatment of gastroparesis are administered using other methods of drug delivery known in the art (i.e., they are not administered via continuous or frequent intra-oral delivery) while LD or CD are infused intra-orally. Examples of drugs for the treatment of gastroparesis are Metoclopramide, Cisapride, Erythromycin, Domperidone, Sildenafil Citrate, Mirtazapine, Nizatidine, Acotiamide, Ghrelin, Levosulpiride, Tegaserod, Buspirone, Clonidine, Relamorelin, Serotonin 5-HT4 agonists and dopamine D2 or D3 antagonists.

Methylation of LD, whereby 3-methoxy-levodopa (3-OMD) is produced, is one of the major metabolic paths of LD. It increases the amount of LD required by Parkinson's disease patients and because the conversion shortens the half-life of plasma LD, it also increases the frequency at which LD or LD/CD or CD need to be administered in order to manage the symptoms of Parkinson's disease. The conversion of LD to 3-OMD is catalyzed by the enzyme catechol-O-methyl transferase, COMT. Administration of a COMT inhibitor can reduce the required dosage of LD or LD/CD, or in earlier stages of PD, even provide for managing the disease without LD or LD/CD. The two most frequently used COMT inhibitors, entacapone and tolcapone are, however, short-lived.

Entacapone does not cross the blood-brain barrier and can be less toxic than Tolcapone, which crosses the barrier. The plasma half-life of Entacapone is, however, merely 0.4-0.7 hours, making it difficult to maintain a sufficient plasma level of the drug without administering large and frequent doses of the drug. In clinical practice, one 200 mg tablet is often administered with each LD/CD or LD/Benserazide dose. The maximum recommended dose is 200 mg ten times daily, i.e., 2,000 mg. Continuous oral administration of Entacapone could reduce the dosage and/or frequency of administration of the drug and its side effects. The reduced dosage could alleviate side effects such as dyskinesia and/or gastrointestinal problems, nausea, abdominal pain or diarrhea.

Entacapone could be continuously orally administered in a daily dose of less than 1000 mg per 16 hours while the patient is awake (such as less than 500 mg per 16 awake hours), for example as an aqueous suspension including small particles, e.g., less than 100 µm average diameter, such as less than 30 µm, 10 µm, 3 µm or 1 µm particles of Entacapone. Alternatively, it could be administered as a suspension in a non-aqueous solution, such an edible oil, cocoa-butter, propylene glycol, or glycerol.

Tolcapone is a reversible COMT inhibitor of 2-3 hour half-life. It exerts its COMT inhibitory effects in the central nervous system as well as in the periphery. Its use is limited by its hepatotoxicity. The typical dose of Tolcapone in PD management is 100-200 mg three times daily. Tolcapone may also be effective in the treatment of Hallucinogen Persisting Perception Disorder, decreasing visual symptoms. Continuous oral administration of Tolcapone could reduce its dosage and/or frequency of administration and its hepatotoxicity. The reduced dosage could alleviate its hepatotoxicity. Its daily dose could be less than 500 mg per 16 awake hours, such as less than 300 mg per 16 awake hours. It could be continuously orally administered, for example, as a suspension of the invention including small particles, e.g., less than 100 µm average diameter, such as less than 30 µm, 10 µm, 3 µm or 1 µm particles of the drug.

Because administration according to this invention is typically into the mouth, it is preferred that the drugs selected for administration are those whose taste is neutral or pleasant, as perceived by a majority of patients. Taste masking or modifying excipients may be added to the formulations of drugs whose taste is unpleasant, as perceived by a majority of patients.

Other drugs that may usefully be delivered in accordance with the invention include methylphenidate, prostaglandins, prostacyclin, treprostinil, beraprost, nimodipine, and testosterone.

Examples of drugs that are often prescribed to be dosed four times per day include:

Amoxicillin—infection
Cephalexin (Keflex)—infection
Chlorpromazine (Thorazine)—neuroleptic for migraine
Diazepam (Valium)—anxiety and sleep
Diclofenac (Voltaren)—arthritis
Diltiazem—calcium channel blocker
Erythromycin—infection
Holperiodol (Haldol)—neuroleptic for migraine
Impramine—psychotropic
Ipratropium (Atrovent)—Anticholinergic
Metoclopramide (Reglan)—gastroesophageal reflux, migraine
Niledpine—calcium channel blocker
Olanzapine (Zyprexa)—neuroleptic for migraine
Prochlorperazine (Compazine)—neuroleptic for migraine
Promethazine (phenergan)—neuroleptic for migraine
Salbutamolasthma
Tetracycline—infection
Theophylline (Theolair)—COPD, asthma
Trazodone—psychotropic Drugs delivered as solids may be formulated with excipients to increase disintegration or dispersion.

Many types of drugs may be delivered in accordance with the invention. Drugs which may in principle be used for treatment according to the invention are any known drugs, wherein the drugs may be present in the form according to the invention as such, or in the form of the active ingredient, optionally in the form of a pharmaceutically acceptable salt of the active ingredient. Drugs which may be delivered in accordance with the invention include, without limitation, analgesics and antiinflammatory agents (e.g., aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac), antihelmintics (e.g., albendazole, bephenium hydroxynaphthoate, cambendazole, dichlorophen, ivermectin, mebendazole, oxamniquine, oxfendazole, oxantel embonate, praziquantel, pyrantel embonate, thiabendazole), anti-arrhythmic agents (e.g., amiodarone HCl, disopyramide, flecainide acetate, quinidine sulphate, antibacterial agents (e.g., benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim), anticoagulants (e.g., dicoumarol, dipyridamole, nicoumalone, phenindione), antidepressants (e.g., amoxapine, maprotiline HCl, mianserin HCl, nortriptyline HCl, trazodone HCl, trimipramine maleate), antidiabetics (e.g., acetohexamide, chlorpropamide, glibenclamide, gliclazide, glipizide, tolazamide, tolbutamide), anti-epileptics (e.g., beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid, topiramate, lamotrigine, gabapentin, levetiracetam, pregabalin), antifungal agents (e.g., amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid), antigout agents (e.g., allopurinol, probenecid, sulphin-pyrazone), antihypertensive agents (e.g., amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCl, reserpine, terazosin HCl), antimalarials (e.g., amodiaquine, chloroquine, chlorproguanil HCl, halofantrine HCl, mefloquine HCl, proguanil HCl, pyrimethamine, quinine sulphate), anti-migraine agents (e.g., dihydroergotamine mesylate, ergotamine tartrate, methysergide maleate, pizotifen maleate, sumatriptan succinate), anti-muscarinic agents (e.g., atropine, benzhexol HCl, biperiden, ethopropazine HCl, hyoscyamine, mepenzolate bromide, oxyphencylcimine HCl, tropicamide), anti-neoplastic agents and immunosuppressants (e.g., aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone), anti-protazoal agents (e.g., benznidazole, clioquinol, decoquinate, diiodohydroxyquinoline, diloxanide furoate, dinitolmide, furzolidone, metronidazole, nimorazole, nitrofurazone, ornidazole, tinidazole), anti-thyroid agents (e.g., carbimazole, propylthiouracil), anxiolytic, sedatives, hypnotics and neuroleptics (e.g., alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone), β-Blockers (e.g., acebutolol, alprenolol, atenolol, labetalol, metoprolol, nadolol, oxprenolol, pindolol, propranolol), cardiac inotropic agents (e.g., amrinone, digitoxin, digoxin, enoximone, lanatoside C, medigoxin), corticosteroids (e.g., beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone), diuretics: acetazolamide, amiloride, bendrofluazide, bumetanide, chlorothiazide, chlorthalidone, ethacrynic acid, frusemide, metolazone, spironolactone, triamterene), anti-parkinsonian agents (e.g., bromocriptine mesylate, lysuride maleate), gastrointestinal agents (e.g., bisacodyl, cimetidine, cisapride, diphenoxylate HCl, domperidone, famotidine, loperamide, mesalazine, nizatidine, omeprazole, ondansetron HCl, ranitidine HCl, sulphasalazine), histamine H,-receptor antagonists (e.g., acrivastine, astemizole, cinnarizine, cyclizine, cyproheptadine HCl, dimenhydrinate, flunarizine HCl, loratadine, meclozine HCl, oxatomide, terfenadine), lipid regulating agents (e.g., bezafibrate, clofibrate, fenofibrate, gemfibrozil, probucol), nitrates and other anti-anginal agents (e.g., amyl nitrate, glyceryl trinitrate, isosorbide dinitrate, isosorbide mononitrate, pentaerythritol tetranitrate), opioid analgesics (e.g., codeine, dextropropyoxyphene, diamorphine, dihydrocodeine, meptazinol, methadone, morphine, nalbuphine, pentazocine), sex hormones (e.g., clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone), and stimulants (e.g., amphetamine, dexamphetamine, dexfenfluramine, fenfluramine, mazindol).

The above-stated compounds are predominantly stated by their international nonproprietary name (INN) and are known to the person skilled in the art. Further details may be found, for example, by referring to International Nonproprietary Names (INN) for Pharmaceutical Substances, World Health Organization (WHO).

Gastroparesis, delayed or erratic gastric emptying, and other abnormalities or diseases of the stomach, intestine, pylorus, jejunum, duodenum impact the transport of food and medication from the stomach to the duodenum and through the small and large intestines. Such conditions of the GI tract are commonly caused by or associated with various diseases and conditions, including Parkinson's disease, diabetes, autonomic neuropathy, and cancer treatments. Reduced, delayed, or erratic transport of medication from the stomach to the duodenum and through the small and large intestines decreases the benefits or effectiveness of many drugs, including levodopa. It is for this reason that the Duopa™ (also known as Duodopa™) LD/CD delivery system infuses a LD/CD suspension into the jejunum or duodenum, even though intrajejunal delivery requires surgical implantation of a PEG tube and suffers from a high rate of PEG tube related complications. The inventors discovered that the oral intake of an aqueous solution of L-DOPA and carbidopa at frequency of about 6-12 times/hour also stabilizes the plasma concentration of L-DOPA and reduces by about 43% the OFF time of PD patients. Without limiting the scope of this invention by a theory or model, we have observed that the reported gastric delay of drugs does not necessarily apply when the drugs are continuously orally infused and are dissolved. Thus, it can be advantageous to infuse into the mouths of patients a suspension or paste including solid drug particles at a rate that equals or is slower than the rate of dissolution of the solid drug particles in body fluids secreted in the mouth, such that the drug passing through the esophagus to the stomach is already substantially dissolved, such that the remaining solid drug particles are substantially dissolved in fluid secreted in the stomach, and/or such that the still remaining drug particles are substantially dissolved in fluid secreted in the duodenum, then, if solid drug particles still remain, these are substantially dissolved in fluids secreted in the jejunum, then if still present, substantially dissolved in fluids secreted in the ileum, and eventually if still present, substantially dissolved in fluids secreted in the colon. The secreted body fluid in which the solid drug may dissolve can be, for example, saliva secreted in the mouth (e.g., by the submandibular and parotid glands) mostly in the awake hours. In healthy persons the rate of secretion can be between about 50 mL/hour and about 100 mL/hour. Considering that the solubility of LD can be about 50 mg/mL and considering that even if a patient would require as much as 200 mg LD per hour, as little as about 4 mL/hour of saliva could dissolve the orally delivered solid LD. The drug could not only be dissolved, but its solution might be diluted before reaching the stomach even in patients (e.g., patients with PD or xerostomia) secreting less saliva than healthy people. For rapid dissolution in saliva it could be advantageous to disperse the drug particles (e.g., by administering their surfactant-including suspension) where the size of the drug particles could be small (e.g., typically less than about 100 µm in average diameter, such as less than 50 µm in average diameter, such as less than 20 µm in average diameter, such as less than 10 µm in average diameter).

Other drugs, such as baclofen or pyridostigmine, that are administered in lesser daily amounts than LD could be adsorbed on small particles of a solid excipient, such as an amino acid like tyrosine. For continuous oral delivery, the paste of the drug-containing excipient could be extruded into the mouth where the excreted saliva would dissolve the sorbed drug as well as any solid drug particles, if present.

Drug Delivery Devices

The drug delivery devices of the present invention are designed to address the requirements for a device that is inserted into the mouth by the patient or caregiver, and that resides in the mouth while it is administering drug, and that can be removed from the mouth by the patient or caregiver. Preferred drug delivery devices include oral liquid impermeable reservoirs.

The drug delivery devices typically have a total volume of less than about 10 mL, and preferably less than 7.5, 5.0, or 3.0 mL. Preferred volumes for the drug delivery devices are 0.5-3.0 mL, to minimize interference with the patient's mastication, swallowing and speech.

The drug delivery devices of the invention preferably contain bite-resistant structural supports that enable them to withstand a patient's bite with a force of at least 200 Newtons, without rupturing and without infusing a bolus of greater than 5% of the drug contents, when unused reservoirs are newly inserted into the mouth. Bite-resistant structural supports, for example, can include a structural housing that encapsulates the entire drug reservoir, propellant reservoir and pump components, either protecting individual components, the entire device, or both. Structural housings can be constructed of any tough, impact-resistant, material that is compatible with the oral anatomy. Metals such as stainless steel or titanium, composites, optionally fiber reinforced polymers such as poly (methyl methacrylate) and strong polymers such as Kevlar, are examples of tough materials that are compatible with the oral anatomy. Other structural elements can include posts or ribs in the housings that are placed in locations such that compression is not possible due to the stiffness of the housing components being increased. In another example, structural elements, such as ribs and posts, allow some flexure of the housing, but do not allow sufficient flexure to deform the components of the pump. In another example, the pump housing can be made of a material that allows some flexure and there is sufficient volume within the housing such that the drug reservoir and or propellant reservoir, can deform or become displaced when pressure is applied but maintain their structural integrity. In another embodiment, some of the previously described elements can be incorporated into a design, and the entire internal volume of the device can be potted with a tough biocompatible material such as an epoxy or a thermoplastic.

To prevent their being accidentally swallowed or aspirated into the trachea, the drug delivery devices of the invention are either secured in the mouth or are of a shape and size that cannot be swallowed or aspirated into the trachea. They may be secured to any interior surface of the mouth, such as one or more teeth, the roof of the mouth, the gums, the lips or the cheek within the mouth of the patient. In order to obtain a secure and comfortable fit, the devices may be molded to fit on or attach to a surface within the mouth of a patient, such as the teeth or the roof of the mouth, or they may conform to at least one cheek. In some embodiments, the drug delivery devices are secured such that they are positioned on the teeth, on a cheek, between the gums and the cheek, between the gums and the lips, or at the roof of the mouth. Alternatively, the drug delivery device includes a shape and size that cannot be swallowed. Examples are a curved, elongated shape of greater than 4 cm length in its curved form (e.g., greater than 5, 6 or 7 cm) that can be placed between the gums and the cheek and lips; or drug delivery devices positioned adjacent to both cheeks and connected with a bridge, optionally forming fluidic contacts with both the left and the right parts.

Although the housing of the typical drug delivery device of the invention can be a strong material such as a metal or a ceramic, the device may include in some embodiments a rigid plastic, a strong elastomer, a deformable plastic or a plastic that optionally deforms such that it can conform to contours of the mouth of the patient (for example, to contours of the cheek, or of the roof mouth, or the floor of the mouth, or the front gum near a lip, or the teeth). The plastic may optionally be fiber reinforced, i.e., it may be re-inforced, for example, by carbon, metal, glass fibers, or by fibers of a strong polymer, such as a polyimide. The plastic may include, for example, elastomeric butyl rubber, elastomeric silicone or polyurethane. It can be a less deformable, for example substantially oxygen or water impermeable, plastic, such as poly(vinylidene chloride), poly(vinyl chloride), poly(triflurorochloro)ethylene, poly(ethylene terephthalate)), polyether polycarbonate, or high density, high crystallinity polyethylene. Alternatively, the drug delivery device may include a metal, such as stainless steel or alloyed titanium, aluminum or magnesium. In an alternative embodiment, the drug delivery device includes multiple segments connected by flexible connectors, so that the drug delivery device is able to conform to the shape of the surface on which it is mounted.

Figure 1B:
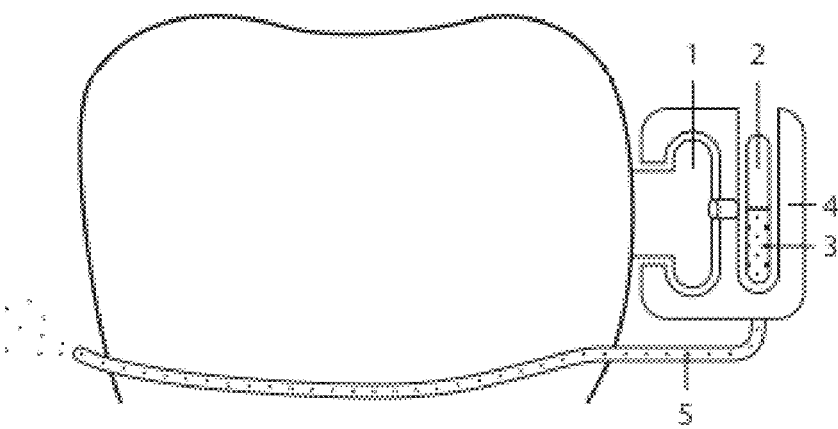
FIG. 1B depicts an embodiment in which a portion 4 of the drug delivery device is reusable, and a removable pump 2 and drug reservoir 3 can be disposable.
Figure 1C:
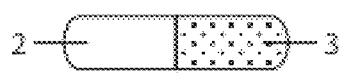
Figure 10:
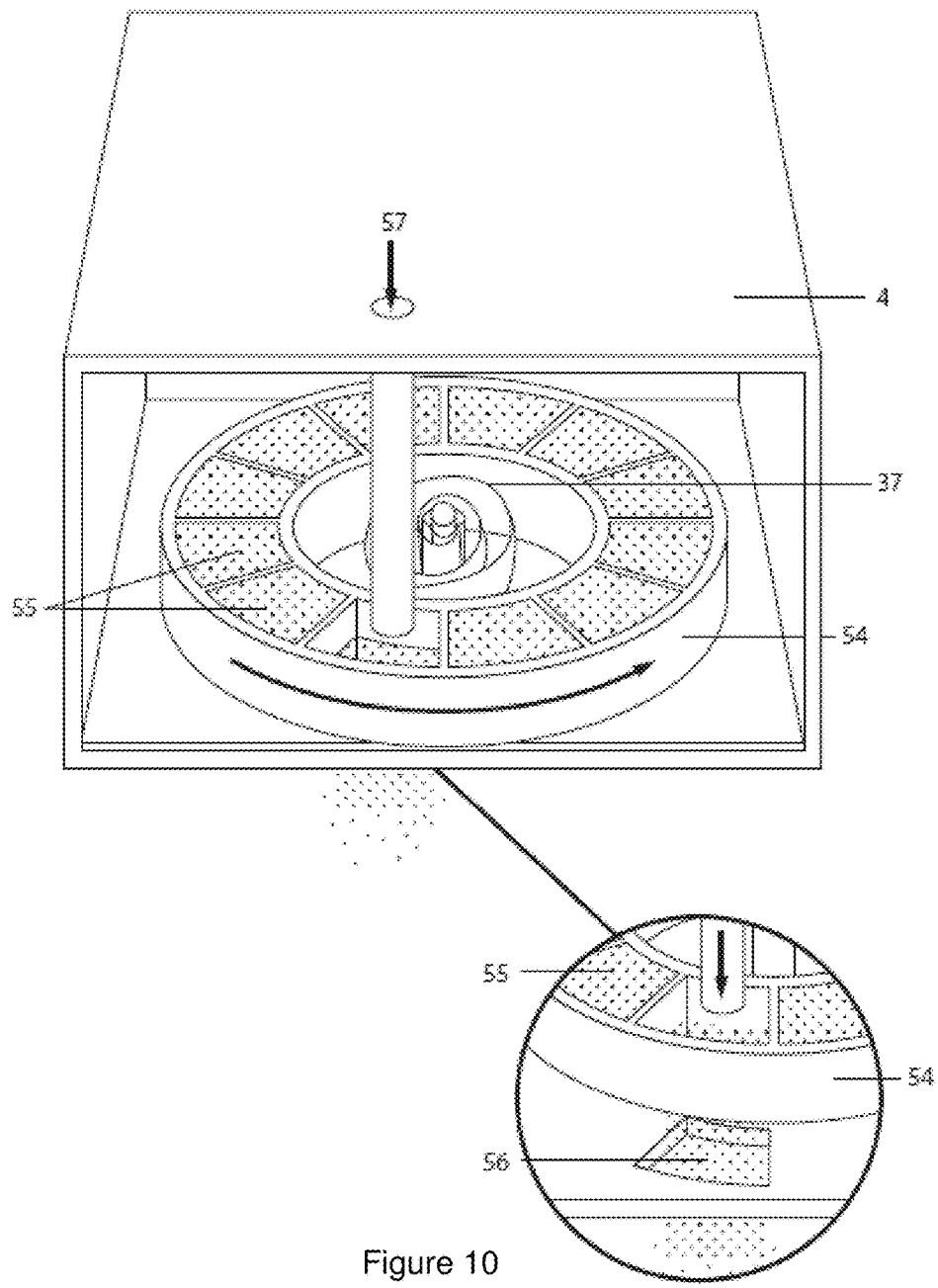
FIG. 10 depicts an embodiment in which a pump 2 and a drug reservoir 3 form a single component.

The drug delivery devices of the invention may be attached to the teeth or other interior surfaces of the mouth by a fastener, as shown in FIGS. 1A and 1B. The fastener 1, the one or more pumps 2, and the one or more drug reservoirs 3 may include a single unit or they may include separate components, with the fastener remaining in the mouth when the one or more pumps or one or more reservoirs are remved. FIG. 1A shows an embodiment where a pump 2, and a drug reservoir 3 include a single removable component that can be attached to the fastener 1. Drug is delivered into the mouth via a tube 5 which may optionaly include a flow restrictor. FIG. 1B shows an embodiment including a reusable housing 4, and a disposable pump 2 and drug reservoir 3. The fastener 1, one or more drug pumps and one or more drug reservoirs may be removably attached to each other using magnets, clips, clasps, clamps, flanges, latches, retaining rings, snap fasteners, screw mounts, or other attachment mechanisms known in the art. In preferred embodiments, the fastener includes a transparent retainer or a partial retainer on one side of the mouth (e.g., attached to 3, 4, or 5 teeth). FIG. 10 depicts an embodiment in which a pump 2 and a drug reservoir 3 form a single component.

Figure 2A:
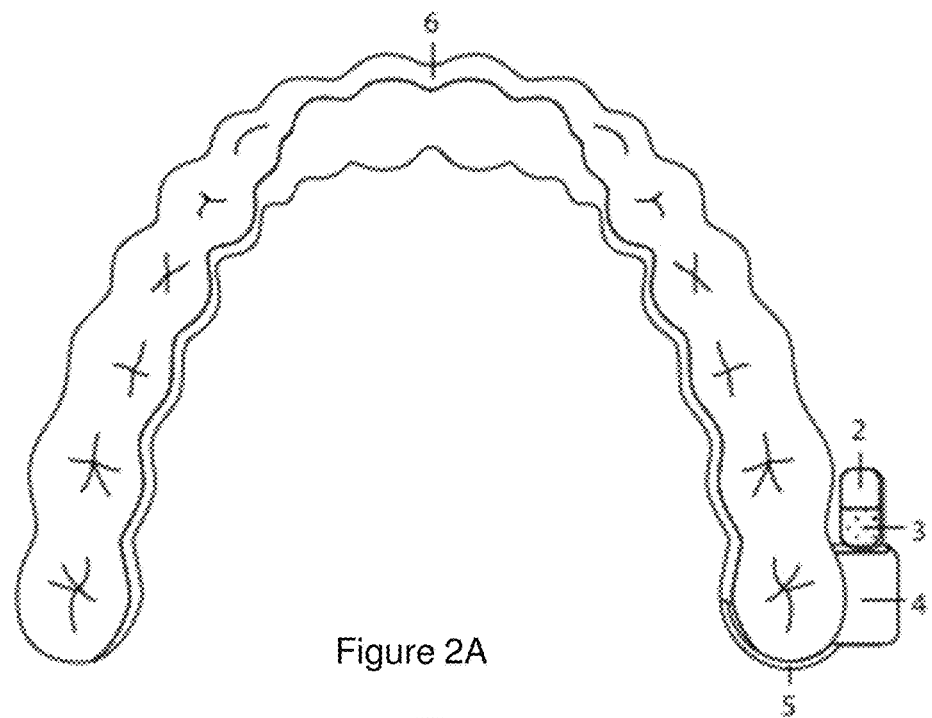
FIG. 2A depicts an embodiment of the drug delivery device in which the pump 2 and/or drug reservoir 3 is fastened to either the upper or lower teeth using a transparent retainer 6. One, two or more pumps and/or one or more drug reservoirs are secured on the buccal side of the transparent retainer 6. One, two, or more drug pumps and/or drug reservoirs may be secured unilaterally, on either the right or left sides, positioned in the buccal vestibule or, alternatively, on the lingual side of the teeth.
Figure 2B:
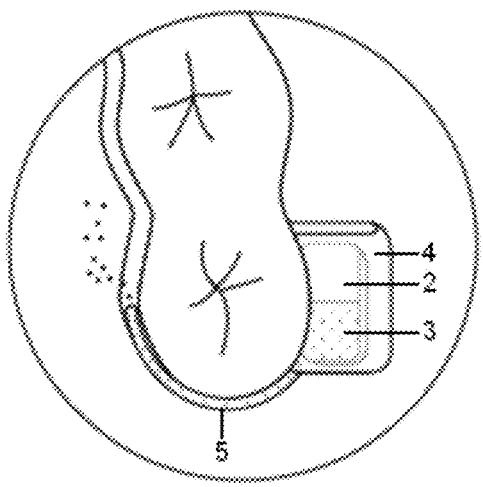
FIG. 2B is a close up showing the pump 2 and drug reservoir 3 attached to the transparent retainer 6 and dispensing drug to the lingual side of the mouth through a tube 5.

An embodiment of the device is shown in FIGS. 2A and 2B, where the pump and/or oral liquid impermeable reservoir is secured to either the upper or lower teeth using a transparent retainer 6. One, two or more pumps and/or one or more drug reservoirs are secured on the buccal side of the transparent retainer. One, two, or more drug pumps 2 and/or drug reservoirs 3 may be secured unilaterally, on either the right or left sides, positioned in the buccal vestibule or, alternatively, on the lingual side of the teeth. The drug pump and reservoir are attached to the transparent retainer via a housing 4. Drug is delivered into the mouth via a tube 5 which may optionaly include a flow restrictor. The tube 5 serves to carry the drug from the buccal to the lingual side of the teeth, where the drug may be more readily swallowed. The tube may be molded into the retainer.

Figure 3:
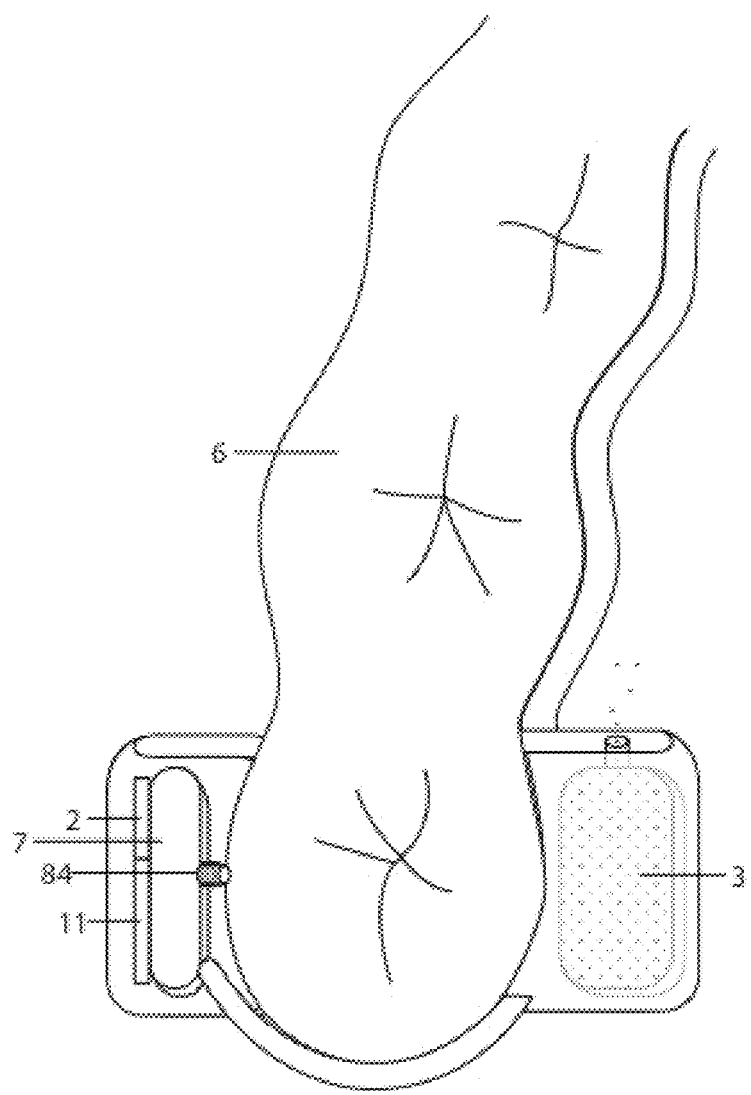
FIG. 3 depicts a drug delivery device in which the pump 2 and drug reservoir 3 are configured to be positioned both on the lingual side of the teeth and in the bucal vestibule. The drug reservoir is fastened on the lingual side of the teeth, while a drug pump and an optional gas pump 11 are positioned on the buccal side of the teeth.
Figure 4A:
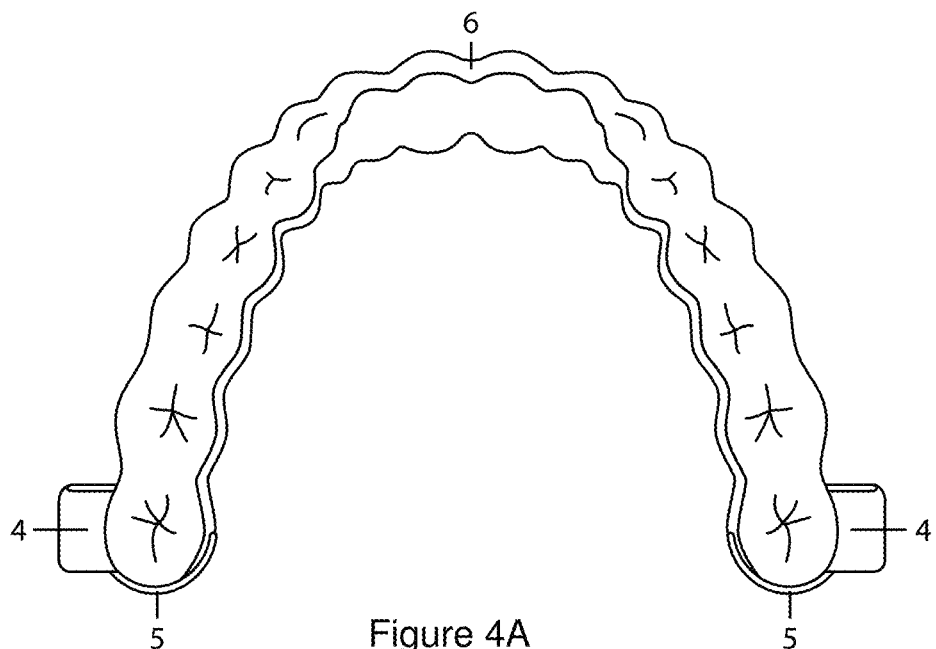
FIG. 4A depicts a fastener in the form of a transparent retainer 6, including two bilateral housings 4 (shown empty) on the buccal side of the teeth into which drug pumps and/or drug reservoirs may be inserted.
Figure 4B:
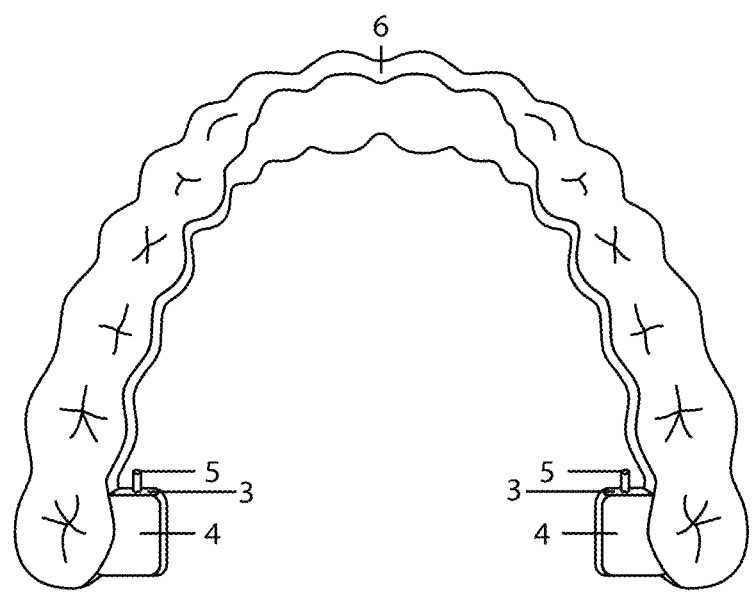
FIG. 4B depicts a fastener in the form of an invisible retainer 6, including two bilateral housings 4 (shown filled) on the lingual side of the teeth into which drug pumps and/or drug reservoirs 3 have been inserted.

In a related embodiment, illustrated in FIG. 3, the pumps 2 and reservoirs 3 can be configured to be positioned both on the lingual side of the teeth and in the buccal vestibule. In this embodiment, the pump 2 is used to fill an expandable polymeric (e.g., elastomeric or non-elastomeric) compartment 7, described in greater detail in FIGS. 11A, 11B, and 11C, which drives the drug from the drug reservoir 3. In another related embodiment, illustrated in FIGS. 4A and 4B, one, two or more pumps and/or oral liquid impermeable reservoirs may be secured bilaterally, on both the right and left sides, positioned in the buccal vestibule or on the lingual side of the teeth, or both buccally and lingually. FIG. 4A depicts a fastener in the form of an invisible retainer 6, including two bilateral housings 4 (shown empty) on the buccal side of the teeth into which drug pumps and/or drug reservoirs may be inserted. FIG. 4B depicts a fastener in the form of an invisible retainer 6, including two bilateral housings 4 (shown filled) on the lingual side of the teeth into which drug pumps and/or drug reservoirs have been inserted.

Optionally, two or more oral liquid impermeable drug reservoirs may be in fluidic contact with each other. Optionally, the transparent retainer 6 may include 2, 3, 4 or more layers of different hardness, to ease insertion and removal of the transparent retainer from the teeth. For example, the transparent retainer 6 may include a dual laminate with a softer, inner, tooth-contacting layer, and a harder, outer layer contacting the cheeks and tongue.

The one or more pumps and/or oral liquid impermeable reservoirs may be removably attached to the transparent retainer using magnets, clips, clasps, clamps, flanges, latches, retaining rings, snap fasteners, screw mounts, or other attachment mechanisms known in the art. In one embodiment, the transparent retainer includes one, two, or more housings into which one, two, or more pumps and/or the oral liquid impermeable reservoir are inserted. The one, two or more housings may be molded or formed to the shape of the one, two or more pumps and/or oral liquid impermeable reservoirs.

For delivery of some drugs, such as LD or CD, it can be desirable to administer the drug-including solid or fluid on the lingual side of the teeth, rather than on the buccal side of the teeth, in order to minimize the residence time of the drug in the mouth, thereby avoiding potential accumulation of the drug in the buccal vestibule and minimizing potentially irritating exposure of the buccal tissue to the drug. In a preferred embodiment, the fastener (e.g., a transparent retainer or a partial retainer) includes one, two, or more fluidic channels to transport the drug-including fluid into the mouth from the one, two or more pumps and/or oral liquid impermeable reservoirs. The fluidic channels can transport the drug-including fluid from one, two, or more oral liquid impermeable reservoirs located on the buccal side of the teeth to the lingual side of the teeth. For example, the fluidic channels can include one, two or more tubes that are molded into the fastener. The fluidic channels can, for example, pass behind the rear molars, above the mandibular arch, so that they do not cross the biting surface of the teeth. The fluidic channels may include an inner diameter of less than 0.25 mm, 0.25-1 mm, 1-2 mm, 2-3 mm, or greater than 3 mm. The fluidic channels may include a fluidic path length in the fastener of less than 1 mm, 1-3 mm, 3-5 mm, 5-10 mm, or greater than 10 mm, such as 1-2 cm, 2-3 cm or 3-4 cm.

The one, two or more pumps and/or one, two, or more oral liquid impermeable drug reservoirs can be in fluid communication with the one, two, or more fluidic channels in the fastener (e.g., a transparent retainer or a partial retainer) via any type of leak-free fluidic connector known in the art, such as leak-free snap fastner or screw-mount. The leak-free fluidic connector preferably includes metal, to improve durability. Optionally, the one, two or more pumps and/or the one, two, or more oral liquid impermeable reservoirs do not deliver drug when they are not mounted on the fastener, while mounting these on the fastener initiates delivery of the drug. Similarly, drug delivery can be temporarily halted when the pumps and/or oral liquid impermeable reservoirs are dismounted from the fastener.

In one embodiment, the one, two or more fluidic channels may include one, two or more flow restrictors. The one, two or more flow restrictors may include metal tubes that are molded into the fastener (e.g., a transparent retainer or a partial retainer). By incorporating flow restrictors into a reusable fastener, the disposable drug delivery device and/or oral liquid impermeable reservoir need not include a flow restrictor that accurately controls the rate of infusion.

In another embodiment, a reusable fastener (e.g., a transparent retainer or a partial retainer) may include a pump and/or power source. With a reusable pump and/or power source incorporated into the fastener, the disposable portion of the drug delivery device and/or the oral liquid impermeable reservoir need not include the pump and/or power source, thereby reducing overall cost. For example, the fastener may include a piezoelectric or battery driven electroosmotic pump, and/or a battery. The battery may optionally be rechargeable.

The fastener or its components, such as the housings, may be manufactured using methods known in the art, such as thermoforming, injection molding, pressure molding, and laminating.

The drug delivery device may be a single unit, or it may have two, three, four, five or more components. The drug delivery device may have one, two, three, four, five or more oral liquid impermeable reservoirs in which the solid or fluid drug formulation is contained. These one or more reservoirs may form a single component, or they may form multiple components.

The drug delivery devices may be reusable, disposable, or they may have one or more reusable components and one or more disposable components. In a preferred embodiment, the fastener is reusable, and may be reused for a period of equal to or greater than 7, 30, 60 or 180 days, or one year or two years. In another preferred embodiment, the one or more oral liquid impermeable reservoirs are single use, disposable components. The pump may be either reusable or disposable. A flow restrictor, if present, may be a single use disposable or may be reused.

The oral liquid impermeable reservoir may be refillable with a solid or fluid drug formulation. In a preferred embodiment, the oral liquid impermeable reservoir is a single use disposable. The oral liquid impermeable reservoir may be filled by the user. In preferred embodiments, the oral liquid impermeable reservoir is prefilled.

The drug delivery device further includes one, two, three, four or more orifices for releasing the drug from the device into the mouth.

Durations of administration from a single drug delivery device or oral liquid impermeable reservoir typically exceed 4, 8, 12, or 16 hours per day, up to and including 24 hours per day. Administration can also take place over multiple days from a single device or oral liquid impermeable reservoir, e.g., administration of a drug for 2 or more days, 4 or more days, or 7 or more days. The devices can be designed such that they can be worn when the patient is awake or asleep.

It is desirable that the patient be able to temporarily remove the drug delivery device from the mouth, for example, to eat meals, brush teeth, or at times when the patient does not want or need the medication (e.g., at night). Consequently, the drug delivery devices and/or some of its components (such as the pump and/or the oral liquid impermeable reservoirs) can be temporarily removable. It is, however, acceptable for some components, such as the fastener, to remain in the mouth if these do not interfere with the patient's activities. For example, a band, a fastener cemented or glued to one or more teeth, a retainer, or a muco-adhesive patch adhered to the oral mucosa, and which holds the pump and/or oral liquid impermeable reservoir in place, may remain in the mouth when the pump and/or the oral liquid impermeable reservoir are removed.

The drug delivery device preferably can have a shape that is comfortable in the mouth. Typically such a shape has rounded edges. Shapes such as obround shapes are typically more comfortable than cylindrical shapes.

It is desirable that the drug delivery device include an indicator of: the quantity remaining of one or more drugs; the infusion time remaining until empty; and/or that one or more of the oral liquid impermeable reservoirs is empty and should be replaced.

The drug delivery devices of the current invention are configured and arranged to administer one or more solid or fluid drug formulations from one or more oral liquid impermeable reservoirs including a total volume of 0.1-10 mL of drugs, e.g., 0.1-1.0, 1.0-2.0, 2.0-3.0, 3.0-4.0, 4.0-5.0, 5.0-6.0, 6.0-7.0, 7.0-8.0, 8.0-9.0, or 9.0-10 mL. They are configured and arranged to administer the one or more solid or fluid drug formulations at a rate in the range of 0.03-1.25 mL/hour, e.g., 0.03-0.10, 0.10-0.20, 0.20-0.30, 0.30-0.40, 0.40-0.50, 0.50-0.60, 0.60-0.70, 0.70-0.80, 0.80-0.90, 0.90-1.0, 1.0-1.1, or 1.1-1.25 mL/hour. In some embodiments, they are configured and arranged to administer the drug, (i.e., the active pharmaceutical ingredient) at an average rate of 0.01-1 mg per hour, 1-10 mg per hour, 10-100 mg per hour, or greater than 100 mg per hour. In other embodiments, the drug product (i.e., the active pharmaceutical ingredient plus excipients) is delivered at an average rate of 0.01-1 mg per hour, 1-10 mg per hour, 10-100 mg per hour or greater than 100 mg per hour.

The one or more drugs may be administered at a constant rate or at a non-constant rate that varies over the course of the administration period. For example, the drug delivery device may be programmed to administer drugs according to a drug delivery profile over the course of the administration period. The drug delivery device may also have an on-demand bolus capability, whereby the patient or caregiver may initiate the delivery of a bolus of drug.

In preferred embodiments, the drug delivery device administers one or more solid or fluid drug formulations via continuous and/or frequent administration, e.g., infusion. In a preferred embodiment, the solid or fluid drug administration rate is held constant or near constant for a period of 4, 8, 12, 16 or 24 hours during the day. For example, the administered volume may vary by less than ±10% or ±20% per hour, or by ±10% or ±20% per 15 minute period, over a period of 4, 8, 12, 16 or 24 hours. In another embodiment, the solid or fluid drug administration rate is held about constant during the awake hours of the day. In another embodiment, the solid or fluid drug formulation administration rate is held about constant during the asleep hours. In another embodiment, the solid or fluid drug formulation administration rate is held about constant during the awake hours of the day, except for the delivery of a bolus at about the time of waking. In one embodiment, the administration rate can be set prior to insertion in the mouth by the patient or by the caregiver. In another embodiment, the administration is semi-continuous and the period between the infusions is less than the biological half-life of the drug $t_{1/2}$; for example it can be less than one half of $t_{1/2}$, less than ⅓rd of $t_{1/2}$, or less than ¼ of $t_{1/2}$, or less than ⅒th of $t_{1/2}$.

For fluid drug formulations, it is desirable to deliver the solutions or suspensions of the invention using drug delivery devices that are small, efficient, inexpensive, and reliable. This can be particularly challenging when these fluids are viscous. It is also desirable to minimize the pressure required to pump the fluid. In preferred drug delivery devices for fluids of greater than 100 cP, for example, 100-1000 cP, 1,000-10,000 cP, 10,000-100,000 cP, 100,000-500,000 cP, 500,000-2,500,000 cP, or greater than 2,500,000 cP, the drug can exit the device through a tube, nozzle, channel, or orifice of less than 4 cm, 3 cm, 2 cm, 1 cm, 0.5 or 0.2 cm length. For example, the fluid may be delivered through an optionally flexible cannula, or it may be delivered through an orifice without utilizing any type of tubing or cannula. To further minimize the pressure required to pump the fluid, the tube, channel or orifice through which the drug exits the device may have an internal diameter of greater than 0.5, 1, 2, 3, 4, or 5 mm, for example, 1 mm-5 mm, 1 mm-3 mm, 2 mm-4 mm, or 3 mm-5 mm. Preferred minimum internal diameters are 0.1-2 mm (0.1-0.7 mm, 0.2-0.5 mm, 0.5-0.75 mm, 0.75-1.0 mm, 1.0-1.5 mm, or 1.5-2.0 mm) and preferred lengths are 0.25-5 cm (such as 1-2.5 cm, 1-5 cm, 0.25-0.5 cm, 0.5-0.75 cm, 0.75-1 cm, 1-2 cm, 2-3 cm, 3-4 cm, or 4-5 cm).

Pumps

The pumps for the drug delivery devices must be suitable for miniature devices carried safely and comfortably in the mouth. Any suitable pump may be used. The pump and the oral liquid impermeable reservoir may be distinct.

Miniature pumps are advantageous for placement in the mouth. For example, the extruded fluid including the drug may occupy more than 33%, 50%, 66%, or 75% of the total volume of the drug delivery device.

Non-electric pumps. Pumps that do not require a battery can be smaller and have fewer moving parts than battery-requiring electrical pumps. One group of nonelectric disposable pumps of the invention is based on the physical principle that mechanical restriction within the flow path can determine the flow rate of a pressurized fluid. The pressure on the fluid may be generated by a variety of mechanisms using nonelectric power, including a stretched elastomer, a compressed elastomer, a compressed spring, a chemical reaction, a propellant, and a cartridge of pressurized gas. The restriction of flow may be provided by an orifice (e.g., in the drug reservoir), by narrow-bore tubing (such as a metal, glass or plastic pipe), or by a channel, or by a capillary, or a flow-controlling nozzle. Optionally, the flow-controlling nozzles, channels or tubes can be made of a plastic such as an engineering plastic, or made of a metal or a ceramic such as a glass. The nozzles, channels or tubes can have an internal diameter less than 1 mm, 0.6 mm, 0.3 mm or 0.1 mm and they can be shorter than 10 cm, 5 cm, 2 cm or 1 cm such as 0.5 cm. Preferred minimum internal diameters are 0.1-2 mm (0.1-0.7 mm, 0.2-0.5 mm, 0.5-0.75 mm, 0.75-1.0 mm, 1.0-1.5 mm, or 1.5-2.0 mm) and preferred lengths are 0.25-5 cm (such as 1-2.5 cm, 1-5 cm, 0.25-0.5 cm, 0.5-0.75 cm, 0.75-1 cm, 1 -2 cm, 2-3 cm, 3-4 cm, or 4-5 cm).

Because different patients may require different doses of drug, it is desirable for the drug delivery devices of the invention to be available as a product line of multiple products, each product having a different drug administration rate. The desired flow rate may be obtained by selecting a flow restrictor of the appropriate inner diameter and length. In one embodiment, the plastic flow restricting nozzle or tubing may be cut to the length providing the desired flow rate. Use of a narrow-bore tubing as a flow restrictor simplifies the manufacturing process for such a product line. During the manufacturing process a narrow-bore tubing with constant inner diameter may be cut into multiple segments of fixed length A, to provide reproducible flow restrictors for products with one flow rate. A different portion of the narrow-bore tubing with constant inner diameter may be cut into multiple segments of fixed length B, to provide reproducible flow restrictors for products with a second flow rate.

In another embodiment, when the reservoir is metallic one or more pinholes in the reservoir wall can include the flow restrictor, i.e., a desired flow rate can be obtained by the number of pinholes and the diameter of the one or more pinholes.

In yet another embodiment, the flow restrictor can include an orifice with an adjustable diameter, similar to the user-adjustable aperture of a camera. Instead each device being able to infuse at only a single infusion rate such a user-adjustable orifice could allow the physician or the patient to set the infusion rate, thereby providing more flexibility and convenience.

The preferred nozzles, channels or tubes can be made of an engineering plastic, can have an internal diameter less than 1 mm, 0.6 mm, 0.3 mm or 0.1 mm and can be shorter than 10 cm, 5 cm, 2 cm or 1 cm such as 0.5 cm. Preferred minimum internal diameters are 0.1-2 mm (0.1-0.7 mm, 0.2-0.5 mm, 0.5-0.75 mm, 0.75-1.0 mm, 1.0-1.5 mm, or 1.5-2.0 mm) and preferred lengths are 0.25-5 cm (such as 1-2.5 cm, 1-5 cm, 0.25-0.5 cm, 0.5-0.75 cm, 0.75-1 cm, 1-2 cm, 2-3 cm, 3-4 cm, or 4-5 cm).

Flow rate can be affected by the pressure gradient across the flow restrictor and by fluid viscosity. A significant source of inaccuracy in existing pump products can be that viscosity is strongly affected by temperature. An important benefit of carrying within the mouth the drug delivery devices of the invention is that the temperature is held nearly constant at about 37° C., thereby minimizing variations in the rheological properties (such as viscosity) and therefore in the infusion rate. The nearly constant about 37° C. is also advantageous in maintaining a stable pumping pressure when a gas, such as from a liquid propellant, is used to drive the pump.

The formulations of the invention are often viscous suspensions. Use of viscous suspensions is often desired to achieve the small volumes, high concentrations, uniform drug dispersion, storage stability, and operational stability desired for the drugs and methods of the invention. Consequently, it is often desired to employ pump mechanisms that can provide the pressures required to pump the viscous fluids.

The pressure generated by elastomeric, spring-driven and gas-driven pumps on fluid is typically in the range of 250 mm Hg to 5,000 mm Hg, depending on flow rate and cannula size, but can be higher. For example, the pressure may be 250-500 mm Hg, 500-750 mm Hg, 750-1,000 mm Hg, 1,000-1250 mm Hg, 1,250-2,500 mm Hg, 2,500-5,000 mm Hg, or greater than 5,000 mm Hg. The pressurizing gas can be a propellant that condenses to a liquid at a pressure greater than 1 bar (such from 1 bar to 2 bar, from 2 bar to 3 bar, from 3 bar to 4 bar, or from 4 bar to 5 bar at about 37° C.), or the pressurizing gas can be chemically generated, for example electrolytically generated, (e.g., by electrolyzing water).

The drug delivery device may be kept in the mouth while the patient is eating and drinking, or may be removed for eating or drinking. Preferably, the introduction into the mouth of food or liquid, including food or liquids that are hot, cold, acidic, basic, oily, or alcoholic, does not have a clinically significant effect on the drug delivery. For example, such conditions may affect the solubility of the drug; the volume of the drug-including fluid in the reservoir; the viscosity of the drug-including fluid in the oral liquid impermeable reservoir; the volume of the gas in the reservoir (if present); the diffusivity of mass-transport limiting membranes (if present); and/or the force exerted by elastomers or springs (if present). Some drug delivery technologies, such as controlled release muco-adhesive drug delivery patches, can deliver large drug boluses when in contact with a hot, cold, acidic, basic, oily, or alcoholic liquid in the mouth. Such boluses may result in undesirable clinical effects, and should be minimized. In one embodiment, the solid or fluid drug delivery devices of the invention deliver a bolus of less than 5%, 4%, 3%, or 2% of the contents of a fresh oral liquid impermeable reservoir when immersed for 5 minutes or for 1 minute in a beaker containing a stirred aqueous 0.14 M saline solution that is hot (e.g., at about 55° C.), cold (e.g., at about 1° C.), acidic (e.g., at about pH 2.5), basic (e.g., at about pH 9), oily (e.g., emulsion of 5% by weight of olive oil in 0.14 M aqueous saline solution), or alcoholic (e.g., a 0.14 M saline solution containing 5% by weight ethanol). For example, a LD delivery device may deliver a bolus of less than 0.5, 0.25, 0.12, or 0.06 millimoles of LD under these conditions.

Battery powered pumps. Other than than powering the pump, the battery can power optional electronic controls and communication capabilities (e.g., radio frequency receivers) for programmed drug delivery and remote control of the drug delivery by a transmitting device. A miniature battery may be used to drive the pump or dispensing mechanism for the delivery of the solid or fluid drug. Any low power pump drive mechanism known in the art may be used, such as syringe, hydraulic, gear, rotary vane, screw, bent axis, axial piston, radial piston, peristaltic, magnetic, piezoelectric, electroosmotic, diaphragm and memory alloy, such as nitinol, based.

An advantage of battery powered pumps for use in the mouth is that it is possible to temporarily stop the drug delivery from the device if the patient wishes to temporarily remove the drug delivery device from the mouth. This can be accomplished, for example, by turning off the electric power to the pump.

One embodiment of a battery powered pump is a miniature diaphragm pump that uses the motion of a piezoelectric crystal to fill a chamber with drug from a reservoir in one motion and to expel the drug from the chamber in the opposite motion. Typically, the frequency of oscillation of the piezoelectric crystal is less than about 20,000 Hz, 5,000 Hz, or 1,000 Hz, so as to avoid the higher frequencies where biological membranes are ultrasonically disrupted or where free radicals are more likely to be generated through a sonochemical process. A significant advantage to the diaphragm pump is that it can be used to very accurately deliver materials of both high and low viscosity, as well as solids such as granules or powders.

Another embodiment of a battery powered pump is a miniature electroosmotic pump as disclosed, for example, in U.S. Patent Publication Nos. 2013/0041353, 2013/0156615, 2013/0153797 and 2013/0153425, in PCT Publication No. WO2011/112723, and in Korean Patent Publication No. KR101305149, each of which is incorporated herein by reference. Typically the volume of the miniature electroosmotic pump, including its battery or batteries, is smaller than the volume of the fluid in the unused oral liquid impermeable reservoir. For example, the volume of the pump can be less than half, less than $1/3^{rd}$, less than $1/4^{th}$, or less than $1/5^{th}$ of the volume of the unused oral liquid impermeable reservoir. When an electroosmotic pump is used with a refillable reservoir, the battery powering the pump can be replaced upon refilling. To provide different patients with different dose rates, oral liquid impermeable reservoirs may be filled with the drug at different concentrations. Alternatively, the flow rate of the electroosmotic pump can be adjusted by controlling the applied voltage or the applied current, or by varying the cross sectional fluid contacting area of the membrane sandwiched between the electrodes. Optionally, the applied voltage or current can be remotely adjusted by incorporating a short range RF receiver in the insert.

Another category of battery powered pumps is that of positive displacement pumps. Two examples of battery powered positive displacement pumps that can be used to deliver the drug are gear pumps and peristaltic pumps. One of the main advantages of the use of a positive displacement pump is that the delivery rate is not affected by changes in ambient pressure. The gear pump, in one embodiment, uses two rotors that are eccentrically mounted and intermeshed with their cycloid gearing. As a result a system of several sealed chambers exists at all times and are moved toward the outlet of the pump, one at a time. An example of a gear pump is the Micro annular gear pump mzr-2521 from HNP Mikrosysteme GmbH. A second type of battery powered positive displacement pump is the peristaltic pump. Peristaltic pumps use a series of rollers to pinch a tube creating a vacuum to draw the material from a reservoir, thereby creating and moving a volume of drug within subsequent roller volumes to deliver the drug toward the outlet of the pump. An example of a battery powered peristaltic pump is the RP-TX series micro peristaltic pump from Takasago Electric, Inc.

Elastomeric infusion pumps. In elastomeric infusion pumps, the pressure on the fluid is generated by the force of a stretched or compressed elastomer. An example of an elastomeric, partially disposable, constant-rate medication infusion pump with flow restrictor is the CeQur PaQ insulin patch pump, described in U.S. Ser. No. 12/374,054 and U.S. Pat. No. 8,547,239, each incorporated herein by reference.

Figure 5A:
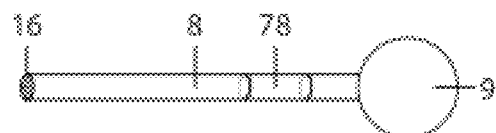
FIGS. 5A and 5B illustrate a drug delivery device including a pressurized, drug-filled polymer such as an elastomer. The elastomer provides pressure that delivers the drug at a constant rate through a narrow internal diameter tubing, with the rate determined by the properties of the elastomer and the inner diameter of the narrow bore tubing.
Figure 5B:
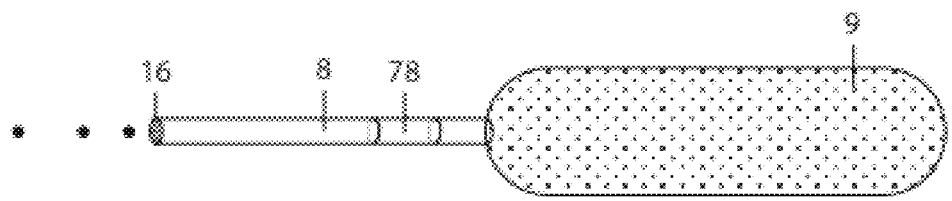

FIGS. 5A and 5B show an embodiment of an elastomeric drug reservoir that can be filled with a drug to pressurize the drug and to pump the fluid at a controlled rate through the use of a narrow-bore tubing 8 that serves as a flow restrictor. FIG. 5A shows the elastomeric reservoir 9 when empty of drug and FIG. 5B shows the elastomeric balloon 9 when pressurized due to expansion of the elastomer by filling with the drug.

Preferably, the elastomeric membrane is protected by an outer protective shell. The outer protective shell can either be a conformable elastomer or a more rigid plastic, which may be molded to a surface of the mouth. The membranes of elastomeric pumps may include both natural and synthetic (e.g., thermoplastic) elastomers (e.g., isoprene rubber, neoprene, latex, silicon, and polyurethanes), and can be made of a single or multiple layers. The type of elastomer and the geometry of the elastomeric balloon 9 determine the pressure generated on the fluid when the balloon is stretched. Multiple-layer elastomeric membranes can generate higher pressures than the single-layer membranes. Higher driving pressures are of benefit for achieving faster flow rates and for pumping viscous fluids.

To minimize the change in flow rate as the fluid is delivered, it is preferred to utilize sufficiently high tension in the elastomeric membrane such that the difference between the starting and ending pressure on the fluid is less than 30%, 20%, or 10% of the starting pressure.

Figure 5C:
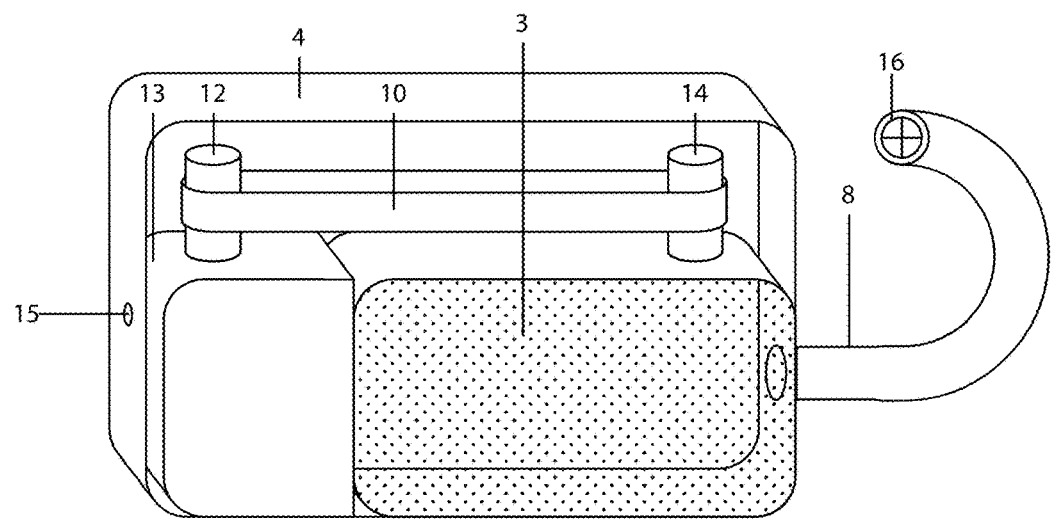
FIGS. 5C and 5D illustrate an elastomeric band-driven pump employing a rubber band 10 to pull a piston 13 to apply pressure to the drug reservoir 3.
Figure 5D:
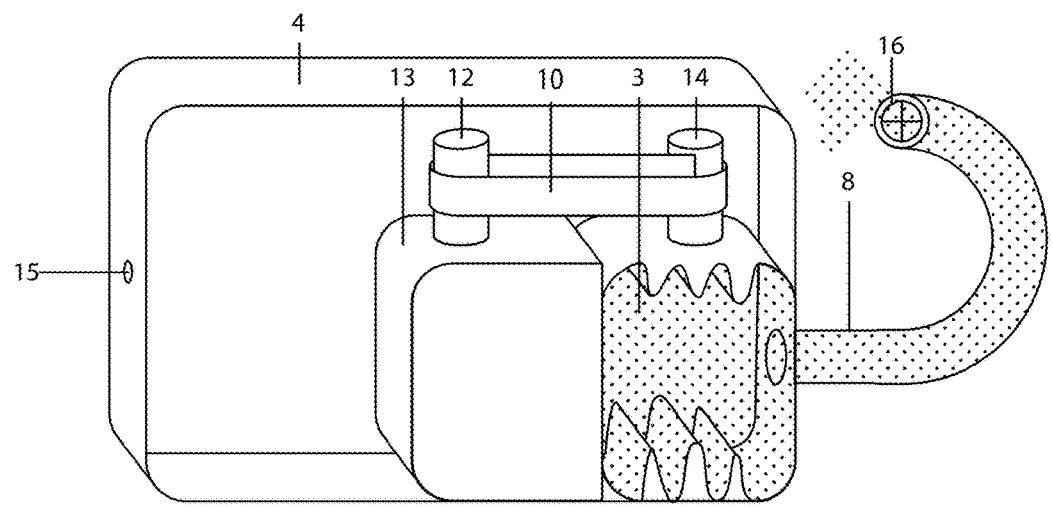

Another embodiment of an elastomer-driven pump is the use of an elastomeric band 10 (e.g., a rubber band, see FIGS. 5C and 5D) to apply a constant force to a drug reservoir 3 driving the drug through a narrow bore tubing 8 with a check valve 16 (or one-way valve) at the downstream end. Elastomers are known to have material properties where large strain values can be imparted on them with relatively small changes in stress and, in some regions of the stress-strain curve with very little change in stress. In one embodiment of an elastomeric band pump, a stretched polyisoprene band is used. Polyisoprene has desirable material properties in that, within a specific region of the stress-strain curve, significant changes in strain result in virtually no change in stress. In this embodiment, the elastomeric rubber band 10 is used within the range in the stress-strain curve where the stress remains within the elastic region from the beginning to the end of the stroke of the motion of the piston. In this embodiment, one end of the elastomeric band 10 is placed onto the post 12 attached to the piston 13 while the other end is placed onto the stationary post 14. The tension on the elastomeric band 10 applies a force to the drug reservoir and in order to eliminate the effect of ambient pressure differences, a vent hole 15 allows the drug reservoir 3 to be exposed, on all sides, to ambient pressure. The check valve 16 also serves to keep saliva from entering the narrow bore tubing 8 while the drug is not flowing. FIGS. 5C and 5D show the device with a full drug reservoir 3 and a partially emptied drug reservoir 3, respectively.

Yet another embodiment of a nonelectric disposable pump including a pressurized fluid and a flow restrictor involves the use of a volume of elastomer in a fixed volume drug reservoir. The elastomer may, optionally, be a closed cell elastomer. The elastomer can be compressed and the subsequent controlled expansion of the elastomer provides the force to deliver the drug. In continuous pumping using a gas-including closed-cell elastomer, a drug-including fluid is pumped at an about constant flow rate by maintaining in the fixed volume, oral liquid impermeable reservoir an about constant pressure. For maintaining the about constant pressure in the reservoir a substantially compressible elastomer is placed in the reservoir. The substantially compressible elastomer can be compressed by applying a pressure in the reservoir that is typically less than about 100 bar (for example less than 10 bar) to a volume of elastomeric material. The volume of the compressed elastomeric material in the pressurized reservoir can be less than about 67%, 50%, or 25% of the volume of the elastomer at about sea-level atmospheric pressure. An exemplary family of such compressible elastomers includes closed cell rubbers, also known as closed-cell rubber foams. Closed cell rubbers have fully rubber-enclosed gas pores, the pores containing a gas, such as $N_2$, $CO_2$, or air. At about sea-level atmospheric pressure the density of the closed pore elastomer can be less than 67% of the density of the elastomer without the gas, for example between 67% and 33% of the elastomer without the gas, between 33% and 25% of the elastomer without the gas, between 25% and 12% of the elastomer without the gas, or less than 12% of the density of the elastomer without the gas. The volume percent of the gas in the elastomer at about sea-level atmospheric pressure can be greater than 20 volume %, for example greater than 50 volume %, or greater than 75 volume %. The elongation of the gas-including elastomer can be greater than about 25%, for example between 50% and 200%, between 200% and 450%, or greater than 450%. The gas containing elastomer can be of any shape fitting in the fixed volume drug reservoir. It can be a single piece, such as a block, or an optionally folded sheet, or it can be multiple pieces, such as small gas-filled spheres. Typical gas pore enclosing elastomers can include cross-linked polymers and copolymers, for example of dienes (exemplified by isoprene, chloroprene (neoprene), butadiene); exemplary copolymers include acrylonitrile-butadiene-styrene, acrylonitrile-butadiene, or elastomeric polyacrylates, or elastomeric olefins such as ethylene-propylene rubbers, or elastomeric silicones and fluorosilicones, or elastomeric polyurethanes. In general the less gas permeable, particularly less water vapor permeable elastomers, are preferred.

Drug delivery devices including closed cell elastomeric pumps are preferably configured and arranged to continuously or semi-continuously administer the drug into the patient's mouth at an average rate for a delivery period of not less than 4 hours and not more than 7 days at a rate in the range of 80%-120% of the average rate.

During the delivery of the drug-including suspension at a constant rate the gas-including elastomer expands such that it occupies most or all of the volume vacated by the already delivered suspension and there are large gas bubbles within the elastomer. In an exemplary method of production and operation of a system delivering the drug at an about constant rate, a closed-cell elastomer can be placed in a drug reservoir equipped with an closed outlet or outlets for drug delivery and optionally equipped with a septum for filling the reservoir. The drug reservoir can have walls made of a material that does not substantially deform at the operating pressure in the reservoir, for example the deformation of the wall under the applicable pressure changing the reservoir volume typically by less than 5%, for example by less than 1%. The drug containing suspension can be then injected through the septum, compressing the gas-containing closed cells of the rubber and pressurizing thereby the reservoir. Opening the outlet or outlets initiates the flow of the drug-including suspension, e.g., into the mouth. The about constant pressure in the reservoir during the delivery of the drug can be controlled, for example, by the type of the closed cell rubber.

An advantage of elastomeric infusion pumps for use in the mouth is that it is possible to temporarily stop the drug delivery from the device if the patient wishes to temporarily remove the drug delivery device from the mouth. This can be accomplished, for example, by blocking or closing the flow restrictor, e.g., the orifice, the glass capillary, or the narrow bore tubing.

To minimize the change in flow rate when the patient drinks a hot beverage, it is preferred to utilize elastomeric materials whose force is relatively independent of temperature in the range of 37° C.-55° C. For example, the force in a fresh reservoir may increase by less than 30%, 20% or 10% when the temperature is raised from 37° C. to 55° C.

Spring driven pumps. Positive-pressure spring-powered pumps are powered by energy stored in a compressed spring. In one embodiment, the spring is compressed during the reservoir filling process, as the volume of the solid or fluid in the reservoir increases. In another embodiment, the spring is relaxed prior to use, for example during storage and shipping of the product, and the spring is compressed during the process of inserting the pump component into the re-usable oral appliance. In yet another embodiment, the spring is relaxed prior to use and the spring is compressed during the process of placing the oral appliance into the mouth.

A significant advantage of spring-driven pumps for use in the mouth is that it is possible to temporarily stop the drug delivery from the device if the patient wishes to temporarily remove the drug delivery device from the mouth. This can be accomplished, for example, by retracting the spring, restricting the further expansion or contraction of the spring, or blocking or closing the flow restrictor, e.g., the glass capillary or narrow bore tubing.

The spring of the invention is preferably an about constant force spring. To minimize the change in flow rate as the solid or fluid is delivered, it is preferred to utilize a sufficiently long spring, or a coaxial coupled spring set, or a sufficiently high tension in the spring such that the difference between the starting and ending force applied by the spring is less than 30%, 20%, or 10% of the starting force.

To minimize the change in drug administration rate when the patient drinks a hot beverage, it is preferred to utilize spring materials whose force is relatively independent of temperature in the range of 37-55° C. For example, the force in a fresh reservoir may increase by less than 30%, 20% or 10% when the temperature is raised from about 37° C. to about 55° C.

The springs of the invention may be any type of spring, including traditional metal springs or a compressible elastomer. For example, the compressible elastomer may be a solid such as isoprene, or it may contain closed gas cells (e.g., neoprene).

An example of a spring-driven, fully disposable, constant-rate medication infusion pump with flow restrictor is the Valeritas V-go insulin patch pump, described in U.S. Ser. No. 13/500,136, incorporated herein by reference.

In embodiments in which the drug is delivered into the mouth via a tube or channel, the oral liquid impermeable drug reservoir may be kept free of oral liquids by using a tube or channel coated with a hydrophobic or non-stick material (e.g. paraffin, PTFE or fluorinated polyether), and/or designed with a diameter that would require a sufficiently high pressure so as to not allow saliva to enter.

Figure 6:
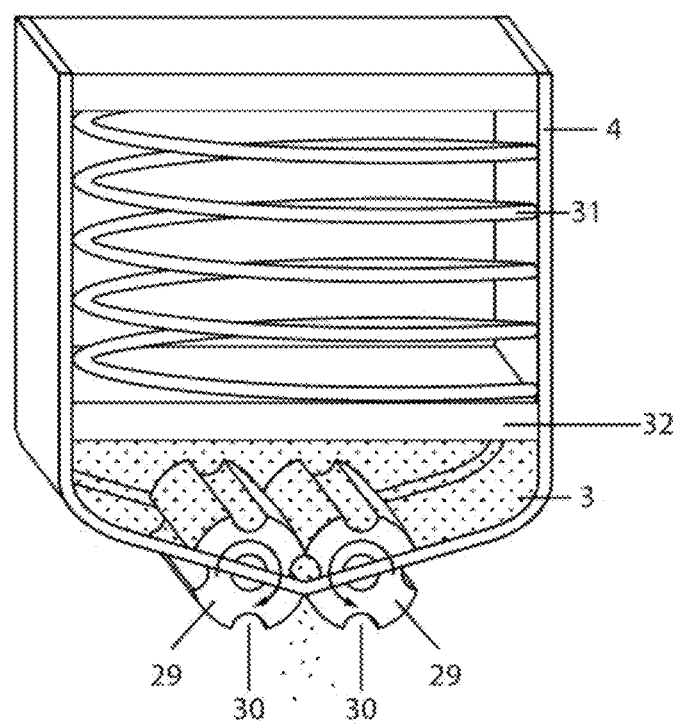
FIG. 6 illustrates the use of a motor to rotate two columnar or conical shaped drums 29 that are attached to the oral liquid impermeable drug reservoir 3.

Another embodiment of a spring driven drug pump, illustrated in FIG. 6, includes the use of a spring motor to rotate two columnar or conical shaped drums 29 that are attached to the oral liquid impermeable drug reservoir 3 containing a suspension. The drums 29 are constructed of a hydrophobic or non-stick material, and can be configured with a tight tolerance to prevent introduction of saliva into the reservoir. The rotation of these drums can draw the suspension from the drug reservoir 3, through the drums 29, and into the mouth. The drums can be configured such that a cutout 30 defines the dosage, and the frequency of rotation of the drums 30 defines the drug delivery rate. In another embodiment, the cutout 30 would not be present and the spacing between the drums 29 along with the speed of rotation of the drums 29 would define the drug delivery rate. In order to maintain constant feeding and eliminate the potential for gaps of drug to the drums, a spring 31 and piston 32 are employed within the housing 4.

Figure 8:
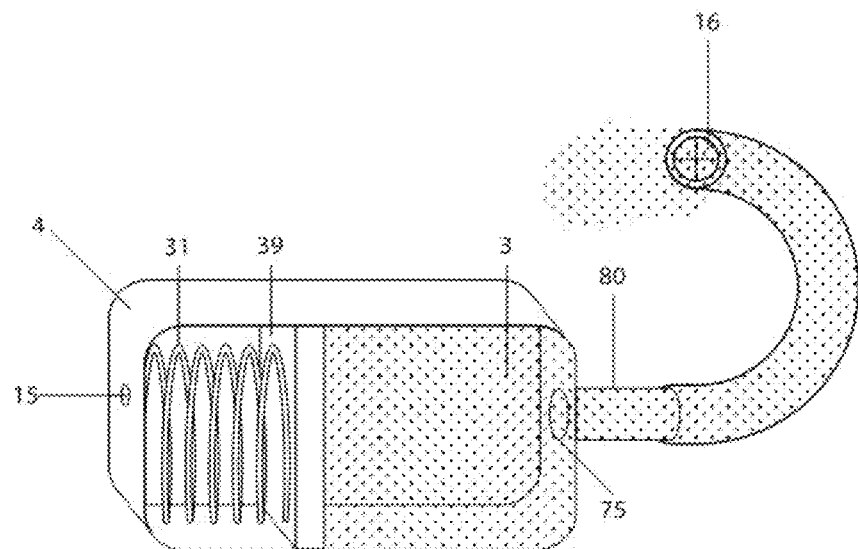
FIG. 8 illustrates a constant force compression-spring driven pump delivering a drug suspension.

In another embodiment of a compression spring-driven drug delivery device, FIG. 8 illustrates a compression-spring driven pump delivering a drug suspension. One or more constant force compression springs 31 are used to push a compression plate 39 toward an orifice 75. The drug is contained in an oral liquid impermeable reservoir with rigid walls 4. For example, the rigid walls and compression plate may include a syringe barrel and a plunger which creates a seal that prevents leakage of the drug into the compartment containing the spring. In order to eliminate the effect of changes in ambient pressure on the drug delivery rate, a vent hole 15 is present within the device to allow both the drug reservoir 3 and the drug reservoir nozzle 80 to be exposed to ambient pressure, which reduces or eliminates the effect of change in ambient air pressure (e.g., by the patient sucking on the device and/or change in altitude). The drug delivery device may optionally include a one-way valve 16.

Figure 9:
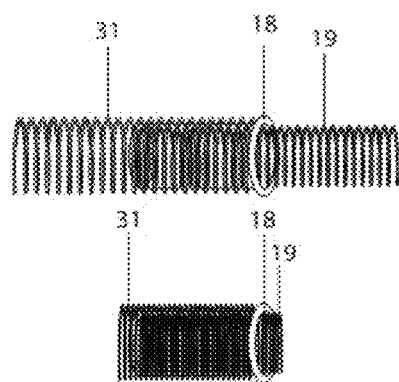
FIG. 9 illustrates two coaxial compression springs wherein, upon compression, a first spring with a first diameter is wholly or partially nested within a second spring with a second, larger diameter.

As illustrated in FIG. 9, a particularly advantageous embodiment is the use of two coaxial compression springs 31 and 19 connected via a coupler 18 wherein, upon compression, a first spring with a first diameter is wholly or partially nested within a second spring with a second, larger diameter. Such an embodiment provides for a smaller overall length and a reduced variation in force across the stroke length, as compared to the use of a single spring.

Figure 7A:
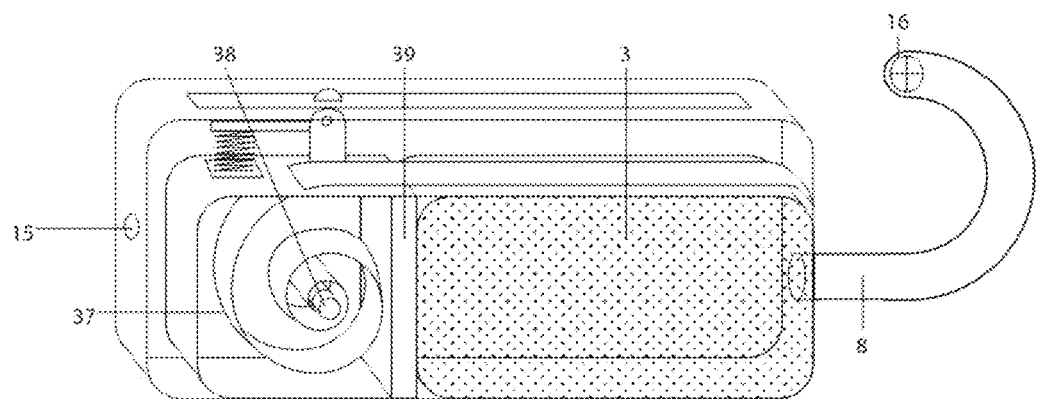
FIGS. 7A, 7B, 7C, and 7D illustrate spring-driven pumps in which a constant force spring is used to compress the drug reservoir 3.
Figure 7B:
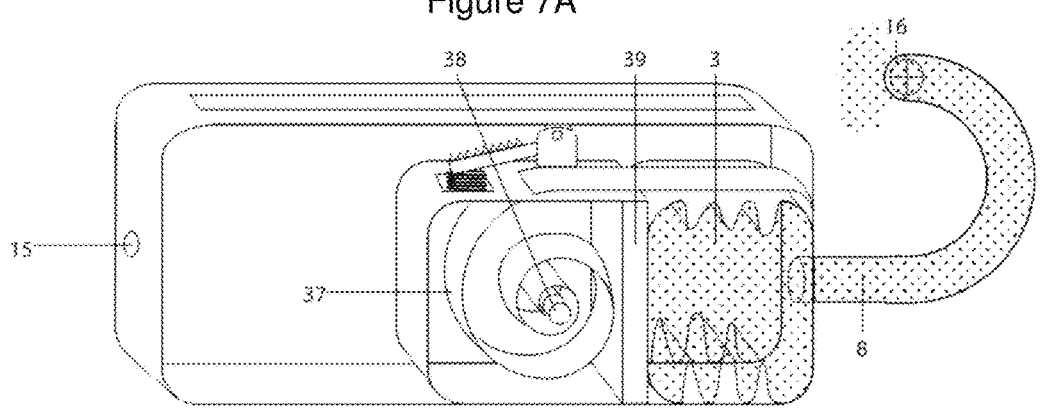

In a further embodiment of a coil spring-driven drug delivery device, FIGS. 7A and 7B illustrate an embodiment in which one or more constant force springs are used to pull a compression plate toward an orifice. A flexible and/or deformable oral liquid impermeable reservoir within a housing contains the drug. The end of the spring rides along a track on the inside of the housing. FIG. 7A, shows the location of the spring 37, spring axle 38 and compression plate 39 when the reservoir 3 is full and the spring 37 is fully extended. FIG. 7B shows the location of the compression plate 39 and spring 37 when the retraction of the spring 37 has delivered all of the drug from the reservoir 3. In a related embodiment, the drug can be contained within the housing itself and the compression plate would create a seal and act as a plunger to deliver the drug in a manner similar to a syringe. In this embodiment, the spring rides inside of the housing and inside of the drug chamber, within a sealed sleeve, protecting the drug from exposure to the spring. In order to eliminate the effect of changes in ambient pressure on the drug delivery rate, an optional vent hole 15 is present within the device to allow both the drug reservoir 3 and the drug reservoir nozzle 8 to be exposed to ambient pressure, which reduces or eliminates the effect of change in ambient air pressure (e.g., by the patient sucking on the device and/or change in altitude).

Figure 7C:
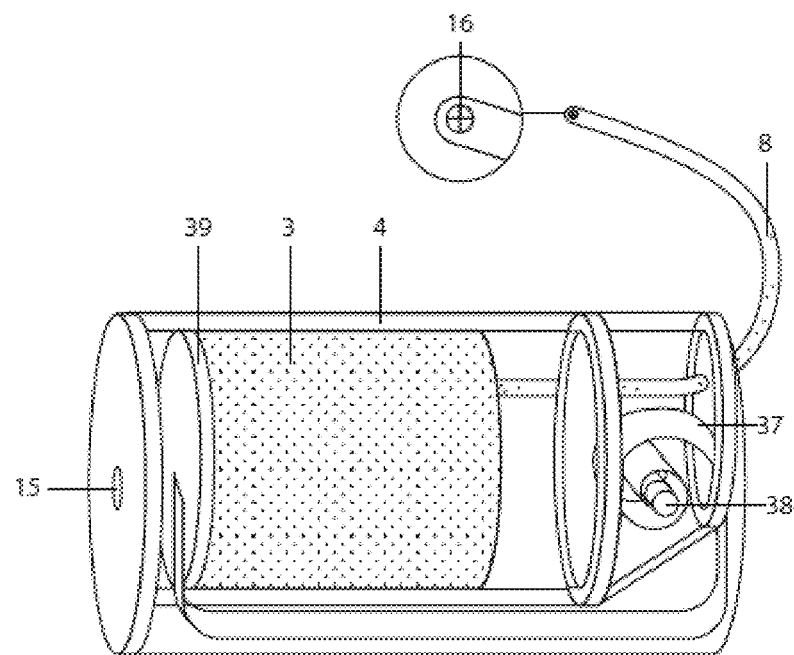
Figure 7D:
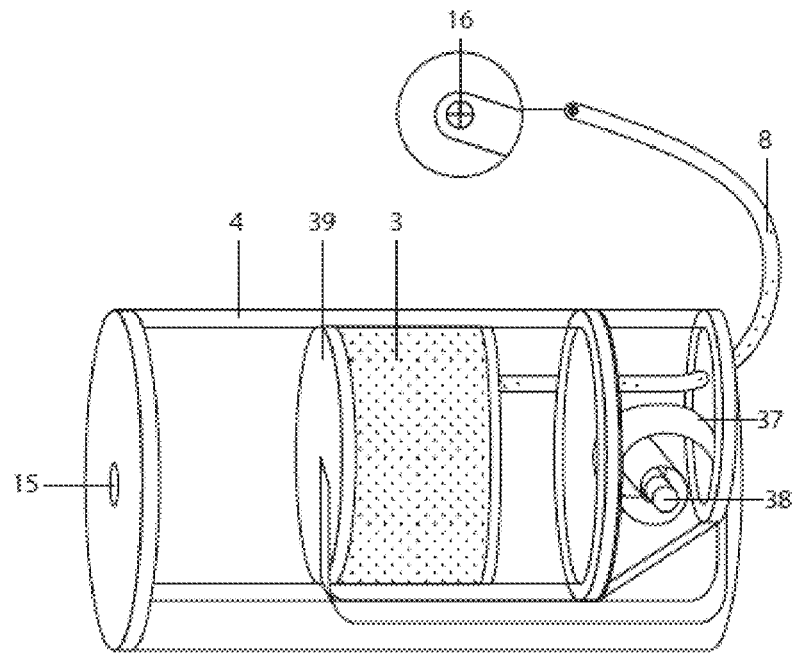

In another embodiment illustrated in FIGS. 7C and 7D, a constant force spring 37 remains fixed in space; one end of the spring 37 is attached to a compression plate 39, and pulls the compression plate 39 toward the drug reservoir nozzle 8. FIG. 7C shows the location of the spring 37 and compression plate 39 when the drug reservoir 3 is full and the spring 37 is fully extended. FIG. 7D shows the location of the compression plate 39 and spring 37 when the retraction of the spring 37 has delivered all or most of the drug from the reservoir 3. FIGS. 7C and 7D also have a vent hole 15 incorporated into the design, to eliminate any effect of ambient pressure on the drug delivery rate.

In a further embodiment of a spring pump, one or more compression springs can be used to apply an approximately constant force to a piston or plunger that applies that force to the drug reservoir. Using a very long compression spring with a low spring rate, one could apply a force across a short stroke with relatively constant force. As an example, a 10 inch long spring with a spring rate of 0.05 lbF/in would be compressed to 8.5 inch and would apply a force of 0.425 lbF. If the spring were allowed to expand to 7.5 inches (a 1 inch total stroke), the resulting force would be 0.375 lbF, which is a decrease of 12.5% throughout the stroke. In preferred embodiments, the spring force is in the range of 0.25-10 lbF and is preferably less than 10 lbF, 5 lbF, or 1 lbF; the spring rate is in the range of 0.01-1 lbF/inch and is preferably less than 1 lbF/inch, 0.5 lbF/inch, or 0.05 lbF/inch; the stroke length is in the range of 0.5-1 inch and is preferably less than 2 inches, 1 inch, or 0.5 inches; and the difference between the starting and ending force across the stroke is less than 15%, 10%, or 5%.

Pneumatic pumps. Pneumatic pumps generate a driving force using a pressure head of air. In one embodiment, a diaphragm pump generates a pressure head that pushes a discreet amount of drug, in solid form (e.g., particles, granules or powder), from a reservoir and into the mouth. An example of such a design, illustrated in FIG. 10, is a rotating disk 54 that contains compartments filled with suspension 55 that is injected by an air pressure bolus 57 at a predetermined rate through an orifice 56 that is fixed in place with respect to the rotating disk 54. The rotation of the disk 54 exposes a single compartment and the bolus of air 57 delivers the drug from that compartment to the mouth at a specific rate. The housing can be formed from a clear material that would allow the user to observe how much drug remains in the device. In another embodiment, the disk can contain a single compartment that rotates and alternately fills the compartment from the reservoir and delivers the drug with a bolus of air. In this configuration, the air not only delivers the drug material, but also removes any saliva prior to re-filling the compartment from the reservoir.

Negative pressure pumps. Negative-pressure pumps generate a driving force from the pressure difference across two sides of the pump's low-pressure chamber wall, with one side being at low pressure (e.g., inside a partial vacuum chamber) and another side being at atmospheric pressure. The low pressure in the vacuum chamber may be created during the reservoir filling process. Expansion of the oral liquid impermeable reservoir, e.g., upon adding the drug-containing fluid to the reservoir, causes simultaneous expansion of the reduced pressure chamber, thus creating a significant vacuum. During administration of the solid or fluid drug, pressure on the movable wall plunger is generated by the large pressure difference between its two sides, causing it to move and compress the solid or fluid in the drug-containing chamber.

A significant advantage of negative pressure pumps for use in the mouth is that it is possible to temporarily stop the drug delivery from the device if the patient wishes to temporarily remove the drug delivery device from the mouth. This can be accomplished, for example, by blocking or closing the flow restrictor, e.g., the glass capillary or narrow bore tubing.

Gas-driven infusion pumps. In one embodiment, a gas-driven drug delivery device includes two or more compartments, with pressurized gas in at least one compartment and the suspension to be administered in at least one separate oral liquid impermeable drug reservoir. The pressurized gas provides the driving force. The two compartments are separated by a movable member (such as a flexible and/or deformable diaphragm) that transmits the force from the gas compartment to the suspension.

The housing containing the two compartments is typically constructed to have a fixed volume that does not vary significantly as the drug is dispensed and the internal pressure declines in the compartment containing the pressurized gas. An example is a reservoir in the shape of a syringe barrel including: a fluid dispensing orifice at the distal end of the syringe barrel; a sealed proximal end of the syringe barrel; a mobile rubber or elastomeric plunger in the syringe barrel, which separates the syringe barrel into two compartments; a drug-including fluid located in the distal compartment; and a pressurized gas in the proximal compartment. In another example, the drug compartment may have a bellows shape and may be surrounded by the gas compartment, such that the pressurized gas compresses the bellows and forces the drug-including fluid through a flow restrictor.

Figure 11A:
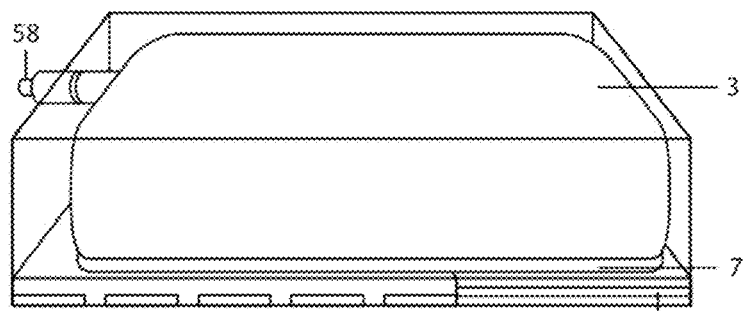
FIGS. 11A, 11B, and 11C illustrate a drug delivery device wherein a first elastomeric drug reservoir 3 is compressed by a second elastomeric reservoir or balloon 7 containing gas or propellant (partially or mostly liquified).
Figure 11B:
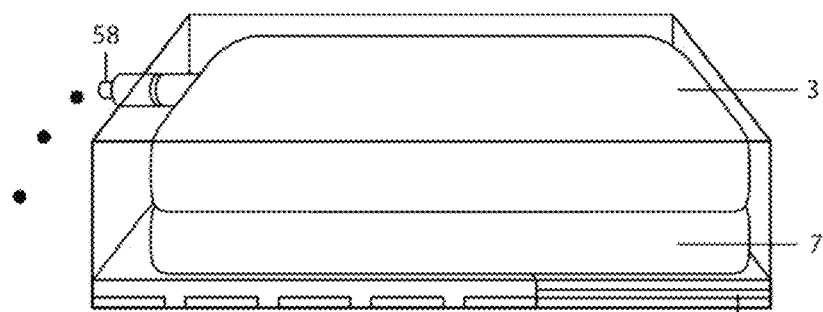
Figure 11C:
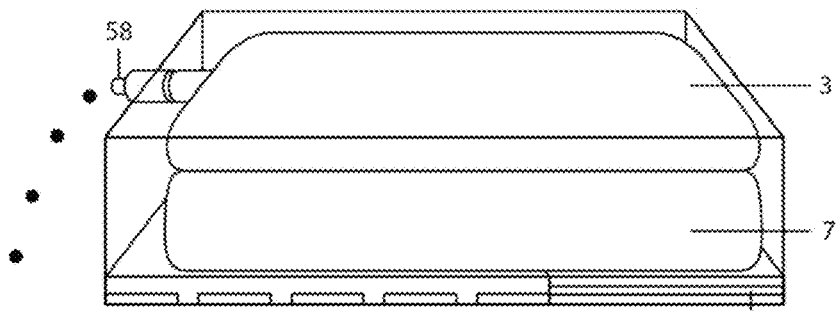

FIGS. 11A, 11 B, and 11C illustrate another embodiment, wherein a first elastomeric drug reservoir 3 is compressed by a second elastomeric compartment 7 containing gas or propellant. In FIG. 11A, the drug delivery device includes a housing containing a first, full elastomeric drug reservoir 3; a second empty, elastomeric compartment 7; and an optional gas pump 11 and electronics. In one embodiment air and/or saliva is pumped by the electronic (e.g., piezoelectric) pump 11 into the second elastomeric reservoir 7. In another embodiment the second elastomeric reservoir 7 contains a compressed gas or propellant, and no pump is required. In either embodiment, the pressure from the second elastomeric reservoir 7 compresses the first elastomeric reservoir containing the drug 3, forcing the drug out of the reservoir through a flow restrictor 58 at a constant rate. FIG. 11B illustrates the system when the drug reservoir 3 is half-full. FIG. 11C illustrates the system when the drug reservoir 3 is close to empty.

In one embodiment, a gas (e.g., carbon dioxide, nitrogen) is contained in a miniature gas cartridge or cylinder. The gas cartridges have an external volume of less than or equal to 5 mL, 2 mL, or 1 mL and have stored pressures of 100-500 psi, 500-1,000 psi, 1,000-4,000 psi, or greater than 4,000 psi.

Figure 12:
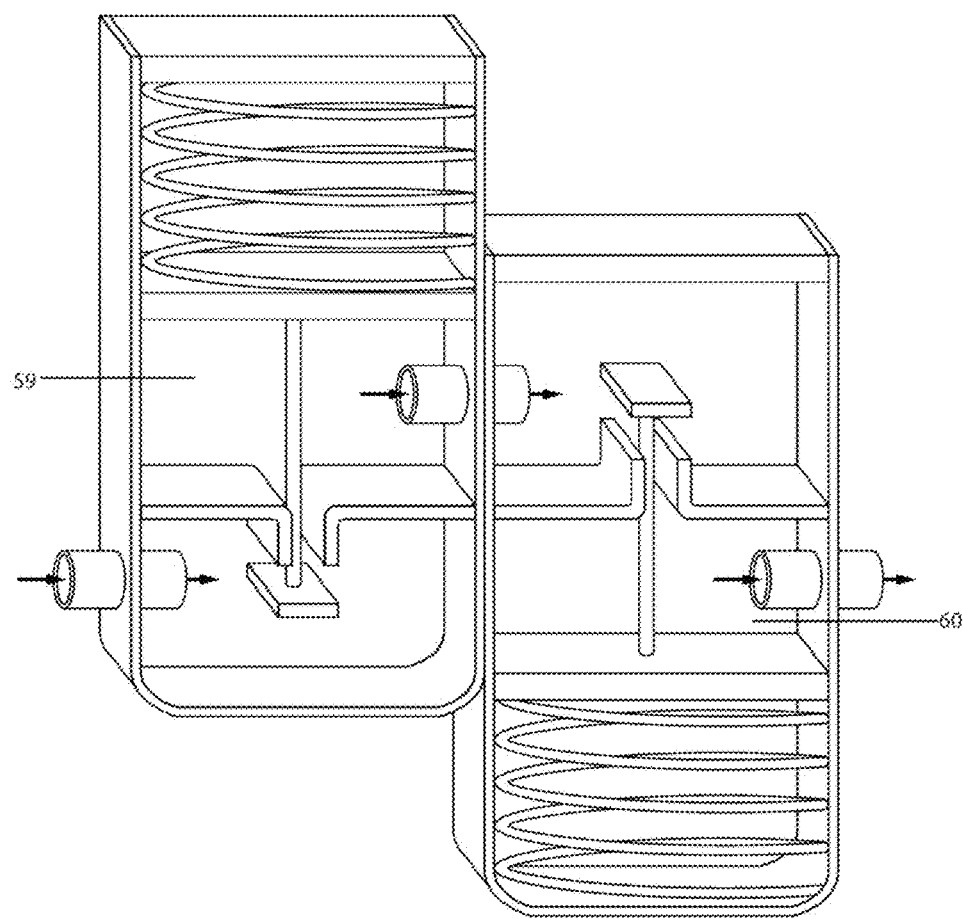
FIG. 12 shows a schematic of a typical two stage gas pressure regulator.

Exemplary gas cartriges are product numbers 40106 (1.00" CO2 Filled; 0.75 grams) and 40106IIN21750 Nitrogen cylinder (1.00" N2 Filled; 0.135 grams) manufactured by Leland Gas Technologies (2614 South Clinton Ave, South Plainfield, N.J. 07080) and product number SM-2 (5/32" Single Acting, Spring Return, Sub-Miniature Cylinder) manufactured by Clippard Instrument Laboratory, Inc. (7390 Colerain Avenue, Cincinnati, Ohio 45239). The gas from the miniature cartridge or cylinder can be used to compress the oral liquid impermeable drug reservoir, thereby delivering the drug. The gas-pressurized cartridge can be used in conjunction with a one or two-stage regulator in order to provide a constant pressure gas flow as the drug reservoir is emptied. FIG. 12 shows a schematic diagram of a commercially available two-stage regulator. Examples of miniature two-stage regulators are the product categories PRD2 and PRD3 manufactured by Beswick Engineering Co, Inc.(284 Ocean Rd, Greenland, N.H. 03840-2442). A two-stage regulator is used to gradually reduce the pressure from high to very low, in this example from the cartridge to the piston chamber of the pump. The first stage 59 reduces the gas pressure to an intermediate pressure. The gas at that intermediate pressure then enters the second stage 60 and is further reduced by the second stage 60 to the working pressure.In a related embodiment, a gas cartridge contains an optionally reversibly $CO_2$-absorbing or adsorbing solid that maintains, e.g. in its Henry region, an about constant $CO_2$ pressure at about 37° C. The reversibly $CO_2$-absorbing or adsorbing solid can be, for example, a high specific surface activated carbon, silica, e.g., silica gel, modified with n-propylamine or with another amine or heterocyclic nitrogen compound. The BET (Brunauer-Emmett-Teller) specific surface of the materials can be greater than 50 $m^2/g$ such as, between 50 $m^2/g$ and 500 $m^2/g$, or greater than 500 $m^2/g$. The materials can contain more than 0.5 millimoles of amine functions per gram, for example between 1-5 millimoles of amine functions per gram. Exemplary reversibly $CO_2$-absorbing or adsorbing solids are described, for example, by Z. Bacsik, N. Ahlsten, A. Ziadi, G. Zhao, A. E. Garcia-Bennett, B. Martin-Matute, and N. Hedin "Mechanisms and Kinetics for Sorption of $CO_2$ on Bicontinuous Mesoporous Silica Modified with n-Propylamine" Langmuir 2011, 27, 11118-11128 incorporated herein by reference and in the references cited by Bacsik et al, also incorporated herein by reference. The materials may also be in the MIL-53 family of soft porous crystals, such as MIL-53(Al), MIL-53(Al)-11.1% NH2, MIL-53(Al)-20% $NH_2$, MIL-53 (Al)-50% $NH_2$, MIL-53(Al)-66.7% $NH_2$, and MIL-53 (Al)—$NH_2$, as described by M. Pera-Titus, T. Lescouet, S. Aguado, and D. Farrusseng "Quantitative Characterization of Breathing upon Adsorption for a Series of Amino-Functionalized MIL-53" (J. Phys. Chem. C 2012, 116, 9507-9516). In general, the reversibly $CO_2$ absorbing amine-modified carbon, zeolite, silica or silica gel adsorbs $CO_2$ when the silica also contains bound water. The materials may also include high surface area carbon or activated carbon as described for example in "Fixed bed adsorption of CO2/H2 mixtures on activated carbon: experiments and modeling" by N. Casas, J. Schell, R. Pini, M. Mazzotti Adsorption (2012) 18:143-161 and "Pure and binary adsorption of $CO_2$, $H_2$, and $N_2$ on activated carbon" by J Schell, N Casas, R Pini, M Mazzotti in Adsorption (2012) 18:49-65.

The materials may provide an about constant $CO_2$ pressure of greater than 1 bar, for example between 1.2 and 2.0 bar, or between 2.0 and 5.0 bar, or between 5 bar and 20 bar.

In yet another related embodiment the gas cartridge may contain a solid metal hydride, providing at about 37° C. an about constant hydrogen pressure. The metal hydride may include an alloy, for example of a rare earth like lanthanum, and a transition metal like nickel, and may also include magnesium.

In some embodiments, the pressurized gas material remains in the gaseous state through the temperature range of 0° C.-37° C. A disadvantage of such embodiments is that the drug infusion rate tends to decline as the drug is dispensed because the gas pressure declines as the gas expands. For this reason, it is preferred to utilize sufficiently high gas pressures in the pump such that the difference between the starting and ending gas pressure is less than 30%, 20%, or 10% of the starting gas pressure.

To minimize the change in flow rate when the patient drinks a hot beverage, it is preferred to minimize the volume of the gas relative to the volume of the drug-including fluid. The volume of the gas can be less than 40%, 30%, 20% or 10% of the volume of the drug-including fluid in a fresh reservoir. For example, the force in a fresh reservoir may increase by less than 30%, 20% or 10% when the temperature is raised from 37 to 55° C.

Figures 13A, 13B:
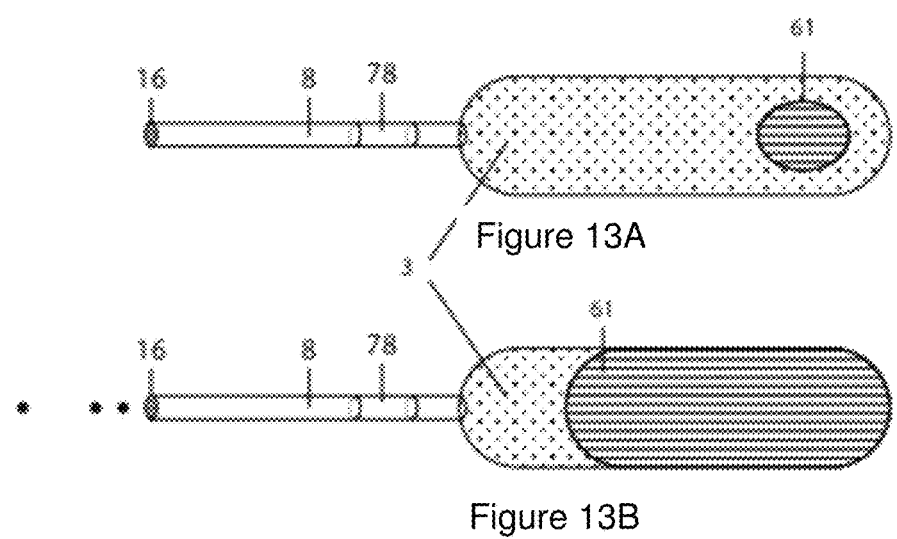
FIGS. 13A and 13B illustrate a drug delivery device including an expandable plastic (elastomeric or non-elastomeric) compartment 61 containing propellant within a rigid drug reservoir 3. The propellant within the expandable plastic compartment has a vapor pressure that pressurizes the drug compartment at a specific pressure when exposed to body temperature, and pushes the drug through a narrow bore tubing.

In a preferred embodiment, the drug delivery device includes a volatile propellant in one compartment and the drug in a second compartment, the propellant boiling at sea level atmospheric pressure at a temperature less than about 37° C. The propellant is under greater than 1 bar pressure, such that part or most of it is liquid at 37° C. and its volume is small. Optionally, the partly or mostly liquid propellant in the device has at about 37° C. a saturated vapor pressure greater than about 1 bar and less than about 50 bar, for example greater than about 1.5 bar and less than about 25 bar, such as greater than about 1.5 bar and less than about 20 bar, such as greater than about 2 bar and less than about 15 bar, such as between 2 bar and 10 bar, such as between 3 bar and 10 bar. In this embodiment, a propellant-driven drug delivery device can include an oral liquid impermeable drug reservoir with a pressure-liquefied propellant, i.e., a propellant-containing compartment within the drug delivery device, such that the pressurized, volatile, propellant liquid and the fluid including the infused drug reside in the different compartments. Optionally, the wall material of the propellant-containing compartment can be expandable or plastically easily deformable, such as elastomeric or non-elastomeric, allowing for expansion of the propellant-containing compartment as the drug-containing fluid is depleted. Typically, some of the propellant is a gas at 1 bar pressure at 37° C. It can maintain an about constant pressure when the drug-including formulation is infused in the mouth. In an embodiment shown in FIGS. 13A and 13B, the gas compartment is encapsulated by an expandable membrane 61 and resides within the oral liquid impermeable drug reservoir 3. The propellant exerts an about constant pressure on the expandable membrane 61 as the expandable membrane 61 expands and pushes the solid or fluid drug from the oral liquid impermeable drug reservoir 3 through a narrow-bore tubing 8. Optionally, a narrow bore tubing may serve as a flow restrictor to control the delivery rate, or there may be a separate flow restrictor. FIG. 13A shows the compressed expandable compartment 61 containing propellant within the full drug reservoir 3. FIG. 13B shows the nearly empty drug reservoir 3 and the expanded expandable compartment 61 containing propellant. The advantage of this embodiment is that the drug delivery rate does not decline as the drug is dispensed.

In a preferred embodiment, the propellant and a solid or fluid drug are contained within a rigid metal housing (e.g., titanium or titanium alloy) that does not significantly deform under the pressure of the propellant. The housing includes a liquid impermeable drug reservoir. The propellant and the drug are separated within the housing by a flexible and/or deformable diaphragm, which transmits the pressure from the propellant compartment to the drug compartment. The flexible and/or deformable diaphragm may include a substantially pinhole free metal sheet, such as a tin-containing sheet or silver-containing sheet, typically of a thickness between 10 μm and 250 μm, e.g., between 20 μm and 125 μm, such as between 25 μm and 75 μm. To obtain a hermetic seal of the propellant compartment, the metal diaphragm may be welded to the metal housing, e.g. by resistance welding (i.e., by application of an electrical current pulse or pulse sequence).

In one embodiment, the gas can be contained in a gas-impermeable, non-flexible material, such as metallized Mylar®, which is folded such that the expansion of the gas unfolds the gas compartment and allows the pressurization of the solid or fluid drug to occur. Optionally, the unfolding compartment can be coil or bellows-like.

Figure 14A:
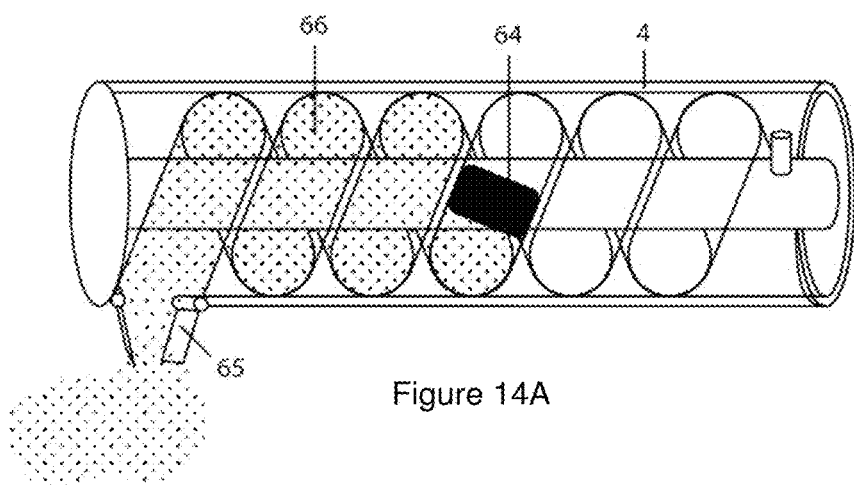
FIGS. 14A, 14B, 14C, and 14D illustrate illustrate a propellant-driven drug delivery device for the delivery of suspensions.
Figure 14B:
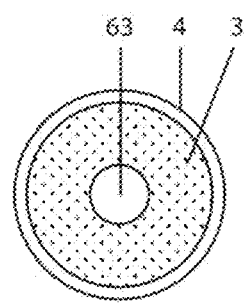
Figure 14C:
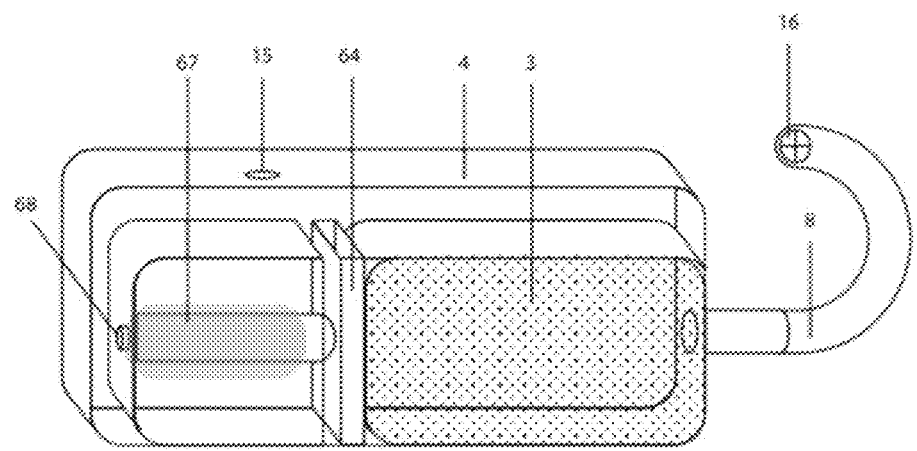
Figure 14D:
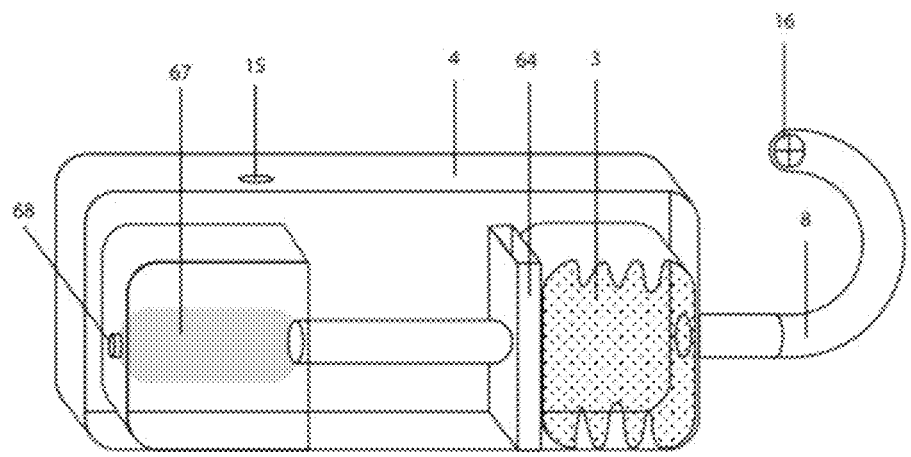

In another embodiment of a gas-driven pump, a propellant can be used to deliver a suspension containing a drug. In FIGS. 14A and 14B, the propellant, contained within propellant chamber 63 pushes the piston 64 which in turn applies a constant pressure to a column of the drug suspension. The flow rate of the drug suspension 66 can be affected by the friction at the interface of the suspension and the inner drug reservoir wall as well as by the check valve 65 located at the oulet port. The resistance to flow can thus change as the drug reservoir 3 is emptied. To alleviate or eliminate this change, the resistance of the plunger movement, i.e. the friction, can be made sufficiently greater than the resistance of the suspension to maintain the flow rate within the desired tolerance. In a related embodiment, a vent within the housing of a propellant driven piston allows the piston to be exposed to ambient pressure, thereby eliminating the effect of changes in ambient pressure on the flow rate of the drug. This embodiment is illustrated in FIGS. 14C and 14D. FIG. 14C shows the drug reservoir 3 in its full state. The piston 64 is positioned against the drug reservoir 3 on one end and within the propellant chamber 67 on its opposite end. The piston 64 forms a seal with the propellant chamber 67 such that the propellant is allowed to pressurize and maintains its pressure within the volume created by the propellant chamber 67 and the piston 64. As the propellant is exposed to body temperature, the propellant pressurizes pushing the piston 64 against the drug reservoir 3. A vent 15 maintains ambient pressure around the drug reservoir 3. FIG. 14D shows the device after some time has elapsed and the collapsible drug reservoir 3 has emptied some of its contents. A filling septum 68 is located on the opposite end of the piston 64 allowing filling of the propellant chamber 67.

In a further embodiment, the drug delivery device includes a propellant and a drug together in the same compartment. The saturated vapor pressure of the propellant at 37° C. can be between about 1 bar and 50 bar, (e.g., 1.5-20 bar, 2-10 bar, or 1.5 and 6 bar). Part of the propellant can be gas and part liquid at 37° C. at the pressure within the compartment. In this embodiment, a propellant-driven drug delivery device can include an oral liquid impermeable drug reservoir with a pressure-liquefied propellant, i.e., volatile liquid propellant in the reservoir, such that both the pressurized, volatile, propellant liquid and the suspension including the infused drug reside in the same compartment. The propellant may not be substantially dissolved in the drug-containing composition, but could be dispersed in it to form an about homogeneous mixture. The propellant can maintain an about constant pressure when the drug including formulation is infused in the mouth.

Because separation or segregation of the liquid propellant and the drug formulation could lead to oral delivery of propellant-enriched or propellant-poor fluid and hence to lesser or greater than intended drug dosing, the liquid propellant can be dissolved or co-dispersed in the suspension. The propellant liquid can be homogeneously dispersed in any of the phases, for example in a non-aqueous phase, which may optionally be part of an emulsion, formed optionally by adding an emulsifier, such as a lecithin, or by Pickering emulsification, where small solid drug or other particles stabilize the emulsion. In general, the emulsions can be stable for at least 24 hours and can be re-formed by agitation, for example by shaking. The optional emulsions can be foamable or non-foamable and can include an emulsifier such as lecithin, a protein, or a surfactant that can be non-ionic, including for example a glyceryl monoester, like glyceryl monooleate, a Tween or a Polysorbate. Examples of emulsifiers in propellant including mixtures are listed for example in U.S. Pat. No. 6,511,655 and in U.S. Patent Publication No. 2003/0049214, each of which is incorporated by reference.

Alternatively the liquid propellant can be dissolved in the carrier liquid of a solid drug including formulation, e.g. when the carrier liquid is non-aqueous, for example when it is edible oil or medicinal paraffin oil. The propellant dissolving carrier liquid may optionally be a temperature sensitive liquid such as cocoa butter.

As the drug is dispensed and the internal pressure falls in the gas compartment, volatile liquid propellant evaporates, thereby maintaining an about constant pressure within the oral liquid impermeable reservoir. The advantage of such an embodiment is that the drug infusion rate does not decline as the drug is dispensed.

In a related embodiment, a gas-driven drug delivery device includes an oral liquid impermeable drug reservoir having one or more compartments, with a non-toxic propellant gas (formed from the optionally substantially immiscible pressurized liquid when the pressure is reduced to about 1 bar) and the drug to be infused both present in at least one compartment. The propellant gas provides the driving force. The pressure-liquefied gas can optionally be insoluble in the fluid containing the drug, such that the pressure in the reservoir remains about constant at the about constant body temperature near 37° C. in the mouth.

Alternatively, a pressurizing gas can be dissolved in the drug-including fluid. For example, when the fluid infused in the mouth is aqueous, or when it includes ethanol, and the reservoir is pressurized, the pressurizing gas can be $CO_2$. When the fluid infused in the mouth includes an edible oil such as a vegetable oil, a monoglyceride, a diglyceride or a triglyceride, or paraffin oil, and the reservoir is pressurized, the pressurizing gas can be a flurorohydrocarbon, a Freon™, or a saturated hydrocarbon or a non-saturated hydrocarbon such as an olefin. When the pressurizing gas dissolves in the fluid in the oral liquid impermeable reservoir the pressure can be about constant at the constant about 37° C. temperature in the mouth, making the flow rate about constant.

Examples of continuously subcutaneously drug infusing compressed air or Freon™ pressurized pumps include those described in U.S. Pat. Nos. 4,265,241, 4,373,527, 4,781,688, 4,931,050, 4,978,338, 5,061,242, 5,067,943, 5,176,641, 6,740,059, and 7,250,037, each of which is incorporated herein by reference. When the reservoir is refillable and when the pumping is by pressurization, the reservoir can be pressurized upon its refilling.

An example of a propellant-driven, implanted medication infusion pump is the Codman pump described in U.S. Pat. No. 7,905,878, European Patent Nos. EP 2177792 B1 and EP 1527794 B1, each of which is incorporated herein by reference.

To provide different patients with different dose rates, fluids with different drug concentrations can be placed in the reservoirs, thereby not necessitating modifications to the drug delivery device or to the flow rate. Alternatively, the drug concentration in the reservoir can be held constant and the flow rate can be changed, for example by changing the diameter or length of the flow restrictor.

Exemplary volatile propellant compounds for use in the devices of the invention include hydrocarbons (e.g., pentane; isopentane; 1-pentene; trans-2-pentene; trans-dimethylcyclopropane; ethylcyclopropane; 1,4 -pentadiene; 2-methyl-1,3-butadiene; and methyl-1-butane; 2-butyne); halocarbons (e.g., trichlorofluoromethane; difluoromethane; 1,1-dichloro-1-fluoroethane; 2,2-dichloro-1,1,1-trifluoroethane; 1-fluorobutane; 2-fluorobutane; perfluoropentane; 1,1-dichloroethylene; cis-1-chloropropene; and 2-chloropropene); esters (e.g., methyl formate); ethers (e.g., diethyl ether), and hydrofluoroalkanes. Preferred propellants are those approved by the FDA for use in medication inhalers, such as 1,1,1,2 tetrafluoroethane (sold as DuPont™ Dymel® (r)134a/P); and 1,1,1,2,3,3,3 heptafluoropropane, sold as 227ea/P (sold as DuPont™ Dymel® 227ea/P). Also preferred are propellants approved by the FDA for topical applications, such as 1,1,1,3,3,3 hexafluoropropane (sold as DuPont™ Dymel® 236fa); and propellants approved for use in food and over the counter anticarie drug products, such as octafluorocyclobutane and isopentane, respectively.

Exemplary pressurized liquid propellants and their vapor pressures at 37° C. are listed in Table 1.

TABLE 1

| Propellant | Approximate Pressure, bars at 37° C. |
|---|---|
| diethyl ether | 1.1 |
| 1-fluorobutane | 1.3 |

TABLE 1-continued

| Propellant | Approximate Pressure, bars at 37° C. |
|---|---|
| isopentane | 1.4 |
| 2-fluorobutane | 1.6 |
| 1,2-difluoroethane | 1.9 |
| neopentane | 2.4 |
| methyl ethyl ether | 3 |
| 2-butene | 3.2 |
| butane | 3.5 |
| 1-fluoropropane | 4.1 |
| 1-butene | 4.2 |
| 2-fluoropropane | 5 |
| 1,1-difluoroethane | 8.4 |
| propane | 12.8 |
| propene | 15.5 |
| 1,1,1,2-tetrafluoroethane | 9.3 |
| 1,1,1,2,3,3,3-hepta-fluoropropane | 6.4 |
| 1,1,1,3,3,3 hexafluoropropane | 4.0 |
| octafluorocyclobutane | 4.3 |

When the pressurized gas and the drug are located in the same compartment, the gas can be selected to be safe, non-toxic, and non-irritating when delivered into the mouth and inhaled into the lungs at the delivery rates of the invention. Furthermore, the gas can be selected so as not to adversely affect the stability of the drug and formulation in the reservoir. Chemically inert gases, meaning gases that do not react at body temperature with any of the components of the orally infused composition, are therefore preferred. Preferably, the propellant used in the drug delivery device of the invention is n-butane, isopentane, 1-butene, 1-fluoropropane, trifluorochloromethane, difluoromethane, dichlorofluoromethane, 1,1,1,2,3,3,3-heptafluoropropane, 1,1,1,3,3,3-hexafluoropropane, or 1,1,1,2-tetrafluoroethane.

A source of inaccuracy in propellant pressurized devices is that the pressure, such as the vapor pressure of a liquid propellant, increases with temperature. An important benefit of carrying within the mouth the drug delivery devices of the invention is that the pressure is held nearly constant at about 37° C., thereby minimizing variations in the infusion rate.

In another embodiment, gas is generated by the gas-driven drug delivery device. For example, a low current electrolyzer may be used to generate hydrogen gas. Exemplary hydrogen gas generating systems are the hydrogen gas generating cells sold by VARTA Microbattery GmbH Daimlerstr. 1, D-73479 Ellwangen/Jagst Germany. The VARTA systems are capable of generating 130 ml, 260 ml or more ultrapure $H_2$ at high back pressure. An advantage of such a system is that gas need not be stored in the drug delivery device prior to its use.

An advantage of gas-driven infusion pumps for use in the mouth is that it is possible to temporarily stop, or greatly reduce, the drug delivery from the device if the patient wishes to temporarily remove the drug delivery device from the mouth. This can be accomplished, for example, by blocking or closing the flow restrictor, e.g., the orifice, the glass capillary or the narrow bore tubing or by cooling to a temperature below that in the mouth, for example to the typically 20° C.-25° C. room temperature or by placing the device in a refrigerator typically at 3° C.-8° C.

Propellant-driven Pumps

The following sections provide additional details on designs and manufacturing processes of propellant-driven pumps for the delivery of pharmaceutical compositions including LD/CD pastes. It will be recognized that similar designs and manufacturing processes may be used with other pumps and drug formulations of the invention.

The devices of the invention can be propellant-pumped, rigid walled, intraoral, continuously drug delivering devices having a drug compartment and a propellant compartment separated by an optionally metallic diaphragm. In one embodiment, the device for continuous or semi-continuous intraoral drug administration is configured to be removably inserted in a patient's mouth. The pump can be propellant-driven. The drug delivery device includes a chamber containing a propellant, a chamber containing a drug-including fluid such as a paste, and a flexible and/or deformable diaphragm separating the propellant chamber from the drug chamber. The housing of the device can be rigid and can be gas and liquid impermeable, for example impermeable to gaseous and liquid propellant, gaseous nitrogen, gaseous or dissolved oxygen, gaseous or dissolved air, water vapor, liquid water, saliva and/or gaseous helium; the drug reservoir can be an oral liquid impermeable reservoir. In a preferred embodiment, the rigid housing forms a wall of a chamber containing the drug-including fluid and a wall of a chamber containing the propellant, and the two chambers are separated by a diaphragm. The separating diaphragm includes a metal, i.e., the diaphragm can be metallic or a metallized polymer. The device dispenses at least 50% (e.g., 50%-99%, 60%-95%, 75%-95%, 51%-60%, 61%-70%, 71%-80%, 81%-90%, 91%-95%, or 95%-99%) of the weight of the drug-including fluid (e.g., paste) in the chamber, preferably while the rate of drug delivery, meaning the flow rate or extrusion rate, varies by less than ±20% (e.g., less than ±15%, less than ±10%, or less than ±5%) over a period of greater than or equal to 4, 8, 16, or 24 hours.

The rigid wall of the drug and the propellant including chambers (which can include part of the housing) can be strong, dense and it can be metallic. In a preferred embodiment, the rigid housing forms a wall of the drug-containing chamber and/or a wall of the propellant-containing chamber. The rigid housing of the chamber wall can be strong and includes a metal, ceramic, or a composite of a polymer reinforced by fibers. The fibers reinforcing the polymer can include, for example, carbon fibers, glass fibers, or metal fibers. The housing can include a material having at about 25±3° C. a tensile yield strength greater than 100 MPa, such as greater than 200 MPa, 300 MPa, 400 MPa, or 500 MPa; and/or the housing can include a material having at 25±3° C. a modulus of elasticity (Young's modulus) greater than 30 GPa such as greater than 50 GPa, 75 GPa, or 100 GPa; and/or the housing can include a material having at 25±3° C. a Brinell hardness greater than 200 MPa, such as greater than 400 MPa or 600 MPa; and/or the housing can include a material having at 25±3° C. a density greater than 2.5 g/cm$^3$, such as greater than 3.5 g/cm$^3$, such as about equal to or greater than 4.5 g/cm$^3$, 5.5 g/cm$^3$, 6.5 g/cm$^3$, or 7.5 g/cm$^3$. When metallic, the metal of the housing can be selected from the group titanium, iron, aluminum, molybdenum, or tungsten, or an alloy of titanium, iron, aluminum, molybdenum, or tungsten; it can include, for example, titanium or an alloy of titanium.

Figure 23A:
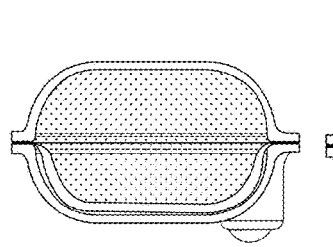
FIGS. 23A, 23B, and 23C illustrate an embodiment of a propellant-driven pump including a propellant-containing chamber and a pharmaceutical composition-containing chamber separated by a flexible and/or deformable diaphragm.
Figure 23B:
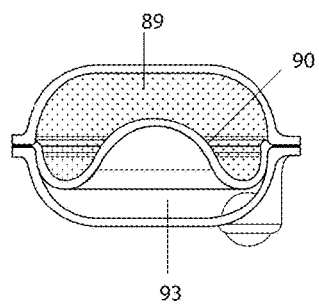
Figure 23C:
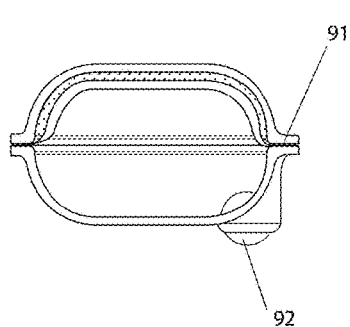

The diaphragm separating the chamber containing the drug-including fluid from the chamber containing the propellant can be a flexible and/or deformable metal foil or it includes a flexible and/or deformable metal foil. In a preferred embodiment, the diaphragm separating the chamber containing the drug-including fluid from the chamber containing the propellant can be metallic or includes a metal. It can be a flexible and/or deformable, pinhole-free metal foil. The density of the diaphragm metal can be greater than 2.0 g per cm$^3$ at 25° C. It can be for example greater than 2.5 g per cm$^3$, such as greater than 4.0 g per cm$^3$, 7.0 g per cm$^3$, or 10.0 g per cm³ at 25° C. Optionally, the tensile strength of the diaphragm material can be greater than 25 MPa, for example it can be greater than 50 MPa, 75 MPa, or 100 MPa at 25±3° C. and/or its elastic modulus can be greater than about 20 GPa, such as greater than 30 GPa, 40 GPa, or 50 GPa. The metallic diaphragm can include, for example, silver or an alloy of silver; alternatively, it can include tin or an alloy of tin; or it can include aluminum or an alloy of aluminum; or it can include magnesium or an alloy of magnesium; or it can include titanium or an alloy of titanium; or it can include copper or an alloy of copper. The diaphragm can be a pinhole-free flexible and/or deformable foil of silver, tin, aluminum, magnesium or copper. When heated, the metallic diaphragm can optionally alloy the metal of the housing, such that the diaphragm is welded at its rim to the housing wall to form a hermetic, gas-impermeable seal (e.g. impermeable to propellant and/or helium). The diaphragm can be shaped to substantially conform to the interior housing wall of the drug chamber, to the interior housing wall of the propellant chamber, or to the interior housing walls of both chambers. As illustrated in FIGS. 23A-C, in a preferred embodiment the propellant-driven pump includes a drug chamber 89 and a propellant chamber 93 separated by a diaphragm 90. The diaphragm 90 is attached to the two housings by a weld 91. The pump further includes a sealable port 92 for introduction of the propellant, e.g., via needle or nozzle injection. FIG. 23A shows the initial configuration of the pump where the drug and propellant chambers are full. FIG. 23B shows the pump partially full and FIG. 23C shows the pump upon completion of the delivery of the drug.

The housing can be made of two or more parts joined together. The parts may be joined together by welding (optionally with a diaphragm) or by forming a compression seal (meaning a seal formed by pressing the parts together), the parts optionally separated by sealant exemplified by a polymer or a soft metal like tin. The interior housing wall of the propellant chamber and interior housing wall of drug chamber can be substantially mirror images of each other, meaning that they can be substantially symmetrical with respect to a central plane, excepting that their ports differ and an interior housing wall of the drug chamber may have grooves or similar flow-enhancing features while the mirroring interior housing wall of the propellant chamber may not have grooves or similar flow-enhancing features.

In a preferred embodiment the housing wall of the drug chamber can include a sealable port that allows for the introduction of a pharmaceutical composition. The port may be temporarily or permanently sealed prior to or after the filling process, e.g., by a grommet, septum, drug delivery nozzle, flow restrictor, or delivery tube. The port may optionally also be used for delivery of the drug during operation of the device, e.g., by attaching a drug delivery nozzle, flow restrictor, or delivery tube. Optionally, the flow-controlling nozzles, channels or tubes can be made of a plastic, such as an engineering plastic. The nozzles, channels or tubes can have an internal diameter less than 1 mm, 0.6 mm, 0.3 mm or 0.1 mm and they can be shorter than 10 cm, 5 cm, 2 cm or 1 cm such as 0.5 cm. Preferred minimum internal diameters are 0.1-2 mm (0.1-0.7 mm, 0.2-0.5 mm, 0.5-0.75 mm, 0.75-1.0 mm, 1.0-1.5 mm, or 1.5-2.0 mm) and preferred lengths are 0.25-5 cm (such as 1-2.5 cm, 1-5 cm, 0.25-0.5 cm, 0.5-0.75 cm, 0.75-1 cm, 1-2 cm, 2-3 cm, 3-4 cm, or 4-5 cm).

Figure 24:
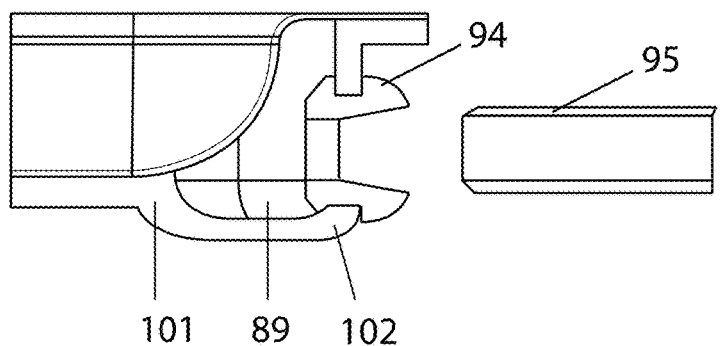
FIG. 24 shows a port 102 in a pump housing 101 forming a wall of a chamber 89 containing a pharmaceutical composition with an elastomeric grommet 94 inserted into the port. A filling nozzle 95 may be inserted through the grommet to fill the drug-containing chamber 89 with the pharmaceutical composition.
Figure 25:
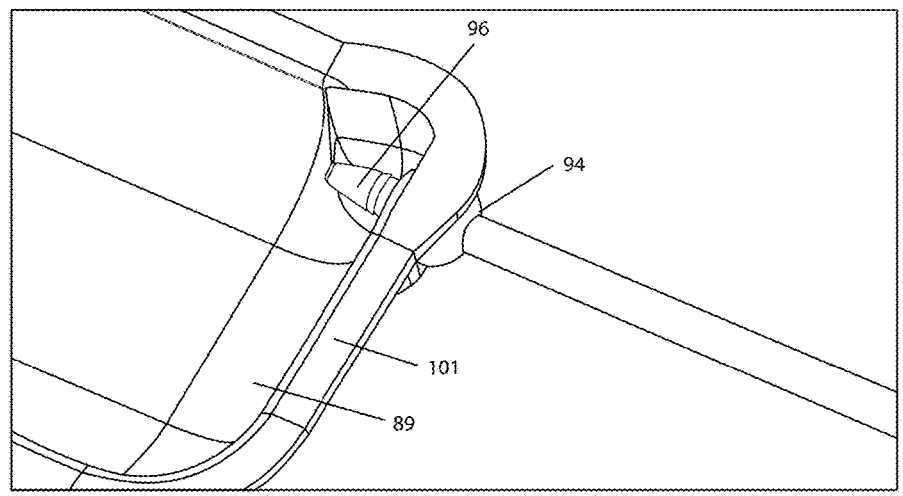
FIG. 25 illustrates a port 102 in a pump housing 101 forming a wall of a chamber 89 containing a pharmaceutical composition with an elastomeric grommet 94 inserted into the port. After filling the drug-containing chamber through the port, the port may then be removed and replaced with the delivery nozzle 96.

FIG. 24 and FIG. 25 show a port 102 in a pump housing 101 forming a wall of a chamber 89 containing a pharmaceutical composition (e.g., a LD/CD suspension) with an elastomeric grommet 94 inserted into the port. A filling nozzle 95 may be inserted through the grommet to fill the drug-containing chamber 89 with the pharmaceutical composition. The filling nozzle 95 may then be removed and replaced with the delivery nozzle 96.

Preferably, the housing wall of the propellant chamber includes a second, sealable port (e.g., containing a grommet, septum, or similar resealable member) for filling the propellant chamber with propellant. A propellant delivery nozzle can be inserted into the septum and the propellant chamber is filled. Preferably, the drug chamber is filled first and the propellant chamber is subsequently filled.

Patient compliance depends on the drug delivery device and retainer being comfortable when worn in the mouth. Preferably, the system does not substantially affect the appearance of the wearer, impede speech, or impede swallowing and drinking. For comfort and in order to avoid substantial change in the appearance of the face of the wearer the oral pump may have a substantially obround shape. An exemplary location of the pump in the mouth is a maxillary location. In general it is preferred that the pump and/or its drug outlet be located such that the likelihood of excessive drug accumulation in the buccal vestibule is avoided. In order to avoid irritation of tissue the surfaces of the pump is smooth. For examples, pump surfaces contacting buccal tissue may have protrusions that are less than about 100 µm, e.g., less than about 30 µm, 10 µm, 5 µm, or 1 µm.

The pump may contain between about 0.1 mL and about 2 mL of the drug-including fluid, such as between about 0.2 mL and about 1.2 mL, for example between about 0.6 mL and about 1 mL. An exemplary pump with a 0.8 mL drug reservoir contains about 1 g of an about 1.25 g/mL density composition. In some compositions, there can be 800 mg/mL of the mostly solid containing composition, the solid being mostly the solid drug itself or mostly solid excipient. When the solid is a drug of about 1.5 g/mL density such as LD or CD, the reservoir can contain about 0.64 g of mostly solid drug.

The pump can be, for example, substantially obround shaped or it can be substantially flattened teardrop shaped. The dimensions of the substantially obround-shaped pump are width, measured from the vestibular surface of the teeth outward, height measured in the direction of tooth eruption, and length measured along the direction of a series of teeth, typically including a molar. The width (outer dimension, OD) of the pump housing can be between about 3 mm and about 10 mm; its height (OD) can be between about 5 mm and about 18 mm; its length (OD) can be between about 10 mm and about 30 mm. Preferably, the length of the pump housing can be such that the pump housing spans one or two teeth, but not three teeth. The thickness of the wall of the housing can be between about 0.2 mm and about 2 mm, such as between about 0.3 mm and about 1.0 mm.

The width of the substantially flattened teardrop shaped pump, its length and the thickness of the housing of the wall can be similar to those of the obround pump. The height of its anterior side when residing in the buccal vestibule can be less than the height of its posterior side. The posterior side can be, for examples, between 1.1 times and twice as high as the anterior side, such as between 1.3 times and 1.8 times as high, e.g., between 1.4 and 1.6 times as high.

In one embodiment the metallic diaphragm is about uniformly thick and it is free of pinholes. The thickness of the pinhole-free metallic diaphragm can be between about 10 µm and about 1 mm. The diaphragm can be, for example, between about 10 µm and 250 µm, e.g., between 20 µm and 125 µm, such as between 25 µm and 75 µm. The thickness and the associated rigidity of the diaphragm, meaning its resistance to change of shape under stress, can vary by less than ±25% across the diaphragm, such as by less than ±10%. In some embodiments the rim of the diaphragm is thicker than the about uniformly thick center in order to facilitate sealing, e.g., creation of a hermetic seal via welding. The about uniformly thick center can constitute about 80% or more of the area of the diaphragm, the thicker rim constituting typically less than about 20% of the area of the diaphragm. The rim of the diaphragm can be more than 1.5 times as thick as its center, e.g., 1.5-2 times as thick as the center, or 2-3 times as thick, or more than 3 times thicker than the center. In another embodiment, the diaphragm has a non-uniform thickness along its length and/or width. This variable thickness allows the diaphragm to counteract internal forces and deflect in a predictable manner.

The peripheral rim of the diaphragm is shaped and sized to match the peripheral rim of the central cross sectional plane of the typically obround or flattened teardrop shaped housing. The diaphragm can be made, for example, by forcing a sheet of metal, such as annealed about pure silver foil or tin foil of a thickness between 0.02 mm and 0.10 mm into a mold. Alternatively, the diaphragm can be made by stamping a formable metal foil or sheet, typically of a thickness between 0.02 mm and 0.10 mm. Parameters that can affect formability include the strain, or work-hardening, exponent of the metal (termed its n-value) and the strain ratio in the width and thickness directions (termed its r-value). Typical r-values of the silver of which the diaphragms are made are from 0.75 to 1.0 and typical n-values are from 0.2 to 0.4. The height of the stamped, metallic, optionally obround, cup-shaped diaphragm (matching about the width of the housing) can be between about 3 mm and about 10 mm; its width (matching the height of the housing) can be between about 5 mm and about 18 mm; and its length can be between about 10 mm and about 30 mm. The optionally obround diaphragm may be folded, pleated, or scored. It can be formed, for example, by hydroforming or by stamping, optionally with heating by hot-stamping. It can be formed by stamping or deep drawing, optionally with heating, or it can be formed by electroplating or by electroless plating.

Optionally, the flexible and/or deformable metallic diaphragm separating the drug and propellant chambers can be welded to the housing to form hermetically sealed chambers with propellant filling and drug delivery ports. The pump can be hermetically sealed, meaning that its drug including chamber and its propellant including chamber are hermetically sealed, except for the one, two or more drug delivery ports from the drug chamber. Each of the chambers can include one or more ports for filling and for release of gas, such as air or nitrogen or any inert gas present in the chamber while it is being filled. The housing wall of the drug including chamber can include one, two, or more hermetically sealable or sealed ports for filling with drug and/or for drug delivery. The ports are hermetically sealable or sealed after filling.

The housing wall of the drug including chamber can include one or more sealable or sealed ports for drug delivery. The propellant containing chamber can be hermetically sealed and can include a hermetically sealable or sealed port for filling with propellant.

When stored, the pump can be hermetically sealed. When in use, the drug can flow or be extruded through the one, two, or more drug delivery ports, to which a flow controlling tubing or pipe can be attached or which can itself control the flow.

As shown in FIGS. 23A-C, for hermetic enclosure the drug chamber 89, propellant chamber 93, and diaphragm 90 are joined by a hermetically sealing weld 91, the hermetically sealing weld 91 preventing, for example, the influx of air or water vapor, or the out-flux of optionally inert gas (e.g., nitrogen or argon), or of water vapor, or of saliva, or the out-flux of any constituent of the drug including composition from the drug chamber, or the out-flux of propellant from the propellant chamber during the rated shelf-life of the device, which can be longer than 3 months, such as longer than 6, 12, 18, or 24 months. Optionally, the weld can prevent the influx of helium into and/or out-flux of helium from the drug-including chamber, and/or from the propellant-including chamber, or from both chambers. The hermetically sealing weld can be a weld between a metallic housing and a metallic diaphragm, where the metals of the housing and the diaphragm are the same or they can differ. The weld can be, for example between a metal forming a wall of the housing, meaning the wall of a drug-including and/or a propellant-including chamber, and a different metal of the diaphragm, typically melting at a lower temperature than the metal of the housing. For example, the housing can include titanium or an alloy of titanium to which a metallic diaphragm is welded. The diaphragm welded to the titanium or titanium alloy housing can include, for example, silver or an alloy of silver. The hermetically sealing weld can include an alloy of silver and titanium. Alternatively, the housing can include iron or an iron alloy, such as steel exemplified by a stainless steel, and the diaphragm can include silver or a silver alloy or tin. The hermetically sealing weld can be between a metallic diaphragm that can be welded to iron or an alloy of iron. The weld can include, for example, an alloy including silver and iron or silver and nickel. The method of forming the hermetic weld can include, for example, resistance welding, laser welding or electron beam welding. The method of welding can include additional steps like preheating, i.e., heating the diaphragm and the housing prior to their welding, and/or annealing after welding, optionally at a temperature between 400° C. and 700° C. typically for 15 min or more.

Figure 26:
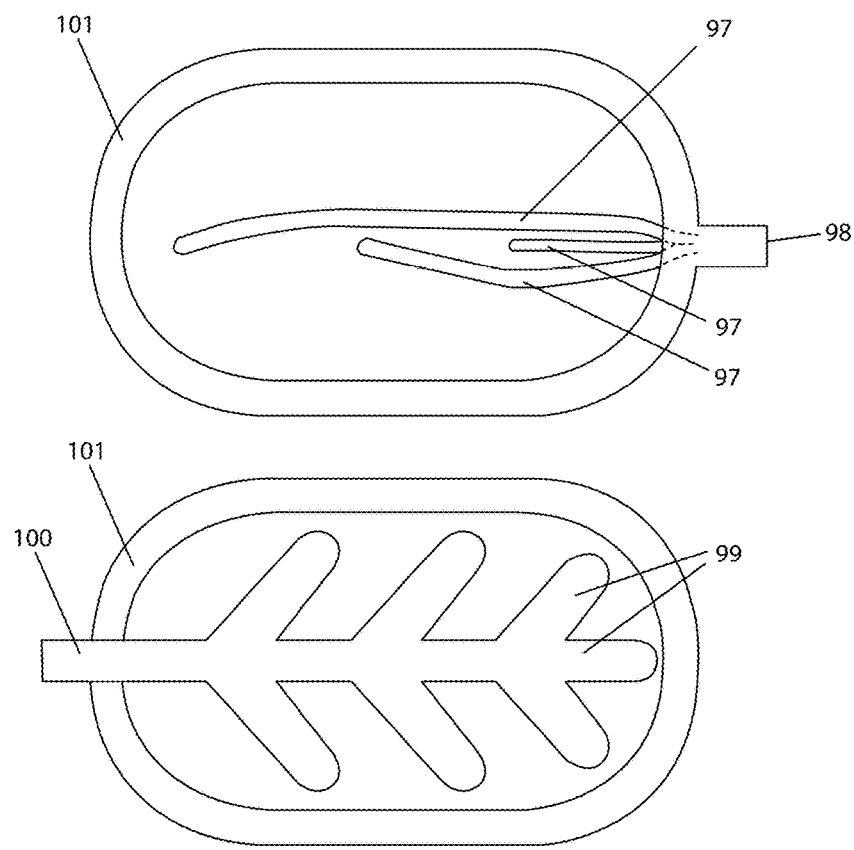
FIG. 26 illustrates a propellant-driven pump including grooves in the surfaces of the chamber including the pharmaceutical composition.

The devices of the invention can include channels, grooves, or tubes providing constant rate delivery of most or nearly all of the drug. During the delivery of the drug the diaphragm may deform such that it partially or completely isolates a volume of the drug-including fluid within the drug-containing chamber from the outlet port or ports. Such isolation can result in stoppage of drug flow or reduction in the flow rate of the drug including fluid while the chamber still contains a substantial fraction of the fluid. In order to deliver at an about constant rate most or nearly all of the drug including fluid in the chamber, the device can include channels that reduce or eliminate blockage by the diaphragm when it extends into the drug-including chamber during the delivery. Exemplary blockage reducing or preventing channels are tubes inserted in the drug including chamber and connected to one outlet port or several outlet ports in the chamber; or a groove-including insert in the chamber; or a groove or grooves in a wall of the chamber. For example, a grooved plate or a tube can be inserted in the drug including chamber to form a channel or multiple channels in which the drug can flow. The tube, tubes, groove or grooves can form a channel or multiple channels that remain open and unblocked by the diaphragm after more than 50% (such as more than 60%, 70%, 75%, 80%, 85%, 90%, or 95%) of the weight of the drug in the chamber can be delivered. Optionally, there are multiple grooves forming multiple flow channels that are optionally interconnected, the interconnections allowing flow between the channels. FIGS. 26A and 26B show exemplary grooves in surfaces of the drug including chamber. In one embodiment illustrated in FIG. 26A, the grooved flow channels 97 cause flow from individual locations within the pump to channel to the nozzle 98. In another embodiment illustrated in FIG. 26B, the interconnected flow channels 99 form a network of channels that feed into a single central channel 100 in the housing wall 101.

The groove or grooves are typically 1 mm to 20 mm long, 0.5 mm to 3 mm wide, and 0.5 mm to 3 mm deep. The tube or tubes are typically 1 mm to 20 mm long, 0.5 mm to 3 mm wide, and of 0.5 mm to 3 mm diameter. The number of optionally interconnected flow channels 99 formed by the grooves is typically between 1 and 10. Typically at least one groove-associated flow channel remains open after the diaphragm has been fully extended into the drug chamber at or near the exhaustion of the drug contained in the chamber.

of the diaphragm may corrode visibly after 3 months while the housing metal and the diaphragm metal are electrically shorted and are immersed in an air-exposed 0.1 M citrate buffer solution of about pH 4.0 at about 23±3° C. The density of the current flowing between two electrically shorted electrodes of about equal area, one of the metal of the rigid housing, the other of the metal of the diaphragm, can less than 2 µA cm$^{-2}$ such as less than 0.5 µA cm$^{-2}$, for example less than 0.1 µA cm$^{-2}$ when the electrodes are immersed in a substantially de-oxygenated about pH 4 0.1 M citrate buffer solution at 23±3° C. for 24 hours or more.

In order to obtain the desired rate of delivery of the pharmaceutical composition without clogging the flow restrictor (e.g., the nozzle) the apparent viscosity and the particle size of the pharmaceutical composition, the vapor pressure, as well as the diameter and length of the flow restrictor are simultaneously controlled. Table D provides exemplary ranges for these simultaneously controlled parameters for an intra-oral drug delivery device and formulation of the invention.

TABLE D

Exemplary parameter ranges for continuous intra-oral drug delivery devices and formulations

| | Viscosity at about 37° C., Poise | Flow Restrictor ID, mm | Flow Restrictor Length, cm | Propellant Vapor Pressure, bar at about 37° C. | Oral Extrusion Rate, mL/hour | Drug or Excipient Particle Size, $D_{90}$, µm* | Drug or Excipient Particle Size, $D_{50}$, µm** |
|---|---|---|---|---|---|---|---|
| Possible | 100-500,000 | 0.05-3.00 | 0.25-20 | 1.2-50 | 0.001-1.000 | 0.1-200 | 0.1-50 |
| Typical | 200-100,000 | 0.1-0.7 | 1.0-5.0 | 2.5-15.0 | 0.03-0.5 | 1.0-50 | 0.5-30 |
| Preferred | 500-75,000 | 0.2-0.5 | 1.00-2.5 | 4.0-10.0 | 0.05-0.2 | 3.0-30 | 2.00-20.0 |

*Measured by light scattering when the particles are suspended in a non-solvent, e.g. with a Malvern Ltd (UK) Mastersizer.
**Typically the viscous compositions contain drug particles and/or excipient particles and can be pastes; they can, however, also be gels or true solutions, e.g., thickened (made viscous by a dissolved macromolecule) particularly when the drug concentration is low and/or the drug is highly soluble (its concentration being, e.g., between 0.001 mg/mL and 500 mg/mL).

In a preferred embodiment, greater than 60% (e.g., 75%-85%, 86%-95%, or greater than 95%) of the drug-including fluid can be dispensed while the delivery rate varies by less than ±20% (e.g., less than ±15%, ±10%, or ±5%) over a period of greater than or equal to 4 hours (e.g., greater than or equal to 8, 16, or 24 hours).

In a related embodiment, the flexible and/or deformable diaphragm may be shaped and sized such that it contacts only a limited portion (or even none) of the interior wall surface of the drug chamber (excluding the surface area of the diaphragm itself) as the drug chamber approaches exhaustion. For example, the diaphragm may be shaped and sized so that it contacts 0%-10%, 11%-20%, 21%-30%, 31%-40%, or 41%-50% of the interior surface area of the drug chamber (excluding the surface area of the diaphragm itself) after delivery of 85%, 90%, or 95% of the starting drug product in the drug chamber. The interior surface of the drug chamber may include, for example, an interior wall of the pump housing. In a particular embodiment, the flexible and/or deformable diaphragm may be shaped and sized such that it does not contact the drug exit orifice from the drug chamber after delivery of 85%, 90%, or 95% of the starting drug product in the drug chamber.

Typically, neither the metal of the rigid housing nor of the diaphragm may corrode visibly after 3 months when the housing metal and the diaphragm metal are electrically shorted and are immersed in a substantially de-oxygenated 0.1 M citrate buffer solution of about pH 4 at about 23±3° C. The de-oxygenated solution can be a solution kept under nitrogen. Typically, neither the metal of the rigid housing nor The oral device can continuously or semi-continuously extrude or infuse a viscous drug-containing composition into the mouth; it can also include a mechanical pump comprising, for example, a spring, pressurized gas, or propellant. The device can include a flow restrictor such as a nozzle, a channel, a tube or any other flow or extrusion restricting component. The extrusion or flow rate through the nozzle can depend on its internal diameter, on its length, and on the vapor pressure of the liquid propellant.

The oral device can include a viscous drug-containing paste, or a viscous orally infused drug-containing solution, or a viscous orally-infused drug containing suspension extruded or infused into the mouth at a rate that can be between 0.001 mL/hour and 1.25 mL/hour (e.g., 0.015-1.25 mL/hour). The viscosity of the paste, the solution or the suspension can be greater than 100 poise and less than 500,000 poise at about 37° C.; its extrusion rate or flow restrictor (e.g., nozzle) can have an internal diameter between 0.05 mm and 3.00 mm and a length between 0.25 cm and 20 cm (e.g., 0.5-4 cm); the device can include a propellant having a vapor pressure at about 37° C. greater than 1.2 bar and less than 50 bar (e.g., 1.5-10 bar). When a paste including drug particles and/or excipient particles is extruded into the mouth, the particle size distribution, measured by light scattering (e.g. with a Malvern Mastersizer after dispersing the paste in a liquid non-solvent) can have a $D_{90}$ between 0.1 µm and 200 µm and a $D_{50}$ between 0.1 µm and 50 µm.

A typical device can include a viscous drug-containing paste, or a viscous orally infused drug-containing solution, or a viscous orally-infused drug-containing suspension, extruded or infused into the mouth at a rate that can be between 0.03 mL/hour and 0.5 mL/hour. The typical viscosity of the paste, solution or suspension can be greater than 200 poise and less than 100,000 poise at about 37° C.; its extrusion rate or flow rate can be controlled mostly by a flow restrictor (e.g., nozzle) which can have an internal diameter between 0.1 mm and 0.7 mm and can be between 1 cm and 5 cm long; the typical device can also include a mechanical pump. The mechanical pump can include a propellant having a vapor pressure at about 37° C. that can be greater than 2.5 bar and can be less than 15 bar. When a paste including drug particles and/or excipient particles is extruded into the mouth, the particle size distribution measured by light scattering (e.g., with a Malvern Mastersizer after dispersing the paste in a liquid non-solvent) can have a $D_{90}$ between 1 µm and 50 µm and a $D_{50}$ between 0.5 µm and 30 µm.

In a preferred embodiment the device can include a viscous drug-containing paste, or a viscous orally infused drug-containing solution, or a viscous orally-infused drug containing suspension, extruded or infused into the mouth at a rate 0.05 mL/hour and 0.2 mL/hour. The paste, or the solution, or the suspension can have a viscosity greater than 500 poise and less than 75,000 poise; its extrusion rate or flow rate can be controlled mostly by a flow restrictor (e.g., nozzle), which can have an internal diameter between 0.2 mm and 0.5 mm and a length between 1 cm and 2.5 cm; the device can also include a propellant having a vapor pressure at about 37° C. that can be greater than 4 bar and can be less than 10 bar. When a paste including drug particles and/or excipient particles is extruded into the mouth, the particle size distribution measured by dispersing the particles in a liquid non-solvent by light scattering (e.g., with a Malvern Mastersizer after dispersing the paste in a liquid non-solvent) can have a $D_{90}$ between 3 µm and 30 µm and a $D_{50}$ between 2 µm and 20 µm.

Also disclosed is the method of continuously or semi-continuouslty orally extruding or infusing a viscous drug-containing paste, or for infusing a viscous drug-containing solution, or a viscous drug-containing suspension, at an extrusion rate or flow rate between 0.001 mL/hour and 1.25 mL/hour; the paste, solution or suspension can have a viscosity greater than 100 poise and less than 500,000 poise; the extrusion rate or the flow rate can be controlled mostly by a flow restrictor (e.g., nozzle) having an internal diameter between 0.05 mm and 3.00 mm and a length between 0.25 cm and 20 cm; the extrusion or infusion can be driven by a mechanical pump. The mechanical pump can include a propellant, the propellant can have a vapor pressure at about 37° C. greater than 1.2 bar and less than 50 bar. The paste or the suspension or the solution can include solid drug and/or excipient particles whose particle size distribution (when dispersed in a non-solvent and when measured by light scattering) can have a $D_{90}$ between 0.1 µm and 200 µm and a $D_{50}$ between 0.1 µm and 50 µm.

In a typical method of oral extrusion or infusion the extrusion or flow rate can be greater than 0.03 mL/hour and less than 0.5 mL/hour and the typical paste, suspension or solution can have a viscosity greater than 200 poise and less than 100,000 poise; the typical flow restrictor (e.g., nozzle) can have an internal diameter can be between 0.1 mm and 0.7 mm and the typical nozzle length can be between 1 cm and 5 cm; a typical propellant can have a vapor pressure at about 37° C. greater than 2.5 bar and less than 15 bar. The typical paste or the suspension or the solution can include solid drug and/or excipient particles whose particle size distribution (when dispersed in a non-solvent and when measured by light scattering) can have a $D_{90}$ between 1 µm and 50 µm and a $D_{50}$ between 0.5 µm and 30 µm.

In a preferred method of oral extrusion or infusion the flow rate can be greater than 0.05 mL/hour and less than 0.2 mL/hour; the preferred paste, suspension or solution can have a viscosity greater than 500 poise and less than 75,000 poise; a preferred flow restrictor (e.g., nozzle) can have an internal diameter between 0.2 mm and 0.5 mm and a length between 1 cm and 2.5 cm; and a preferred propellant can have a vapor pressure at about 37° C. greater than 4 bar and less than 10 bar. The preferred paste or suspension can include solid drug and/or excipient particles whose particle size distribution (when dispersed in a non-solvent and when measured by light scattering) can have a $D_{90}$ between 3 µm and 30 µm and a $D_{50}$ between 2 µm and 20 µm.

Ambient-Pressure and Suction Independent Pump Designs

The invention includes intra-oral drug delivery devices whose rates of drug delivery are substantially independent of increases or decreases in ambient pressure in the mouth and/or in the atmosphere, e.g., devices that do not deliver clinically significant, undesired boluses as the ambient pressure changes. A source of inaccuracy in many device designs, including many pumps pressurized by a spring, a propellant or by compressed gas can be that the rate of drug delivery can vary as (a) the ambient air pressure changes, e.g., at sea level (14.7 psia or 1 bar) versus at 7,000 feet elevation or in an airplane (both about 11.3 psia or 0.78 bar), and (b) the patient sucks on the drug delivery device. The invention includes pressure-invariant pumps whose drug delivery rate can be substantially insensitive to changes in atmospheric pressure. The invention also includes suction-induced flow limiters that substantially reduce or eliminate the delivery of a drug bolus when a patient sucks on the drug delivery device.

In some embodiments, the spring or propellant compartment is hermetically sealed so that the components are not exposed to saliva, food, liquids, and potentially deleterious conditions (e.g., acids, bases, alcohols, oils, and solvents in the mouth). In preferred embodiments, drug delivery devices of the invention include spring or propellant-pressurized surfaces in the spring or propellant compartments that are in fluidic (gas and/or liquid) contact with the ambient atmosphere via one or more ports or openings in the housing of the drug delivery device. Preferred designs for ambient pressure independent spring-driven and propellant-driven pumps are those in which both the drug outlet and the spring or propellant-pressurized surface (e.g., a pressure plate or plunger) are exposed to the ambient pressure, i.e., the pressurized surface is not enclosed within a hermetically sealed chamber. With such a design, changes in ambient pressure are the same at the drug outlet and at the pressurized surface, resulting in no change to the rate of drug delivery.

In another embodiment, the system can be designed to keep the change in the rate of drug delivery within a desired limit by using a sufficiently high pressure inside the device. For example, for the flow rate to vary by less than about 10% across the range of about 1.013 to about 0.782 bar pressure (sea level to about 7,000 feet) the system can be calibrated such that it delivers drug at its target rate at the pressure midpoint, i.e., about 0.898 bar. Then, for a 0.116 bar ambient pressure change to cause less than a 10% change in the rate of drug delivery it is necessary for the drug delivery device to have an internal pressure of greater than about 1.00+(0.116/0.1)=2.16 bar. In such a manner it is possible to achieve any desired accuracy across a specified ambient pressure change. For example, to achieve accuracies within±20%,±15%,±10%,±5%, or ±3% across the ambient pressure range of 1.013 to 0.782 bar requires propellant pressures of about 1.58, 1.77, 2.16, 3.31, and 4.85 bar, respectively. Preferred spring-driven, gas-driven, or propellant-driven drug delivery devices of the invention maintain an internal pressure of greater than or equal to about 1.5, 1.75, 2, 3, 4, or 5 bar.

Figure 15A:
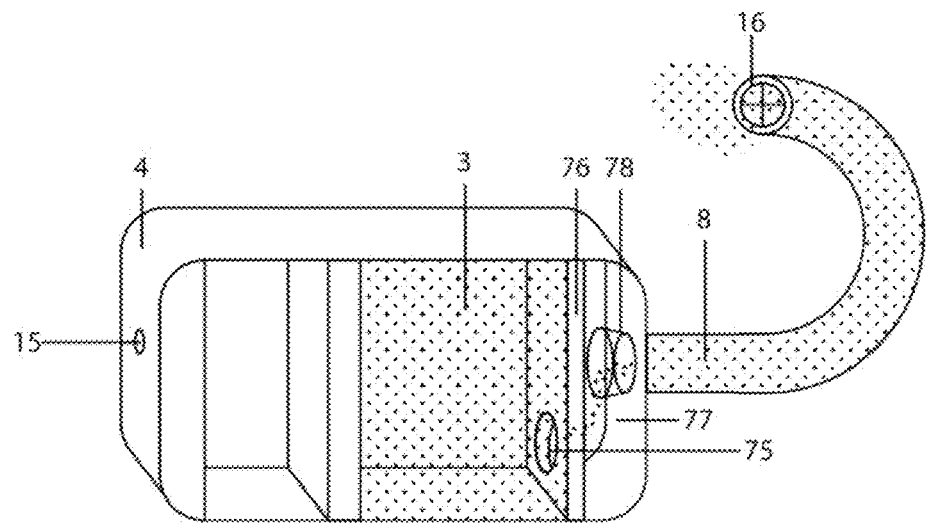
FIGS. 15A, 15B, 16A, 16B, 16C, 16D, 17A, 17B, and 17C illustrate mechanisms which make the drug delivery rate of drug delivery devices insensitive to ambient pressure changes in the mouth.
Figure 15B:
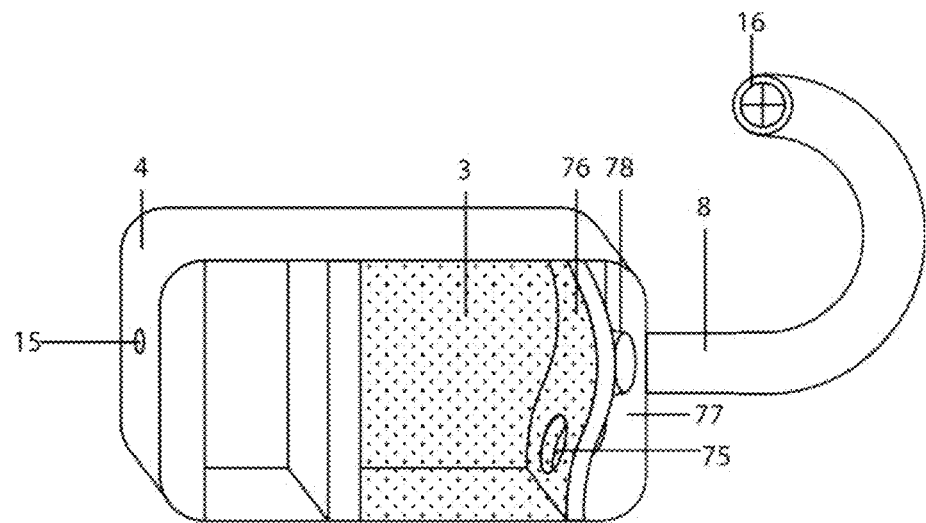

A low pressure condition can be created within the mouth if the patient sucks air out of the mouth or sucks directly on the drug delivery device. Humans are able to draw a negative pressure of up to about 0.14 bar in the mouth. The lowered pressure can cause a drug bolus to be delivered from the drug reservoir into the mouth. In some embodiments, a means is provided for preventing premature evacuation of the drug from the drug reservoir under the suction conditions created within the mouth. One example of such means is a fluidic channel designed such that when the drug is being infused via a pressure head the fluidic channel inflates, and when the pressure in the mouth is low the fluidic channel collapses, the collapse causing it to kink and temporarily halting the infusion of the drug. In another embodiment, low ambient pressure in the mouth causes a diaphragm to deflect and block the drug flow channel, examples of which can be seen in FIGS. 15A and 15B. FIG. 15A shows drug delivery during normal operation. Drug from the drug reservoir 3 is pushed through the orifice 75 in the diaphragm 76 and into a chamber 77 prior to entering the nozzle tube 78 and then out the nozzle with one-way valve 16. In FIG. 15B, an external vacuum is applied to the environment that the device occupies. This causes the diaphragm 76 to be displaced, blocking the orifice 75 from flow and halting flow through the nozzle 78. Another example of a means of addressing the issue of bolus delivery of the drug due to low pressure in the mouth is the use of an inline vacuum-relief valve, such as a float valve that closes the fluidic channel when a vacuum is created and releases the fluidic channel once the vacuum is released.

Figure 16A:
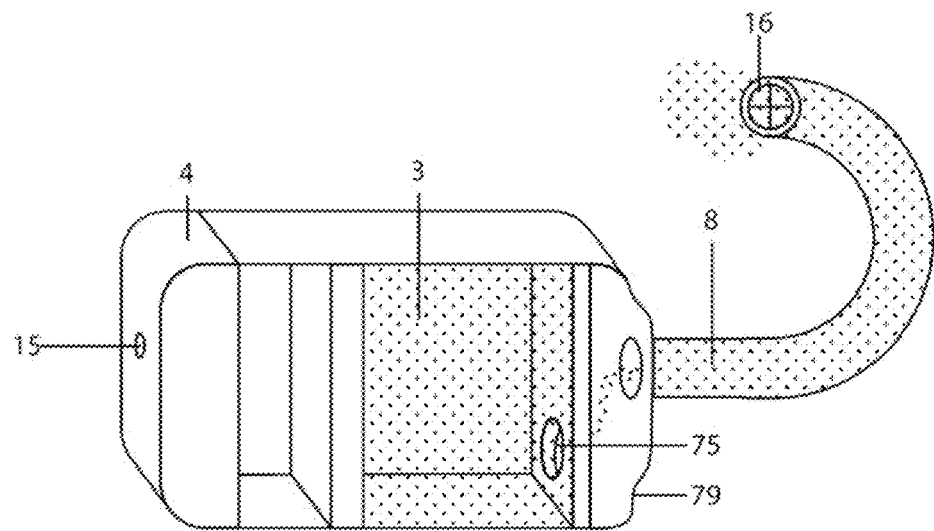
Figure 16B:
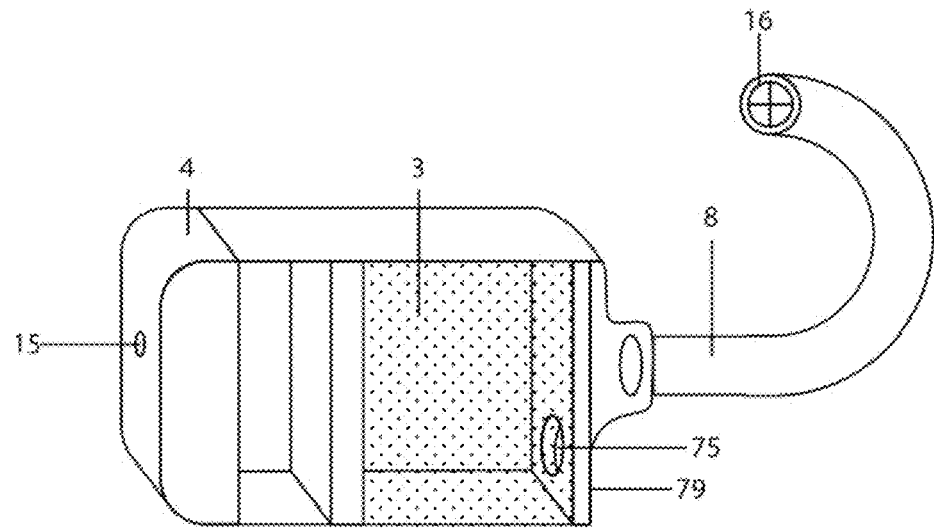
Figure 16C:
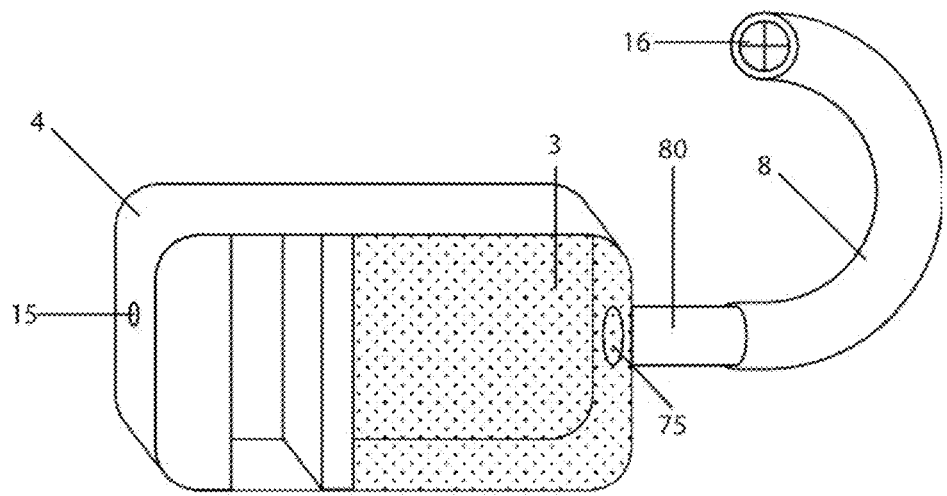
Figure 16D:
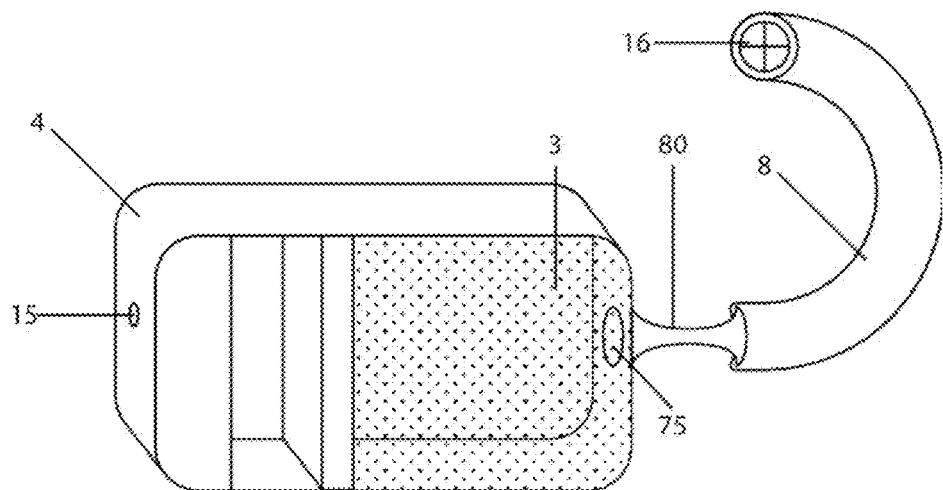

In another embodiment, the drug delivery device includes a compliant accumulator reservoir downstream of the drug reservoir. This accumulator includes a compliant material that collapses and plugs the outlet port from the drug reservoir when the ambient pressure decreases below a specified level. FIGS. 16A and 16B illustrates the mechanism of operation of the accumulator. FIG. 16A shows the concept during normal operation. Drug from the drug reservoir 3 is pushed through an orifice 75 and into the accumulator 79 prior to entering the nozzle tube 8 and then exiting the nozzle via one-way valve 16. In FIG. 16B, an external vacuum is applied to the environment that the device occupies. This causes the accumulator 79 to collapse, blocking the orifice 75 from flow and halting flow through the nozzle 8. Another embodiment is a compliant member that collapses with external vacuum pressure. A compliant tubing 80 is placed in line and is in fluid communication with the drug reservoir 3 and the ambient environment. FIG. 16C shows the device in normal operation. FIG. 16D shows the collapsed compliant tubing 80 when an external vacuum pressure is applied to the system, collapsing the compliant tubing 80 and blocking flow from exiting the one-way valve 16.

Figure 17A:
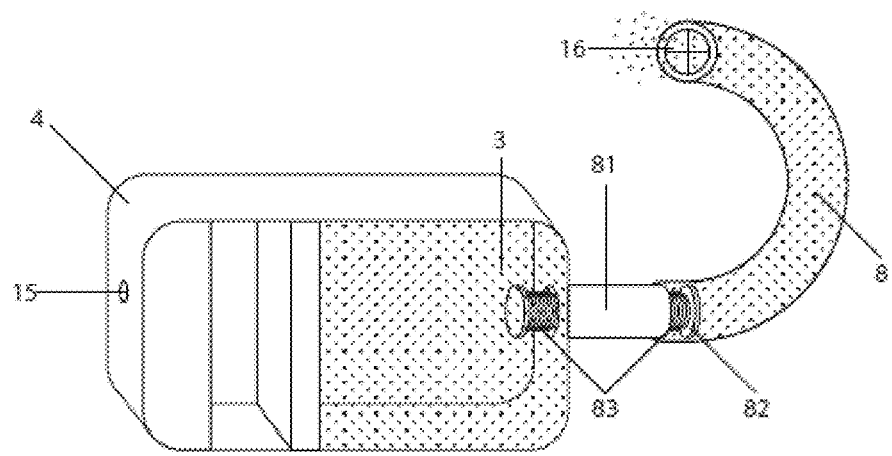
Figure 17B:
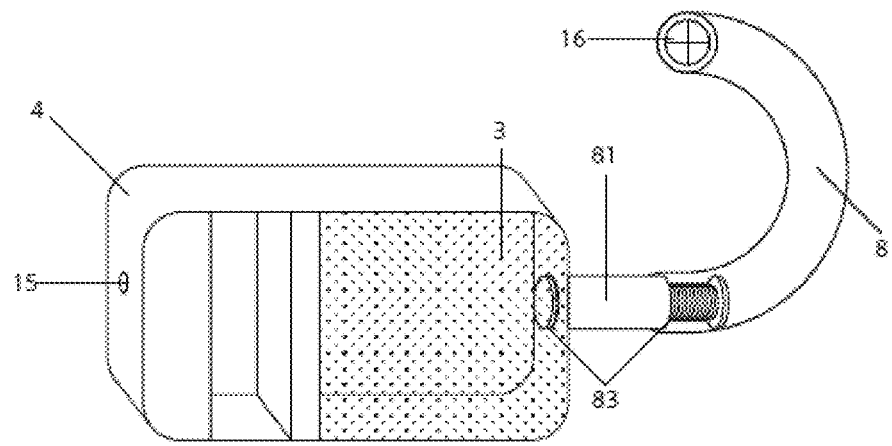
Figure 17C:
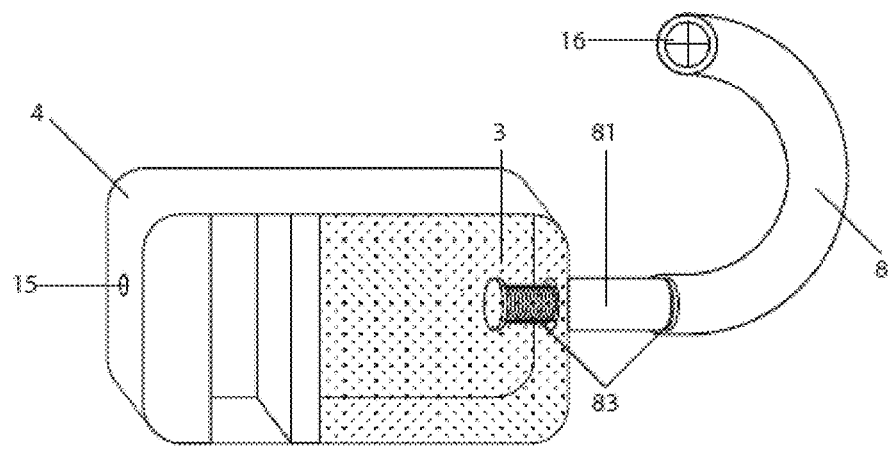

FIGS. 17A, 17B, and 17C illustrate an additional mechanism that prevents bolus delivery in the mouth when a patient sucks on the drug delivery device, and changes in drug delivery rate when the ambient pressure changes. FIG. 17A shows the concept during normal operation. Drug from the drug reservoir 3 is pushed through an orifice tube 81 prior to entering the nozzle tube 8 and then exiting the nozzle with one-way valve 16. In FIG. 17B, an external vacuum is applied to the environment that the device occupies. This causes the float valve 82 to compress the spring 83 and move in the direction of blocking flow from entering the orifice tube 81 and halting flow through the one-way valve 16. In FIG. 17C, an external positive pressure is applied to the environment that the device occupies. This causes the float valve 82 to compress the spring 83 and move in the direction of blocking flow from exiting the orifice tube 81.

In preferred embodiments of these designs for substantially ambient-pressure independent drug delivery devices, the drug delivery device is configured to deliver a bolus of less than about 5%, 3%, or 1% of the contents of a fresh drug reservoir, when the device is sucked on by a patient for a period of about one minute; or when the ambient pressure drops by about 2 psi for a period of about one minute.

Ambient-Temperature Independent Pump Designs and Methods

While the flow rate of electric pumps is typically substantially independent of the ambient temperature the same is not true of passive pumps, such as elastomeric, spring-driven, gas-driven, propellant-driven, or osmotic pumps. The invention includes designs and methods of achieving accurate drug delivery as the ambient temperature surrounding the drug delivery device increases or decreases, i.e., devices that do not deliver clinically significant, undesired boluses as the ambient temperature changes. Osmotic pumps, drug delivery patches and other diffusion-based drug delivery systems are particularly sensitive to changes in the ambient temperature, and transient temperature excursions may permanently change the drug transport characteristics of the diffusion-controlling membranes or pores in these devices. In a preferred embodiment the drug delivery devices of the invention do not substantially change their average long-term rate of drug delivery after exposure to a transient temperature excursion. In preferred embodiments, the invention includes one or more temperature-induced flow limiters which substantially reduce or eliminate the delivery of a drug bolus when a patient consumes a hot drink.

Figure 18A:
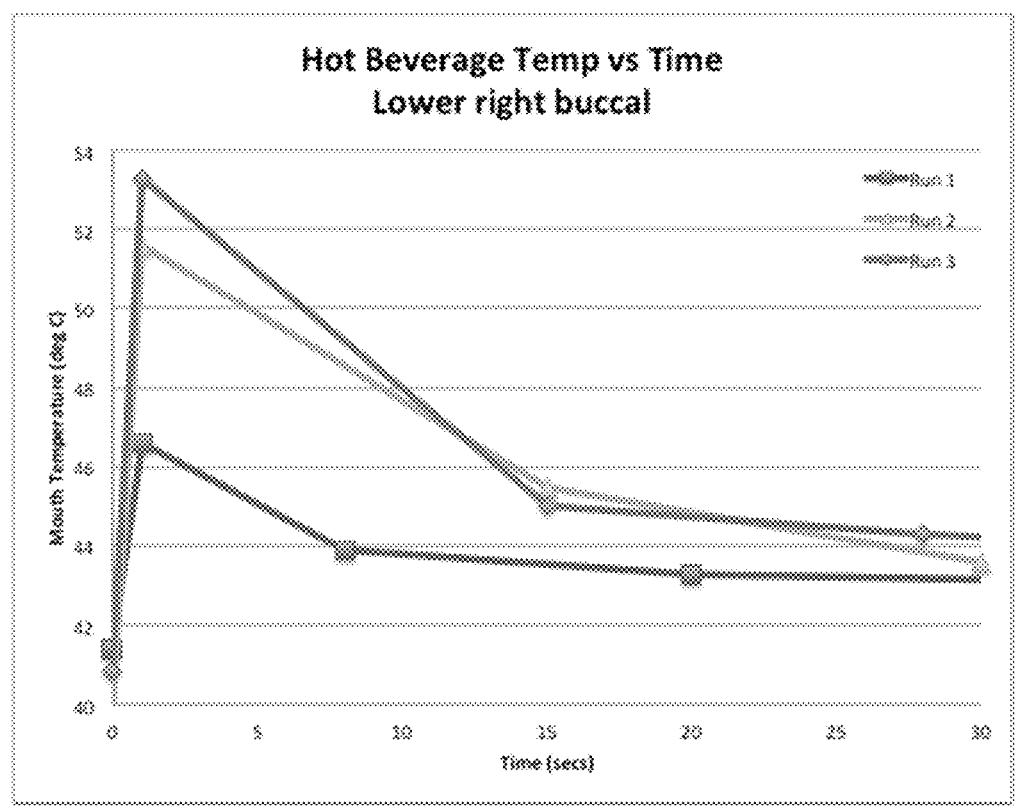
FIGS. 18A and 18B are graphs of the temperature in two locations in the mouth after ingestion of a hot beverage.
Figure 18B:
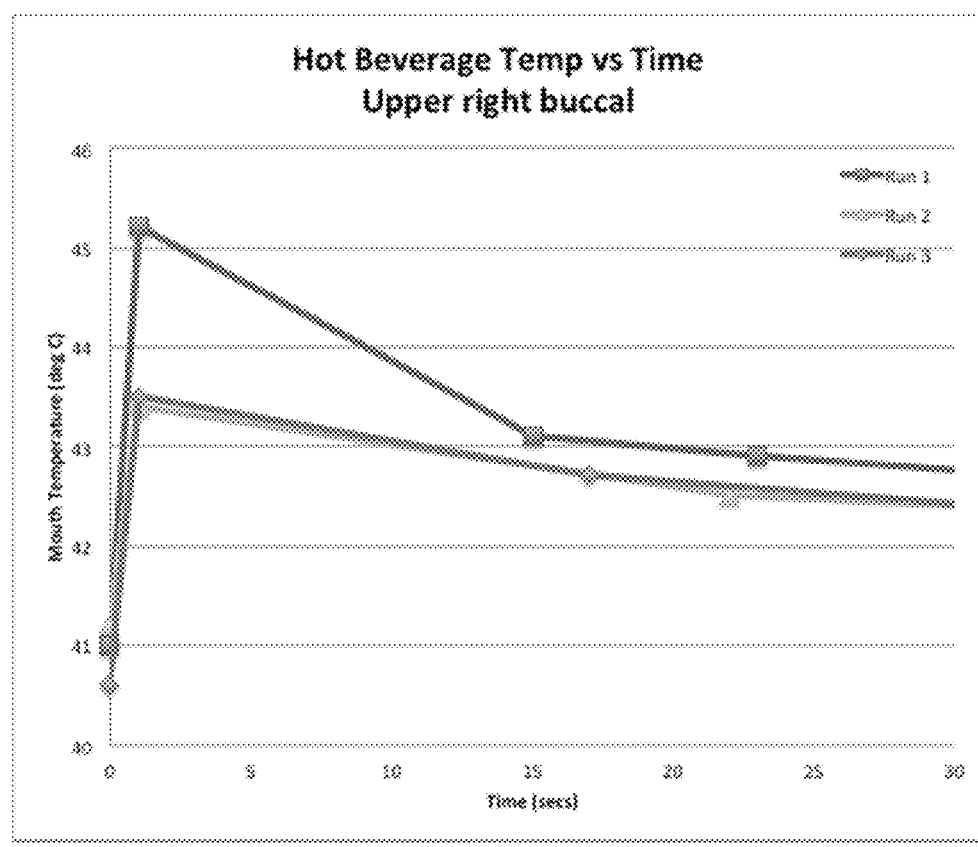
Figure 19A:
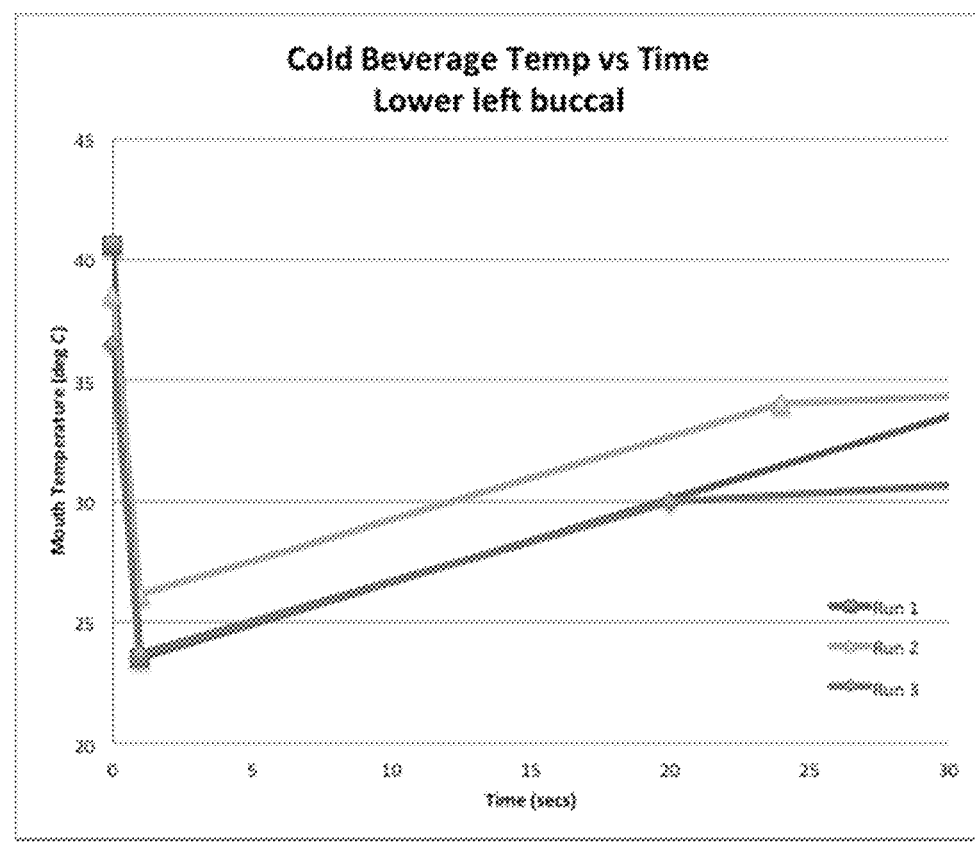
FIGS. 19A and 19B are graphs of the temperature in two locations in the mouth after ingestion of a cold beverage.
Figure 19B:
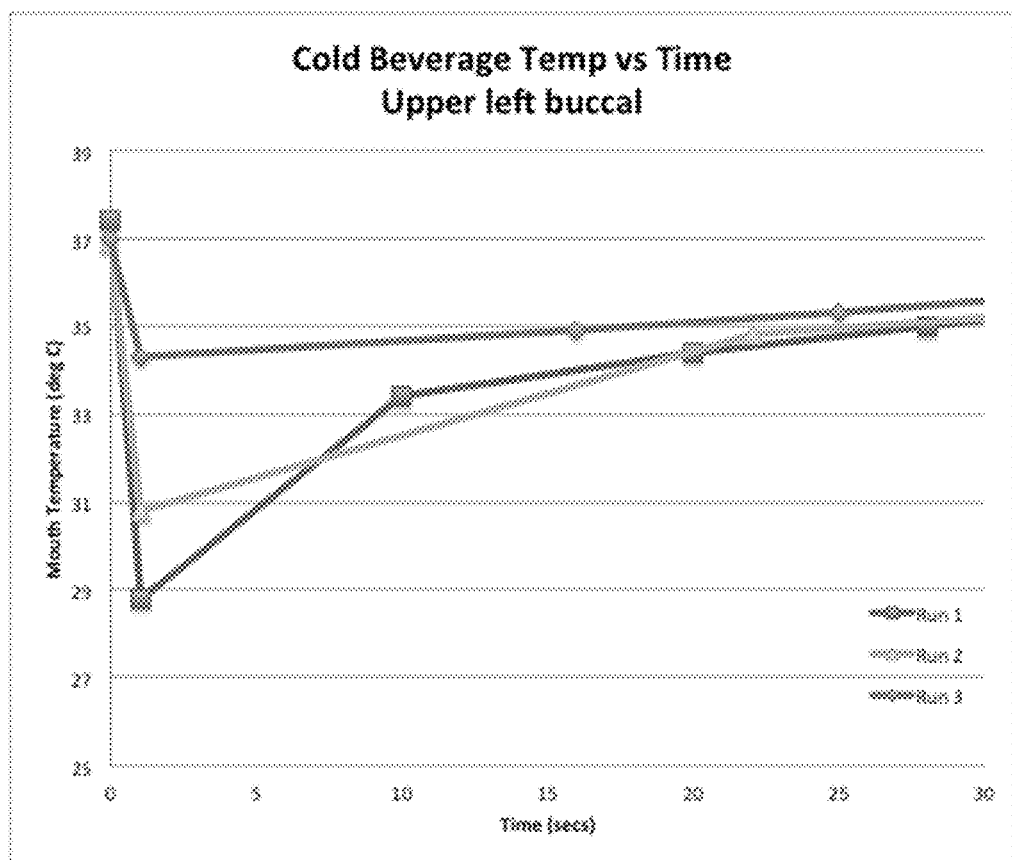

FIG. 18A shows the temperature-time profile in the lower buccal vestibule when a hot drink is sipped. FIG. 18B shows the temperature-time profile in the upper buccal vestibule when a hot drink is sipped. FIG. 19A shows the temperature-time profile in the lower buccal vestibule when a cold drink is sipped. FIG. 19B shows the temperature-time profile in the upper buccal vestibule when a cold drink is sipped. All experiments were performed in a single male patient. A thermocouple was placed in the vestibular space to obtain baseline oral temperature. A beverage was held in the mouth and swished over the location of the thermocouple for approximately three seconds. The data demonstrate that transient temperature excursions routinely occur in the mouth when a hot or cold beverage is consumed, with excursions possible of over about 53° C. and below about 24° C. The data also demonstrate that temperature excursions tend to be significantly reduced in the upper buccal vestibule than in the lower buccal vestibule, with a maximum temperature recorded of about 45° C. vs. 53° C. and a minimum temperature recorded of 29° C. vs. 24° C. Consequently, in a preferred embodiment the drug delivery devices of the invention are located in the upper buccal vestibule rather than in the lower buccal vestibule.

Generally, it is a greater concern when the intra-oral temperature increases rather than decreases, because many non-electric pumps will provide an undesired drug bolus that may be clinically signficant. When the temperature decreases, many non-electric pumps will provide a transient reduction in drug delivery that is generally not clinically significant.

In a preferred embodiment, the drug delivery device is configured to deliver a bolus of less than 5% of the contents of a fresh drug reservoir, when immersed for five minutes or for one minute in a stirred physiological saline solution at about 55° C. In another preferred embodiment, the drug delivery device is configured to change its average rate of drug delivery over a period of one hour in a physiological saline solution of pH 7 at 37° C. by less than about 5% after immersion for five minutes or for one minute in a stirred physiological saline solution at about 55° C., as compared to its average rate of drug delivery immediately prior to exposure to the temperature excursion.

For elastomeric pumps, to minimize the change in flow rate when the patient drinks a hot beverage, it is preferred to utilize elastomeric materials whose force is relatively independent of temperature in the range of about 37° C. to about 55° C. For example, the force in a fresh reservoir may increase by less than about 30%, 20%, or 10% when the temperature is raised from about 37° C. to about 55° C. Examples of elastomeric materials whose mechanical properties change little within these temperature ranges are natural rubbers, such as highly cross-linked polyisoprene and synthetic elastomers such as neoprene.

For spring-driven pumps, to minimize the change in drug administration rate when the patient drinks a hot beverage, it is preferred to utilize spring materials whose force is relatively independent of temperature in the range of about 37° C. to about 55° C. For example, the force in a fresh reservoir may increase by less than 30%, 20%, or 10% when the temperature is raised from about 37° C. to about 55° C. Examples of materials with low sensitivity to temperature changes in this range, that are safe for use in the oral anatomy are 300 series stainless steels, such as 301, titanium, Inconel, and fully austenitic Nitinol (above its austenite finish temperature).

For gas-driven pumps, to minimize the change in flow rate when the patient drinks a hot beverage, it is preferred to minimize the volume of the gas relative to the volume of the drug-including fluid. The volume of the gas can be less than about 40%, 30%, 20%, or 10% of the volume of the drug-including fluid in a fresh reservoir. For example, the force in a fresh reservoir may increase by less than about 30%, 20%, or 10% when the temperature is raised from about 37° C. to about 55° C.

For propellant-driven pumps, it is preferred to use propellants whose vapor pressure increases by less than about 80%, 60%, or 40% when the temperature is raised from about 37° C. to about 55° C. As examples, the vapor pressure of Dupont Dymel HFC-134a (1,1,1,2-tetrafluoroethane) increases from 938 kPa (absolute) at 37° C. to 1,493 kPa (absolute) at 55° C., an increase of 59%. The vapor pressure of Dupont Dymel HFC-227ea/P (1,1,1,2-tetrafluoroethane) increases from about 700 kPa (absolute) at 37° C. to 1,000 kPa (absolute) at 55° C., an increase of 42%. In order to minimize the effect of temperature fluctuations on the propellants, a number of methods can be employed. In one embodiment, an insulating material can be used to decrease the sensitivity to changes in ambient temperature by insulating the propellant and drug reservoirs with materials of low thermal conductivity. Materials such as closed cell neoprene foams, can be used in this embodiment. In another embodiment, a material with very low thermal conductivity can be utilized, such as a ceramic.

Pump Automatic Stop/Start Safety Feature

When the pump is removed from the mouth, it is preferred that the drug delivery be temporarily stopped. This is desirable so that drug is not wasted and, more importantly, so that dispensed drug does not accumulate on the surface of the device. Such an unquantified accumulation of drug on the surface of the device might lead to the undesired delivery of a bolus of an unknown quantity of drug to the patient when the device is reinserted in the mouth. In preferred embodiments, the drug delivery device includes one or more automatic stop/start elements.

In one embodiment, the drug delivery device has an on/off switch or other mechanism for use by the patient. In a preferred embodiment, the drug delivery device automatically stops delivering drug when (1) the drug delivery device, the pump, and/or the oral liquid impermeable reservoir are removed from the mouth; (2) the drug delivery device, the pump, and/or the oral liquid impermeable reservoir are disconnected from their attachment to the interior surface of the mouth, either directly (e.g., when secured to the teeth), or indirectly (e.g., when secured to a fastener which is secured to the teeth); or (3) the oral liquid impermeable reservoir is disconnected from the pump or from the reusable component (e.g., the fastener). In another preferred embodiment, the drug delivery device automatically starts delivering drug when (1) the drug delivery device, the pump, and/or the oral liquid impermeable reservoir are inserted into the mouth; (2) the drug delivery device, the pump, and/or the oral liquid impermeable reservoir are connected to their attachment to the interior surface of the mouth, either directly (e.g., when secured to the teeth), or indirectly (e.g., when secured to a fastener which is secured to the teeth); or (3) the oral liquid impermeable reservoir is connected to the pump or to the reusable component (e.g., the fastener).

In another embodiment, the flow of drug begins when a cap is removed from the orifice from which the drug is delivered into the mouth and halts when the cap is placed back onto the orifice. In a different embodiment, a clip can be placed over the fluidic channel carrying the drug, causing a kink or blockage, thereby halting the flow of drug to the patient. The flow of drug is restored to the patient once the clip is removed. In yet another embodiment, the flow of drug is halted due to the release of a pressure sensitive switch that breaks the circuit of power to the pump, halting the flow of drug when the device is removed from the mouth. The act of replacing the device back onto the dentition closes the pressure sensitive switch, restoring power to the pump and the flow of drug to the patient. In a further embodiment, the fluidic channel kinks, halting the flow of drug, when the device is removed from the patient due to a change in the radius of curvature of the fluidic channel.

Figure 7E:
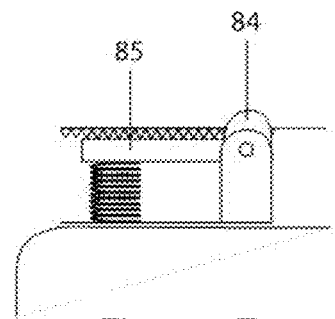
FIGS. 7E and 7F illustrate a spring loaded clutch mechanism 85 useful in the devices of the invention. The clutch mechanism engages the piston 39 to inhibit the force transmission to the drug reservoir 3 prior to use. When the device is removed from the mouth, the protrusion 84 is disengaged, stopping the release of drug from the drug reservoir 3.
Figure 7F:
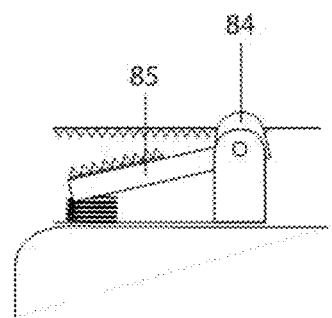

In another embodiment, illustrated in FIGS. 7E and 7F, a protrusion 84 in the drug delivery device is attached to a spring loaded clutch mechanism 85 employed in the device that engages the piston 39 to inhibit the force transmission to the drug reservoir 3 prior to use. This protrusion 84 is depressed when the drug delivery device is placed onto the tooth or teeth, releasing the piston 39 and allowing the piston 39 to transmit force to the drug reservoir 3. When the device is removed from the mouth, the protrusion 84 is disengaged, which again engages the clutch mechanism 85, stopping the piston 39 from applying force to the drug reservoir 3.

In another embodiment, an actuator-connected sensor detects when the device is placed in the mouth. For example an optical sensor can send a signal to turn the device off, the connected actuator halting flow from the pump. In another example, an actuator-connected moisture sensor can signal the connected actuator to turn the device on, initiating flow from the pump.

Concentrated Drug Formulations

Formulations of drugs to be delivered via the drug delivery devices of the invention (such as LD, LD prodrugs, DDC inhibitors, and other drugs) may include non-toxic aqueous or non-aqueous carrier liquids, such as water, ethanol, glycerol, propylene glycol, polyethylene glycols, ethyl lactate and edible oils such as vegetable oils, lipids, monoglycerides, diglycerides or triglycerides, paraffin oil, and their mixtures. The monoglycerides, diglycerides or triglycerides can be of any non-toxic carboxylic acid, the carboxylic acid having typically an even number of carbon atoms. The formulations may also include esters of non-toxic polyols and carboxylic acids, such as carboxylic acids having an even number of carbon atoms. The esterified, partially esterified or non-esterified non-toxic polyol can be, for example, erythritol, sorbitol, arabitol, lactitol, maltitol, mannitol and xylitol. The liquids or their infused mixtures melt or sufficiently soften for pumping typically below about 37° C.

Formulations of the inventions are typically suspensions including one or more drugs (which can be mostly solid particles) and a liquid (which can be an emulsion). The emulsion is typically an oil in water emulsion but can also be a water in oil emulsion. The emulsion typically includes: particles of the one or more drugs; water; a non-toxic, substantially water-insoluble organic compound that is liquid at 37° C., or a mixture of substantially water insoluble organic compounds that are liquid at 37° C.; and at least one surfactant. The weight fraction of the solid drug can be greater than the weight fraction of the substantially water immiscible organic compound or mixture of organic compounds; the weight fraction of the substantially water immiscible organic compounds or mixture of organic compounds can be greater than the weight fraction of water; and the weight fraction of the water can be greater than the weight fraction of the surfactant or surfactants. Typically the weight fraction of the one or more mostly solid drugs in the suspension can be greater than 0.3, such as greater than 0.4, such as greater than 0.5, or such as greater than 0.6. The suspended solid drug can include LD and/or CD. The weight fraction of the suspended LD can be greater than the weight fraction of the suspended CD; it can be, for example, at least twice that of CD, such as at least three times that of CD. The density of the suspension can be greater than 1.1 g/cm$^3$, for example it can be greater than 1.12 g/cm$^3$, 1.15 g/cm$^3$, 1.20 g/cm$^3$, or 1.22 g/cm$^3$. The water immiscible organic compound or mixture of organic compounds can include, for example, triglycerides (exemplified by triglycerides of caproic acid and caprylic acid) or an oil (such as canola oil).

In some embodiments the infused fluid can include drug-containing micelles or liposomes.

Typically the continuous phase of the emulsion is hydrophilic and it can be an oil in water emulsion, which is preferred because it is rapidly dispersed in saliva and other fluids of the gastrointestinal tract, which are aqueous. It can also be hydrophobic and it can be a water in oil emulsion. Typically the weight fraction of the oil in the emulsion is greater than the weight fraction of water. The weight fraction of the oil can be, for example, at least twice the weight fraction of water, for example the weight fraction of the oil can be three times the weight fraction of water or more, even when the continuous phase is water, i.e., the emulsion is an oil in water emulsion. The drug or drugs can be mostly solid, with only some drug dissolved in one of the carrier liquid emulsion phases, e.g., in the water phase of the emulsion.

The physical and chemical stability of suspensions including emulsions, particularly oil in water emulsions, can be superior to their stability in aqueous suspensions, i.e., in suspensions without oil. The superior stability to oxidation by dissolved oxygen may be attributed to the lesser solubilty of drugs like LD and CD in oil than in water and to the greater viscosity of the emulsion, reducing the rate of reaction of diffusionally reacting dissolved molecules. Some liquids provide the benefit of particularly low drug solubility, the low solubility providing the further benefit of slower Ostwald ripening when the drug particles are small. In Ostwald ripening solid particles grow over time by dissolution from highly curved (and therefore highly energetic) particle surfaces and their re-deposition on surfaces of larger particles having with lower curvature.

In preferred embodiments, the intra-orally administered formulation includes a suspension at body temperature, the suspension including solid drug particles of a concentration greater than or equal to 2 M, such as greater than 3 M, greater than 4 M, or greater than 4.4 M (e.g., from 2 M to 4.4 M). For example, the concentration of the one or more drugs in the suspension of the invention can be from about 35% (w/w) to about 70% (w/w). The suspensions can remain free of sedimented solid drug for about 1 month or more or for about 1 year or more at about 25° C. and 1 G. Accelerated testing of the suspensions for physical stability can be conducted via centrifugation. For example, physically stable suspensions can sustain centrifugation at 25° C. at about 16,000 G (meaning 16,000 times the acceleration of sea level) gravity for at least 30, 60, or 90 minutes without sedimenting or creaming.

In addition to the components described herein, the pharmaceutical compositions of the invention can further contain preservatives and antimicrobial agents such as benzoic acid, sodium benzoate, EDTA or its salts, or other transition metal chelating agents or their salts, methylparaben, propylparaben, potassium sorbate, methyl hydroxybenzoate, or propyl hydroxybenzoate; and/or sweeteners like saccharine sodium, flavorings like citric acid, sodium citrate, and antifoaming or defoaming agents like polydimethylsiloxanes and their combinations. They may also include poly-N-vinylpyrrolidone or polyethylene glycol.

Viscosity of the Suspensions

The suspensions may have a shear (dynamic) viscosity greater than 100 Poise, or even greater than 1,000 Poise. For example, the suspensions may have viscosities of 100-1000 cP, 1,000-10,000 cP, 10,000-100,000 cP, 100,000-500,000 cP, 500,000-2,500,000 cP, or greater than 2,500,000 cP. Typically the suspensions can't be poured at about 25° C., even though they can easily deform under pressure.

Aqueous Phase

The suspensions of the invention are typically suspensions of solid drug particles (e.g., solid LD and/or CD particles) in emulsions. The suspensions can contain less than or equal to about 16% (w/w) (e.g., less than or equal to about 13% (w/w), less than or equal to about 11% (w/w), or less than or equal to about 9% (w/w)) of water. The suspensions of the invention can contain greater than or equal to about 1% (w/w) (e.g., greater than or equal to about 2% (w/w) or greater than or equal to about 3% (w/w)) of water. For example, the suspension can contain between about 6% (w/w) and about 9% (w/w) water, such as about 8% (w/w) of water. Even though the weight percentage of water is small, water or the aqueus phase may constitute the continuous phase of the emulsions, i.e., the emulsion in which solid drug particles are suspended can be an oil in water emulsion, the oil droplets being co-suspended in the continuous aqueous phase.

Water Immiscibe Hydrophobic or Oil Phase

Suspensions of the invention include emulsions that include a water-immiscible hydrophobic phase. The hydrophobic (i.e., water immiscible) phase can be an oil. Exemplary oils include edible oils, such as vegetable oils; monoglycerides, diglycerides, or triglycerides; and paraffin oil. The oils can be coconut oil, palm oil, olive oil, soybean oil, sesame oil, corn oil, medium-chain triglycerides (MCT) oil, canola oil, or mineral oil. In certain embodiments, the oil is medium-chain triglycerides (MCT) oil or canola oil. The oil can be coconut oil, or a medium chain triglyceride such as a Miglyol® (e.g., Miglyol® 812). The oil can be a triglyceride of one or more $C_6$-$C_{24}$ (e.g., $C_8$-$C_{16}$) fatty acids. Alternatively, the oil can be a triglyceride of $C_8$-$C_{12}$ fatty acids, $C_{14}$-$C_{18}$ fatty acids, or $C_{20}$-$C_{24}$ fatty acids, or a mixture thereof. The suspension can contain less than or equal to about 30% (w/w) (e.g., less than or equal to 29% (w/w), less than or equal to about 27% (w/w), or less than or equal to about 25% (w/w)) of the oil. The suspension can contain greater than or equal to about 19% (w/w) (e.g., greater than or equal to about 21% (w/w) or greater than or equal to about 23% (w/w)) of the oil. The suspension can contain about 24% (w/w) of the oil. Even though the weight percentage of oil can be greater than that of water, the oil phase may not constitute the continuous phase of the emulsions, i.e., the emulsion can include a continuous aqueous phase in which solid drug particles and oil droplets are suspended.

Drug Particles

Drug particles for use in the pharmaceutical compositions of the invention can be made by using any method known in the art for achieving the desired particle size distributions. Useful methods include, for example, milling, homogenization, supercritical fluid fracture, or precipitation techniques. Exemplary methods are described in U.S. Pat. Nos. 4,540,602; 5,145,684; 5,518,187; 5,718,388; 5,862,999; 5,665,331; 5,662,883; 5,560,932; 5,543,133; 5,534,270; and 5,510,118; 5,470,583, each of which is specifically incorporated by reference.

In one approach, the drug, or a salt thereof, is milled in order to obtain micron or submicron particles. The milling process can be a dry process, e.g., a dry roller milling process, or a wet process, i.e., wet-grinding. A wet-grinding process is described in U.S. Pat. Nos. 4,540,602; 5,145,684; 6,976,647; and EP Patent Publication No. EP498482 (the disclosures of which are hereby incorporated by reference). Thus, the wet grinding process can be practiced in conjunction with a liquid dispersion medium and dispersing or wetting agents such as described in these publications. Useful liquid dispersion media include safflower oil, ethanol, n-butanol, hexane, or glycol, among other liquids selected from known organic pharmaceutical excipients (see U.S. Pat. Nos. 4,540,602 and 5,145,684), and can be present in an amount of about 2.0%-70%, 3%-50%, or 5%-25% by weight based on the total weight of the drug in the formulation.

Drug particles can also be prepared by homogeneous nucleation and precipitation in the presence of a wetting agent or dispersing agent using methods analogous to those described in U.S. Pat. Nos. 5,560,932 and 5,665,331, which are specifically incorporated by reference. Such a method can include the steps of: (1) dispersing drug in a suitable liquid media; (2) adding the mixture from step (1) to a mixture including at least one dispersing agent or wetting agent such that at the appropriate temperature, the drug is dissolved; and (3) precipitating the formulation from step (2) using an appropriate anti-solvent. The method can be followed by removal of any formed salt, if present, by dialysis or filtration and concentration of the dispersion by conventional means. In one embodiment, the drug particles are present in an essentially pure form and dispersed in a suitable liquid dispersion media. In this approach the drug particles are a discrete phase within the resulting mixture. Useful dispersing agents, wetting agents, solvents, and anti-solvents can be experimentally determined.

Drug particles can also be prepared by high pressure homogenization (see U.S. Pat. No. 5,510,118). In this approach drug particles are dispersed in a liquid dispersion medium and subjected to repeated homogenization to reduce the size of the drug particles to the desired $D_{50}$ and distribution. The drug particles can be reduced in size in the presence of at least one or more dispersing agents or wetting agents. Alternatively, the drug particles can be contacted with one or more dispersing agents or wetting agents either before or after attrition. Other materials, such as a diluent, can be added to the drug/dispersing agent mixture before, during, or after the size reduction process. For example, unprocessed drug can be added to a liquid medium in which it is essentially insoluble to form a premix (i.e., about 0.1%-60% w/w drug, and about 20%-60% w/w dispersing agents or wetting agents). In particular embodiments, the dispersing agent is a surfactant (e.g., a non-ionic surfactant). The apparent viscosity of the premix suspension is preferably less than about 1,000 cP. The premix can then be transferred to a microfluidizer and circulated continuously first at low pressures, and then at maximum capacity (i.e., 3,000 to 30,000 psi) until the desired particle size reduction is achieved. The resulting dispersion of drug particles can be included in a pharmaceutical composition of the invention.

The drug particles can be prepared with the use of one or more wetting and/or dispersing agents, which are, e.g., adsorbed on the surface of the drug particle. The drug particles can be contacted with wetting and/or dispersing agents either before, during, or after size reduction. Generally, wetting and/or dispersing agents fall into two categories: non-ionic agents and ionic agents. The most common non-ionic agents are excipients which are contained in classes known as binders, fillers, surfactants and wetting agents. Limited examples of non-ionic surface stabilizers are hydroxypropylmethylcellulose, polyvinylpyrrolidone, Plasdone, polyvinyl alcohol, Pluronics, Tweens and polyethylene glycols (PEGs). Ionic agents are typically organic molecules bearing an ionic bond such that the molecule is charged in the formulation, such as long chain sulfonic acid salts (e.g., sodium lauryl sulfate and dioctyl sodium sulfosuccinate) or fatty acid salts.

The drug particles can include, for example, LD and/or CD, and may optionally further include a COMT inhibitor.

The drug particles present in the suspension of the invention can be sized to have $D_{50}$ less than or equal to 500 µm, e.g., less than or equal to 250 µm, 200 µm, 150 µm, 100 µm, 75 µm, or 50 µm. The drug particles present in the suspension of the invention can be sized to have $D_{50}$ greater than or equal to 1 µm, e.g., greater than or equal to 3 µm, 5 µm, 10 µm, or 25 µm. In some embodiments, the drug particles are sized to have $D_{50}$ in the range of from about 1 µm to about 500 µm (e.g., from about 3 µm to about 250 µm, from about 10 µm to about 250 µm, from about 25 µm to about 200 µm, from about 3 µm to about 100 µm, from about 5 µm to about 50 µm, or from about 7 µm to about 30 µm). In particular embodiments, the drug particles are sized to have $D_{50}$ in the range of from about 1 µm to about 25 µm (e.g., from 1 µm to about 10 µm). In certain embodiments, the drug (e.g., LD or CD) particles can be sized to have $D_{50}$ less than or equal to about 75 µm. In further embodiments, the drug (e.g., LD or CD) particles can be sized to have $D_{90}$ less than or equal to about 20 µm, 50 µm, 100 µm, 150 µm, 200 µm, or 250 µm. In certain embodiments, the drug (e.g., LD or CD) particles can be sized to have $D_{10}$ less than or equal to about 1 µm, 5 µm, or 25 µm. In certain embodiments, the drug (e.g., LD or CD) particles can be sized to have $D_{95}$ less than or equal to about 100 µm (such as less than 50 µm) and/or a $D_{80}$ less than or equal to about 30 µm or about 45 µm.

The maximal solid drug particle diameters may be bimodally or multimodally distributed.

When the pharmaceutical composition is infused and the flow is controlled by a flow-limiting tube or orifice, the peak diameter of the largest particles of the unimodal, bimodal or multimodal particle size distribution is typically smaller than $\frac{1}{10}^{th}$ of its diameter, in order to avoid blockage. Typically, less than about 3% of the partices of the distribution, for example less than 1% of the particles, have diameters that are larger than $\frac{1}{5}^{th}$ of the diameter of the flow-controlling component of the drug delivery device. For example when the diameter of the flow controlling nozzle, orifice or pipe is 1 mm then fewer than 3% or 1% of the particles have diameters greater than about 200 µm, 150 µm, 125 µm, 100 µm, 75 µm, or 50 µm. Typically, the peak of the particle distribution, or when the distribution is multimodal the peak of the distribution of the largest particles, can be of 100 µm or less, for example 50 µm or less, 30 µm or less, or 10 µm or less, or 3 µm or less. In a bimodal distribution the peaks for the smaller particles might be correspondingly about 20 µm or less, 6 µm or less, 2 µm or less or 0.6 µm or less, respectively. Typically the infused suspensions include both LD and CD. The LD particles can be larger than the CD particles (or vice versa) wherefore the particle size distribution can be bimodal. For example the diameters of the LD particles can peak in the distribution at diameters 1.5 times or even larger than the peak diameters of CD particles. The resulting bimodal distribution can provide for denser packing of solid particles in the emulsion, can increase the concentration of the drug, reduce the size of the reservoir containing the daily dose, and reduce the likelihood of flow-impeding aggregation of the particles.

Surfactants

The suspensions of the invention can contain a surfactant in an amount sufficient to provide physical stability adequate for continuous or frequent intermittent intraoral administration of the pharmaceutical composition of the invention. The surfactant can be selected based on its hydrophilic-lipophilic balance (HLB) to match the surface properties of drug particles and the continuous phase (e.g., of water). The surfactant can be an ionic or a neutral surfactant. In general, non-ionic surfactants are preferred and surfactants where the hydrophilic function includes polyethylene oxide are especially preferred.

Non-limiting examples of ionic surfactants are sodium dodecyl sulfate (SDS), phospholipids (e.g., lecithin), quaternary ammonium salts (e.g., cetrimonium bromide), pyridinium salts (e.g., cetylpyridinium chloride), and fatty acid salts. Non-limiting examples of non-ionic surfactants are poloxamers (also known under tradenames Cremophor®, Kolliphor®, Lutrol®, Pluronic®, and Synperonic®), poloxamines, polysorbates (also known under tradename Tween®), fatty acid esters of sorbitan (also known under tradename Span®), polyethylene glycol alkyl ethers (also known under tradename Brij®), fatty acid esters of polyethylene glycol (also known under tradenames Solutol® and Myrj®), alkyl polyglycosides (e.g., alkyl polyglucosides (also known under tradenames Triton® and Ecoteric®)), and fatty acid monoglycerides (e.g., monolaurin).

The suspension of the invention can contain a surfactant that is an emulsifier (e.g., a hydrophobic emulsifier (such as a surfactant having HLB from 3 to 8) or a hydrophilic emulsifier (such as a surfactant having HLB from 10 to 18)). In certain embodiments, the surfactant is a poloxamer or a polysorbate. The suspension of the invention can contain less than or equal to about 7% (w/w) (e.g., less than or equal to about 6% (w/w) or less than or equal to about 5% (w/w)) of the surfactant. The suspension of the invention can contain greater than or equal to about 2% (w/w) (e.g., greater than or equal to about 2% (w/w) or greater than or equal to about 4% (w/w)) of the surfactant. In particular embodiments, the suspension of the invention contains about 5% (w/w) of the surfactant.

The surfactant may be selected from a wide variety of soluble non-ionic surface active agents including surfactants that are generally commercially available under the IGEPAL™ trade name from GAF Company. The IGEPAL™ liquid non-ionic surfactants are polyethylene glycol p-isooctylphenyl ether compounds and are available in various molecular weight designations, for example, IGEPAL™ CA720, IGEPAL™ CA630, and IGEPAL™ CA890. Other suitable non-ionic surfactants include those available under the trade name TETRONIC™ 909 from BASF Wyandotte Corporation. This material is a tetra-functional block copolymer surfactant terminating in primary hydroxyl groups. Suitable non-ionic surfactants are also available under the VISTA ALPHONIC™ trade name from Vista Chemical Company and such materials are ethoxylates that are non-ionic biodegradables derived from linear primary alcohol blends of various molecular weights. The surfactant may also be selected from poloxamers, such as polyoxyethylene-polyoxypropylene block copolymers, such as those available under the trade names Synperonic PE series (ICI), Pluronic® series (BASF), Supronic, Monolan, Pluracare™, and Plurodac™; polysorbate surfactants, such as Tween® 20 (PEG-20 sorbitan monolaurate); nonionic detergents (e.g., nonyl phenoxypolyethoxylethanol (NP-40), 4-octylphenol polyethoxylate (Triton-X100™), Brij nonionic surfactants); and glycols such as ethylene glycol and propylene glycol. In particular embodiments, the surfactant is a non-ionic surfactant including a polyglycolized glyceride, a poloxamer, an alkyl saccharide, an ester saccharide, a polysorbate surfactant, or a mixture thereof.

The weight fraction of the one or more solid drugs in the suspension can be greater than about 0.6. The suspension can be non-pourable. The suspensions can be pumped or extruded into the mouth, for example, by slippage also known as plug-flow, or by a combination of flow and slippage. Slippage or plug-flow means that parts of the suspension, or even all of the suspension move, e.g., through a flow-controlling tube or orifice as a unit or as multiple units, each unit a plastically deformable block such as a cylindrical block. The movement, i.e., flow of the block or blocks can be retarded by friction between the moving block and the wall of the flow-controlling tube. An optional lubricant can reduce the friction and facilitate the extrusion as described below.

Pharmaceutical compositions including the drugs in Table A may be formulated using a variety of formulations. Five formulations (A, B, C, D, and F) for these and other drugs are described below.

Type A Formulations

Type A formulations are pharmaceutical compositions including a suspension, which is typically a highly viscous but nevertheless extrudable paste, the suspension including (i) from about 35% to about 80% (w/w) (e.g., from about 35% to about 70%, from about 35% to about 65%, from about 35% to about 60%, from about 35% to about 55%, from about 35% to about 50%, from about 35% to about 45%, from about 35% to about 40%, from about 40% to about 45%, from about 40% to about 45%, from about 40% to about 50%, from about 40% to about 55%, from about 40% to about 60%, from about 40% to about 65%, from about 40% to about 65%, from about 40% to about 70%, from about 40% to about 75%, from about 45% to about 75%, from about 50% to about 75%, from about 55% to about 75%, from about 60% to about 75%, from about 65% to about 75%, from about 70% to about 75%, or from about 50% to about 65%) undissolved solid drug particles and dissolved drugs, or salts of the solid or dissolved drugs, the solid drugs or their salts decomposing without melting, or melting above 45° C., or softening above 45° C.;

(ii) from about 19% to about 40% (w/w) (e.g., from about 19% to about 28%, from about 19% to about 26%, from about 19% to about 24%, from about 19% to about 22%, from about 19% to about 21%, from about 21% to about 24%, from about 21% to about 30%, from about 24% to about 30%, from about 26% to about 30%, from about 28% to about 30%, or from about 31% to about 40%) of one or more water-immiscible compounds melting or softening at or below 45° C., (iii) from about 2% to about 40% (w/w) (e.g., from about 2% to about 15%, from about 2% to about 13%, from about 2% to about 12%, from about 2% to about 10%, from about 2% to about 8%, from about 2% to about 6%, from about 2% to about 4%, from about 4% to about 13%, from about 6% to about 13%, from about 8% to about 13%, from about 6% to about 10%, from about 10% to about 13%, from about 13% to about 16%, from about 16% to about 25%, from about 25% to about 30%, or from about 31% to about 40%) water, and (iv) from about 1% to about 10% (w/w) (e.g., from about 1% to about 7%, from about 1% to about 5%, from about 1% to about 3%, from about 3% to about 8%, or from about 5% to about 8%) surfactant, wherein the pharmaceutical composition is physically stable and suitable for continuous or frequent intermittent intra-oral delivery.

In some embodiments, the Type A formulations include at about 25° C. greater than about 500 mg/mL of the drug, e.g., between about 500 mg/mL and about 850 mg/mL of the drug.

In some embodiments, the pharmaceutical composition includes a drug particle-containing emulsion. In other embodiments, the solid drug particle containing pharmaceutical composition can be macroscopically substantially homogeneous, when examined at a resolution of 5 mm, 3 mm, 1 mm, or 0.5 mm. In any of the preceding aspects, the suspension may be an extrudable, non-pourable emulsion. In some embodiments, the suspension is physically stable for about 12 months at about 5° C. In other embodiments, the suspension is physically stable for about 12 months at about 25° C. In certain embodiments, after 12 months (e.g., after 13 months, after 14 months, after 15 months, or more) the suspension is physically stable for about 48 hours at about 37° C.

In any of the preceding Type A formulations, the pharmaceutical composition may include a continuous hydrophilic phase.

In any of the preceding Type A formulations, the concentration of drug in a pharmaceutical composition may be at least 1.75 M (e.g, more than 1.80 M, 1.85 M, 1.90 M, 1.95 M, 2.0 M, 2.5 M, 3.0 M, or even 3.5 M). In some embodiments, the pharmaceutical composition includes from about 50% to about 70% (w/w) (e.g., from about 50% to about 65%, from about 50% to about 60%, from about 50% to about 55%, from about 55% to about 70%, from about 60% to about 70%, or from about 65% to about 70%) drug particles, the concentration of drug in the pharmaceutical composition being at least 3.0 M (e.g., 3.1 M, 3.2 M, 3.5 M, or more).

In some embodiments, the suspension of any of the preceding aspects includes one or more water-immiscible compounds that melts or softens below 45° C. (e.g., at 40° C., 37° C., 35° C., or less). In some embodiments, the weight ratio of the one or more water-immiscible compounds to water is greater than 1.0 (e.g., greater than 1.5, greater than 2.0, greater than 3.0, or greater than 5.0).

In some embodiments, the one or more water-immiscible compounds of any of the preceding aspects includes an oil. In some embodiments, the suspension includes a continuous hydrophilic phase. In certain embodiments, the suspension includes an oil in water emulsion. In some embodiments, the suspension is free of polymers of a molecular mass greater than 1,000 Daltons (e.g., greater than about 1,100 Daltons, greater than about 1,200 Daltons, greater than about 1,500 Daltons, greater than about 1,700 Daltons, or greater than about 2,000 Daltons). In some embodiments, the suspension has a dynamic viscosity of at least 100 cP (e.g., greater than 500 cP, 1,000 cP, 5,000 cP, 10,000 cP, 50,000 cP, or 100,000 cP) at 37° C.

In any of the preceding Type A formulations, the suspension may include greater than 50% (w/w) (e.g., greater than 55%, greater than 60%, greater than 65%, or greater than 70%) drug particles. In some embodiments, the $D_{50}$ of the drug particles is less than or equal to about 500 μm, about 250 μm, about 200 μm, about 150 μm, about 125 μm, or about 100 μm. In some embodiments, the $D_{50}$ of the drug particles is greater than or equal to about 1 μm, about 3 μm, about 5 μm, about 10 μm, or about 25 μm. In particular embodiments, the $D_{50}$ of the drug particles is 25±24 μm; 1-10 μm; 11-20 μm; 21-30 μm; 31-40 μm; or 41-50 μm. In other embodiments, the D50 of the drug particles is 75±25 μm; 51-75 μm; or 76-100 μm. In certain embodiments, the $D_{50}$ of the drug particles is 125±25 μm. In further embodiments, the $D_{50}$ of the drug particles is 175±25 μm.

In any of the preceding Type A formulations, the suspension may include less than or equal to about 40% (w/w), such as less than about 35% (w/w), about 25% (w/w), 16% (w/w), about 13% (w/w), about 12% (w/w), about 11% (w/w), or about 9% (w/w) water. In some embodiments, the suspension includes greater than or equal to about 1% (w/w), about 2% (w/w), or about 3% (w/w) water. In certain embodiments, the suspension includes 4±2% (w/w) water. In particular embodiments, the suspension includes 8±2% (w/w) water. In other embodiments, the suspension includes 13±3% (w/w) water. In some embodiments the suspension includes 25±15% (w/w) water.

In any of the preceding Type A formulations, the one or more water-immiscible compounds may include an oil selected from a saturated fatty acid triglyceride, an unsaturated fatty acid triglyceride, a mixed saturated and unsaturated fatty acid tryglyceride, a medium-chain fatty acid triglyceride, canola oil, coconut oil, palm oil, olive oil, soybean oil, sesame oil, corn oil, or mineral oil. In some embodiments, the oil is a saturated fatty acid triglyceride. In other embodiments, the oil is a medium-chain fatty acid triglyceride oil. For example, the oil can be a Miglyol® or chemical equivalent. In certain embodiments, the oil is a canola oil. In particular embodiments, the oil is a coconut oil. In some embodiments, the oil is a triglyceride or one or more $C_6$-$C_{24}$ fatty acids, such as a triglyceride of one or more $C_8$-$C_{16}$ fatty acids. For example, the oil can be a triglyceride of $C_8$-$C_{12}$ fatty acids, $C_{14}$-$C_{18}$ fatty acids, or $C_{20}$-$C_{24}$ fatty acids, or a mixture thereof. In some embodiments, at least 50% (w/w) of the one or more water-immiscible compounds is a triglyceride of one or more $C_8$-$C_{12}$ fatty acids. In certain embodiments, the suspension includes less than or equal to about 30% (w/w) (e.g., about 29% (w/w), about 27% (w/w), or about 25% (w/w)) of the oil. In particular embodiments, the suspension includes greater than or equal to about 19% (w/w) (e.g., about 21% (w/w), or about 23% (w/w)) of the oil. In certain embodiments, the suspension includes 20±2% (w/w) of the oil. In other embodiments, the suspension includes 24±2% (w/w) of the oil. In some embodiments, the suspension includes 28±2% (w/w) of the oil.

In any of the preceding Type A formulations, the pharmaceutical composition may include a surfactant. A surfactant of a pharmaceutical composition may be a non-ionic surfactant. In some embodiments, the non-ionic surfactant includes a polyglycolized glyceride, a poloxamer, an alkyl saccharide, an ester saccharide, or a polysorbate surfactant. In certain embodiments, the non-ionic surfactant includes a poloxamer. In other embodiments, the non-ionic surfactant includes a polyglycolized glyceride that is a polyethoxylated castor oil. In particular embodiments, the non-ionic surfactant includes a polysorbate surfactant that is Polysorbate 60. In some embodiments, the suspension includes less than or equal to about 10% (w/w) (e.g., about 9% (w/w), 8% (w/w), 7% (w/w), about 6% (w/w), or about 5% (w/w)) of the surfactant. In some embodiments, the suspension includes greater than or equal to about 2% (w/w) (e.g., about 3% (w/w) or about 4% (w/w)) of the surfactant. In certain embodiments, the suspension includes about 6±3% (w/w) of the surfactant.

In some embodiments of the Type A formulations, a pharmaceutical composition of any of the preceding aspects further includes an antioxidant such as Vitamin E, TPGS, ascorbylpalmitate, a tocopherol, thioglycerol, thioglycolic acid, cysteine, N-acetyl cysteine, vitamin A, propyl gallate, octyl gallate, butylhydroxyanisole, or butylhydroxytoluene. In some embodiments, the antioxidant is oil soluble. In other embodiments, the pH of the suspension of any of the preceding aspects is less than or equal to about 7.0, about 5.0, or about 4.0. In certain embodiments, the pH is greater than or equal to about 3.0. In some embodiments, the shelf life of the pharmaceutical composition is 1 year or longer at 5±3° C. In particular embodiments, the shelf life of the pharmaceutical composition is 1 year or longer at 25±3° C.

In any of the preceding Type A formulations, the suspension may not cream or sediment when centrifuged for 1 hour at an acceleration of about 5,000 G or greater (e.g., about 7,000 G, about 9,000 G, about 10,000 G, or about 16,000 G) at 25±3° C. In some embodiments, the pharmaceutical composition does not cream or sediment when stored for 12 months at 5±3° C. or 25±3° C. In some embodiments, after the centrifugation or storage the concentrations of drug in the layer containing the top 20 volume % and the layer containing the bottom 20 volume % of the composition differ by less than 10%. In particular embodiments, after the centrifugation or storage the concentrations of drug in the layer containing the top 20 volume % and the layer containing the bottom 20 volume % of the composition differ by less than 6% (e.g., 5%, 4%, 3%, 2%, 1%, or less). In any of these embodiments, after the centrifugation or storage a pharmaceutical composition may exhibit no visible creaming or sedimentation.

In any of the preceding Type A formulations, the pharmaceutical composition may have substantially no taste.

Type A formulations typically include at about 25° C. (a) between 500 mg/mL and 850 mg/mL of the drug when the drug is mostly or entirely a compound having a density of about 1.7 g/mL or less, e.g., of between about 1.3 g/mL and about 1.7 g/mL; (b) when the formulation includes a compound of a metal, such as a compound of magnesium, zinc or iron, the density of which can exceed about 1.7 g/mL, then the composition can include more than 850 mg/mL of the drug, such as between 850 mg/mL and about 2.5 g/mL. The density of the formulations at about 25° C. can be greater than about 1.15 g/mL, such as greater than 1.20 g/mL, such as 1.25 g/mL or greater. The formulations can be non-pourable at about 25° C. but can be extruded at body temperature, typically 37±2° C.

An exemplary physically stable paste composition of an organic compound drug can include about 60-64 weight % of the drug, 23-26 weight % of an oil like Miglyol 812™, 7-9 weight % of water, and 4-6 weight % of a surfactant like Poloxamer 188. An exemplary physically stable paste composition of an inorganic or metal-organic compound drug, such as a compound of magnesium or zinc, can include about 60-80 weight % of the drug, 8-26 weight % of an oil like Miglyol 812™, 3-15 weight % of water and 2-6 weight % water of a surfactant like Poloxamer 188.

Type B Formulations

Type B formulations are pharmaceutical compositions including a suspension, the suspension including (i) from about 25% to about 80% (w/w) (e.g., from about 25% to about 35%, from about 35% to about 70%, from about 35% to about 65%, from about 35% to about 60%, from about 35% to about 55%, from about 35% to about 50%, from about 35% to about 45%, from about 35% to about 40%, from about 40% to about 45%, from about 40% to about 45%, from about 40% to about 50%, from about 40% to about 55%, from about 40% to about 60%, from about 40% to about 65%, from about 40% to about 70%, from about 40% to about 75%, from about 45% to about 75%, from about 50% to about 75%, from about 55% to about 75%, from about 60% to about 75%, from about 65% to about 75%, from about 70% to about 75%, or from about 50% to about 65%) of one or more solid excipients.

(ii) from about 5% to about 60% (w/w) (e.g., from about 5% to about 10%, from about 11% to about 20%, from about 21% to about 30%, from about 31% to about 40%, from about 41% to about 50%, from about 51% to about 50%, from about 51% to about 60%,)drug particles, or salts thereof;

(iii) from about 19% to about 30% (w/w) (e.g., from about 19% to about 28%, from about 19% to about 26%, from about 19% to about 24%, from about 19% to about 22%, from about 19% to about 21%, from about 21% to about 24%, from about 21% to about 30%, from about 24% to about 30%, from about 26% to about 30%, or from about 28% to about 30%) of one or more water-immiscible compounds;

(iv) from about 2% to about 25% (w/w) (e.g., from about 2% to about 20%, from about 2% to about 15%, from about 2% to about 13%, from about 2% to about 12%, from about 2% to about 10%, from about 2% to about 8%, from about 2% to about 6%, from about 2% to about 4%, from about 4% to about 13%, from about 6% to about 25%, from about 6% to about 20%, from about 6% to about 13%, from about 8% to about 13%, from about 6% to about 10%, from about 10% to about 13%, from about 13% to about 16% from about 13% to about 25%, from about 17% to about 25%) water; and (v) from about 1% to about 10% (w/w) (e.g., from about 1% to about 7%, from about 1% to about 5%, from about 1% to about 3%, from about 3% to about 8%, or from about 5% to about 8%) surfactant;

wherein the pharmaceutical composition is physically stable and suitable for continuous or frequent intermittent intra-oral delivery; and In some embodiments, the Type B formulations include at about 25° C. between about 50 mg/mL and about 500 mg/mL of the drug. In some embodiments, the Type B formulations include between 200 mg/mL and about 800 mg/mL (such as between 200 mg/mL and 750 mg/mL) of the solid excipient.

In some embodiments of the the Type B formulations, the solid excipient includes an organic compound. Exemplary organic excipients include cellulose and its derivatives, such as non-swelling cellulose derivative, or amino acids like L-tyrosine or L-phenylalanine. In other embodiments the solid excipient includes an inorganic excipient, such as titanium dioxide or calcium silicate, or calcium phosphate, which can be of higher density and its weight percentage can exceed 80% (w/w).

In some embodiments of the the Type B formulations, the solid drug particle containing pharmaceutical composition includes a drug particle-containing emulsion. In other embodiments, the pharmaceutical composition is macroscopically substantially homogeneous when examined at a resolution of 5 mm, 3 mm, 1 mm, or 0.5 mm. In any of the preceding aspects, the suspension may be an extrudable, non-pourable emulsion. In some embodiments, the suspension is physically stable for about 12 months at about 5° C. In other embodiments, the suspension is physically stable for about 12 months at about 25° C. In certain embodiments, after 12 months (e.g., after 13 months, after 14 months, after 15 months, or more) the suspension is physically stable for about 48 hours at about 37° C.

In any of the preceding Type B formulations, the pharmaceutical composition may include a continuous hydrophilic phase.

In any of the preceding aspects, the concentration of drug in a pharmaceutical composition may be between 0.15 M and 1.0 M (e.g., 0.15-0.25M, 0.25-0.35M, 0.35-0.45M, 0.45-0.55M, 0.55-0.65M, 0.65-0.75M, 0.75-0.85M, or 0.85-1.0 M).

In some embodiments of the the Type B formulations, the suspension of any of the preceding aspects includes one or more water-immiscible compounds that melts or softens below 45° C. (e.g., at 40° C., 37° C., 35° C., or less). In some embodiments, the weight ratio of the one or more water-immiscible compounds to water is greater than 1.0 (e.g., greater than 1.5, greater than 2.0, greater than 3.0, or greater than 5.0).

In some embodiments of the Type B formulations, the one or more water-immiscible compounds of any of the preceding aspects includes an oil. In some embodiments, the suspension includes a continuous hydrophilic phase including greater than 50% (w/w) (e.g., 55%, 60%, 65%, 70%, or 75%) drug particles. In certain embodiments, the suspension includes an oil in water emulsion. In some embodiments, the suspension is free of polymers of a molecular mass greater than 1,000 Daltons (e.g., greater than about 1,100 Daltons, greater than about 1,200 Daltons, greater than about 1,500 Daltons, greater than about 1,700 Daltons, or greater than about 2,000 Daltons). In some embodiments, the suspension has a dynamic viscosity of at least 100 cP (e.g., greater than 500 cP, 1,000 cP, 5,000 cP, 10,000 cP, 50,000 cP, or 100,000 cP) at 37° C.

In some embodiments of the the Type B formulations, the $D_{50}$ of the drug particles and/or of the one or more solid excipients is less than or equal to about 500 μm, about 250 μm, about 200 μm, about 150 μm, about 125 μm, or about 100 μm. In some embodiments, the $D_{50}$ of the drug particles and/or of the one or more solid excipients is greater than or equal to about 1 μm, about 3 μm, about 5 μm, about 10 μm, or about 25 μm. In particular embodiments, the $D_{50}$ of the drug particles and/or of the one or more solid excipients is 25±24 μm; 1-10 μm; 11-20 μm; 21-30 μm; 31-40 μm; or 41-50 μm. In other embodiments, the $D_{50}$ of the drug particles and/or of the one or more solid excipients is 75±25 μm; 51-75 μm; or 76-100 μm. In certain embodiments, the D50 of the drug particles and/or of the one or more solid excipients is 125±25 μm. In further embodiments, the $D_{50}$ of the drug particles and/or of the one or more solid excipients is 175±25 μm.

In any of the preceding Type B formulations, the suspension may include less than or equal to about 16% (w/w), about 13% (w/w), about 12% (w/w), about 11% (w/w), or about 9% (w/w) water. In some embodiments, the suspension includes greater than or equal to about 1% (w/w), about 2% (w/w), or about 3% (w/w) water. In certain embodiments, the suspension includes 4±2% (w/w) water. In particular embodiments, the suspension includes 8±2% (w/w) water. In other embodiments, the suspension includes 13±3% (w/w) water.

In any of the preceding Type B formulations, the one or more water-immiscible compounds may include an oil selected from a saturated fatty acid triglyceride, an unsaturated fatty acid triglyceride, a mixed saturated and unsaturated fatty acid tryglyceride, a medium-chain fatty acid triglyceride, canola oil, coconut oil, palm oil, olive oil, soybean oil, sesame oil, corn oil, or mineral oil. In some embodiments, the oil is a saturated fatty acid triglyceride. In other embodiments, the oil is a medium-chain fatty acid triglyceride oil. For example, the oil can be a Miglyol® or chemical equivalent. In certain embodiments, the oil is a canola oil. In particular embodiments, the oil is a coconut oil. In some embodiments, the oil is a triglyceride or one or more $C_6$-$C_{24}$ fatty acids, such as a triglyceride of one or more $C_8$-$C_{16}$ fatty acids. For example, the oil can be a triglyceride of $C_8$-$C_{12}$ fatty acids, $C_{14}$-$C_{18}$ fatty acids, or $C_{20}$-$C_{24}$ fatty acids, or a mixture thereof. In some embodiments, at least 50% (w/w) of the one or more water-immiscible compounds is a triglyceride of one or more $C_8$-$C_{12}$ fatty acids. In certain embodiments, the suspension includes less than or equal to about 30% (w/w) (e.g., about 29% (w/w), about 27% (w/w), or about 25% (w/w)) of the oil. In particular embodiments, the suspension includes greater than or equal to about 19% (w/w) (e.g., about 21% (w/w), or about 23% (w/w)) of the oil. In certain embodiments, the suspension includes 20±2% (w/w) of the oil. In other embodiments, the suspension includes 24±2% (w/w) of the oil. In some embodiments, the suspension includes 28±2% (w/w) of the oil.

In any of the preceding Type B formulations, the pharmaceutical composition may include a surfactant. A surfactant of a pharmaceutical composition may be a non-ionic surfactant. In some embodiments, the non-ionic surfactant includes a polyglycolized glyceride, a poloxamer, an alkyl saccharide, an ester saccharide, or a polysorbate surfactant. In certain embodiments, the non-ionic surfactant includes a poloxamer. In other embodiments, the non-ionic surfactant includes a polyglycolized glyceride that is a polyethoxylated castor oil. In particular embodiments, the non-ionic surfactant includes a polysorbate surfactant that is Polysorbate 60. In some embodiments, the suspension includes less than or equal to about 8% (w/w) (e.g., about 7% (w/w), about 6% (w/w), or about 5% (w/w)) of the surfactant. In some embodiments, the suspension includes greater than or equal to about 2% (w/w) (e.g., about 3% (w/w) or about 4% (w/w)) of the surfactant. In certain embodiments, the suspension includes about 5±2% (w/w) of the surfactant.

In some embodiments of the the Type B formulations, a pharmaceutical composition of any of the preceding aspects further includes an antioxidant such as Vitamin E, TPGS, ascorbylpalmitate, a tocopherol, thioglycerol, thioglycolic acid, cysteine, N-acetyl cysteine, vitamin A, propyl gallate, octyl gallate, butylhydroxyanisole, or butylhydroxytoluene. In some embodiments, the antioxidant is oil soluble. In other embodiments, the pH of the suspension of any of the preceding aspects is less than or equal to about 7.0, about 5.0, or about 4.0. In certain embodiments, the pH is greater than or equal to about 3.0. In some embodiments, the shelf life of the pharmaceutical composition is 1 year or longer at 5±3° C. In particular embodiments, the shelf life of the pharmaceutical composition is 1 year or longer at 25±3° C.

In any of the preceding Type B formulations, the suspension may not cream or sediment when centrifuged for 1 hour at an acceleration of about 5,000 G or greater (e.g., about 7,000 G, about 9,000 G, about 10,000 G, or about 16,000 G) at 25±3° C. In some embodiments, the pharmaceutical composition does not cream or sediment when stored for 12 months at 5±3° C. or 25±3° C. In some embodiments, after the centrifugation or storage the concentrations of drug in the layer containing the top 20 volume % and the layer containing the bottom 20 volume % of the composition differ by less than 10%. In particular embodiments, after the centrifugation or storage the concentrations of drug in the layer containing the top 20 volume % and the layer containing the bottom 20 volume % of the composition differ by less than 6% (e.g., 5%, 4%, 3%, 2%, 1%, or less). In any of these embodiments, after the centrifugation or storage a pharmaceutical composition may exhibit no visible creaming or sedimentation.

In any of the preceding Type B formulations, the pharmaceutical composition may have substantially no taste.

The density of the formulations at about 25° C. can be greater than about 1.15 g/mL, such as greater than 1.20 g/mL, such as 1.25 g/mL or greater. The formulations can be non-pourable at about 25° C., but can be extruded at body temperature, typically 37±2° C.

An exemplary physically stable paste composition where the excipient is an amino acid like L-tyrosine can include about 10-15 weight % of the drug, 45-55 weight% of the excipient, 23-26 weight % of an oil like Miglyol 812, 7-9 weight % of a surfactant like Poloxamer 188, and 4-6 weight % water. Another exemplary physically stable paste composition, where the excipient is non-swelling cellulose derivative, can include 5-12 weight % of the drug, 20-30 weight % excipient, 20-30 weight % water, 7-9 weight % of a surfactant like Kolliphor RH40, and 25-35 weight% of an oil like Miglyol™ 812. The paste can be non-pourable at about 25° C. and can be extruded at about 37° C. into the mouth, Type C Formulations Type C formulations include between 20 mg/mL and 150 mg/mL (for example between 20 mg/mL and 100 mL, or between 20 mg/mL and 50 mg/mL) of the drug. Type C formulations include true solutions, oil-in-water emulsions or water-in-oil emulsions, or solid particle including suspensions. The formulations can include an excipient that is liquid at or below about 45° C., such as at or below 37° C. Examples of such excipients include DMSO and liquids having at about 25° C. a dynamic viscosity greater than about 50 cP, such as greater than 100 cP, such as glycerol and polyethylene glycols. They can optionally further include surfactants. Typically, the added excipient raises the dynamic viscosity of the formulations to above 100 cP, such as above 1000 cP, above 10,000 cP, or or above 100,000 cP at about 37° C. When dispensed through a flow restrictor, the preferred nozzles, channels or tubes for Type C formulations that are true solutions can have an internal diameter of 10 µm-2 mm (e.g, 10 µm-100 µm, 0.1 mm-0.5 mm, or 0.5-2 mm). Although it can be longer or shorter, the length of the flow restrictor for a Type C true solution is typically 0.2 cm-10 cm.

Type D Formulations

Type D formulations include aqueous solutions, gels or suspensions of metal compounds, such as compounds of magnesium, zinc or iron. Their pH is typically between pH 3 and pH 10, such as between pH 4 and pH 9. Optionally, they contain a gelling agent or viscosity increasing agent, which can be a water soluble polymer, or a water-swollen polymer, such as hyaluronic acid, polyacrylic acid, polymethacrylic acid, alginic acid or a salt of these acids. Typically, the added excipient raises the dynamic viscosity of the formulations to above 100 cP, such as above 1000 cP or above 10,000 cP, above 10,000 cP, or or above 100,000 cP at about 37° C. When dispensed through a flow restrictor, the preferred nozzles, channels or tubes for Type D formulations that are true solutions can have an internal diameter of 10 µm-2 mm (e.g, 10 µm-100 µm, 0.1 mm-0.5 mm, or 0.5-2 mm). Although it can be longer or shorter, the length of the flow restrictor for a Type D true solution is typically 0.2 cm-10 cm.

Type F Formulations

Type F formulations are liquid solutions or gels including between 0.1 mg/mL and 20 mg/mL of the drug. The formulations can contain water or they can be non-aqueous (e.g., <1% water). They can include water and/or an excipient that is liquid at or below about 45° C., such as at or below 37° C. Examples of such excipients include DMSO and liquids having a dynamic viscosity greater than about 50 cP (such as greater than 100 cP at about 25° C.) such as glycerol and polyethylene glycols. They can optionally further include surfactants. When water-including, they can optionally contain a gelling agent or viscosity increasing agent, such as a water soluble polymer or a water-swollen polymer such as hyaluronic acid, polyacrylic acid, polymethacrylic acid, alginic acid or a salt of these acids. Typically, the added excipient raises the dynamic viscosity of the formulations to above 100 cP, such as above 1000 cP, above 10,000 cP, or or above 100,000 cP at about 37° C. When dispensed through a flow restrictor, the preferred nozzles, channels or tubes for Type F formulations that are true solutions can have an internal diameter of 10 µm-2 mm (e.g, 10 µm-100 µm, 0.1 mm-0.5 mm, or 0.5-2 mm). Although it can be longer or shorter, the length of the flow restrictor for a Type F true solution is typically 0.2 cm-10 cm.

Levodopa Formulations

LD is poorly soluble in most non-toxic solvents, including water and alcohols. For example, we have found that in a citrate buffered solution of about pH 4.5 the solubility of LD at 25° C. is only about 0.68 g/100 mL, or 34 mM. LD is even less soluble in alcohols. To deliver a typical daily dose of 1,000 mg approximately 150 mL of saturated LD aqueous solution would be required, which is incompatible with the volume requirements for a drug delivery device placed in the mouth.

DDC inhibitors such as CD are typically co-administered with LD, and it is usually desirable to co-infuse LD and CD. CD is also poorly soluble in non-toxic solvents such as water, further increasing the required volume of infused solution.

This invention features pharmaceutical compositions including COMT inhibitors. The exemplary COMT-inhibitor entacapone is poorly soluble in water, is administered in large daily doses, often of greater than 1 g/day, and has a physiological half-life of less than 1 hour, making it advantageous to continuously or frequently orally co-administer it with LD or LD-CD in suspensions of this invention. It can be co-administered, for example, at a rate between 25 mg/hour and 100 mg/hour.

The invention features a pharmaceutical suspension containing a carrier and levodopa particles optionally admixed with CD (e.g., LD/CD molar ratio is from about 2:1 to about 6:1, such as about 4:1). Preferred suspensions include LD and CD. One or more additional drugs for the treatment of Parkinson's disease may be included in the pharmaceutical compositions of the invention, e.g., a DDC inhibitor, a COMT inhibitor, a drug to treat gastroparesis, a MAO-B inhibitor, adenosine A2 receptor antagonists, or a dopamine agonist.

The preferred dynamic viscosities of the suspensions at about 25° C. are typically greater than 100 cP (i.e., 1 Poise), e.g., they can be greater than 10, 100, 1,000, or even 10,000 Poise. Typically the more viscous suspensions, such as suspensions having viscosities of 1,000 Poise or more, are not pourable. While they can't be poured, they can be extruded into the mouth. The advantage of highly viscous, non-pourable but extrudable emulsions is that they are physically stable, meaning that upon standing, for example for a month, 3 months, 6 months, 1 year, 2 years, or longer than 2 years their suspended solid drug does not sediment. Furthermore, when the viscous suspensions include an emulsion, their aqueous and organic or oil phases may not separate. Another advantage of the viscous suspensions is that the oxidation of their drugs by dissolved oxygen, the rate of which can be diffusion and therefore viscosity-dependent, is greatly slowed. While air-exposed solutions of LD or CD can turn dark, even black, in one day because of air oxidation, the suspensions remain off-white when air-exposed for a month. At the high viscosity also the rate of $O_2$-oxidation of CD whereby toxic hydrazine is produced is reduced, greatly increasing the shelf life, which can be at the typical ambient temperature of 25° C.±3° C. longer than 3 months, such as longer than 6 months, or even longer than 1 year, in which the hydrazine can be less than 8 µg (e.g., 7 µg, 6 µg, 5 µg, 4 µg, 3 µg, 2 µg, or 1 µg) per mg of carbidopa.

Other than the exemplary emulsion-including suspensions of the solid drugs, viscous suspensions of solid drugs could be made with thickeners, such as carboxymethylcellulose. Concentrated sugar solutions, such as sucrose solutions, are also viscous. For example, the solid drugs may be suspended in a sugar (e.g., sucrose, dextrose, glucose) solution containing 40%-70% sugar by weight, e.g., 40%-50% sugar by weight, 50%-60% sugar by weight, or 60%-70% sugar by weight. As previously discussed, the LD and CD formulations may include multimodal particle size distributions.

The pH of the formulations including those of the emulsion including LD and/or CD suspensions can be between 2.5 and 9.5, the more acidic solutions damaging the enamel of teeth and the more basic solutions having bad taste. The pH range between about 3 and 7.5 is preferred and the range between 3 and 5 is most preferred, because of slower air-oxidation of LD and CD, resulting in the case of CD also in a lesser rate of formation of toxic hydrazine and consequently in a longer shelf life when the shelf life is limited by the hydrazine content, as it is in the jejunally infused Duodopa™.

The LD/CD including pharmaceutical compositions can have an apparent pH (meaning a pH measured by inserting a glass walled pH electrode into the composition) of more than pH 2 but less than pH 5 (e.g., less than pH 4, less than pH 3.5, between about pH 2.7 and about pH 3.3, or about pH 3) and it can remain less than pH 5 (e.g., less than pH 4, less than pH 3.5, or about pH 3) after 3 months storage at 25±3° C. The compositions can include a bacteriostatic and/or a fungistatic agent, such as benzoic acid or a benzoate salt. The combined concentrations of benzoic acid and benzoate salt such as its sodium salt is between 0.1 weight % and 1.0 weight % (such as between 0.2 weight % and 0.6 weight %) of the pharmaceutical composition and can optionally include more benzoic acid than benzoate salt, e.g. sodium benzoate. The compositions can also include a transition metal ion complexing agent such as EDTA and/or its salts, such as its sodium salts. The concentration of the EDTA and its salts (e.g. sodium salts) is between 0.05 weight % and 0.25 weight % of the pharmaceutical composition. The pharmaceutical composition may include a sulfur-including compound, such as a thiol reacting at 25±3° C. with dopaquinone or with the quinone formed by oxidation of carbidopa, exemplified by cysteine or N-acetylcysteine.

In general, the color of the emulsion-based suspensions of LD and CD when exposed to air at ambient temperature (about 25° C.) remains off-white for at least one week, e.g., 2 weeks or more or 1 month or more.

The densities of the emulsion-including suspensions in the absence of trapped air can be between about 1.15 g/cm$^3$ and about 1.3 g/cm$^3$, such as between about 1.20 g/cm$^3$ and 1.27 g/cm$^3$. Most of the trapped air can be removed by centrifugation.

Method of Preparing the Concentrated Formulations of the Invention

The invention also features a method of preparing the pharmaceutical composition of the invention. The method can involve contacting (e.g., mixing) solid particles of the drug with an aqueous solution containing a surfactant and water, whereby a mixture of the solid particles with the aqueous surfactant solution is produced, followed by mixing with an oil. Pharmaceutical compositions that can be prepared according to this method are described herein.

Control of Hydrazine Formation

Stored CD is known to degrade such that hydrazine is produced. In animal studies, hydrazine shows notable systemic toxicity, particularly upon inhalation. Hydrazine is also hepatotoxic, has CNS toxicities (although not described after oral treatment), and is genotoxic as well as carcinogenic. Consequently, it is important to minimize hydrazine formation during storage of CD or LD/CD formulations.

Duodopa™, a LD/CD suspension for continuous intraduodenal infusion, produces hydrazine during storage. The average recommended daily dose of Duodopa is 100 mL, containing 2 g levodopa and 0.5 g CD. The maximum recommended daily dose is 200 mL. This includes hydrazine at up to an average exposure of 4 mg/day, with a maximum of 8 mg/day. In order to meet these exposure limits, Duodopa's labeling (outside the USA) states that its refrigerated, unopened shelf life is just 15 weeks, and that once removed from the refrigerator and opened the product may only be used for up to 16 hours. In the United States, Duodopa (sold in the USA as Duopa) requires frozen storage and its labeled shelf life is 12 weeks refrigerated (after thawing). The concentrations of LD and CD in Duodopa are 20 mg/mL and 5 mg/mL, respectively.

A stable fluid formulation of CD that does not contain high levels of hydrazine and that can be stored unrefrigerated for extended periods of time is desirable. Hydrazine is produced almost entirely by oxidation of CD in solution; as more of the dissolved CD is degraded over time, more of the suspended CD is dissolved and is itself degraded. In this way significant amounts of hydrazine can accumulate over time. Hydrazine is not produced in significant quantities by oxidation of suspended CD particles. Therefore, the amount of hydrazine produced is greatly reduced by simultaneously minimizing the amount of aqueous or non-aqueous liquid in which the hydrazine can dissolve, and maximizing the concentration of the suspended solid CD. Such an approach maximizes the ratio of the suspended solid CD to the dissolved CD. The invention features an oral liquid impermeable reservoir containing a suspension of CD in a fluid volume of 0.20-5.0 mL, wherein the concentration of solid CD suspended in the fluid is 50-500 mg/mL. The invention features a CD suspension containing less than about 4 mg, 1 mg, or 0.25 mg of hydrazine per 500 mg of CD after storage of the suspension at 5±3° C. for 1 year, or at 25±3° C. for 3 months, 6 months, 12 months, or 24 months. Preferred reservoirs are substantially free of oxygen and are substantially impermeable to oxygen. Preferably, LD is also present in the drug reservoir. Preferrably the drug is formulated with a carrier (e.g., an emulsion) in which CD has a very low solubility, such as water-oil emulsion. Because of the poor solubility of CD in the carrier used in the suspensions of the invention, most of the CD is in the solid, particulate form. Because hydrazine is formed mostly or exclusively of dissolved CD, not of solid particulate CD, the decomposition of CD, with concomitant formation of hydrazine, is minimized.

To further reduce the formation of hydrazine, the CD-including pharmaceutical compositions can have an apparent pH (meaning a pH measured by inserting a glass walled pH electrode into the composition) of more than pH 2 but less than pH 5 (e.g., less than pH 4, less than pH 3.5, between about pH 2.7 and about pH 3.3, or about pH 3) and it can remain less than pH 5 (e.g., less than pH 4, less than pH 3.5, or about pH 3) after 3 months storage at 25±3° C. The compositions can also include a transition metal ion complexing agent such as EDTA and/or its salts, such as its sodium salts. The concentration of the EDTA and its salts (e.g. sodium salts) is between 0.05 weight % and 0.25 weight % of the pharmaceutical composition. The pharmaceutical composition may include a sulfur-including compound, such as a thiol reacting at 25±3° C. with dopaquinone or with the quinone formed by oxidation of carbidopa, exemplified by cysteine or N-acetylcysteine.

Pump-Driven Suspension Separation

The inventors observed that some suspensions with high solid drug concentrations maintain their uniformity of composition, i.e., may not show sedimentation upon storage at about 25° C., for at least two days, yet when a flow-causing pressure is applied the suspensions can become non-uniform. The invention includes compositions and methods for preventing pressure-induced separation of pumped, viscous suspensions. When viscous suspensions are pumped under pressure, separation of the solids from the liquid carrier is often observed. Typically, the pump delivers a fluid that contains a reduced amount of solids and the solids accumulate behind the orifice and are not delivered to the patient. In preferred embodiments, the drug delivery devices of the invention include one or more suspension flow-enhancement elements that substantially prevent pressure-induced separation of pumped, viscous suspensions.

For example, this phenomenon was observed during an experiment to deliver a suspension of LD and water with a viscosity of approximately 50,000 cP. The driving pressure was approximately 41 inches $H_2O$ through a nozzle with an inner diameter of 0.603 mm. The suspension separated and a murky fluid dripped from the end of the nozzle. As the pressure was increased to 60 and then 80 in $H_2O$, the separation persisted, with increasing clarity of the exuding fluid. As the pressure was decreased by increasing the nozzle diameter, the effect was lessened, but was not eliminated.

Figure 20:
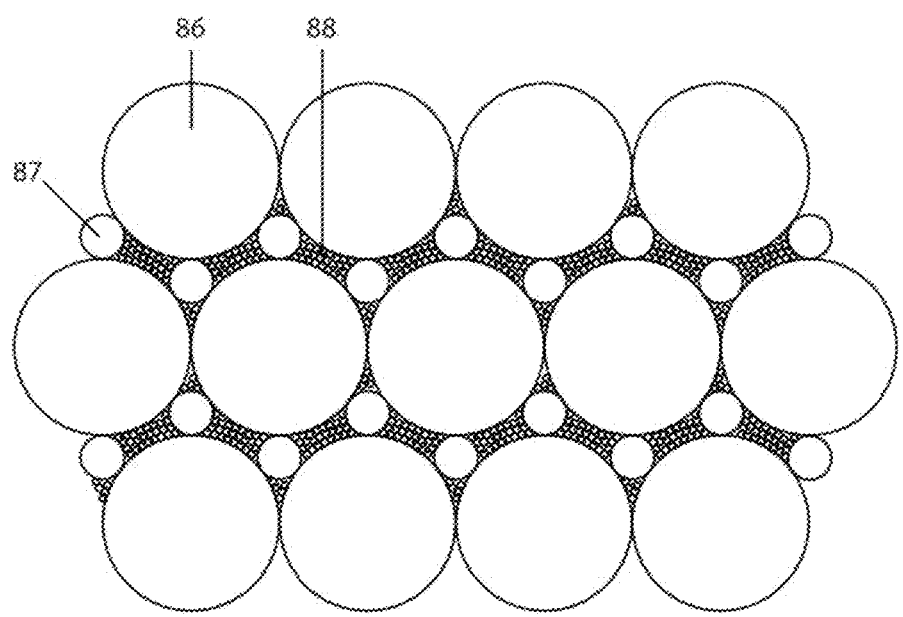
FIG. 20 illustrates an embodiment of efficient drug packing using drug particles with a tri-modal size distribution.

This and other experiments showed that pressure induced flow can cause formation of a filtering plug, the plug passing more of the carrier fluid and less of the solid drug. Such pressure or flow-induced sedimentation, i.e., filtering-plug formation, makes it difficult, if not impossible, to maintain a fixed dose rate by controlling the flow. Sedimentation leading to filtering may be alleviated when the suspended particle sizes are bimodally or multimodally distributed. Suspensions with multimodal particle size distributions tend to have superior flow characteristics over particles with unimodal particle size distributions, thereby reducing or eliminating the of separation or sedimentation of the solids from the liquid carrier that can occur when a suspension is pumped. Filtering could be reduced or avoided by increasing, through the bimodally or multimodally distributed particle sizes, the volume fraction, i.e., packing density, of the suspended solid drug, typically to greater than about 0.64, for example to between 0.65 and 0.69. A two-dimensional example of an optimal trimodal distribution of particle sizes is illustrated in FIG. 20. The largest particle 86 is shown packed with a second smaller particle 87 and a further smaller third particle size 88. Particle 88 is approximately $\frac{1}{5}^{th}$ the diameter of 87 and particle 87 is approximately $\frac{1}{5}^{th}$ the diameter of the particle 86.

The invention includes suspensions for infusion into the mouth including bimodal or multimodal particle size distributions, optionally wherein the ratio of the average particle diameters for the peaks is in the range of 2:1 to 7:1, e.g., about 3:1, 4:1, 5:1, 6:1, or 7:1. In the bimodal or multimodal distributions particle sizes can peak, for example, between 0.5 µm and 100 µm, such as between 1 µm and 50 µm, or between 1 µm and 30 µm, or between 1 µm and 15 µm. In general, proximal particle sizes at the maxima of the bimodal or multimodal distribution differ twofold or more, for example between two and fourfold, or between four and six-fold. In an exemplary bimodal distribution the weight-based amount of the larger particles can equal or be greater than that of the smaller particles. Typically the large particle: small particle weight ratio is typically greater than 1; it can be, for example, between 1 and 2, such as between 1.2 and 1.8, such as about 1.5.

The invention includes reduction or elimination of pump-driven suspension separation in the intra-oral drug delivery devices by use of one or more of the following suspension flow enhancement elements:

Formulation of pumped suspensions with multimodal particle size distributions that increase the volume fraction of solids. As previously described, the invention includes suspensions for infusion into the mouth including multimodal particle size distributions, preferably wherein the ratio of the volume weighted average particle diameters at the peaks is in the range of 1.5:1 to 7:1, such as between 3:1 to 7:1.

Use of surfactants that facilitate the extrusion of the particle-including suspensions through the orifice or tube, exemplified by surfactants used as food additives, such as monoesters of glycerol and fatty acids like glyceryl monooleate or glyceryl monostearate, or a polysorbate like Polysorbate 80, 65, 60 or 20, or a Kolliphor™ such Kolliphor RH 40, or a Poloxamer such as Poloxamer 188.

Use of coatings that modify the surface of the orifice or tube, facilitating the extrusion of the particle-rich suspension through the orifice or tube, such as a fatty acids, or coating the orifice with a perfluorinated polymer, exemplified by Teflon™ or its lubrication with a fluorinated hydrocarbon like Kryton™ or fluorinated polyether such a Fomblin™. Alternatively, the orifice or tube can be made of a fluorinated polymer, such as a perfluorinated polymer.

Flaring of the orifice to enhance the flow of particles through the orifice or tube.

Use of an orifice inner diameter of at least 5, 10, or preferably 20 times the maximum particle size (i.e., the $D_{90}$, $D_{95}$, or $D_{98}$).

Selection of a formulation viscosity, concentration, and flow rate, and an orifice inner diameter, such that the pressure on the suspension is less than 10 bars, and preferably less than 5 bars.

The invention features combinations of these designs and methods such that the drug concentration in the suspension delivered by the drug delivery device varies by less than 20%, 10%, 5%, and preferably 3% from the average during each one hour interval over a period of 8, 16, or 24 hours.

Oral Liquid Impermeable Drug Reservoirs

The preferred drug reservoirs of the invention are oral liquid impermeable reservoirs. For such oral liquid impermeable drug reservoirs, 1, 4, 8, 16, 24, 48, or 72 hours after placing a drug delivery device including a fresh reservoir in a patient's mouth and initiating the administration, less than 5%, 3%, or 1% by weight of the drug-including solid or drug-including fluid in the reservoir includes an oral liquid (e.g., less than 1% after 1 hour, less than 1% after 24 hours, less than 3% after 8 hours, less than 5% after 4 hours, or less than 5% after 72 hours). The oral liquid impermeable reservoirs may contain one or more drugs in solid form or in fluid form. Oral liquids include any fluid originating from the mouth, including saliva (or its water component) and other fluids commonly found in the mouth or that are commonly drunk or consumed by the patient, including diluted oils and alcohols. Exemplary oral liquid impermeable reservoirs can be made of a metal, or a plastic that can be elastomeric or fiber-reinforced. Metallic reservoirs can include, for example aluminum, magnesium, titanium or iron alloys of these. When made of a plastic it can have a metallic barrier layer; or a non-metallized plastic or elastomer used for packaging of food, or for drink-containing bottles, or in a fabric of washable clothing (e.g., Nylon or Dacron), or in stoppers or seals of drink containing bottles, or in septums of vials containing solutions of drugs. Ingress of oral liquids into openings in the reservoir can be prevented or minimized by the use of one or more valves, squeegees, baffles, rotating augers, rotating drums, propellants, pneumatic pumps, diaphragm pumps, hydrophobic materials, and/or hydrophobic fluids. In some embodiments, multiple doses of fluid or solid drug are contained within multiple, impermeable reservoirs or compartments.

While the extrusion into the mouth of a highly viscous plug substantially decreases the potential for saliva ingress, other methods that substantially prevent the ingress of saliva can be utilized. Saliva ingress could result of capillary climb, associated with wetting of the inner surface of the drug delivering tube or orifice by saliva. Capillary climb occurs when the adhesive forces between the surface of the tubing and the saliva are stronger than the cohesive forces (surface tension) of the saliva. One method to reduce or eliminate capillary climb is to reduce the cohesive forces by utilizing a large diameter tubing between the drug reservoir and the exit orifice. Another method to eliminate capillary climb is to reduce the adhesive force of the surface of the tubing through the use of a hydrophobic coating on the inner surface of the tubing. The goal of the coating is to prevent wetting of the tubing. By diminishing the released surface energy of the tubing upon wetting by saliva (e.g., by making it of, or by its coating with, a difficult to wet perfluorocarbon like Teflon™, or its lubrication by a difficult to wet fluorinated hydrocarbon like Kryton™, or by a difficult to wet fluorinated polyether like a Fomblin™) a greater than 90 degree contact angle between the saliva and the inner surface of the tubing can be achieved and capillary climb can be reduced or prevented. Another method to limit ingress of saliva is the use of a check valve 16 (illustrated in FIGS. 15A and 15B). In times where the flow is halted or paused, the pressure gradient across the check valve 16 is eliminated, closing the valve and preventing the flow of drug and the ingress of saliva.

For ergonomic reasons, the drug reservoirs and/or devices of the invention may include syringes, barrels and plungers that are not the customary cylindrical shapes. An example of an alternative shape for the drug reservoir (e.g., a syringe and plunger) is an obround shape. Alternatively, a non-cylindrical (e.g., obround) housing may include two or more cylindrically shaped syringes, barrels and/or plungers arranged side-by-side.

A drug reservoir used in the drug delivery device of the invention can be a syringe assembly including a plunger and a barrel, where the plunger is in a slidable arrangement with the barrel. Administration of a drug from the drug reservoir can involve relative, slidable displacement of the barrel and the plunger by a drug pump (e.g., a mechanical pump, such as a spring-driven drug pump or a propellant-driven pump), such that the volume enclosed by the barrel and the plunger is decreased. The syringe assembly may include a seal fitted over the plunger, the seal being in contact with the barrel to seal the interface between the barrel and the plunger. The seal can be an O-ring. To reduce variability in drug delivery due to friction or stickiness of the syringe, some or all of the interior surfaces of the syringe (e.g., the barrel, the plunger, or the seal) may include a non-stick coating such as a fluorinated polymer, e.g., Teflon™ or a a fluorinated polymer like Kryton™ or Fomblin™. The interior surfaces can be non-wettable by oil or by water (e.g., by the preferred pharmaceutical composition of the invention, which is typically an emulsion including a suspension of solid particles).

In some embodiments, the rug delivery device can include a tapered flow path for the pharmaceutical composition as it approaches the flow restrictor, exit orifice, or tube. The taper can make the flow of the pharmaceutical composition more reproducible. FIG. 22 illustrates a drug reservoir 4 in the shape of a syringe barrel with a tapered flow path at the exit orifice 75. The angle of the taper, a, can be equal to or less than about 60 degrees, 45 degrees, or 30 degrees.

To achieve reproducible and accurate drug delivery, it is preferred that the components of the syringe be made of materials that do not substantially deform, e.g. creep or yield, under the stress resulting of the force exerted to deliver the drug. It is also preferred that the components of the syringe have matched or similar thermal expansion characteristics so that the friction between the barrel and the piston or seal remains about constant as the temperature varies, and so that there is minimal leakage of the drug suspension during storage. This can be accomplished, for example, by using barrels, plungers and/or seals with glass transition temperatures of greater than 37° C., preferably greater than 45° C., more preferably greater than 60° C., and most preferably greater than 90° C.; and by using syringe components made from the same material so that they have the same thermal expansion coefficients. Examples of such materials are polycarbonate, polystyrene, non-creeping perfluorinated polymers, polyamides like Nylon 6-6, polymethylmethacrylate, and PET. Materials such as polypropylene are less desirable due to their low glass transition temperature and consequent easy deformation at 37° C.

Alternatively, the moving surface and the nearby stationary surface (e.g., the inner surface of a syringe barrel) can be rendered non-sticky by a lubricant. As the lubricant may come in contact with the pharmaceutical composition of the invention inside the drug delivery device of the invention, the lubricant should exhibit low or no solubility in the pharmaceutical composition of the invention. In some embodiments, the lubricant has an oil solubility less than 3% (w/w) at about 25° C. (e.g., less than 2% (w/w) at about 25° C., less than 1% (w/w) at about 25° C., or less than 0.5% (w/w) at about 25° C.). In other embodiments, the lubricant has aqueous solubility less than 2% (w/w) at about 25° C. (e.g., less than 1% (w/w) at about 25° C., less than 0.5% (w/w) at about 25° C., or less than 0.2% (w/w) at about 25° C.). The lubricant can be a halogenated polymeric oil (e.g., a halogenated polymeric oil having an average molecular mass of equal to or greater than about 1,000 Daltons, or having an average molecular mass of equal to or greater than about 2,000 Daltons). Certain lubricants can be a perfluorinated polymer, a chlorofluorinated polymer, or a fluorinated polyether.

In another embodiment, the lubricant includes two organic fluid phases, such as two organic immiscible phases. These phases may be pourable or non-pourable. An example is lubricant including both a silicone oil or grease and a fluorinated polyether oil or grease. Another example is a lubricant including both hydrocarbon oil or grease and a fluorinated polyether oil or grease.

In yet another embodiment, the compartment including the driving element (e.g., the propellant or spring) may be separated from the compartment including the drug suspension (e.g., LD and CD suspension in a syringe barrel) by a plug of material. The plug replaces a solid plunger and provides reduced friction and more reproducible drug delivery. The plug may be deformable and/or mobile, and may optionally be non-pourable. The pressure of the propellant causes the plug to move and/or deform, and transmits the pressure to the suspension. Use of a non-pourable plug serves to keep the propellant and the suspension separate by preventing penetration of the propellant gas into the drug, assuring that the suspension, and not the gas, is delivered to the patient. Preferably the rate of permeation of the components of the drug suspension in the plug, and optionally also of the propellant in the plug, is low. The rate of permeation of water through the plug can be, for example, less than about 10 mg per day at about 25±2° C., for example less than 1 mg per day or less than 0.1 mg per day. Similarly, the rate of permeation of oil through the plug can be, for example, less than about 10 mg per day at about 25±2° C., for example less than 1 mg per day or less than 0.1 mg per day. Furthermore, the rate of permeation of the optionally used propellant, used to drive the plug, can be less than about 1 mg per day at about 25±2° C., for example less than about 1 mg per day or less than about 0.1 mg per day, or less than about 0.01 mg per day. Exemplary plug materials in which the solubilities of water and/or oil and/or propellant are low include perfluorinated or fluorinated or chlorofluorinated oils and greases. The oils and greases may include solid and preferably inorganic particles to reduce their permeabilities, such as particles of carbon, silica, alumina, titania, or halogenated, particularly fluorinated, solid polymer particles, exemplified by polytetrafluoroethylene particles. The carbon particles can be, for example, particles of graphite, such as graphite flakes. The solid particles may have densities between about 1.5 g/mL and about 3 g/mL, for example between about 1.6 g/mL and about 2.5 g/mL, such as between 1.6 g/mL and 2.1 g/mL. The average or mean size of these particles in the grease can be between about 0.5 µm and about 250 µm, for example between about 1 µm and about 100 µm. Typically, the incorporated solid particles scatter and/or absorb visible light. Exemplary oils and greases may include fluorinated polyethers or polymeric fluorinated alkanes such as perfluoroalkanes. Some fluorinated polyether oils and greases are sold under the trade name "Fomblin™" and some fluorinated hydrocarbon oils and greases are sold under the trade name "Krytox™". The oil or grease may wet the walls of the compartment or may not be repelled from the walls, as indicated, for example, by a concave meniscus or no meniscus when the oil is in an optionally cylindrical compartment, and the absence of a convex meniscus when the oil is in an optionally cylindrical compartment. Optionally, the plug may include one or more solid supports to provide the plug with greater structural integrity, to further reduce the rate of permeation of gasses or drug through the plug, and to reduce leaching of materials from the plug into the drug or into the propellant. For example, the plug may include a metal or polymeric mesh or cage, or a metal or polymeric cap on one or both ends.

Methods of Use and Methods of Treating Disease

The drug delivery devices of the invention can be used to orally administer drugs to patients in therapeutically effective amounts. Similarly, the formulations of the invention can be administered to patients in therapeutically effective amounts. For example, an amount is administered which prevents, delays, reduces, or eliminates the symptoms of a disease, such as PD, mucositis, bacterial infections, cancer, pain, organ transplantation, disordered sleep, epilepsy and seizures, anxiety, mood disorders, post-traumatic stress disorder, cancer, arrhythmia, hypertension, heart failure, spasticity, diabetic nephropathy, and allergy. They can also be used to manage allergies, e.g. by delivering agents used for sublingual immunotherapy such that the delivered agents contact a mucous membrane or tissue of the mouth. Using the drug delivery devices of the invention, a drug appropriate for the treatment of a given disease to be treated can be formulated and administered using the methods, compositions, and devices described herein. Many drugs with narrow therapeutic indices benefit from drug delivery devices and methods that result in small fluctuation indices. For example, Table 2 summarizes the fluctuation indices of extended release tablet formulations of anti-epileptic drugs reported in various studies (from "Extended-release antiepileptic drugs: A comparison of pharmacokinetic parameters relative to original immediate-release formulations", Ilo E. Leppik and Collin A. Hovinga, Epilepsia, 54(1):28-35, 2013).

TABLE 2

Fluctuation indices of anti-epileptic drug extended release tablets.

| Drug | Fluctuation Index (SD) |
| --- | --- |
| Carbamazepine | 0.31 (0.1) |
|  | 0.26 (0.1) |
|  | 0.47 |
|  | 0.49 |
| Divalproate sodium | 0.39 (0.15) |
|  | 0.67 (0.16) |
|  | 0.34 (0.15) |
|  | 0.67 (0.17) |
|  | 0.59 (0.27) |
|  | 0.46 (0.16) |
|  | 0.71 (0.20) |
| Lamotrigine | 0.341 |
|  | 0.817 |
|  | 0.209 |
|  | 0.545 |
|  | 0.986 |
|  | 0.318 |
| Oxcarbazepine | 0.39 (0.08) |
|  | 0.54 (0.09) |
| Levetiracetam | 1.19 |
|  | 1.27 |

The invention includes a method of treating a disease or medical condition using any of the devices, drugs, formulations, and methods disclosed herein, wherein the fluctuation index is less than or equal to 2.0, 1.5, 1.0, 0.75, 0.50, 0.25, or 0.15. For example, the disease or medical condition to be treated may be Parkinson's disease, bacterial infections, cancer, pain, organ transplantation, disordered sleep, epilepsy and seizures, anxiety, mood disorders, post-traumatic stress disorder, cancer, arrhythmia, hypertension, heart failure, spasticity, dementia, diabetic nephropathy, gastroparesis, xerostomia, and dementia.

Drug dosages administered using the methods of the invention may be higher or lower than those administered using traditional, infrequent dosing regimens. A lower daily dose is possible without loss of efficacy when continuous or semi-continuous administration reduces troughs in the drug's steady state circulating plasma concentration, enabling the drug's plasma concentration to remain above the minimum effective plasma concentration without the need for high peak concentrations. A higher daily dose is possible without increased side effects when continuous or semi-continuous administration reduces peaks in the drug's steady state circulating plasma concentration, enabling an increase in the drug's average plasma concentration without the need for high peak concentrations.

The methods of the invention provide a dosing regimen having an improved safety profile as adverse events associated with peak plasma concentrations (i.e., a Cmax characteristic of oral unit dosage forms) are eliminated. Thus, the methods, compositions, and devices of the invention can be used to deliver drugs having a narrow therapeutic window in the patient population being treated (i.e., patients refractory to standard therapeutic regimens). Details provided below for the treatment of PD can be applicable to the formulation and administration of drugs for the treatment of other diseases.

Treatment of PD

For the treatment of PD, typical administered dose ranges are from about 20 μmole/kg to about 200 μmole/kg of LD or LD prodrug per day. The typical daily dose of the optionally co-administered DDC inhibitor is between about 5 μmole/kg and about 50 μmole/kg. For example, the typical daily dose for a patient weighing 75 kg is from about 1.5 millimoles to about 15 millimoles of LD or LD prodrug. Optionally, a molar amount of a DDC inhibitor between about 10% and about 40% of the molar amount of the LD or LD prodrug, for example between 15% and 30%, may be added.

Preferred modes of administration of the drug-including solid or fluid are via drug delivery devices that are removably secured in the mouth, and which administer the drug into the mouth or into the nasal cavity for a period of at least 4 hours. The drug may be administered at a variable rate, although constant rate administration is preferred. Administration is preferably continuous or semi-continuous.

The administration into the mouth can be for 24 hours daily or it can be limited to the awake period, typically about 16 hours. When limited to the awake period it can be advantageous to administer a morning bolus to more rapidly raise the plasma concentration of the LD than a constant rate administration would. The morning bolus can be delivered, for example, through an orally taken pill or pills of LD and a DDC inhibitor or it can be through administration of a solid or fluid drug into the mouth using the drug devices of the invention. Alternatively, the exterior of the drug delivery device may include a drug, such that a bolus of the drug is delivered into the mouth when the device is first inserted into the mouth.

The invention includes methods of administering into the mouth one or more drugs (e.g., LD and CD) from one or more drug reservoirs residing in the cavity of the mouth including a total volume of 0.1-10 mL of drugs(e.g., 0.1-1.0 mL, 1.0-2.0 mL, 2.0-3.0 mL, 3.0-4.0 mL, 4.0-5.0 mL, 5.0-6.0 mL, 6.0-7.0 mL, 7.0-8.0 mL, 8.0-9.0 mL, or 9.0-10 mL). The invention includes methods of administering the one or more drugs (in either solid or fluid form) at a rate in the range of 0.03-1.25 mL/hour (e.g., 0.03-0.10 mL/hour, 0.10-0.20 mL/hour, 0.20-0.30 mL/hour, 0.30-0.40 mL/hour, 0.40-0.50 mL/hour, 0.50-0.60 mL/hour, 0.60-0.70 mL/hour, 0.70-0.80 mL/hour, 0.80-0.90 mL/hour, 0.90-1.0 mL/hour, 1.0-1.1 mL/hour, or 1.1-1.25 mL/hour). The invention includes methods of administering the one or more drugs at an average rate of less than 1 mg per hour, 1-10 mg per hour, 10-25 mg per hour, 25-50 mg per hour, 50-75 mg per hour, 75-100 mg per hour, 100-125 mg per hour, or greater than 125 mg per hour. The invention includes methods of administering one or more drugs via continuous and/or semi-continuous administration. In a preferred embodiment, the method includes holding the average administration rate constant or near constant for a period of 4, 8, 12, 16, or 24 hours during the day. For example, the volume administered every hour may vary from the average hourly administration rate during the infusion period by less than ±10% or ±20% per hour, or by ±10% or ±20% per 15 minute period. The invention includes methods of administering one or more drugs into the mouth using any of the drug delivery devices described herein.

Continuous or semi-continuous administration using the drug delivery devices and formulations of the invention can reduce concentration fluctuations of the therapeutic drug in body fluid, for example in blood, plasma or serum. It can provide, for example, a plasma concentration profile where the difference between peak concentrations and nadir concentrations of the therapeutic drug is less than ±70% of the average concentration through a period in which the drug is administered, for example it can be less than ±50%, less than ±30%, less than ±20%, or less than ±10% of the time averaged concentration over a period of greater than or equal to 4 hours (e.g., 8, 12, 16, or 24 hours).

The invention features a method of treating a disease in a patient, the method including: (a) inserting a drug delivery device into the patient's mouth; (b) starting a drug administration from the device; (c) administering into the patient's mouth one or more drugs, using continuous or semi-continuous administration, for a period of 4 hours to 7 days at an hourly rate in the range of 0.015-1.25 mL/hour or 1-125 mg/hour; and (d) removing the drug delivery device from the mouth; wherein the drug delivery device includes a oral liquid impermeable reservoir of 0.1-5 mL volume (e.g., 0.1-1 mL, 0.5-3 mL, or 3-5 mL), and the reservoir includes a solid or fluid including a drug. Optionally, the method may also include the optional step of: (e) stopping the drug delivery from the device. The invention further includes a method wherein steps a, b, c, d and e are performed at least twice over a period of 4 hours to 7 days. The drug may include a total of greater than 1 millimole of LD.

The invention features a method of treating a disease in a patient, the method including: (a) inserting a drug delivery device into the patient's mouth; (b) starting a drug administration from the device; (c) administering into the patient's mouth one or more drugs, using continuous or semi-continuous administration, for a period of 4 hours to 7 days at an hourly rate in the range of 0.015-1.25 mL/hour or 1-125 mg/hour; (d) removing the drug delivery device from the mouth; and (e) stopping the drug delivery from the device, wherein: (1) the drug delivery device includes a reservoir of 0.1-5 mL volume (e.g., 0.1-1 mL, 0.5-3 mL, or 3-5 mL), and the reservoir includes a solid or fluid including a drug, and (2) steps a, b, c, d and e are performed at least twice over a period of 4 hours to 7 days. The drug may include a total of greater than 1 millimole of LD.

The invention features a method for treating Parkinson's disease in a patient (including in patients with scores of 4 and 5 on the Hoehn and Yahr scale), the method including: (a) removably inserting a drug delivery device into the patient's mouth, the drug delivery device including an oral liquid impermeable reservoir of 0.1-5 mL volume (e.g., 0.1-1 mL, 0.5-3 mL, or 3-5 mL), and the reservoir including a solid or fluid including a total of greater than 1 millimole of LD; (b) administering into the patient's mouth the solid or fluid for a period of at least 8 hours at an hourly rate in the range of 0.03-1.25 mL/hour or 30-150 mg/hour, such that a circulating plasma LD concentration greater than 400 ng/mL and less than 7,500 ng/mL is continuously maintained for a period of at least 8 hours during the administration; and (c) removing the drug delivery device from the patient's mouth. In certain embodiments, the LD suspension is administered into the mouth at such a rate that a circulating plasma LD concentration greater than 800 ng/mL, 1,200 ng/mL, 1,600 ng/mL, or 2,000 ng/mL (e.g., from 800 to 1,500, from 1,000 to 2,000, from 1,600 to 2,500, or from 1,500 to 3,000 ng/mL, depending upon the condition of the patient) is continuously maintained for a period of at least 2 hours, 3 hours, 4 hours, 8 hours, 16 hours, or 24 hours during the administration. In particular embodiments, the LD suspension is administered into the mouth at such a rate that a circulating plasma LD concentration greater than 400 ng/mL, 800 ng/mL, 1,200 ng/mL, 1,600 ng/mL, or 2,000 is achieved within 60 minutes of the initiation of the infusion. The LD suspension can be administered into the mouth at such a rate that a circulating plasma LD concentration less than 7,500 ng/mL, 5,000 ng/mL, 3,500 ng/mL, 3,000 ng/mL, 2,500 ng/mL, or 2,000 ng/mL is continuously maintained for a period of at least 8 hours during the administration. In particular embodiments, the patient receives an average daily dose of less than 10 mL, 7.5 mL, 5 mL, 3 mL, or 2 mL of the LD suspension. The LD suspension can be administered into the mouth at such a rate that the circulating LD plasma concentration varies by less than ±20%,±15%, or ±10% from its mean for a period of at least 1 hour, 2 hours, 3 hours, or 4 hours.

The method can further include the co-administration of an effective amount of a DDC inhibitor such as benserazide, carbidopa or carbidopa prodrug. Carbidopa can be co-administered as a solid, suspension or emulsion, or as a solution of one of its highly water soluble prodrug salts, exemplified by carbidopa ethyl ester hydrochloride, by carbidopa methyl ester hydrochloride or by carbidopa amide hydrochloride. The molar amount of the co-administered DDC inhibitor can be between one-tenth and one-half of the molar amount of LD, preferably about $\frac{1}{4}^{th}\pm\frac{1}{8}^{th}$ of the molar amount of LD. Preparations of the carbidopa prodrugs, recognized to be LD decarboxylase inhibitors, are described, for example, in U.S. Pat. Nos. 3,895,052 and 7,101,912, and Patent Publication Nos. DE2062285A and FR2052983A1. In one particular embodiment, a LD suspensionincludes a greater than 0.5 M LD (e.g., 0.5±0.1, 0.6±0.1, 0.7±0.1, 0.8±0.2, 1.0±0.3, 1.5±0.5, 2.0±0.5, 0.6±0.3, 0.75±0.25, 1.0±0.5, 1.5±0.5, 2.0±0.5, 2.5±0.5, 3.0±0.5, 3.5±0.5, greater than 1.5, greater than 2, greater than 2.5, or greater than 3.5 moles per liter). In particular embodiments, the LD and the DDC inhibitor are co-administered separately, or are contained in a single solid or fluid and administered into the patient.

The method can alleviate a motor or non-motor complication in a patient afflicted with Parkinson's disease, such as tremor, akinesia, bradykinesia, dyskinesia, dystonia, cognitive impairment, and disordered sleep.

Mucosal Delivery

In some embodiments, e.g. those where the daily dose of the drug is less than 100 mg, for example less than 50 mg, a part or most of the drug in the continuously pumped composition can be transported into, i.e. absorbed by, the buccal or sublingual mucosa and optionally through the mucosa to the blood. It could reach through venules the facial vein, then the jugular vein and the heart, delivering part of the drug-including blood to the brain, the lungs or other organs, without the drug-containing blood passing the liver or the kidneys where the drug could be eliminated. Transport of the drug to and/or through the mucosa can be enhanced by additives and or physical means described, for example, in "Enhancing the Buccal Mucosal Delivery of Peptide and Protein Therapeutics" Pharm Res (2015) 32: 1-21 by T. Caon, L. Jin, C.M. 0. Simoes, R. C. Norton and/or J. A. Nicolazzo; and/or "Mucoadhesive polymers for buccal drug delivery." Drug Dev Ind Pharm. (2014) 40(5):591-8 by F. Laffleur, both incorporated herein by reference. Typically the composition is pumped within a zone from which more than about one half of the drug is transported to the mucosa in less than about 60 minutes, such as less than 30 minutes, 10 minutes, 5 minutes, or 2 minutes.

The invention further includes delivering the drug-containing composition into a location in the mouth such that the drug has a residence time at or near the mucosa of greater than 2 minutes, 5 minutes, 10 minutes, 30 minutes, or 60 minutes before being removed from contact with the oral mucosa (e.g., by substantial saliva-dilution followed by swallowing). Several techniques and device configurations may be used to obtain the desired residence time, optionally in combination with each other. In one embodiment, the drug-containing composition is delivered into a portion of the mouth where the flux of saliva is slow, e.g., into the cheek pocket between the bottom teeth/gums and the cheek, and preferably not proximate a salivary gland. In a related embodiment, the composition may be mucoadhesive or include a mucoadhesive to retain the drug proximate the mucosa. In yet another related embodiment, the drug-containing composition may be delivered into a material that retains the drug proximate the mucosa, such as a sorbent.

The accuracy and repeatability of dosing of the drug into the buccal or sublingual mucosa can be enhanced by locating the distal end of the composition-delivering e.g. plastic tubing or metallic pipe proximal to the buccal or sublingual mucosa within a zone bounded in part by a water vapor and gas permeable membrane that is not saliva-wetted i.e. is saliva-repelling. The saliva-repelling gas permeable membrane can delay dilution or extraction of the pumped composition by saliva, keeping it near the mucosa until the uptake of its drug by the mucosa. The membrane can include fibers coated with a fluorinated polymer, or its fibers can include, e.g. be made of, a fluorinated polymer. Exemplary waterproof, breathable fabric membranes are sold by W. L. Gore and Associates under the trade name GORE-TEX®. The GORE-TEX®. The membranes repel liquid water and can repel saliva, yet allow passage of water vapor and other gases. Pumping of the pharmaceutical composition into a zone enclosed in part or entirely by the saliva-repelling membrane can increase the fraction of the drug that is buccally or sublingually absorbed, reducing the flux of the composition or its drug from the proximity of the mucous membrane into a part the oral cavity where it is diluted by saliva, then swallowed. The saliva-repelling membrane can have a rim adhering to the buccal or sublingual tissue. For adhesion to the buccal or sublingual tissue, the rim can have a mucoadhesive polymer coating described, for example, in U.S. Pat. Nos. 4,900,552, 5,723,143, 5,744,155, 5,900,247, 5,989,535, 5,989,535, 7,914,645, 8,735,374, 9,017,771, 9,044,475, 9,044,500 or 9,161,890, each of which is incorporated herein by reference.

For buccal or sublingual delivery an optionally flow-controlling metallic pipe or polymeric tubing can be connected at one end to the reservoir and at the other end to a mucosa-contacting, e.g. buccal or sublingual mucosa-contacting, manifold having one or more openings through which the composition flows as a liquid or is extruded as a paste or gel. The pipe or tubing can be, for example 1-15 cm long, such as 5-10 cm long. Its inner diameter can be between about 5 μm and about 1 mm, such as between about 10 μm mm and about 0.5 mm. When metallic, the pipe can include, for example, titanium or one of its alloys, such as annealed titanium of greater than about 98 weight % purity; or a stainless steel; when polymeric, it could include, for example polyethylene terephthalate, a polyamide or a fluorinated polymer.

This invention includes the following itemized aspects and embodiments.

1. A pharmaceutical composition comprising a suspension that is a drug particle-containing emulsion comprising (i) from 35% to 70% (w/w) drug particles comprising levodopa and/or carbidopa, or salts thereof, (ii) from 19% to 30% (w/w) of one or more water-immiscible compounds, (iii) from 2% to 16% (w/w) water, and (iv) from 1% to 8% (w/w) surfactant, wherein the pharmaceutical composition is physically stable and suitable for continuous or frequent intermittent intra-oral delivery.

2. A pharmaceutical composition comprising a suspension comprising (i) from about 35% to 70% (w/w) drug particles, (ii) from 19% to 30% (w/w) of one or more water-immiscible compounds, (iii) from 2% to 16% (w/w) water, and (iv) from 1% to 8% (w/w) surfactant, wherein the pharmaceutical composition is physically stable and suitable for continuous or frequent intermittent intra-oral delivery.

3. A pharmaceutical composition comprising a suspension comprising (i) an excess of one or more water-immiscible compounds over water, and (ii) from about 35% to 70% (w/w) drug particles, wherein the pharmaceutical composition is physically stable for 6 months or more at 5° C.

4. The pharmaceutical composition of item 2 or 3, wherein said pharmaceutical composition comprises an emulsion.

5. The pharmaceutical composition of any one of items 1 to 4, wherein said suspension is an extrudable, non-pourable emulsion.

6. The pharmaceutical composition of any one of items 1 to 5, wherein said suspension is physically stable for 12 months at 5° C.

7. The pharmaceutical composition of any one of items 1 to 5, wherein said suspension is physically stable for 12 months at 25° C.

8. The pharmaceutical composition of items 6 and 7, wherein after said 12 months said suspension is physically stable for 48 hours at 37° C.

9. The pharmaceutical composition of any one of items 1 to 8, wherein said suspension comprises a continuous hydrophilic phase.

10. The pharmaceutical composition of any one of items 1 to 9, wherein the concentration of drug in the pharmaceutical composition is at least 1.75 M.

11. The pharmaceutical composition of any one of items 1 to 9, comprising from about 50% to about 70% (w/w) drug particles, wherein the concentration of drug in the pharmaceutical composition is at least 3.0 M.

12. The pharmaceutical composition of any one of items 1 to 11, wherein said one or more water-immiscible compounds melts or softens below 45° C.

13. The pharmaceutical composition of item 12, wherein said one or more water-immiscible compounds melts or softens below 37° C.

14. The pharmaceutical composition of any one of items 1 to 13, wherein the weight ratio of said one or more water-immiscible compounds to water is greater than 1.0.

15. The pharmaceutical composition of item 14, wherein the weight ratio of said one or more water-immiscible compounds to water is greater than 1.5.

16. The pharmaceutical composition of item 15, wherein the weight ratio of said one or more water-immiscible compounds to water is greater than 2.0.

17. The pharmaceutical composition of item 16, wherein the weight ratio of said one or more water-immiscible compounds to water is greater than 3.0.

18. The pharmaceutical composition of any one of items 1 to 17, wherein said one or more water-immiscible compounds comprises an oil.

19. The pharmaceutical composition of any one of items 1 to 18, wherein the suspension comprises a continuous hydrophilic phase comprising greater than 50% (w/w) drug particles.

20. The pharmaceutical composition of any one of items 1 to 19, wherein said suspension comprises an oil in water emulsion.

21. The pharmaceutical composition of any one of items 1 to 20, wherein said suspension is free of polymers of a molecular mass greater than 1,000 Daltons.

22. The pharmaceutical composition of any one of items 1 to 21, wherein said suspension has a dynamic viscosity of at least 100 cP at 37° C.

23. The pharmaceutical composition of item 22, wherein said suspension has a dynamic viscosity of at least 1,000 cP at 37° C. 24. The pharmaceutical composition of item 23, wherein said suspension has a dynamic viscosity of at least 10,000 cP at 37° C.

25. The pharmaceutical composition of item 24, wherein said suspension has a dynamic viscosity of at least 100,000 cP at 37° C.

26. The pharmaceutical composition of any one of items 1 to 25, wherein the suspension comprises greater than 50% (w/w) drug particles.

27. The pharmaceutical composition of item 26, wherein the suspension comprises greater than 60% (w/w) drug particles.

28. The pharmaceutical composition of any one of items 1 to 27, wherein the $D_{50}$ of the drug particles is less than or equal to 500 µm.

29. The pharmaceutical composition of any one of items 1 to 27, wherein the $D_{50}$ of the drug particles is less than or equal to 250 µm.

30. The pharmaceutical composition of any one of items 1 to 27, wherein the $D_{50}$ of the drug particles is less than or equal to 200 µm.

31. The pharmaceutical composition of any one of items 1 to 27, wherein the $D_{50}$ of the drug particles is less than or equal to 150 µm.

32. The pharmaceutical composition of any one of items 1 to 27, wherein the $D_{50}$ of the drug particles is less than or equal to 125 µm.

33. The pharmaceutical composition of any one of items 1 to 27, wherein the $D_{50}$ of the drug particles is less than or equal to 100 µm.

34. The pharmaceutical composition of any one of items 1 to 27, wherein the $D_{50}$ of the drug particles is less than or equal to 50 µm.

35. The pharmaceutical composition of any one of items 1 to 27, wherein the $D_{50}$ of the drug particles is less than or equal to 25 µm.

36. The pharmaceutical composition of any one of items 1 to 35, wherein the $D_{50}$ of the drug particles is greater than or equal to 1 µm.

37. The pharmaceutical composition of any one of items 1 to 35, wherein the $D_{50}$ of the drug particles is greater than or equal to 3 µm.

38. The pharmaceutical composition of any one of items 1 to 35, wherein the $D_{50}$ of the drug particles is greater than or equal to 5 µm.

39. The pharmaceutical composition of any one of items 1 to 35, wherein the $D_{50}$ of the drug particles is greater than or equal to 10 µm.

40. The pharmaceutical composition of any one of items 1 to 34, wherein the $D_{50}$ of the drug particles is greater than or equal to 25 µm.

41. The pharmaceutical composition of any one of items 1 to 27, wherein the $D_{50}$ of the drug particles is 25±24 µm.

42. The pharmaceutical composition of any one of items 1 to 27, wherein the $D_{50}$ of the drug particles is 75±25 µm.

43. The pharmaceutical composition of any one of items 1 to 27, wherein the $D_{50}$ of the drug particles is 125±25 µm.

44. The pharmaceutical composition of any one of items 1 to 27, wherein the $D_{50}$ of the drug particles is 175±25 µm.

45. The pharmaceutical composition of any one of items 1 to 44, wherein said suspension comprises less than or equal to about 16% (w/w) water.

46. The pharmaceutical composition of item 45, wherein said suspension comprises less than or equal to about 12% (w/w) water.

47. The pharmaceutical composition of item 46, wherein said suspension comprises less than or equal to about 9% (w/w) water.

48. The pharmaceutical composition of any one of items 3 to 47, wherein said suspension comprises greater than or equal to about 1% (w/w) water.

49. The pharmaceutical composition of any one of items 1 to 47, wherein said suspension comprises greater than or equal to about 2% (w/w) water.

50. The pharmaceutical composition of any one of items 1 to 47, wherein said suspension comprises greater than or equal to about 3% (w/w) water.

51. The pharmaceutical composition of any one of items 1 to 44, wherein said suspension comprises 4±2% (w/w) water.

52. The pharmaceutical composition of any one of items 1 to 44, wherein said suspension comprises 8±2% (w/w) water.

53. The pharmaceutical composition of any one of items 1 to 44, wherein said suspension comprises 13±3% (w/w) water.

54. The pharmaceutical composition of any one of items 1 to 53, wherein said one or more water-immiscible compounds comprises an oil selected from a saturated fatty acid triglyceride, an unsaturated fatty acid triglyceride, a mixed saturated and unsaturated fatty acid tryglyceride, a medium-chain fatty acid triglyceride, canola oil, coconut oil, palm oil, olive oil, soybean oil, sesame oil, corn oil, or mineral oil.

55. The pharmaceutical composition of item 54, wherein said oil is a saturated fatty acid triglyceride.

56. The pharmaceutical composition of item 54, wherein said oil is a medium-chain fatty acid triglyceride oil.

57. The pharmaceutical composition of item 54, wherein said oil is a canola oil.

58. The pharmaceutical composition of item 54, wherein said oil is coconut oil.

59. The pharmaceutical composition of item 56, wherein said oil is a Miglyol® or chemical equivalent.

60. The pharmaceutical composition of item 54, wherein said oil is a triglyceride of one or more $C_{6\text{-}24}$ fatty acids.

61. The pharmaceutical composition of item 60, wherein said oil is a triglyceride of one or more $C_{8\text{-}16}$ fatty acids.

62. The pharmaceutical composition of item 54, wherein at least 50% (w/w) of said one or more water-immiscible compounds is a triglyceride of one or more $C_8$-$C_{12}$ fatty acids.

63. The pharmaceutical composition of item 60, wherein said oil is a triglyceride of $C_8$-$C_{12}$ fatty acids, $C_{14}$-$C_{18}$ fatty acids, or $C_{20}$-$C_{24}$ fatty acids, or a mixture thereof.

64. The pharmaceutical composition of any one of items 54 to 63, wherein said suspension comprises less than or equal to about 30% (w/w) of said oil.

65. The pharmaceutical composition of any one of items 54 to 63, wherein said suspension comprises less than or equal to about 29% (w/w) of said oil.

66. The pharmaceutical composition of any one of items 54 to 63, wherein said suspension comprises less than or equal to about 27% (w/w) of said oil.

67. The pharmaceutical composition of any one of items 54 to 63, wherein said suspension comprises less than or equal to about 25% (w/w) of said oil.

68. The pharmaceutical composition of any one of items 54 to 67, wherein said suspension comprises greater than or equal to about 19% (w/w) of said oil.

69. The pharmaceutical composition of any one of items 54 to 67, wherein said suspension comprises greater than or equal to about 21% (w/w) of said oil.

70. The pharmaceutical composition of any one of items 54 to 67, wherein said suspension comprises greater than or equal to about 23% (w/w) of said oil.

71. The pharmaceutical composition of any one of items 54 to 63, wherein said suspension comprises 20±2% (w/w) of said oil.

72. The pharmaceutical composition of any one of items 54 to 63, wherein said suspension comprises 24±2% (w/w) of said oil.

73. The pharmaceutical composition of any one of items 54 to 63, wherein said suspension comprises 28±2% (w/w) of said oil.

74. The pharmaceutical composition of any one of items 1 to 73, wherein said pharmaceutical composition comprises a non-ionic surfactant.

75. The pharmaceutical composition of item 74, wherein said non-ionic surfactant comprises a polyglycolized glyceride, a poloxamer, an alkyl saccharide, an ester saccharide, or a polysorbate surfactant.

76. The pharmaceutical composition of item 75, wherein said non-ionic surfactant comprises a poloxamer or wherein the poloxamer is poloxamer 188.

77. The pharmaceutical composition of item 75, wherein said non-ionic surfactant comprises a polyglycolized glyceride that is a polyethoxylated castor oil.

78. The pharmaceutical composition of item 75, wherein said non-ionic surfactant comprises a polysorbate surfactant that is Polysorbate 60.

79. The pharmaceutical composition of any one of items 1 to 78, wherein said suspension comprises less than or equal to about 8% (w/w) of said surfactant.

80. The pharmaceutical composition of any one of items 1 to 78, wherein said suspension comprises less than or equal to about 7% (w/w) of said surfactant.

81. The pharmaceutical composition of any one of items 1 to 78, wherein said suspension comprises less than or equal to about 6% (w/w) of said surfactant.

82. The pharmaceutical composition of any one of items 1 to 81, wherein said suspension comprises greater than or equal to about 2% (w/w) of said surfactant.

83. The pharmaceutical composition of any one of items 1 to 81, wherein said suspension comprises greater than or equal to about 3% (w/w) of said surfactant.

84. The pharmaceutical composition of any one of items 1 to 81, wherein said suspension comprises greater than or equal to about 4% (w/w) of said surfactant.

85. The pharmaceutical composition of any one of items 1 to 78, wherein said suspension comprises about 5±2% (w/w) of said surfactant.

86. The pharmaceutical composition of any one of items 1 to 85, further comprising an antioxidant or a taste modifying agent.

87. The pharmaceutical composition of item 86, wherein said antioxidant is oil soluble.

88. The pharmaceutical composition of item 86, wherein said antioxidant is Vitamin E, TPGS, ascorbylpalmitate, a tocopherol, thioglycerol, thioglycolic acid, vitamin A, propyl gallate, octyl gallate, butylhydroxyanisole, or butylhydroxytoluene.

89. The pharmaceutical composition of any one of items 1 to 88, wherein pH of said suspension is less than or equal to about 7.

90. The pharmaceutical composition of item 89, wherein the pH of said pharmaceutical composition is less than or equal to about 5.0.

91. The pharmaceutical composition of item 88, wherein the pH of said pharmaceutical composition is less than or equal to about 4.0.

92. The pharmaceutical composition of any one of items 87 to 89, wherein the pH of said pharmaceutical composition is greater than or equal to about 3.

93. The pharmaceutical composition of item 90, wherein the pH of the composition measured by inserting a glass walled pH electrode into the formulation is less than pH 5 and remains less than pH 5 after 3 months storage at 25° C.

94. The pharmaceutical composition of item 91, wherein the pH is and remains less than pH 4 after 3 months storage at 25° C.

95. The pharmaceutical composition of item 94, wherein the pH equals or is less than pH 3 after 3 months storage at 25° C.

96. The pharmaceutical composition of any one of items 1 to 95, comprising a bacteriostatic or a fungistatic agent.

97. The pharmaceutical composition of item 96, wherein the agent comprises benzoic acid or a benzoate salt.

98. The pharmaceutical composition of item 97, wherein the combined concentrations of benzoic acid and benzoate salt are between 0.1 percent by weight and 1 percent by weight.

99. The pharmaceutical composition of any one of items 1 to 98, further comprising a transition metal ion complexing agent or a salt thereof.

100. The pharmaceutical composition of item 99, wherein the transition metal ion complexing agent is EDTA or a salt thereof.

101. The pharmaceutical composition of item 100, wherein the combined concentrations of EDTA and its salt or salts is between 0.05 weight % and 0.25 weight %.

102. The pharmaceutical composition of any one of items 1 to 101, further comprising a sulfur comprising compound.

103. The pharmaceutical composition of item 102, wherein the sulfur comprising compound reacts at 25±3° C. with dopaquinone or with quinone formed by oxidation of carbidopa.

104. The pharmaceutical composition of item 103, wherein the sulfur comprising compound is cysteine and N-acetylcysteine.

105. The pharmaceutical composition of any one of items 1 to 104, wherein the shelf life of said pharmaceutical composition is 1 year or longer at 5±3° C.

106. The pharmaceutical composition of any one of items 1 to 104, wherein the shelf life of said pharmaceutical composition is 1 year or longer at 25±3° C.

107. The pharmaceutical composition of any one of items 2 to 106, wherein said drug particles comprise levodopa or a levodopa prodrug, or carbidopa or a carbidopa prodrug, benserazide, or any mixture thereof.

108. The pharmaceutical composition of item 107, wherein said drug particles comprise levodopa and/or carbidopa.

109. The pharmaceutical composition of item 107 or 108, comprising carbidopa and less than 2 pg of hydrazine per mg of drug after 1 week storage under ambient air at 60° C.

110. The pharmaceutical composition of item 107 or 108, comprising carbidopa and less than 1 pg of hydrazine per mg of drug after 1 week storage under ambient air at 60° C.

111. The pharmaceutical composition of item 107 or 108, wherein said drug particles comprise carbidopa, and further comprising less than 8 µg of hydrazine per mg of carbidopa after 6 or 12 month storage at 5±3° C.

112. The pharmaceutical composition of item 107 or 108, wherein said drug particles comprise carbidopa, and further comprising less than 8 µg of hydrazine per mg of carbidopa after 6 or 12 month storage at 25±3° C.

113. The pharmaceutical composition of item 111 or 112, wherein said composition comprises less than 4 µg of hydrazine per mg of carbidopa after said 12 month storage.

114. The pharmaceutical composition of item 113, wherein said composition comprises less than 1 µg of hydrazine per mg of carbidopa after said 12 month storage.

115. The pharmaceutical composition of any one of items 2 to 106, wherein said drug particles comprise one or more allergens, allergen extracts, or allergen derivatives.

116. The pharmaceutical composition of item 115, wherein said one or more allergens is pollen, a part of a mite, or a component of the feline or canine skin, or an extract or a conversion product thereof.

117. The pharmaceutical composition of any one of items 1 to 116, wherein said suspension does not cream or sediment when centrifuged for 1 hour at an acceleration of about 5,000 G at 25±3° C.

118. The pharmaceutical composition of item 117, wherein said suspension does not cream or sediment when centrifuged for 1 hour at an acceleration of about 10,000 G at 25±3° C.

119. The pharmaceutical composition of item 118, wherein said suspension does not cream or sediment when centrifuged for 1 hour at an acceleration of about 16,000 G at 25±3° C.

120. The pharmaceutical composition of any one of items 1 to 116, wherein said pharmaceutical composition does not cream or sediment when stored for 12 months at 5±3° C.

121. The pharmaceutical composition of any one of items 1 to 116, wherein said pharmaceutical composition does not cream or sediment when stored for 12 months at 25±3° C.

122. The pharmaceutical composition of any one of items 117 to 121, wherein after said centrifugation or said storage the concentrations of drug in the layer containing the top 20 volume % and the layer containing the bottom 20 volume % of the composition differ by less than 10%.

123. The pharmaceutical composition of item 122, wherein after said centrifugation or said storage the concentrations of drug in the layer containing the top 20 volume % and the layer containing the bottom 20 volume % of the composition differ by less than 6%.

124. The pharmaceutical composition of item 123, wherein after said centrifugation or said storage the concentrations of drug in the layer containing the top 20 volume % and the layer containing the bottom 20 volume % of the composition differ by less than 4%.

125. The pharmaceutical composition of item 124, wherein after said centrifugation or said storage the concentrations of drug in the layer containing the top 20 volume % and the layer containing the bottom 20 volume % of the composition differ by less than 2%.

126. The pharmaceutical composition of any one of items 117 to 121, wherein after said centrifugation or said storage there is no visible creaming or sedimentation.

127. The pharmaceutical composition of any one of items 1 to 126, wherein said pharmaceutical composition has substantially no taste.

128. A pharmaceutical composition comprising a suspension comprising (i) from about 20% to about 80% (w/w) solid excipients; (ii) from about 5% to 60% (w/w) drug particles, (iii) from 19% to 30% (w/w) of one or more water-immiscible compounds, (iv) from 2% to 25% (w/w) water, and (v) from 1% to 10% (w/w) surfactant, wherein the pharmaceutical composition is physically stable and suitable for continuous or frequent intermittent intra-oral delivery.

129. The pharmaceutical composition of item 128, wherein said pharmaceutical composition comprises a paste.

130. The pharmaceutical composition of item 128 or 129, wherein said pharmaceutical composition comprises an emulsion.

131. The pharmaceutical composition of any of items 128 to 130, wherein said suspension is physically stable for 12 months at 5° C.

132. The pharmaceutical composition of any of items 128 to 131, wherein said suspension is physically stable for 12 months at 25° C.

133. The pharmaceutical composition of item 131 or 132, wherein after said 12 months said suspension is physically stable for 48 hours at 37° C.

134. The pharmaceutical composition of item 128 or 133, wherein the concentration of drug in the pharmaceutical composition is between about 50 mg/mL and about 500 mg/mL 135. The pharmaceutical composition of any of one of items 128 to 134, wherein the concentration of solid excipient in the pharmaceutical composition is between 200 mg/mL and about 800 mg/mL.

136. The pharmaceutical composition of any of one of items 128 to 135, wherein said solid excipient comprises cellulose, a cellulose derivative, an amino acid, titanium dioxide, calcium silicate, or calcium phosphate.

137. The pharmaceutical composition of any one of items 128 to 136, wherein said drug comprises Tizanidine, Midodrine, Metoclopramide, Captopril, Treprostinil, Bitolterol, Oxybutinin, Darifenacin, or a pharmaceutically acceptable salt thereof.

138. The pharmaceutical composition of any one of items 128 to 136, wherein said drug comprises baclofen and said pharmaceutical composition comprises baclofen.

139. The pharmaceutical composition of any one of items 128 to 137 having a viscosity greater than 10,000 cP at 37° C.

140. A pharmaceutical composition suitable for continuous infusion in the mouth comprising: a solution, an oil-in-water emulsion, a water-in-oil emulsion, or a solid particle comprising a suspension of between 20 mg/mL and 150 mg/mL of a drug selected from Baclofen, Tizanidine, Midodrine, Metoclopramide, Captopril, Treprostinil, Bitolterol, Oxybutinin, Darifenacin.

141. The pharmaceutical composition of item 140, further comprising a thickener.

142. The pharmaceutical composition of item 140 or 141 wherein the viscosity of said pharmaceutical composition is greater than 100 cP, 1,000 cP, 10,000, or 100,000 cP at about 37° C.

143. The pharmaceutical composition of any one of items 140 to 142, further comprising a surfactant.

144. An extrudable pharmaceutical composition suitable for continuous infusion in the mouth having a pH of from 3 to 10 comprising a magnesium compound, a zinc compound, or an iron compound at a concentration between 60 mg/mL to 1,600 mg/mL.

145. The pharmaceutical composition of item 144, further comprising a gelling agent or a thickener.

146. The pharmaceutical composition of item 144 or 145, wherein the viscosity of said pharmaceutical composition is greater than 100 cP, 1,000 cP, 10,000 cP, or 100,000 cP at about 37° C.

147. The pharmaceutical composition of item 146, wherein the pharmaceutical composition comprises a magnesium compound and the $Mg^{2+}$ concentration in the pharmaceutical composition is greater than 200 mg/mL.

148. A pharmaceutical composition suitable for continuous infusion in the mouth comprising a solution, suspension or gel comprising between 0.1 mg/mL and 20 mg/mL of a drug selected from Tizanidine, Iloprost, Beraprost, Ciclesonide, Flunisolide, Budesonide, Beclomethasone, Mometasone, Vilanterol, Levosalbutamol sulfate, Salbutamol, Salmeterol, Glycopyrronium bromide, Ipatropium bromide, Aclidinium bromide, Hexoprenaline sulfate, Pirbuterol, Fenoterol, Terbutaline, Metaproterenol, Tolterodine tartarate.

149. The pharmaceutical composition of item 148, further comprising a thickener.

150. The pharmaceutical composition of item 148 or 149 wherein the viscosity of said pharmaceutical composition is greater than 100 cP, 1,000 cP, 10,000 cP, or 100,000 cP at about 37° C.

151. The pharmaceutical composition of any one of items 148 to 150, further comprising a surfactant.

152. A drug delivery device configured to be removably inserted in a patient's mouth and for continuous or semi-continuous intraoral administration a drug, said device comprising a propellant-driven pump comprising a rigid housing, said rigid housing comprising a wall of a first chamber containing a drug-comprising fluid and a wall of a second chamber containing a propellant.

153. The drug delivery device of item 152, comprising a flexible and/or deformable propellant-impermeable diaphragm separating said first chamber from said second chamber.

154. The drug delivery device of item 153, wherein the density of the propellant-impermeable diaphragm is greater than 2.0 g per $cm^3$ at 25° C.

155. The drug delivery device of item 153 or 154, wherein said diaphragm comprises a wall of said first chamber and a wall of said second chamber.

156. The drug delivery device of any one of items 153 to 155, wherein said diaphragm is metallic.

157. The drug delivery device of item 156, wherein the metallic diaphragm comprises tin or silver or aluminum or copper or an alloy of tin or of silver or of aluminum or of copper.

158. The drug delivery device of item 157, wherein the metallic diaphragm comprises silver or an alloy of silver.

159. The drug delivery device of item 157, wherein the metallic diaphragm comprises tin or an alloy of tin.

160. The drug delivery device of any one of items 153 to 159, wherein said diaphragm is shaped to substantially conform to the interior housing wall of said first chamber.

161. The drug delivery device of any one of items 153 to 159, wherein said diaphragm is shaped to substantially conform to the interior housing wall of said second chamber.

162. The drug delivery device of any one of items 153 to 161, wherein the thickness of said diaphragm is between 10 µm and 250 µm, between 20 µm and 125 µm, or between 25 µm and 75 µm.

163. The drug delivery device of any one of items 153 to 162, wherein the thickness of said diaphragm varies across the interior of the housing by less than ±25%.

164. The drug delivery device of any one of items 153 to 162, wherein the thickness of said diaphragm varies across the interior of the housing by less than ±10%.

165. The drug delivery device of any one of items 153 to 162, wherein said diaphragm comprises a rim that is thicker than the center of said diaphragm.

166. The drug delivery device of item 165, wherein the thickness of the rim is at least 1.5 times greater than the thickness of the center of said diaphragm.

167. The drug delivery device of item 166, where the thickness of the rim is between 1.5 times and 2 times the thickness of the center of said diaphragm.

168. The drug delivery device of item 167, where the thickness of the rim is between 2 times and 3 times the thickness of the center of said diaphragm.

169. The drug delivery device of item 168, where the thickness of the rim is 3 times or more the thickness of the center of said diaphragm.

170. The drug delivery device of any one of items 153 to 169, wherein said diaphragm is folded, pleated, or scored.

171. A method of forming said diaphragm of any one of items 153 to 170, by stamping, hot-stamping, electroplating, electroless plating, or hydroforming.

172. The drug delivery device of any of items 152 to 171, wherein the device is hermetically sealed except for one or more orifices for drug filling or drug delivery.

173. The drug delivery device of item 172, wherein the one or more orifices for drug filling or drug delivery are hermetically or non-hermetically sealed.

174. The drug delivery device of item 173, wherein the one or more orifices for drug filling or delivery are hermetically sealed.

175. The drug delivery device of any one of items 152 to 174, wherein the propellant chamber is hermetically sealed and comprises a hermetically sealed orifice for filling with propellant.

176. The drug delivery device of any one of items 172 to 175, wherein the drug chamber comprises two, three, or more hermetically sealable or sealed orifices for filling with drug or for drug delivery.

177. The drug delivery device of any one of items 153 to 176, wherein said rigid housing and said diaphragm are joined by a hermetically sealing weld.

178. The drug delivery device of item 177, where the hermetically sealing weld prevents the influx of air and water vapor or the outflux of water vapor, drug or propellant.

179. The drug delivery device of item 178, where the hermetically sealing weld prevents the influx of air or oxygen.

180. The drug delivery device of any one of items 177 to 179, wherein the hermetically sealing weld prevents the influx or the outflux of helium.

181. A method of forming the weld of any one of items 177 to 180, comprising welding said rigid housing and said diaphragm to form a hermetic seal.

182. The method of item 181, wherein the method comprises resistance welding, laser welding or electron beam welding.

183. The method of item 182, wherein the method comprises resistance welding.

184. The method of item 183, wherein the method also comprises preheating the housing and said diaphragm.

185. The method of any one of items 181 to 184, wherein the method also comprises annealing at a temperature between 400° C. and 700° C. for 15 minutes or more.

186. The drug delivery device of any one of items 152 to 185, wherein said rigid housing comprises a metal, a ceramic, or a composite of a polymer reinforced by fibers.

187. The drug delivery device of item 186, wherein the fibers reinforcing the polymer comprise carbon fibers, glass fibers, or metal fibers.

188. The drug delivery device of any one of items 152 to 187, wherein said rigid housing comprises a material having at 25±3° C. a yield strength greater than 100 MPa.

189. The drug delivery device of any one of items 152 to 187, wherein said rigid housing comprises a material having at 25±3° C. a tensile yield strength greater than 100 MPa.

190. The drug delivery device of any one of items 152 to 187, wherein said rigid housing comprises a material having at 25±3° C. a modulus of elasticity greater than 30 GPa.

191. The drug delivery device of any one of items 152 to 187, wherein said rigid housing comprises a material having at 25±3° C. a Brinell hardness greater than 200 MPa.

192. The drug delivery device of any one of items 152 to 191, wherein said rigid housing comprises a material having a density greater than 2.5 g/cm$^3$ at 25±3° C.

193. The drug delivery device of any one of items 152 to 192, wherein said rigid housing comprises a metal having a density greater than 2.5 g/cm$^3$.

194. The drug delivery device of item 193, wherein said rigid housing comprises a metal having a density greater than 3.5 g/cm$^3$.

195. The drug delivery device of item 194, wherein said rigid housing comprises a metal having a density equal to or greater than 4.5 g/cm$^3$.

196. The drug delivery device of any one of items 193 to 195, wherein said rigid housing comprises a metal selected from the group titanium or iron or aluminum or molybdenum or tungsten or an alloy of titanium or iron or aluminum or molybdenum or tungsten.

197. The drug delivery device of item 196, wherein said rigid housing comprises titanium or an alloy of titanium.

198. The drug delivery device of item 197, wherein a metallic diaphragm is welded to said rigid housing comprising titanium or an alloy of titanium.

199. The drug delivery device of item 197 or 198, wherein said diaphragm comprises silver or an alloy of silver.

200. The drug delivery device of item 196, wherein the metal comprises iron or an alloy of iron.

201. The drug delivery device of item 200, wherein said diaphragm comprises iron or an alloy of iron.

202. The drug delivery device of item 200, wherein the metallic diaphragm comprises silver or an alloy of silver.

203. The drug delivery device of any one of items 193 to 202, wherein neither the metal of said rigid housing nor of the metal of said metallic diaphragm corrodes visibly after 3 months when the housing metal and said diaphragm metal are electrically contacted and are immersed in an air exposed 0.1 M citrate buffer solution of pH 4.0 at 23±3° C.

204. The drug delivery device of any one of items 193 to 202, wherein neither the metal of said rigid housing nor the metal of said metallic diaphragm corrodes visibly after 3 months when the housing metal and said diaphragm metal are electrically contacted and are immersed in a substantially de-oxygenated 0.1 M citrate buffer solution of pH 4.0 at 23±3° C.

205. The drug delivery device of item 204, wherein the density of the current flowing between two electrically shorted electrodes of about equal area, one of the metal of said rigid housing and the other of the metal of said diaphragm, is less than 2 µA cm$^{-2}$ after the electrodes are immersed in a substantially de-oxygenated 0.1 M citrate buffer solution of pH 4.0 at 23±3° C. for 24 hours.

206. The drug delivery device of item 205, wherein said current density is less than 0.5 µA cm$^{-2}$.

207. The drug delivery device of item 206, wherein said current density is less than 0.1 µA cm$^{-2}$.

208. The drug delivery device of any of items 152 to 207, wherein the shapes of the interior housing wall of said first chamber and the interior housing wall of said second chamber are substantially mirror images of each other excepting for grooves or ports for flow of drug-comprising fluid to the drug exit orifice.

209. The drug delivery device of any one of items 152 to 208, wherein said first chamber comprises one or more interior channels, grooves, or tubes for flow of drug-comprising fluid to the drug exit orifice.

210. The drug delivery device of item 209, wherein at least one channel, groove, or tube is not blocked by the diaphragm after more than 60 weight % of the drug is depleted.

211. The drug delivery device of item 210, wherein at least one channel, groove, or tube is not blocked by the diaphragm after more than 75 weight % of the drug is depleted.

212. The drug delivery device of item 211, wherein at least one channel, groove, or tube is not blocked by the diaphragm after more than 85 weight % of the drug is depleted.

213. The drug delivery device of item 212, wherein at least one channel, groove, or tube is not blocked by the diaphragm after more than 95 weight % of the drug is depleted.

214. The drug delivery device of item 209, wherein at least one channel, groove, or tube is not blocked by the diaphragm when said diaphragm has been fully extended into the drug chamber and drug flow has substantially stopped.

215. The drug delivery device of item 209, wherein a housing wall comprises the at least one channel, groove, or tube.

216. The drug delivery device of any one of items 209 to 215, wherein an insert comprises the at least one channel, groove, or tube.

217. The drug delivery device of any one of items 209 to 216, wherein said at least one channel, groove, or tube comprises one or more flow restrictors that substantially control the rate of drug delivery.

218. The drug delivery device of any one of items 153 to 217, wherein said diaphragm is shaped and sized so that it contacts 0%-10%, 11%-20%, 21%-30%, 31%-40%, or 41%-50% of the interior surface area of the drug chamber (excluding the surface area of the diaphragm itself) after delivery of 85%, 90%, or 95% of the starting drug product in the drug chamber.

219. The drug delivery device of any one of items 153 to 218, wherein said diaphragm is shaped and sized so that it does not substantially block the flow of said pharmaceutical composition from the exit orifice after 85%, 90%, or 95% of the starting drug product in the drug chamber has been delivered.

220. A drug delivery device configured to be removably inserted in a patient's mouth and for continuous or semi-continuous intraoral administration of a drug, said device comprising:
  (i) a first chamber containing a drug-comprising fluid;
  (ii) a second chamber containing a propellant; and
  (iii) a flexible and/or deformable diaphragm separating said first chamber from said second chamber;

(iv) wherein 75%-85%, 86%-95%, or >95% of the drug-comprising fluid is dispensed while the delivery rate varies by less than ±20%,±15%,±10%, or ±5%, over a period of at least 4, 8, 16, or 24 hours.

221. The drug delivery device of any one of items 152 to 220, wherein said pump comprises a liquid propellant, said liquid propellant having a boiling point of less than 37° C. at sea level atmospheric pressure.

222. The drug delivery device of item 221, wherein said liquid propellant is a hydrocarbon, a halocarbon, a hydrofluoralkane, an ester, or an ether.

223. The drug delivery device of item 221, wherein said liquid propellant is isopentane, trifluorochloromethane, dichlorofluoromethane, 1-fluorobutane, 2-fluorobutane, 1,2-difluoroethane, methyl ethyl ether, 2-butene, butane, 1-fluoropropane, 1-butene, 2-fluoropropane, 1,1-difluoroethane, cyclopropene, propane, propene, or diethyl ether.

224. The drug delivery device of item 221, wherein said liquid propellant is 1,1,1,2-tetrafluoroethane, 1,1,1,2,3,3,3-heptafluoropropane, 1,1,1,3,3,3-hexafluoropropane, octafluorocyclobutane or isopentane.

225. The drug delivery device of item 221, wherein said propellant is isopentane, trifluorochloromethane, dichlorofluoromethane, or 1,1,1,2-tetrafluoroethane.

226. The drug delivery device of any one of items 221 to 225, wherein said propellant has a vapor pressure of greater than 1.5 bar and less than 10 bar, or greater than 1.5 bar and less than 20 bar, at 37° C.

227. The drug delivery device of item 226, wherein said propellant has a vapor pressure of greater than 2.0 bar and less than 7 bar, or greater than 2.0 bar and less than 15 bar at 37° C.

228. The drug delivery device of item 227, wherein said propellant has a vapor pressure of greater than 3.0 bar and less than 6 bar, or greater than 3.0 bar and less than 10 bar, at 37° C.

229. The drug delivery device of any one of items 221 to 228, wherein (i) said propellant has a vapor pressure of greater than 2.1 bar at 37° C., and (ii) the average rate of drug delivery increases or decreases by less than ±20% across the atmospheric pressure range between 0.782 bar and 1.013 bar.

230. The drug delivery device of item 229, wherein (i) said propellant has a vapor pressure of greater than 3.2 bar at 37° C., and (ii) the average rate of drug delivery increases or decreases by less than ±10% across the atmospheric pressure range between 0.782 bar and 1.013 bar.

231. The drug delivery device of item 230, wherein (i) said propellant has a vapor pressure of greater than 4.7 bar at 37° C., and (ii) the average rate of drug delivery increases or decreases by less than ±6% across the atmospheric pressure range between 0.782 bar and 1.013 bar.

232. The drug delivery device of any one of items 152 to 231, comprising a pharmaceutical composition of any of items 1-151.

233. A drug delivery device configured to be removably inserted in a patient's mouth and for continuous or semi-continuous intraoral administration of a drug, said device comprising:
(i) a fastener to removably secure said drug delivery device to a surface of said patient's mouth;
(ii) an electrical or mechanical pump; and
(iii) an oral liquid impermeable drug reservoir containing any of the pharmaceutical compositions of any one of items 1 to 151, the volume of said drug reservoir being from 0.1 mL to 5 mL.

234. A drug delivery device configured to be removably inserted in a patient's mouth and for continuous or semi-continuous intraoral administration a drug, said device comprising:
(i) a fastener to removably secure said drug delivery device to a surface of said patient's mouth;
(ii) an electrical or mechanical pump;
(iii) an oral liquid impermeable drug reservoir containing any of the pharmaceutical compositions of any one of items 1 to 151, the volume of said drug reservoir being from 0.1 mL to 5 mL; and
(iv) an automatic stop/start.

235. The drug delivery device of item 234, wherein said drug delivery device is configured to be automatically stopped upon one or more of the following: (a) the drug delivery device, the pump, and/or the oral liquid impermeable reservoir are removed from the mouth; (b) the drug delivery device, the pump, and/or the oral liquid impermeable reservoir are disconnected from the fastener; or (c) the oral liquid impermeable reservoir is disconnected from the pump.

236. The drug delivery device of item 234 or 235, wherein said drug delivery device is configured to be automatically started upon one or more of the following: (a) the drug delivery device, the pump, and/or the oral liquid impermeable reservoir are inserted into the mouth; (b) the drug delivery device, the pump, and/or the oral liquid impermeable reservoir are connected to the fastener; or (c) the oral liquid impermeable reservoir is connected to the pump.

237. The drug delivery device of any one of items 234 to 236, wherein said automatic stop/start is selected from: a pressure sensitive switch, a clip, a fluidic channel that kinks, a clutch, a sensor, or a cap.

238. The drug delivery device of any one of items 234 to 237, further comprising a suction-induced flow limiter, a temperature-induced flow limiter, bite-resistant structural supports, or a pressure-invariant mechanical pump.

239. A drug delivery device configured to be removably inserted in a patient's mouth and for continuous or semi-continuous intraoral administration of a drug, said device comprising:
(i) a fastener to removably secure said drug delivery device to a surface of said patient's mouth;
(ii) a mechanical pump;
(iii) an oral liquid impermeable drug reservoir containing any of the pharmaceutical compositions of any one of items 1 to 151, the volume of said drug reservoir being from 0.1 mL to 5 mL; and
(iv) a suction-induced flow limiter.

240. The drug delivery device of item 239, wherein said suction-induced flow limiter comprises pressurized surfaces that are in fluidic (gas and/or liquid) contact with the ambient atmosphere via one or more ports or openings in the housing of the drug delivery device.

241. The drug delivery device of item 239, wherein said suction-induced flow limiter is selected from the group consisting of a deformable channel, a deflectable diaphragm, a compliant accumulator, an inline vacuum-relief valve, and a float valve.

242. The drug delivery device of any one of items 239 to 241, wherein said suction-induced flow limiter is configured to prevent the delivery of a bolus greater than about 5%, 3%, or 1% of the contents of a fresh drug reservoir, when the ambient pressure drops by 0.14 bar for a period of one minute.

243. The device of any one of items 239 to 242, further comprising an automatic stop/start, a temperature-induced flow limiter, bite-resistant structural supports, or a pressure-invariant mechanical pump.

244. A drug delivery device configured to be removably inserted in a patient's mouth and for continuous or semi-continuous intraoral administration of a drug, said device comprising:
(i) a fastener to removably secure said drug delivery device to a surface of said patient's mouth;
(ii) an electrical or mechanical pump;
(iii) an oral liquid impermeable drug reservoir containing any of the pharmaceutical compositions of any one of items 1 to 151, the volume of said drug reservoir being from 0.1 mL to 5 mL; and
(iv) a temperature-induced flow limiter.

245. The drug delivery device of item 244, wherein said temperature-induced flow limiter comprises insulation with a material of low thermal conductivity proximate the drug reservoir and/or the pump.

246. The drug delivery device of item 244 or 245, wherein said temperature-induced flow limiter comprises an elastomer whose force in a fresh reservoir increases by less than 30% when the oral temperature is raised from 37° C. to 55° C. for a period of one minute.

247. The drug delivery device of item 244 or 245, wherein said pump comprises a spring and said temperature-induced flow limiter comprises a spring configured to produce a force in a fresh reservoir that increases by less than 30% when the oral temperature is raised from 37° C. to 55° C. for a period of one minute.

248. The drug delivery device of item 244, wherein said temperature-induced flow limiter comprises a spring comprising a 300 series stainless steel, titanium, Inconel, and fully austenitic Nitinol.

249. The drug delivery device of item 244 or 245, wherein said pump is gas-driven and said temperature-induced flow limiter comprises a gas having a volume of less than 40% of the volume of a filled drug reservoir in a fresh reservoir at 37° C. and 1.013 bar.

250. The drug delivery device of item 244 or 245, wherein said pump is propellant-driven and said temperature-induced flow limiter comprises a propellant having a pressure that increases by less than about 80%, 60%, or 40% when the oral temperature is raised from 37° C. to 55° C. for a period of one minute.

251. The drug delivery device of any one of items 244 to 250, further comprising a suction-induced flow limiter, an automatic stop/start, bite-resistant structural supports, or a pressure-invariant mechanical pump.

252. A drug delivery device configured to be removably inserted in a patient's mouth and for continuous or semi-continuous intraoral administration of a drug, said device comprising:
(i) a fastener to removably secure said drug delivery device to a surface of said patient's mouth;
(ii) an electrical or mechanical pump;
(iii) an oral liquid impermeable drug reservoir containing any of the pharmaceutical compositions of any one of items 1 to 151, the volume of said drug reservoir being from 0.1 mL to 5 mL; and
(iv) bite-resistant structural supports.

253. The drug delivery device of item 252, wherein said bite-resistant structural supports are selected from: a housing that encapsulates the entire drug reservoir and pump components; posts; ribs; or a potting material.

254. The drug delivery device of item 252 or 253, further comprising a suction-induced flow limiter, an automatic stop/start, a temperature-induced flow limiter, or a pressure-invariant mechanical pump.

255. A drug delivery device configured to be removably inserted in a patient's mouth and for continuous or semi-continuous intraoral administration of a drug, said device comprising:
(i) a fastener to removably secure said drug delivery device to a surface of said patient's mouth;
(ii) a pressure-invariant mechanical pump; and
(iii) an oral liquid impermeable drug reservoir containing any of the pharmaceutical compositions of any one of items 1 to 151, the volume of said drug reservoir being from 0.1 mL to 5 mL.

256. The drug delivery device of item 255, wherein said pressure-invariant mechanical pump comprises pressurized surfaces that are in fluidic (gas and/or liquid) contact with the ambient atmosphere via one or more ports or openings in the housing of the drug delivery device.

257. The drug delivery device of item 255 or 256, wherein said pressure-invariant mechanical pump is configured to maintain an internal pressure of greater than or equal to about 2 bar.

258. The drug delivery device of item 257, wherein said pressure-invariant mechanical pump is configured to maintain an internal pressure of greater than or equal to about 3 bar.

259. The drug delivery device of item 258, wherein said pressure-invariant mechanical pump is configured to maintain an internal pressure of greater than or equal to about 4 bar.

260. The drug delivery device of any one of items 255 to 259, wherein said pressure-invariant mechanical pump is configured such that the average rate of drug delivery increases or decreases by less than about 20%, about 10%, or about 5% at 1.013 bar and at 0.782 bar, as compared to said average rate of delivery at 0.898 bar.

261. The drug delivery device of any one of items 255 to 260, further comprising a suction-induced flow limiter, an automatic stop/start, a temperature-induced flow limiter, or bite-resistant structural supports.

262. A drug delivery device configured to be removably inserted in a patient's mouth and for continuous or semi-continuous intraoral administration of a drug, said device comprising:
(i) a fastener to removably secure said drug delivery device to a surface of said patient's mouth;
(ii) a mechanical pump; and
(iii) an oral liquid impermeable drug reservoir containing any of the pharmaceutical compositions of any one of items 1 to 151, the volume of said drug reservoir being from 0.1 mL to 5 mL.

263. The drug delivery device of item 262, wherein said mechanical pump is selected from: a spring, an elastomer, compressed gas, and a propellant.

264. The drug delivery device of any one of items 255 to 263, wherein said oral liquid impermeable reservoir comprises one or more of: metal reservoirs, plastic reservoirs, elastomeric reservoirs, metallic barrier layers, valves, squeegees, baffles, rotating augers, rotating drums, propellants, pneumatic pumps, diaphragm pumps, hydrophobic materials, and hydrophobic fluids.

265. The drug delivery device of any one of items 255 to 264, wherein said device is configured such that 4 hours after inserting a drug delivery device including a fresh reservoir in a patient's mouth and initiating the administration, less than 5%, 3%, or 1% by weight of an originally contained pharmaceutical composition in the reservoir includes an oral liquid.

266. The drug delivery device of any one of items 255 to 265, further comprising a suction-induced flow limiter, an automatic stop/start, a temperature-induced flow limiter, a pressure-invariant mechanical pump, or bite-resistant structural supports.

267. The drug delivery device of any one of items 233 to 238 or items 244 to 254, wherein said pump is an electrical pump.

268. The drug delivery device of item 267, wherein said electrical pump is a piezoelectric pump or an electroosmotic pump.

269. The drug delivery device of item 268, wherein said piezoelectric pump is configured to operate at a frequency of less than about 20,000 Hz.

270. The drug delivery device of item 269, wherein said electrical pump comprises a motor.

271. The drug delivery device of any one of items 233 to 266, wherein said pump is a mechanical pump.

272. The drug delivery device of item 271, wherein said pump is an elastomeric drug pump.

273. The drug delivery device of item 272, wherein said elastomeric drug pump comprises an elastomeric balloon, an elastomeric band, or a compressed elastomer.

274. The drug delivery device of item 271, wherein said pump is a spring-driven pump.

275. The drug delivery device of item 274, wherein said spring-driven pump comprises a constant force spring.

276. The drug delivery device of item 275, wherein said spring-driven pump comprises a spring that retracts upon relaxation.

277. The drug delivery device of any one of items 274 or 275, wherein said spring-driven pump comprises two coaxial compression springs wherein, upon compression, a first spring with a first diameter is wholly or partially nested within a second spring with a second, larger diameter.

278. The drug delivery device of item 271, wherein said pump is a negative pressure pump.

279. The drug delivery device of item 271, wherein said pump is a pneumatic pump.

280. The drug delivery device of item 271, wherein said pump is a gas-driven pump.

281. The drug delivery device of item 280, comprising a gas in a first compartment and said drug in a second compartment, said gas providing a pressure exceeding 1.013 bar.

282. The drug delivery device of any one of items 280 or 281, wherein said gas-driven pump comprises a compressed gas cartridge.

283. The drug delivery device of any one of items 280 to 282, wherein said pump comprises a gas, the volume of said gas being less than 35% of the volume of said pharmaceutical composition.

284. The drug delivery device of any one of items 280 to 283, wherein said pump comprises a gas generator.

285. The drug delivery device of item 271, wherein said pump is a propellant-driven pump.

286. The drug delivery device of item 285, wherein said pump comprises a liquid propellant, said liquid propellant having a boiling point of less than 37° C. at sea level atmospheric pressure.

287. The drug delivery device of item 286, wherein said liquid propellant is a hydrocarbon, a halocarbon, a hydrofluoralkane, an ester, or an ether.

288. The drug delivery device of item 287, wherein said liquid propellant is isopentane, trifluorochloromethane, dichlorofluoromethane, 1-fluorobutane, 2-fluorobutane, 1,2-difluoroethane, methyl ethyl ether, 2-butene, butane, 1-fluoropropane, 1-butene, 2-fluoropropane, 1,1-difluoroethane, cyclopropene, propane, propene, or diethyl ether.

289. The drug delivery device of item 287, wherein said liquid propellant is 1,1,1,2-tetrafluoroethane, 1,1,1,2,3,3,3-heptafluoropropane, 1,1,1,3,3,3-hexafluoropropane, octafluorocyclobutane or isopentane.

290. The drug delivery device of item 287, wherein said propellant is isopentane, trifluorochloromethane, dichlorofluoromethane, or 1,1,1,2-tetrafluoroethane.

291. The drug delivery device of any of items 285 to 290, wherein said propellant has a vapor pressure of greater than 1.5 bar and less than 10 bar at 37° C.

292. The drug delivery device of item 291, wherein said propellant has a vapor pressure of greater than 2.0 bar and less than 7 bar at 37° C.

293. The drug delivery device of item 292, wherein said propellant has a vapor pressure of greater than 3.0 bar and less than 6 bar at 37° C.

294. The drug delivery device of any of items 285 to 290, wherein (i) said propellant has a vapor pressure of greater than 2.1 bar at 37° C., and (ii) the average rate of drug delivery increases or decreases by less than ±20% across the atmospheric pressure range between 0.782 bar and 1.013 bar.

295. The drug delivery device of item 294, wherein (i) said propellant has a vapor pressure of greater than 3.2 bar at 37° C., and (ii) the average rate of drug delivery increases or decreases by less than ±10% across the atmospheric pressure range between 0.782 bar and 1.013 bar.

296. The drug delivery device of item 294, wherein (i) said propellant has a vapor pressure of greater than 4.7 bar at 37° C., and (ii) the average rate of drug delivery increases or decreases by less than ±6% across the atmospheric pressure range between 0.782 bar and 1.013 bar.

297. The drug delivery device of any of items 285 to 296, comprising a rigid metal housing containing said pharmaceutical composition and said propellant.

298. The drug delivery device of item 297, wherein said rigid metal housing comprises titanium.

299. The drug delivery device of any one of items 297 or 298, wherein said pharmaceutical composition and said propellant are separated by a flexible and/or deformable diaphragm comprising a metal.

300. The drug delivery device of item 299, wherein said flexible and/or deformable diaphragm comprises tin or silver.

301. The drug delivery device of any one of items 233 to 290, comprising two or more drug pumps.

302. The drug delivery device of any one of items 233 to 301, comprising two or more drug reservoirs.

303. The drug delivery device of any one of items 233 to 302, wherein said drug reservoir is substantially impermeable to oxygen gas.

304. The drug delivery device of any one of items 233 to 303, wherein said drug reservoir includes a pharmaceutical composition and said pharmaceutical composition comprises greater than 33% of the total volume of the drug reservoir and pump.

305. The drug delivery device of any one of items 233 to 304, wherein the total volume of said one or more drug reservoirs and said one or more drug pumps is less than 5 mL.

306. The drug delivery device of item 305, wherein the total volume of said one or more drug reservoirs and said one or more drug pumps is less than 3 mL.

307. The drug delivery device of item 306, wherein the total volume of said one or more drug reservoirs and said one or more drug pumps is less than 2 mL.

308. The drug delivery device of any one of items 233 to 307, wherein said drug reservoir is a syringe assembly comprising a plunger and a barrel, said plunger being in slidable arrangement with said barrel.

309. The drug delivery device of item 308, wherein said syringe assembly further comprises a seal fitted over said plunger, said seal being in contact with said barrel.

310. The drug delivery device of item 309, wherein said seal is an O-ring.

311. The drug delivery device of item 309 or 310, wherein said barrel, plunger, and/or seal is not wetted by water.

312. The drug delivery device of item 309 or 310, wherein said barrel, plunger, and/or seal is not wetted by oil.

313. The drug delivery device of item 309 or 310, wherein said barrel, plunger, and/or seal is not wetted by oil or by water.

314. The drug delivery device of item 309 or 310, wherein said barrel, plunger, and/or seal is non-wettable by the pharmaceutical composition of any one of items 1 to 151.

315. The drug delivery device of any one of items 309 to 314, wherein said barrel, plunger, and/or seal is formed from or coated with a fluoropolymer or fluoroelastomer.

316. The drug delivery device of any one of items 309 to 315, wherein a surface of said barrel, plunger, and/or seal is coated with a lubricant.

317. The drug delivery device of item 316, wherein the solubility of said lubricant in said one or more water-immiscible compounds of the pharmaceutical composition is less than 3% (w/w) at 25° C.

318. The drug delivery device of item 316, wherein the solubility of said lubricant in said water is less than 1% (w/w) at 25° C.

319. The drug delivery device of any one of items 316 to 318, wherein said lubricant is a halogenated oil or grease.

320. The drug delivery device of item 319, wherein said halogenated oil or grease has an average molecular mass equal to or greater than about 1,000 Daltons.

321. The drug delivery device of item 319 or 320, wherein said halogenated oil is a perfluorinated polymer, a chlorofluorinated polymer, or a fluorinated polyether.

322. The drug delivery device of any one of items 233 to 317, wherein said drug reservoir is a syringe barrel and further comprising a deformable and/or mobile plug separating two compartments of said syringe barrel.

323. The drug delivery device of item 322, wherein said deformable and/or mobile plug comprises a perfluorinated, fluorinated, or chlorofluorinated oil or grease.

324. The drug delivery device of item 322 or 323, further comprising a propellant in one of said compartments and said pharmaceutical composition in the other of said compartments.

325. The drug delivery device of any one of items 233 to 324, wherein said surface is one or more teeth of the patient.

326. The drug delivery device of item 325, wherein said fastener comprises a band, a bracket, a clasp, a splint, or a retainer.

327. The drug delivery device of item 326, wherein said fastener comprises a transparent retainer.

328. The drug delivery device of item 326, wherein said fastener comprises a partial retainer attachable to fewer than 5 teeth.

329. The drug delivery device according to any one of items 233 to 328, comprising one or more drug reservoirs and one or more pumps, wherein said drug reservoirs or said pumps are configured to be worn in the buccal vestibule.

330. The drug delivery device according to any one of items 233 to 328, comprising one or more drug reservoirs and one or more pumps, wherein said drug reservoirs or said pumps are configured to be worn on the lingual side of the teeth.

331. The drug delivery device according to any one of items 233 to , comprising one or more drug reservoirs and one or more pumps, wherein said drug reservoirs or said pumps are configured to be worn simultaneously in the buccal vestibule and on the lingual side of the teeth.

332. The drug delivery device according to any one of items 233 to 328, comprising one or more drug reservoirs and one or more pumps, wherein said drug reservoirs or said pumps are configured bilaterally.

333. The drug delivery device according to any one of items 233 to 328, comprising one or more drug reservoirs and one or more pumps, wherein said drug reservoirs or said pumps are configured to administer said pharmaceutical composition into the mouth of said patient on the lingual side of the teeth.

334. The drug delivery device of item 333, comprising a fluidic channel from the buccal side to the lingual side of said patient's teeth for dispensing said pharmaceutical composition.

335. The drug delivery device according to any one of items 233 to 328, comprising one or more drug reservoirs and one or more pumps, wherein said drug reservoirs or said pumps are configured to administer said pharmaceutical composition onto the buccal or sublingual mucosa of said patient.

336. The drug delivery device of item 335, comprising a tube, channel, or orifice having a distal end positioned proximal to the buccal or sublingual mucosa within a zone bounded in part by a water vapor and gas permeable membrane that is saliva-repelling.

337. The drug delivery device of any one of items 152 to 336, comprising a fluidic channel in said fastener through which said pharmaceutical composition is administered into the mouth of said patient.

338. The drug delivery device of item 337, comprising a leak-free fluidic connector for direct or indirect fluidic connection of said fastener to said one or more drug reservoirs.

339. The drug delivery device of item 337 or 338, comprising a flow restrictor in said fastener for controlling the flow of said pharmaceutical composition.

340. The drug delivery device of any one of items 233 to 339, wherein said fastener comprises a pump or a power source.

341. The drug delivery device of any one of items 233 to 339, comprising a tapered flow path for said drug with a taper equal to or less than 60 degrees.

342. The drug delivery device of item 341, wherein said tapered flow path comprises a taper of less than or equal to 45 degrees.

343. The drug delivery device of item 342, wherein said tapered flow path comprises a taper of less than or equal to 30 degrees.

344. The drug delivery device of any one of items 152 to 343, wherein the drug reservoir is in fluid communication with a tube, channel, or orifice of less than 4 cm, 3 cm, 2 cm, 1 cm, 0.5 cm, or 0.2 cm in length and the dynamic viscosity of the pharmaceutical composition is greater than about 1,000 cP, 10,000 cP, or 100,000 cP, and where the device is configured to administer said drug via the tube, channel, or orifice.

345. The drug delivery device of item 344, wherein said tube, channel, or orifice has a minimum internal diameter of greater than about 0.1 mm, 0.2 mm, 0.3 mm, 0.4 mm, 0.5 mm, 1 mm, 2 mm, 3 mm, 4mm, or 5 mm.

346. The drug delivery device of item 345, wherein said internal diameter is greater than about 0.1 mm and less than 1 mm, 0.8 mm, 0.6 mm, 0.5 mm, 0.4 mm, 0.3 mm or 0.2 mm.

347. The drug delivery device of any one of items 233 to 345, further comprising a flow restrictor that sets the administration rate of said pharmaceutical composition.

348. The drug delivery device of item 347, wherein the length of said flow restrictor sets the administration rate of said pharmaceutical composition.

349. The drug delivery device of item 348, wherein said flow restrictor is flared.

350. The drug delivery system of item 347, wherein said flow restrictor comprises a diameter smaller than 1 mm and larger than 0.05 mm and a length between 0.5 cm and 10 cm.

351. The drug delivery system of item 350, wherein said flow restrictor comprises a diameter smaller than 0.7 mm and is larger than 0.2 mm.

352. The drug delivery system of item 350, wherein said flow restrictor comprises a plastic.

353. The drug delivery system of item 352, wherein said plastic comprises an engineering plastic.

354. The drug delivery system of Item 353, wherein said engineering plastic comprises a polyamide or a polyester, or a polycarbonate, or a polyetheretherketone, or a polyetherketone, or a polyimide, or a polyoxymethylene, or a polyphenylene sulfide, or a polyphenylene oxide, or a polysulphone, or polytetrafluoroethylene, or polyvinylidene difluoride, or ultra-high-molecular-weight polyethylene, or a strong elastomer.

355. The drug delivery device of item 347, wherein said flow restrictor may be adjusted by the physician or the patient to set the rate of flow.

356. The drug delivery device of any one of items 152 to 355, wherein said drug delivery device is configured to deliver an average hourly rate of volume of from about 0.015 mL/hour to about 1.25 mL/hour over a period of from about 4 hours to about 168 hours at 37° C. and a constant pressure of 1.013 bar, wherein said average hourly rate varies by less than ±20% or ±10% per hour over a period of 4 or more hours.

357. The drug delivery device of item 356, wherein said drug delivery device comprises oral fluid contacting surfaces that are compatible with said oral fluids, such that said average rate of delivery of said drug increases or decreases by less than ±20% or ±10% per hour after said device is immersed for five minutes in a stirred physiological saline solution at 37° C. comprising any one of the following conditions : (a) pH of about 2.5; (b) pH of about 9.0; (c) 5% by weight olive oil; and (d) 5% by weight ethanol.

358. A method of treating Parkinson's disease comprising administering the pharmaceutical composition of any of items 1 to 114 or 117 to 127 to a patient using the device of any of items 152 to 357.

359. A method of administering a pharmaceutical composition to a patient, said method comprising removably attaching the device of any one of items 152 to 357 to an intraoral surface of said patient.

360. The method of item 359, further comprising detaching said device from said intraoral surface.

361. The method of item 359 or 360, said method further comprising administering said drug to said patient for a delivery period of not less than about 4 hours and not more than about 7 days.

362. The method of item 359, wherein said device comprises a drug reservoir comprising a volume of a drug, and said method further comprises oral administration at a rate in the range of from 15 µL per hour to about 1.25 mL per hour during the delivery period.

363. The method of item 359 or 360, wherein the fluctuation index of said drug is less than or equal to 2.0, 1.5, 1.0, 0.75, 0.50, 0.25, or 0.15 during the delivery period.

364. The method of item 359 or 360, wherein said method comprises oral administration at a rate in the range of from about 0.015 mL/hour to about 0.25 mL/hour.

365. The method of item 359 or 360, wherein said method comprises oral administration at a rate in the range of from about 0.25 mL/hour to about 0.5 mL/hour; from about 0.5 mL/hour to about 0.75 mL/hour; or from about 0.75 mL/hour to about 1.0 mL/hour.

366. The method of item 359 or 360, wherein said method comprises oral administration at a rate in the range of from about 1.0 mL/hour to about 1.25 mL/hour.

367. The method of any one of items 359 to 362, wherein said device comprises a drug reservoir comprising a pharmaceutical composition comprising a drug and the drug is administered to said patient at an average rate of not less than 0.01 mg per hour and not more than 250 mg per hour.

368. The method of item 367, wherein said drug is administered to said patient at an hourly rate in the range of 0.01 mg per hour to 1 mg per hour.

369. The method of item 367, wherein said drug is administered to said patient at an hourly rate in the range of 1 mg per hour to 10 mg per hour.

370. The method of item 367, wherein said drug is administered to said patient at an hourly rate in the range of 10 mg per hour to 100 mg per hour.

371. The method of item 367, wherein said drug is administered to said patient at an hourly rate in the range of 100 mg per hour to 250 mg per hour.

372. The method of any one of items 358 to 371, wherein said pharmaceutical composition is administered to said patient at least once every 60 minutes.

373. The method of item 372, wherein said pharmaceutical composition is administered to said patient at least once every 30 minutes.

374. The method of item 373, wherein said pharmaceutical composition is administered to said patient at least once every 15 minutes.

375. The method of any one of items 359 to 371, wherein said pharmaceutical composition is administered to said patient continuously.

376. The method of any one of items 359 to 375, wherein said pharmaceutical composition is administered to said patient over a delivery period of 4, 8, 16, 24, or more hours.

377. The method of any one of items 359 to 376 further comprising treating a disease in said patient, wherein said disease is mucositis, allergy, immune disease, anesthesia, bacterial infections, cancer, pain, organ transplantation, disordered sleep, epilepsy and seizures, anxiety, mood disorders, post-traumatic stress disorder, arrhythmia, hypertension, heart failure, spasticity, or diabetic nephropathy.

378. The method of any one of items 359 to 376 further comprising treating a disease in said patient, wherein said disease is multiple sclerosis, cerebral palsy, spasticity, neurogenic orthostatic hypotension, Wilson's disease, cystinuria, rheumatoid arthritis, Alzheimer's disease, Type-1 Gaucher disease, Type C Niemann-Pick disease, eosinophilic gastroenteritis, chronic mastocytosis, ulcerative colitis, gastro-oesophageal reflux, gastroenteritis, hyperemesis gravidarum, glioblastoma multiformae, anaplastic astrocytoma, pulmonary hypertension, coronary heart disease congestive heart failure, angina, Type 2 diabetes, COPD, asthma, irritable bowel syndrome, overactive bladder, and urinary urge incontinence.

379. The method of any one of items 359 to 376 further comprising treating a disease in said patient, wherein said disease is myasthenia gravis and said pharmaceutical composition comprises pyridostigmine.

380. The method of any one of items 359 to 376, wherein said pharmaceutical composition comprises one or more drugs selected from methylphenidate, prostaglandins, prostacyclin, treprostinil, beraprost, nimodipine, and testosterone.

381. The method of any one of items 359 to 380, wherein said pharmaceutical composition comprises a mucoadhesive polymer.

382. The method of item 381, wherein said pharmaceutical composition further comprises a permeation enhancer.

383. The method of any one of items 359 to 382, wherein said pharmaceutical composition comprises drug dissolved in an aqueous solution.

384. The method of item 383, wherein said aqueous solution further comprises glycerol, ethanol, propylene glycol, polyethylene glycol (PEO, PEG) or DMSO.

385. The method of any one of items 359 to 384, wherein said pharmaceutical composition further comprises a thickening agent.

386. The method of item 385, wherein said thickening agent is a sugar, a sugar alcohol, or a polymer.

387. The method of item 386, wherein said thickening agent is cellulose or a cellulose derivative.

388. The method of item 386, wherein said thickening agent is selected from carboxymethyl cellulose, microcrystalline cellulose, hyaluronic acid, polyacrylic acid, polymethacrylic acid, alginic acid, or salts thereof.

389. The method of item 386, wherein said thickening agent is selected from sucrose, glucose, fructose, sorbitol, and mannitol.

390. The method of any one of items 359 to 376, further comprising treating Parkinson's disease.

391. A method for treating Parkinson's disease in a patient, said method comprising:
(a) inserting the drug delivery device of any one of items 233 to 357 into said patient's mouth, said device having a drug reservoir comprising levodopa or a levodopa prodrug;
(b) administering into said patient's mouth said levodopa or a levodopa prodrug for a period of at least 4 hours at an hourly rate in the range of 30 mg/hour to 150 mg/hour, such that a circulating plasma levodopa concentration greater than 1,200 ng/mL and less than 2,500 ng/mL is continuously maintained for a period of at least 4 hours during said administration; and
(c) removing said drug delivery device from the mouth.

392. The method of item 391 comprising administering into said patient's mouth said levodopa or a levodopa prodrug for a period of at least 8 hours at an hourly rate in the range of 30 mg/hour to 150 mg/hour, such that a circulating plasma levodopa concentration greater than 1,200 ng/mL and less than 2,500 ng/mL is continuously maintained for a period of at least 8 hours during said administration. 393. A method for treating Parkinson's disease in a patient, said method comprising:

(a) inserting a drug delivery device comprising the pharmaceutical composition of any one of items 1 to 113 into said patient's mouth, said pharmaceutical composition comprising levodopa or levodopa prodrug;
(b) administering into said patient's mouth said levodopa or levodopa prodrug for a period of at least 4 hours at an hourly rate in the range of 30 mg/hour to 150 mg/hour, such that a circulating plasma levodopa concentration greater than 1,200 ng/mL and less than 2,500 ng/mL is continuously maintained for a period of at least 4 hours during said administration; and
(c) removing said drug delivery device from the mouth.

394. The method of item 393 comprising administering into said patient's mouth said levodopa or levodopa prodrug for a period of at least 8 hours at an hourly rate in the range of 30 mg/hour to 150 mg/hour, such that a circulating plasma levodopa concentration greater than 1,200 ng/mL and less than 2,500 ng/mL is continuously maintained for a period of at least 8 hours during said administration.

395. The method of item 393 or 394, wherein the fluctuation index of levodopa is less than or equal to 2.0, 1.5, 1.0, 0.75, 0.50, 0.25, or 0.15 for a period of at least 4 hours during said administration.

396. The method of item 395, wherein the fluctuation index of levodopa is less than or equal to 2.0, 1.5, 1.0, 0.75, 0.50, 0.25, or 0.15 for a period of at least 8 hours during said administration.

397. The method of any one of items 393 to 396, wherein during said administration the circulating levodopa plasma concentration varies by less than +/−20% or +/−10% from its mean for a period of at least 1, 2, or 4 hours.

398. A method for treating Parkinson's disease in a patient, said method comprising continuous or semi-continuous administration of the pharmaceutical composition of any one of items 1 to 114 or 117 to 127 into said patient at a rate of 10 mg/hour to 200 mg/hour for a period of about 4 hours to about 168 hours.

399. The method of any one of items 391 to 398, wherein said method of treating Parkinson's disease comprises treating a motor or non-motor complication of Parkinson's disease.

400. The method of item 406, wherein said motor or non-motor complication comprises tremor, akinesia, bradykinesia, dyskinesia, dystonia, cognitive impairment, or disordered sleep.

401. A method of treating Parkinson's disease in a patient comprising administering the pharmaceutical composition of any of items 1 to 114 or 117 to 127 to a patient using the method of any of items 359 to 375 or 391 to 400.

402. A method of preparing a pharmaceutical composition comprising from about 35% (w/w) to about 70% (w/w) of a drug comprising levodopa and/or carbidopa; said composition comprising a surfactant, an oil, and water; said composition, when at 37° C., comprising solid particles of said drug; said drug having a partition coefficient in favor of water; said surfactant being present in an amount sufficient to render said composition physically stable; and said method comprising contacting an aqueous solution comprising said surfactant and water with solid particles of said drug, to produce a mixture of said solid particles in said aqueous solution.

403. The method of item 402, further comprising contacting said mixture with said oil.

404. A method for treating Parkinson's disease in a subject, said method comprising:
(a) inserting a drug delivery device into said subject's mouth, said device having (i) a fastener to removably secure said drug delivery device to a surface of said patient's mouth; (ii) an electrical or mechanical pump; and (iii) an oral liquid impermeable drug reservoir having a volume of from 0.1 ml to 5 ml comprising a suspension or solid containing levodopa or a levodopa prodrug;

(b) administering into said patient's mouth said levodopa or a levodopa prodrug continuously or semi-continuously; and (c) removing said drug delivery device from the mouth of the subject, wherein said subject has a score of 4 and 5 on the Hoehn and Yahr scale.

405. The method of item 404, wherein step (b) comprises administering into said subject's mouth said levodopa or a levodopa prodrug semi-continuously at a frequency of at least once every 30 minutes.

406. The method of item 404 or 405, wherein the suspension or solid is administered to the subject for a period of at least 8 hours at an hourly rate in the range of 10-125 mg/hour, such that a circulating plasma levodopa concentration greater than 1,200 ng/m L and less than 2,500 ng/mL is continuously maintained for a period of at least 8 hours during said administration.

407. The method of any one of items 404 to 406, wherein the subject has delayed gastric emptying or retarded gastrointestinal transit.

408. The method of any one of items 404 to 407, wherein the drug reservoir comprising a composition comprising a suspension that is a drug particle-containing emulsion comprising (i) from 35% to 70% (w/w) drug particles comprising levodopa and/or carbidopa, or salts thereof, (ii) from 19% to 30% (w/w) of one or more water-immiscible compounds, (iii) from 2% to 16% (w/w) water, and (iv) from 1% to 8% (w/w) surfactant.

409. The method of item 408, wherein the suspension comprises a continuous hydrophilic phase comprising greater than 50% (w/w) drug particles.

410. The method of any one of items 404 to 409, wherein the drug delivery device comprises an automatic stop/start.

411. The method of any one of items 404 to 409, wherein the drug delivery device comprises a suction-induced flow limiter.

412. The method of any one of items 404 to 409, wherein the drug delivery device comprises a temperature-induced flow limiter.

413. The method of any one of items 404 to 409, wherein the drug delivery device comprises bite-resistant structural supports.

414. A method for treating spasticity in a subject, said method comprising:

(a) inserting a drug delivery device into said subject's mouth, said device having (i) a fastener to removably secure said drug delivery device to a surface of said patients mouth; (ii) an electrical or mechanical pump; and (iii) an oral liquid impermeable drug reservoir having a volume of from 0.1 ml to 5 ml comprising a suspension or solid containing baclofen;

(b) administering into said patient's mouth said baclofen continuously or semi-continuously; and (c) removing said drug delivery device from the mouth of the subject.

415. A method for treating myasthenia gravis in a subject, said method comprising:

(a) inserting a drug delivery device into said subject's mouth, said device having (i) a fastener to removably secure said drug delivery device to a surface of said patients mouth; (ii) an electrical or mechanical pump; and (iii) an oral liquid impermeable drug reservoir having a volume of from 0.1 ml to 5 ml comprising a solution or suspension of pyridostigmine;

(b) administering into said patient's mouth said pyridostigmine continuously or semi-continuously; and (c) removing said drug delivery device from the mouth of the subject.

416. A method for treating disease in a subject suffering from delayed gastric emptying or retarded gastrointestinal transit, the method including:

(a) inserting a drug delivery device into the subjects mouth, the device having (i) a fastener to removably secure the drug delivery device to a surface of the patient's mouth; (ii) an electrical or mechanical pump; and (iii) an oral liquid impermeable drug reservoir having a volume of from 0.1 ml to 5 ml including a suspension or solid containing a drug useful for treating said disease;

(b) administering into the patient's mouth the drug continuously or semi-continuously at a frequency of at least once every 30 minutes; and (c) removing the drug delivery device from the mouth of the subject.

417. The method of item 416, wherein an efficacious circulating plasma concentration of the drug is continuously maintained for a period of at least 8 hours during the administration.

418. The method of item 416 or 417, wherein the drug delivery device includes an automatic stop/start, a suction-induced flow limiter, a temperature-induced flow limiter, and/or bite-resistant structural supports.

419. A drug delivery device configured for continuously or semi-continuously administering a drug into the mouth of a patient, said drug delivery device comprising:

(i) a pharmaceutical composition comprising a paste, solution or suspension having a viscosity greater than 100 poise and less than 500,000 poise at 37° C. and comprising said drug; and (ii) a mechanical pump comprising a flow restrictor, said flow restrictor comprising an internal diameter between 0.05 mm and 3.00 mm and a length between 0.25 cm and 20 cm, configured and arranged to administer said pharmaceutical composition at a rate between 0.001 mL/hour and 1.25 mL/hour.

420. The drug delivery device of item 419, wherein said mechanical pump comprises a propellant.

421. The drug delivery device of item 420, wherein said propellant has a vapor pressure at about 37° C. greater than 1.2 bar and less than 50 bar.

422. The drug delivery device of item 419, wherein said pharmaceutical composition comprises solid drug particles and/or excipient particles having a $D_{90}$ between 0.1 μm and 200 μm and a $D_{50}$ between 0.1 μm and 50 μm when measured by light scattering with the particles dispersed in a non-solvent.

423. The drug delivery device of item 420, wherein said device is configured such that:

(i) said administration rate is greater than 0.03 mUhour and less than 0.5 mL/hour;

(ii) said viscosity is greater than 200 poise and less than 100,000 poise;

(iii) said flow restrictor has an internal diameter between 0.1 mm and 0.7 mm and a length between 1 cm and 5 cm; and (iv) said propellant has a vapor pressure at about 37° C. greater than 2.5 bar and less than 15 bar.

424. The drug delivery device of item 429, wherein said solid drug particles and/or excipient particles having a $D_{90}$ between 1 μm and 50 μm and a $D_{50}$ between 0.5 μm and 30 μm when measured by light scattering with the particles dispersed in a non-solvent.

425. The drug delivery device of item 423, wherein said device is configured such that:

(i) said administration rate is greater than 0.05 mL/hour and less than 0.2 mL/hour;

(ii) said viscosity is greater than 500 poise and less than 75,000 poise;

(iii) said flow restrictor has an internal diameter between 0.2 mm and 0.5 mm and a length between 1 cm and 2.5 cm; and (iv) said propellant has a vapor pressure at about 37° C. greater than 4 bar and less than 10 bar.

426. The drug delivery device of item 425, wherein said solid drug particles and/or excipient particles having a $D_{90}$ between 3 μm and 30 μm and a $D_{50}$ between 2 μm and 20 μm when measured by light scattering with the particles dispersed in a non-solvent.

427. A method of administering a pharmaceutical composition to a patient, said method comprising:

(i) inserting said drug delivery device into the mouth of said patient;

(ii) continuously or semicontinuously administering said pharmaceutical composition into the mouth of a patient using at a rate between 0.001 mL/hour and 1.25 mL/hour;

(iii) wherein said pharmaceutical composition comprises a paste, solution or suspension having a viscosity greater than 100 poise and less than 500,000 poise at 37° C.; and (iv) said drug delivery device comprises a mechanical pump comprising a flow restrictor comprising an internal diameter between 0.05 mm and 3.00 mm and a length between 0.25 cm and 20 cm.

428. The method of item 427, wherein said mechanical pump comprises a propellant, said propellant having a vapor pressure at about 37° C. greater than 1.2 bar and less than 50 bar.

429. The method of item 427, wherein said solid drug particles and/or excipient particles having a $D_{90}$ between 0.1 μm and 200 μm and a $D_{50}$ between 0.1 μm and 50 μm when measured by light scattering with the particles dispersed in a non-solvent.

430. The method of item 428, wherein:

(i) said administration rate is greater than 0.03 mL/hour and less than 0.5 mL/hour;

(ii) said viscosity is greater than 200 poise and less than 100,000 poise;

(iii) said flow restrictor has an internal diameter between 0.1 mm and 0.7 mm and a length between 1 cm and 5 cm; and (iv) said propellant has a vapor pressure at about 37° C. greater than 2.5 bar and less than 15 bar.

431. The method of item 430 wherein said solid drug particles and/or excipient particles having a $D_{90}$ between 0.1 μm and 50 μm and a $D_{50}$ between 0.5 μm and 30 μm when measured by light scattering with the particles dispersed in a non-solvent.

432. The method of item 431 wherein:

(i) said administration rate is greater than 0.05 mL/hour and less than 0.2 mL/hour;

(ii) said viscosity is greater than 500 poise and less than 75,000 poise;

(iii) said flow restrictor has an internal diameter between 0.2 mm and 0.5 mm and a length between 1 cm and 2.5 cm; and (iv) said propellant has a vapor pressure at about 37° C. greater than 4 bar and less than 10 bar.

433. The method of item 432 wherein said solid drug particles and/or excipient particles having a $D_{90}$ between 3 μm and 30 μm and a $D_{50}$ between 2 μm and 20 μm when measured by light scattering with the particles dispersed in a non-solvent.

The following examples are meant to illustrate the invention. They are not meant to limit the invention in any way.

EXAMPLE 1

Preparation and Extrusion of a 157 mg/mL CD (0.74 M) and 629 mg/mL (3.19 M) LD Solid Particle Containing Suspension, Comprising Only 464 mg/mL of a Carrier Fluid Made of Oil, Water and Surfactant that is Physically Stable and is Also Resistant to Air-oxidation for a Month, Appropriate for Extrusion into the Mouth Ingredients: LD ($D_{50}$ about 75 μm; $D_{90}$ about 200 μm); CD ($D_{95}$ about 100 μm, $D_{80}$ about 45 μm); Kolliphor RH 40 (from Sigma); Miglyol 812 (Peter Cremer, Cincinnati, Ohio); de-ionized water.

0.8 g Kolliphor RH 40 also known as Cremophor RH 40 was dissolved by warming and agitation in 1.5 g water. 2.4 g CD and 9.6 LD was added and the mixture was homogenized, then allowed to age for 10 hours with periodic mixing. 4.75 g of Miglyol 812, a medium chain triglyceride, was added, the suspension was homogenized and allowed to age for 3 hours with periodic mixing.

Most of the LD and most of the CD was particulate, i.e., most of the LD and the CD was suspended, not dissolved. The suspension of the solid drug particles was deformable but could not be poured at the ambient temperature of about 23±2° C. The suspension was soft, compliant, easy to mechanically deform and it retained its shape upon deformation. After storage for a month at 23±2° C. there was no visible indication of sedimentation of solid drug particles, nor was there any visible indication of phase separation of the oil and the water, i.e., the suspension remained unchanged and appeared homogeneous after storage for a month. The suspension was off-white, nearly colorless, and it was nearly tasteless, i.e., it did not have a strong or unpleasant taste.

The calculated approximate volume of the suspension in the absence of trapped air was about 15.3 mL and the measured weight was 19.05 g. From these values a density of about 1.25 g/mL is calculated, providing, if all or most air were removed, a suspension with a CD concentration of about 157 mg/mL and with an LD concentration of about 629 mg/mL.

Although it was not removed, any trapped air could have been removed for example by centrifugation, or by chilling to a temperature where the partial pressure of water is low, e.g., less than 10° C., for example about 0° C., and pulling a vacuum.

About 6.5 g of the soft suspension was loaded in a 20 mL cm® CRONO ® syringe (sold by CANE S.p.A, Rivoli, Italy) equipped with a luer lock. The visible bubbles of trapped air were moved by hard tapping against a rubber pad, which raised them to the orifice where they were expelled with some of the suspension by applying pressure to the plunger. The remaining volume was about 5 mL and the weight was about 6 g for an apparent density of about 1.2 g/mL. The suspension was extruded as a plug through a 25 mm long 16 gauge nozzle, i.e., a nozzle having an inner diameter of 1.29 mm and a cross sectional area of 1.31 $mm^2$. The nozzle through which the suspension was extruded had a female luer for attachment to the male luer of the syringe. In plug flow, known also as slip flow, a deformable plug may be extruded through an orifice by slipping through it, slip-flow accounting for at least some of the flow. The suspension-containing syringe having the attached nozzle was loaded in a CRONO PAR (Rivoli, Italy) pump. The pump was set to deliver continuously a volume of 0.1 mL/hour.

The suspension in the syringe was extruded through the nozzle at about 23±2° C. The extrudate was a long cylindrical fiber that retained its shape for more than 10 hours after its extrusion at ambient temperature. The extruded fiber was off-white, nearly colorless, and remained colorless when air-exposed at ambient temperature for more than a week, showing that the oxidations of CD and LD to colored degradation products were slow, i.e., that the suspension was substantially stable to air-oxidation for a week. This in contrast with a saturated aqueous solution of the LD and CD which turns dark under air in 24 hours.

The change of the extrudate weight, as a function of extrusion time, is shown in Table 3. When the extrusion ended the pump signaled that the syringe was empty, i.e., that about all of the suspension was extruded. The pump did not signal, at any time, an occlusion.

TABLE 3

Change in extrudate weight with extrusion time.

| Extrusion time (hrs) | Extruded weight (g) |
|---|---|
| 0 | 0 |
| 8.92 | 0.93 |
| 20.07 | 2.19 |
| 30.08 | 3.31 |
| 36.95 | 4.11 |
| 43.45 | 4.87 |
| 45.4 | 5.07 |

The slope of the plotted data, which would equal the extrudate density if the pump extruded at the set rate of 0.1 mL/hour, was about constant at about 1.12 g/mL for the about 45 hour long extrusion period. The observed density was less than the above estimated density of about 1.2 g/mL, suggesting that the actual pumping rate of the Crono Par pump, when set at 0.1 mL/hour, was only about 0.093 mL/hour and/or that water evaporated from the ambient air exposed extrudate.

The constancy of the density shows shows that the concentration of the extrudate during the 45 hour long extrusion remained constant in spite of the LD and CD solid particles having estimated densities of about 1.5 g/mL, which is considerably higher than the 0.97 g/mL density of the carrier fluid.

EXAMPLE 2

Showing the Advantage of Adding Oil to the Carrier Fluid and that without Oil the Suspension is not Physically Stable Ingredients: LD, CD, Kolliphor RH 40 and de-ionized water all as in Example 1.

0.8 g Kolliphor RH 40 was dissolved by warming in 6.5 g water at about 60° C.; the calculated volume of the solution is about 7.26 mL; 2.4 g CD and 9.6 LD (estimated combined volumes of the two drugs, 8 mL) was added and the mixture was homogenized. As in Example 1, most of the LD and most of the CD was particulate, not dissolved. The respective concentrations of CD and LD in the resulting suspension were 157 mg/mL and 629 mg/mL, similar to those in Example 1.

Unlike the suspension of Example 1, which was not pourable at about 23±2° C., the suspension without oil was pourable; it could be poured and was, unlike the suspension of Example 1, homogenized by shaking. A nearly clear, particle-free liquid layer was observed at the top in the suspension after about an hour, unlike in the oil-containing suspension of Example 1 where there was no sedimentation or any other indication of inhomogeneity after a month of storage at about 23±2° C. The clear layer became thicker after 3 hours.

Use of the suspension made without oil would require frequent re-suspension (e.g., by shaking), unlike the physically stable oil-containing suspension.

EXAMPLE 3

Preparation and Extrusion of a Physically Stable 156 mg/mL (0.74 M) CD and 624 mg/mL (3.16 M) LD Containing Suspension Comprising Only 460 mg/mL of a Carrier Emulsion, Made with a Food-grade Oil, Suitable for Infusion in the Mouth Ingredients: All as in Example 1, except for the canola oil (Safeway Kitchens, distributed by Safeway, Pleasanton, Calif.) which replaced the Miglyol 812.

Most of the LD and most of the CD were particulate, i.e., were not dissolved. The composition was similar to that of Example 1, except that 4.7 g of canola oil (density about 0.92 g/mL) was used instead of 4.75 g of Miglyol 812 (density about 0.95 g/mL).

To prepare the suspension, 0.8 g Kolliphor RH 40 was dissolved by warming and agitation in 1.5 g water. 2.4 g CD and 9.6 LD was added and the mixture was homogenized, then allowed to age with periodic mixing for 4 hours. 4.7 g of canola oil was added, the suspension was re-homogenized by mixing and allowed to age for 3 hours with periodic mixing. The resulting suspension was plastically deformable, retaining its shape upon deformation. Although it was not pourable at the ambient temperature of about 23±2° C., it was soft, compliant and it was easy to mechanically deform and as seen below easy to extrude through the below described nozzle as a plug. After a month, there was no visible indication of sedimentation of the solid drug particles, nor was there any visible indication of phase separation of the oil and the water. The suspension remained unchanged, i.e., homogeneous, after storage for a month at about 23±2° C. The suspension remained off-white, showing that its rate of air-oxidation was much slower than that of dissolved LD or CD. The suspension was nearly tasteless, i.e., it did not have a strong or unpleasant taste.

The estimated density of the suspension in the absence of trapped air and assuming that the densities of LD and of CD are of about 1.5 g/mL was about 1.24 g/mL and the respective CD and LD concentrations were 156 mg/mL and 624 mg/mL. Trapped air should be possible to remove, e.g., by centrifugation or by chilling to a temperature where the partial pressure of water is low, e.g., less than 10° C., for example about 0° C., and pulling a vacuum.

About 5 g of the soft suspension were loaded in a 20 mL cm® CRONO® syringe having a male luer. Air bubbles were visible; some of the larger one could be moved to the orifice and were expelled with some of the suspension by moving the piston back and forth while the syringe was capped, and by hard tapping then applying pressure to the plunger to expel the layer containing the visible air bubbles. The remaining volume was about 4.5 mL.

The syringe was loaded in a CRONO PAR pump, set to deliver continuously a volume of 0.1 mL/hour, and extruded through a 25 mm long 16 gauge (1.29 mm diameter, about 1.31 mm$^2$ cross sectional area) nozzle equipped with a female luer for attachment to the syringe. The extrudate was a long cylindrical fiber that retained its shape for more than 10 hours after its extrusion at the ambient temperature, about 23±2° C. The color of the extruded fiber was off-white and it remained off-white when air-exposed at ambient temperature for more than a week, showing that the oxidations of CD and LD to colored products were slow.

The extruded suspension weight is shown as a function of extrusion time in Table 4. When the extrusion ended the pump signaled that the syringe was empty, i.e., that about all of the suspension was extruded. The pump did not signal, at any time, an occlusion.

TABLE 4

Change in extruded weight with extrusion time.

| Extrusion time (hrs) | Extruded weight (g) |
|---|---|
| 0 | 0 |
| 4.3 | 0.48 |
| 14 | 1.54 |
| 19.28 | 2.09 |
| 26 | 2.8 |
| 37.61 | 3.98 |
| 42.23 | 4.46 |

When plotted in a graph, the slope (equal to the extrudate density assuming that the pump extrudes 0.1 mL/hour) was about 1.06 g/mL. The pump set at 0.1 mL/hr may have, however, extruded only 0.093 mL/hr, as estimated in Example 1. In this case the extrudate density would be about 1.14 g/mL, less than the estimated density of 1.24 g/mL, suggesting trapped air residue and/or evaporation of water during the extrusion. The slope was about constant for the about 42 hour long extrusion period, showing that the concentrations of the dense components of the suspensions, CD and of LD, are about constant.

EXAMPLE 4

Showing that Both Oil and Water are Required for Physical Stability to Prevent Sedimentation and Caking Upon Extrusion of an 837 mg/mL (4.25 M) LD Suspension Ingredients: LD (sieved particles passing 125 μm openings, not passing 32 μm openings); canola oil (as in Example 3); Polysorbate 60 (as in Example 1); de-ionized water.

(a) Example Showing the Requirement for Water in the Carrier Emulsion Used to Suspend the LD Particles.

An about 837 mg/mL LD suspension in oil was prepared as follows: 1.95 g of Polysorbate 60 was dissolved in 20 g of canola oil. The resulting solution was clear. 5 g of the solution were homogenized with 10 g of LD to form a soft and viscous suspension that remained unchanged after standing for 3 days at 23±2° C.; there was no sedimentation of the dense drug particles, nor did the oil separate from the water; the suspension remained homogeneous. Most of the LD was particulate, i.e. it was not dissolved.

Part of the suspension was loaded into a 20 mL cm® CRONO® syringe barrel, then pushed through its >2 mm diameter outlet, to which no flow-restricting nozzle or tubing was attached, by manually applying pressure on the piston. Unlike the extruded suspensions of Examples 1 and 3, or the also extruded, below-described, water and oil containing suspension of this Example, the delivered suspension did not retain its shape. Furthermore, the concentration of strongly light-scattering solid particles visibly changed. The delivered suspension changed from a solid-rich, intensely light scattering suspension to a less light scattering, more oil-containing suspension; then only nearly clear oil was delivered with few light scattering solid drug particles. After pushing part of the suspension through the opening, it became increasingly difficult to push through more. After about half of the suspension was delivered it became impossible to manually push through any of the remaining suspension. When the syringe was disassembled, i.e., when its piston was pulled out, a dense and hard solid-rich cake was found near the outlet of the syringe. This cake filtered, i.e., retained, the solid drug particles, but passed the nearly particle-free oil.

The experiment shows that at about 837 mg/mL LD concentration a suspension of solid drug particles of about 32-125 μm size in a surfactant-containing oil, not containing water, changes its composition during delivery and that it is difficult or impossible to deliver the entire volume of suspension in a reservoir through an about 2 mm diameter orifice.

(b) Example Showing the Requirement of Water in the Carrier Emulsion Used to Suspend the LD Particles.

1.22 g of Polysorbate 60 was dispersed in 12.2 g of water; the Polysorbate 60 was dispersed, but was not dissolved. To 5 g of the dispersion 10 g of LD was added. The resulting suspension was fluid, i.e. it could be poured. Sedimentation of drug particles was observed after about 30 min; shaking re-homogenized the suspension.

(c) Example Showing Improved Physical Stability of a LD Suspension Containing Both Oil and Water 10 g of the suspension of part (a) above was mixed with 10 g of the suspension of part (b) above to form an 837 mg/ml LD suspension containing both oil and water. At about 23±2° C. the suspension was non-pourable. It was, however, plastically deformable and retained its shape upon deformation. When force was applied, it extruded through a nozzle as a plug. Unlike in the suspension of part (b) of this example, that did not contain oil and in which sedimentation was observed after 30 min, there was no visible sedimentation nor was there any visible indication of phase separation of the oil and the water after a month; the suspension remained unchanged, i.e., homogeneous, after storage for a month at about 23±2° C.

The suspension was then loaded into a 20 mL cm® CRONO® syringe. Unlike the suspension of part (a) the suspension was easy to push through the ~2 mm syringe outlet by applying manual pressure on the piston. Also unlike the suspension of part (a) the suspension emerging from the opening retained its shape and did not visibly change throughout delivery; furthermore no delivery-blocking cake formed, i.e., all of the suspension in the syringe was delivered.

Next, 4.2 g of the suspension was re-loaded in a cm® CRONO® syringe, to which a ½ inch long 17 gauge nozzle was attached. The syringe was then inserted in the Crono Par pump. The pump was set for continuous delivery at 0.12 mL/hour rate and the suspension was extruded for about 18 hours, after which the pump occluded.

The example shows that compositional changes of an about 837 mg/mL, i.e., about 4.2 M, LD suspension can be reduced when the suspension comprises oil, water and a surfactant.

EXAMPLE 5

Showing 87 Hour Long Continuous Extrusion of a 777 mg/mL (3.9 M) LD Suspension Made with 32 μm-125 μm LD Particles Ingredients: Polysorbate 60 (Fluka, Sigma Aldrich Catalog # 95754-F); LD particles (passing 125 μm sieve and not passing 32 μm sieve); canola oil (Safeway Kitchens, distributed by Safeway, Pleasanton), CA; de-ionized water.

2.56 g of Polysorbate 60 was dissolved in 12.34 g of canola oil. The solution was allowed to stand for 24 hours before use; it was nearly colorless and transparent. 9.33 g of the solution was mixed with 20 g of LD, 2.5 mL water was added the mixture was stirred until it was homogeneous. The resulting suspension weighed 31.8 g. It contained 1.6 g Polysorbate 60; 7.73 g canola oil; 2.5 g water and 20 g LD. Its calculated volume is 25.7 mL assuming absence of trapped air and 1.5 g/mL density of LD. The calculated volume and measured weight provided an estimated density of about 1.24 g/mL and an LD concentration of 777 mg/mL. Most of the LD was particulate, i.e., it was not dissolved.

The suspension was aged for about 65 hours. It was plastically deformable, retained its shape upon deformation, and was not pourable at the ambient temperature of about 23±2° C. It was soft, compliant, easy to mechanically deform, and easy to squeeze through a 16 gauge 25 mm long nozzle. When force was applied, it extruded through the nozzle as a plug. Stirring released the largest trapped air bubbles, but smaller air bubbles remained.

About 10 mL of the suspension weighing about 11.6 g were transferred to a 20 mL cm® CRONO® syringe. Part of the remaining air bubbles were removed by intensely shaking the upright reservoir and squeezing out the topmost layer of the air bubble-rich suspension along with some suspension, leaving about 8.7 g suspension in the syringe. The residual trapped air was not removed, but it could be removed by, e.g., centrifugation, or chilling to a temperature where the partial pressure of water is low (e.g., less than 10° C., for example about 0° C.) and pulling a vacuum.

A 25 mm long 16 gauge stainless steel nozzle with a female Luer was attached to the syringe and extrusion was started with the Crono Par pump set to deliver 0.1 mL/hour. All of the suspension in the syringe was extruded, i.e., the pump did not occlude. Table 5 below provides the extrusion duration dependence of the weight of the extrudate.

TABLE 5

Change in extrudate weight with extrusion time.

| Extrusion duration (hrs) | Extrudate weight (g) |
|---|---|
| 0 | 0 |
| 11.1 | 1.16 |
| 19.5 | 2.04 |
| 26.6 | 2.81 |
| 35.43 | 3.78 |
| 44.53 | 4.76 |
| 50.3 | 5.36 |
| 60.35 | 6.48 |
| 69.68 | 7.51 |
| 87.78 | 9.36 |

When plotted in a graph, the slope (which is also the density of the extrudate at the ambient extrusion temperature) is about constant at about 1.07 g/mL. From Example 1 it appears that when the pump is set for a 0.1 mL/hour delivery rate the actual delivery rate is only 0.093 mL/hour, such making the actual delivered density about 1.15 g/mL. The density is constant within less than about±3%, apparently less than about 2%. The lesser than the 1.24 g/mL calculated density is attributed to trapped air and/or water evaporation from the extrudate.

Over 11 days there was no visible sedimentation or phase separation; nor was there cake formation or notable inhomogeneity in the about 87 hours of extrusion through a 16 gauge, 25 mm long nozzle at a nominal delivery rate of 0.1 mL/hour. The initially off-white air-exposed suspension turned light grey, suggesting very slow air-oxidation of the LD.

EXAMPLE 6

Preparation and Extrusion of a 790 mg/mL Small Particle Size LD Suspension

Ingredients: Polysorbate 60, (Fluka, Sigma Aldrich Catalog #95754-F); LD (Ajinomoto, jet milled to <10 μm particle size, most of the mass being of 1-5 μm diameter (see scanning electron micrograph below)); canola oil (Safeway Kitchens, distributed by Safeway, Pleasanton, Calif.); de-ionized water.

Figure 21A:
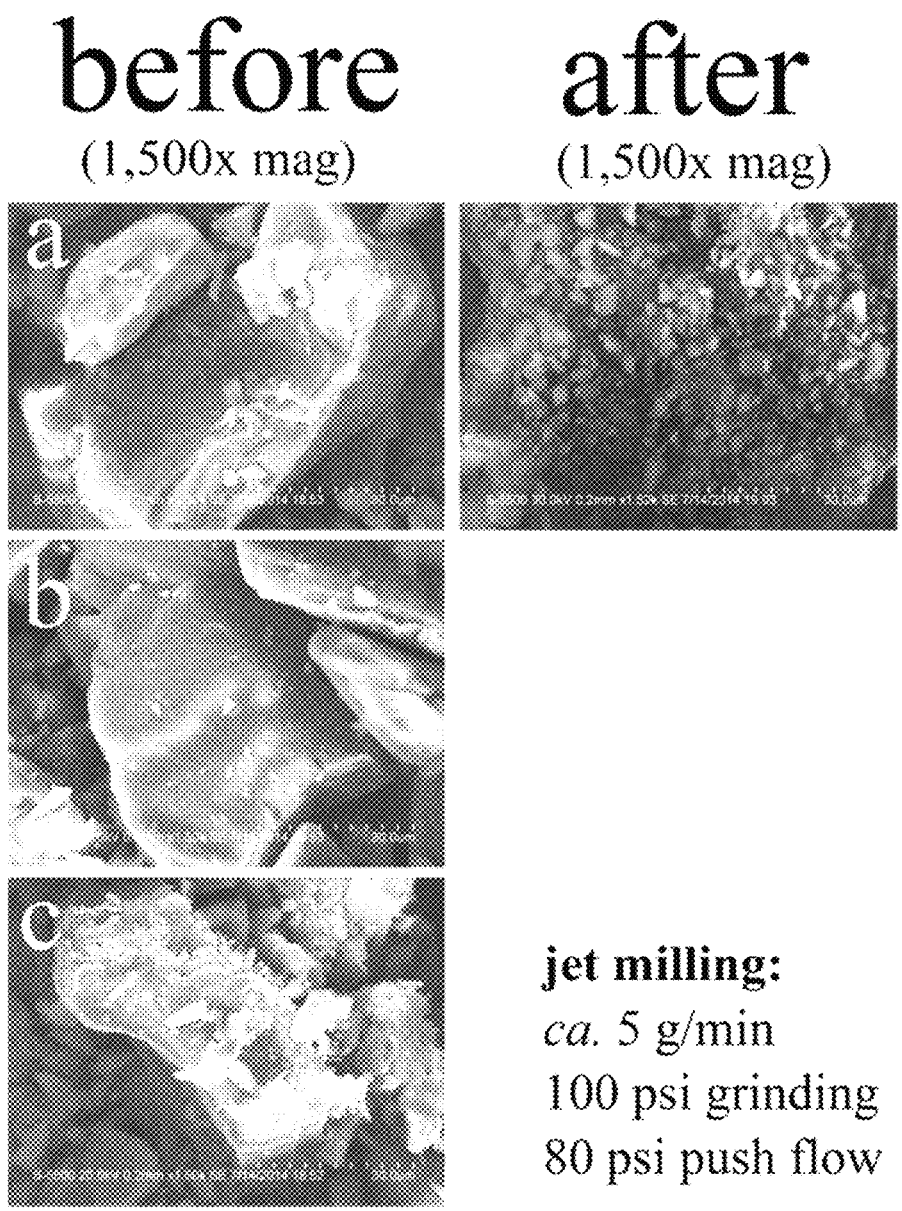
FIGS. 21A and 21B are micrographs depicting LD particles formed by jet milling to reduce the average size of the particles (excluding fines) (see Example 6).
Figure 21B:
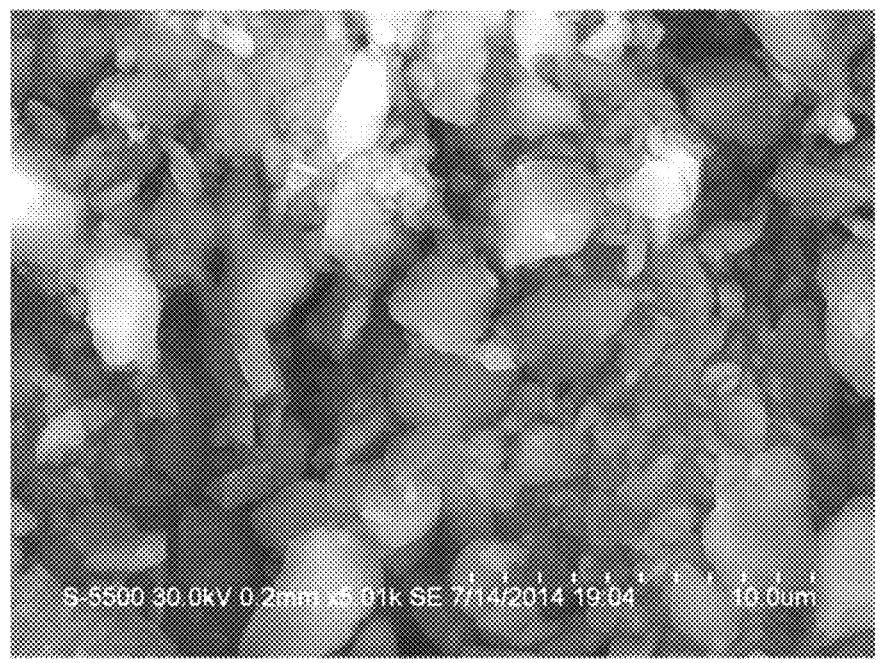
Figure 22:
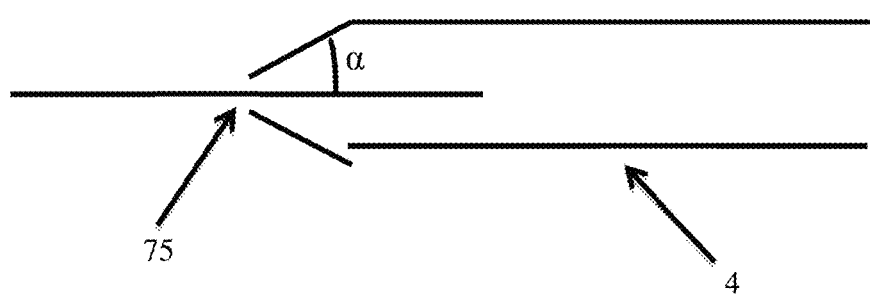
FIG. 22 illustrates a drug reservoir 4 with a tapered flow path leading to the orifice 75.

100 g of Ajinomoto LD was jet milled using a Glen Mills Jet Mill, set at 105 psi supply line, 100 psi grinding line, 80 psi feed push line and feed rate about 7 g per 20 minutes. Yield: 86 g. 1.16 g of Polysorbate 60 was dissolved in 7.7 g canola oil. FIGS. 21A and 21B are micrographs depicting LD particles formed by jet milling.

20 g of the jet-milled LD was added and the mixture was stirred until it was homogeneous, then 2.5 g water was added and the mixture was again stirred until it was homogeneous. The resulting suspension was much more viscous than bread-making dough and its manual mixing was difficult. Most of the LD was particulate, i.e., it was not dissolved. The calculated volume of its 31.4 g mass, assuming 1.5 g/mL LD density, is 25.31 mL in absence of trapped air. The trapped air was not removed, but it can be removed, e.g., by centrifugation, or by chilling to a temperature where the partial pressure of water is low (e.g., less than 10° C., for example about 0° C.) and pulling a vacuum. The calculated LD concentration in the absence of trapped air is 790 mg/mL (4 M) and the estimated density is 1.24 g/mL.

The suspension was extremely viscous, much more viscous than honey at ambient temperature. It was not pourable at the ambient temperature of about 23±2° C., but it was soft, compliant, easy to mechanically deform, and easy to squeeze through a 2.4 mm internal diameter 28 cm long tubing. It plastically deformed when force was applied and was extruded through the tubing as a plug.

The Crono Par pump was set for continuous delivery at 1 mL/ hour delivery rate, and a 28 cm long 2.4 mm internal diameter plastic tubing was attached to the luer of its syringe and filled with the suspension. The suspension was then extruded through the tubing for about 20 hours, at the end of which the syringe was empty. The weight of the extrudate was 27.9 g. The extrudate retained its cylindrical shape, i.e., it was an about 2.4 mm diameter string.

EXAMPLE 7

Showing that a 570 mg/mL (2.89 M) Suspension of Small Particle Size LD in Canola Oil without Surfactant and without Water Becomes Inhomogeneous Upon Extrusion Ingredients: LD jet milled as in Example 6; canola oil (Safeway Kitchens, distributed by Safeway, Pleasanton, Calif.).

About 3.7 g of the jet milled LD (see Example 6) was homogenized by mixing in a 20 mL cm® CRONO® syringe with about 3.72 g of canola oil. An easy to stir and just barely pourable suspension was formed. Most of the LD was particulate, i.e., it was not dissolved. The estimated volume of the suspension, assuming an about 1.5 g/mL density for LD, was about 6.5 mL, the calculated LD concentration was about 570 mg/mL, and the calculated density was about 1.15 g/mL. Using a Crono PAR pump, and with a 2.4 mm inner diameter, 28 cm long plastic tubing coupled to the luer of the syringe the suspension was pumped at a rate of 1 mL/hour. Filtering, resulting in oil with fewer LD particles being extruded, was observed after 1 hour. After 2 hours mostly clear oil was flowing and the pump occluded. A hard cake of solid particle was found when the syringe was disassembled. The cake, consisting mostly of LD and little oil, weighed about 5 g (i.e., about 2 g of oil and only about 0.4 g of LD were delivered). The estimated amount of LD in the cake was about 3.3 g. The experiment showed cake formation, filtering and occlusion during delivery in the absence of water and surfactant.

EXAMPLE 8

Showing that Adding a Surfactant to a 600 mg/mL (3 M) Suspension of Small Particle Size LD in Oil Delays but does not Prevent Caking, Filtration and Occlusion Upon Delivery Ingredients: Polysorbate 60, LD (jet milled as in Example 6), canola oil.

0.25 g Polysorbate 60 was dissolved in about 2.9 g of canola oil, and then 3.3 g LD was added. The mixture was homogenized by mixing in the barrel of a 20 mL cm® CRONO® syringe. The volume of the resulting suspension was about 5.5 mL and the LD concentration was about 600 mg/mL. The suspension was easy to stir and viscous. The LD was mostly particulate, i.e., not dissolved.

Using a Crono PAR pump with a 2.4 mm inner diameter, 28 cm long plastic tubing coupled to the luer of its suspension-containing syringe, the suspension was pumped at flow rate of 3 mL/hour for about 30 min, then for 3 hours at 1 mL/hour. The delivered suspension was inhomogeneous, with clear oil being pumped periodically. The pump signaled occlusion, but only after about 4 mL were delivered, i.e., when about 1 mL was left. Comparison with the delivery of the suspension of Example 7 shows that adding Polysorbate 60 was beneficial. In the absence of added water cake formation, filtering and occlusion during delivery were retarded but were not prevented.

EXAMPLE 9

Showing that a 541 mg/mL (2.75 M) Suspension of LD Particles in Surfactant Containing Oil is not Physically Stable; Also Showing that Adding a Small Amount of Water to the Unstable Suspension Produces a 477 mg/mL (2.4 M) Physically Stable Non-sedimenting and Extrudable Suspension; Also Showing that Trapped Air can be Removed from the Suspension by Centrifugation; and Additionally Showing that the Continuous Phase in the Carrier Fluid of the Stable Suspension is Aqueous, Even Though it Contains Much more Oil than Water Ingredients: LD (95 weight % of the particles passing 250 µm sieve openings and about 30 weight % passing 125 µm sieve openings); canola oil; Polysorbate 60; de-ionized water.

Most of the LD was particulate, i.e., not dissolved.

(a) 1.2 g Polysorbate 60 was dissolved in 12 g of canola oil. 12 g of LD was added and the mixture was ground in a mortar until it was homogeneous. The resulting suspension of about 541 mg/mL (2.75 M) LD concentration was transferred to a glass vial. After 4 hours a clear oil layer was observed on the top of the suspension; after 12 hours the thickness of the clear oil layer increased three-fold, indicating sedimentation and showing that the suspension not phyically stable.

(b) The unstable 541 mg/mL suspension was returned to the mortar, 2 g of water was added, and the suspension was re-ground for 15 min. The water hardened the suspension; 1 g more water was added, for a total of 3 g and grinding was resumed for 20 min. The adding of water and homogenizing by grinding resulted in a soft, mechanically compliant, homogeneous suspension in which the concentration of LD was about 477 mg/mL (2.4 M). It was plastically deformable, retained its shape upon deformation, and was not pourable at the ambient temperature of about 23±2° C. When heated to about 37° C. the suspension became pourable, but just barely.

Centrifugation of 4.5 mL of the suspension for 1 hour in a 15 mL, 110 mm long centrifuge tube at 5000 rpm did not cause observable sedimentation of LD, nor did it cause separation of an aqueous phase from an oil phase, or any other visible change in the appearance of the suspension, which remained homogeneous. The relative centrifugal force was about 3000 G, i.e., about 3,000 times that of gravitational acceleration.

To test if the suspension was a water-in-oil emulsion or an oil-in-water emulsion some of the suspension was added to two test tubes, one containing canola oil and the other containing water. The suspension did not disperse in canola oil, but it dispersed promptly in water, showing that it was an oil-in-water dispersion, i.e., that its continuous phase was aqueous even though it contained much less water than oil.

About 19 mL of the suspension was transferred to a 20 mL cm® CRONO® syringe. The estimated density was 1.12 g/mL, calculated by assuming that the density of LD is about 1.5 g/mL. The suspension was delivered with the Crono Par at a flow rate of 1 mL/hour via a 28 cm long 2.4 mm internal diameter tubing coupled through the luer lock of the syringe. The entire volume in the syringe was delivered, i.e., the pump did not occlude. There was no filtering or solid cake formation and the extrudate appeared to be homogenous and unchanged through the 18 hour long extrusion period, in which 20.4 g of the suspension were delivered. Assuming that 18 mL were delivered in the 18 hour delivery period, the density of the extrudate was 1.13 g/mL, consistent with the calculated density of 1.12 g/mL and suggesting that there was little or no trapped air in the suspension, i.e., that the trapped air was removed by the centrifugation.

EXAMPLE 10

Showing Continuous Extrusion with no Significant Change in Density of a 523 mg/mL (2.7 M) LD Suspension Ingredients: LD (>95 weight % of the particles passing 250 μm sieve openings and about 30 weight % passing 125 μm sieve openings); canola oil (from Safeway); Polysorbate 60 (from Sigma); De-ionized water.

Most of the LD was particulate, i.e. it was not dissolved.

1.43 g of Polysorbate 60 was dissolved with stirring in 14.12 g of canola oil. The solution was clear, i.e., it had no suspended light scattering matter. 13.2 g of the solution, containing 1.2 g of Polysorbate 60 and 11.1 g of canola oil, were transferred to an about 100 mL mortar and 13.03 g LD was added. The mixture was hand-ground to homogeneity in about 15 min, then 3 g of water was added and the mixture was re-ground for about 30 min. During the grinding the mixture-containing mortar was periodically weighed and water was added as needed to compensate for evaporated water. The LD concentration in the resulting suspension was about 523 mg/mL (2.7 M). Its density was about 1.17 g/mL assuming that the density of LD is about 1.5 g/mL. The suspension was non-pourable at the ambient temperature of about 23±2° C. It was soft, compliant, easy to mechanically deform, mayonnaise-like but harder, and easy to squeeze through a nozzle. When force was applied it extruded through a nozzle as a plug.

Most of the suspension was transferred to a 20 mL cm® CRONO® syringe. To remove trapped large air bubbles the filled syringe was warmed to about 40° C. and while it was held with its outlet pointing upward the bubbles rose, coalesced near the outlet, and were expelled. The weight of the suspension filling the syringe to its 20 mL graduation mark was 22.37 g, i.e., its density was about 1.12 g/mL, less than the calculated density of 1.17 g/mL, suggesting a trapped air residue.

The syringe was inserted in a Cane CronoPAR pump and a 28 cm long 2.4 mm internal diameter plastic tubing was coupled to its luer lock. The pump was set to deliver 1 mL/hr for 20 hours. The extrudate was weighed after 5, 8, 13 and 20 hours of extrusion. The weight gain corresponded to that expected for the delivery of a 1.11 g/mL density suspension at 1 mL/hour rate through the first 13 hours, then for the delivery of a 1.08 g/mL suspension in the last 7 hour period. The lesser gain than expected for 1.12 g/mL density are attributed to water evaporation from the extrudate collecting vial, that was open to air. It was not caused by an actual concentration change, as there was no caked, concentrated or hard LD-rich residue left in the syringe when the 20 mL extrusion was completed and the syringe was empty.

The example shows that it is feasible to extrude a suspension containing about 523 mg/mL (2.7 M) LD and to maintain for a 13 hour period a nearly constant extrudate density, the extrudate comprising an edible oil, water and an also edible surfactant. It also shows that in 20 hours of extrusion the density can be constant within about ±1.4% or less.

EXAMPLE 11

Showing that a Suspension Containing 625 mg/mL (3.17 M) LD and 156 mg/mL (0.74 M) CD is Physically Stable When Centrifuged for 1 Hour at 16,000 G and that it Also Physically Stable at 60° C. for 24 Hours Ingredients: LD ($D_{50}$ about 75 μm, $D_{90}$ about 200 μm). CD ($D_{95}$ about 100 μm, $D_{80}$ about 45 μm); Polysorbate 60 (Sigma Aldrich Catalog #95754-F); Miglyol 812 (Peter Cremer, Cincinnati, Ohio); butylated hydroxyanisole (BHA) antioxidant FCC (Spectrum, XV3021); de-ionized water.

Most of the LD and most of the CD were particulate, i.e., they were not dissolved. The composition comprised 50.0 weight % (w/w) LD; 12.5 weight % CD; 24.4 weight % Miglyol 812; 5 weight % of Polysorbate 60; and 8.0 weight % water. It was prepared as follows: (a) The LD (5 g) and CD (1.25 g) powders were mixed for 15 min to homogeneity; (b) The Polysorbate 60 (0.5 g) was mixed with deionized water (0.8 g), the mixture was warmed to about 60° C. and homogenized by thorough mixing; (c) the LD and CD powder mixture of (a) and 10 mg of BHA were added to the Polysorbate 60 and water of (b) and mixed thoroughly. The mixture was kept at ambient temperature for 4 hours; (d) after the 4 hours, 2.44 g of Miglyol 812 containing 10 mg of BHA was added, mixed thoroughly, then the mixture was aged at ambient temperature for at least 2 hours.

There was no visible sedimentation of the solid drug particles nor was there any visible phase separation of the oil and the water upon 1 hour centrifugation at about 16,000 G (G being the gravity at about sea level), suggestive of shelf life physical stability for about 22 months at 1 G and room temperature. The suspension also remained unchanged, i.e., homogeneous, after storage for 24 hours at about 25° C., 40° C., and 60° C.

EXAMPLE 12

Describing a Deformable Plug Material for Separating the Propellant from the Suspension For a mobile plug that could replace the piston in a device where the formulation is delivered into the mouth by the about constant pressure of a propellant, a paste was made of 2 g graphite (Timrex SFG44, Timcal, Westlake, Ohio, average particle (flake) size 44 microns) mixed with 6 g of Fomblin Y (Sigma). The plug may be impermeable to the propellant and also to the drug containing formulation.

EXAMPLE 13

Showing that in the Absence of Solid Drug Particles the Carrier Emulsions can be Physical Unstable and that the Suspension are Physically Stabilized by Adding Solid Drug Particles (a) First phase separating, unstable emulsion in the absence of solid drug particles. An emulsion was made by dissolving with warming 0.8 g Kolliphor RH 60 in 1.5 g water, then adding 4.6 g canola oil and shaking. Part of the emulsion visibly phase separated after 1 hour at room temperature even without centrifugation.

(b) Second phase separating, unstable emulsion in the absence of solid drug particles. An emulsion was made by dissolving 0.8 g Polysorbate 60 in 4.6 g canola oil, then adding 1.5 g water and shaking. The emulsion was intensely light scattering, milky and viscous. It did not visibly phase separate at room temperature for at least 12 hours, but when centrifuged in a 10 cm long test tube at 10,000 rpm for 10 min it phase separated, i.e., it was physically unstable.

(c) To test if dissolved (not solid) LD and CD stabilized the second emulsion, the water was replaced with an aqueous solution saturated in LD and CD. The emulsion was intensely light scattering, milky and viscous. It did not visibly phase separate at room temperature for at least 12 hours, but when centrifuged in a 10 cm long test tube at 10,000 rpm for 10 min phase separation was observed. Saturation of the phases of the emulsion with LD and with CD did not prevent phase separation upon 10 min centrifugation.

(d) As shown in Example 11 the suspension made with the emulsions of (b) or (c) but containing 625 mg/mL (3.17 M) LD and 156 mg/mL (0.74 M) CD is stable when centrifuged for 1 hour at 16,000 G and is also stable at 60° C. for 24 hours.

EXAMPLE 14

Presence and Absence of LD and CD Decomposition Products, Including Toxic Hydrazine in Various Formulations after 0, 1, and 2 Weeks of Aging Chemicals:
Micronized LD with the following particle size distribution:
  $D_{10}$ 0.9 μm
  $D_{50}$ 7.1 μm
  $D_{90}$ 15.9 μm
Micronized CD with the following particle size distribution:
  $D_{10}$ 1 μm
  $D_{50}$ 4 μm
  $D_{90}$ 13 μm
Phosphoric acid (85%), HPLC grade
Citric acid monohydrate, USP
Glacial acetic acid, USP
Sodium hydroxide, NF
EDTA, USP
Light mineral oil, NF
Vitamin E, USP
Glycerin, USP
Super refined PEG 600

Buffers of 50 mM concentration shown in Table 6 were prepared. The weights in mg shown in Table 6 are for 50 mL of the buffer solutions.

TABLE 6

Buffer preparation parameters.

| mg/50 mL | F-1 | F-2 | F-3 | F-4 | F-5 | F-6 | F-7 | F-8 | F-9 |
|---|---|---|---|---|---|---|---|---|---|
| Phosphoric acid (85%) |  | 290 | 290 | 290 |  |  |  | 290 | 290 |
| Glacial acetic acid |  |  |  |  | 150 | 150 |  |  |  |
| Citric acid |  |  |  |  |  |  | 525 |  |  |
| EDTA |  |  |  |  |  |  |  |  | 75 |
| DI-water |  | QS | QS | QS | QS | QS | QS | QS | QS |
| pH by NaOH | As is | 2 | 2.5 | 3 | 4 | 5 | 6 | 7 | 2.5 |

The buffers were compounded according to Table 7 with micronized LD and micronized CD. The weights of added LD and CD in mg per 1 g of compounded suspension are shown in Table 7. In Table 7, QS means "quantity sufficient to make a total of 1 g suspension". In Table 8, QS means "quantity sufficient to make a total of 1.25 g suspension".

TABLE 7

Suspension preparation parameters.

| mg/g | F-1 | F-2 | F-3 | F-4 | F-5 | F-6 | F-7 | F-8 | F-9 |
|---|---|---|---|---|---|---|---|---|---|
| Micronized LD | 600 | 600 | 600 | 600 | 600 | 600 | 600 | 600 | 600 |
| Micronized CD | 150 | 150 | 150 | 150 | 150 | 150 | 150 | 150 | 150 |
| Phosphate buffer |  | QS | QS | QS |  |  |  | QS |  |
| Acetate buffer |  |  |  |  | QS | QS |  |  |  |
| Citrate buffer |  |  |  |  |  |  | QS |  |  |
| Phosphate buffer with EDTA |  |  |  |  |  |  |  |  | QS |
| DI-water | QS |  |  |  |  |  |  |  |  |

TABLE 8

Suspension preparation parameters.

| mg/1.25 g | F-10 | F-11 | F-12 | F-13 | F-14 |
|---|---|---|---|---|---|
| Micronized LD | 600 | 600 | 600 | 600 | 600 |
| Micronized CD | 150 | 150 | 150 | 150 | 150 |
| Miglyol 812 | QS | | | | |
| Light mineral oil | | QS | | | |
| Vitamin E | | | QS | | |
| Glycerin | | | | QS | |
| PEG 600 | | | | | QS |

For the assessment of the stabilities the following protocol was followed to prepare buffers and suspensions: 290 mg of 85% phosphoric acid was added to a 50-mL Falcon tube; it was diluted with de-ionized water to about 80% of the volume of the tube; the pH was adjusted to 2.0, 2.5, 3.0 or 7.0 with 5N NaOH; the solution was diluted to the intended 50 mL volume with de-ionized water. Alternatively 75 mg EDTA was dissolved and its pH was adjusted to 2.5 or 5.0 by 5N NaOH; 150 mg glacial acetic acid was added to a 50-mL Falcon tube, diluted with DI water to 80% of the volume of the tube, the pH was adjusted to 4.0 by 5N NaOH; the solution was diluted with DI water to the intended 50 mL volume. Alternatively 480 mg citric acid was added to a 50 mL Falcon tube and dissolved in about 40 mL DI water, the pH was adjusted to 6.0 by 5N NaOH and the solution was diluted with DI water to the intended 50 mL volume.

For making the suspensions, 9.00 g micronized LD and 2.25 g micronized CD was added to a 50 mL Falcon tube, tumble mixed for 15 min to create a uniform mixture of the two drugs, then 750 mg of the LD-CD mixture added to each of a group of 1.5 mL Eppendorf tubes and enough of the vehicle was added for the weight to total 1.25 g in each tube. After mixing with a BeadBeater (BB) for 2X 2 min, the pH was recorded the tubes were incubated at 60° C. for physical and chemical stability tests by withdrawing samples after 0, 1 and 2 weeks. For each withdrawn sample the appearance and pH were recorded, then the content was diluted to 0.5 mg/mL and the vial containing the sample was weighed. The content of each vial was then HPLC analyzed. The HPLC peaks of the drugs and of the impurities were recorded. The areas of all impurities combined as their percentage of the drugs are summarized in Table 9, showing the % peak impurity area of the total drug peak area.

TABLE 9

Impurities drug formulations.

| ID | 0 day, % | 1 week, % | 2 week, % |
|---|---|---|---|
| F1 | <0.05 | <0.05 | |
| F2 | <0.05 | <0.05 | |
| F3 | <0.05 | <0.05 | <0.05 |
| F4 | <0.05 | 0.07 | ND |
| F5 | <0.05 | 0.06 | ND |
| F6 | <0.05 | 0.05 | ND |
| F7 | <0.05 | 0.07 | ND |
| F8 | <0.05 | 0.05 | ND |
| F9 | <0.05 | <0.05 | ND |
| F10 | <0.05 | <0.05 | ND (<1.1% USP spec) |
| F11 | <0.05 | <0.05 | <0.05% (<1.1% USP spec) |
| F12 | <0.05 | <0.05 | 0.2 |
| F13 | <0.05 | 0.16 | ND |
| F14 | <0.05 | 0.07 | ND |

A known toxic impurity is hydrazine, whose buildup requires frozen storage of Duodopa™ and limits its labeled refrigerated shelf life to 12 weeks after thawing. Hydrazine concentrations, in micrograms per mg of the combined weights of LD and CD, in the various aged formulations are seen in Table 10. ND means not detected.

TABLE 10

Hydrazine concentrations in drug formulations.

| Sample ID | Initial (µg/mg of LD + CD) | After one week at 60° C. (µg/mg of LD + CD) | After 2 weeks at 60° C. (µg/mg of LD + CD) |
|---|---|---|---|
| F1 | 0.47 | 0.54 | ND |
| F2 | 0.45 | 0.89 | ND |
| F3 | 0.49 | 0.45 | 0.74 |
| F4 | 0.56 | 1.02 | ND |
| F5 | 0.49 | 0.90 | ND |
| F6 | 0.54 | 0.75 | ND |
| F7 | 0.49 | 1.33 | ND |
| F8 | 0.65 | 1.43 | ND |
| F9 | 0.47 | 0.87 | ND |
| F10 | 0.78 | 0.58 | 0.15 (<1.6 in-house spec) |
| F11 | 0.51 | 0.74 | 0.19 (<1.6 in-house spec) |
| F12 | 0.50 | 0.69 | 0.26 |
| F13 | 0.47 | 1.20 | ND |
| F14 | 0.45 | 1.00 | ND |

Overall, impurities contributed less than <0.1% to the total peak areas, suggesting good chemical stability. Formulations F13, containing glycerin, and F14 containing PEG600, contained after their aging more impurities than the other formulations, i.e., were chemically less stable. Hydrazine levels were below the target level of 1.6 µg/mg of the weight of the combined LD and CD, which is below the hydrazine exposure limit for Duodopa™.

EXAMPLE 15

Showing the Chemical Stability of Formulations Comprising Solid LD and CD Dispersed in Oils with Various Surfactants, and that Addition of Water is Associated with an Increase in Hydrazine Formation and with Discoloration Indicative of Air Oxidation Ingredients: The LD, CD, Miglyol 812, Kolliphor RH 40 (also known as Cremophor RH 40) and water were those of Example 11. Other ingredients were Polysorbate 60, NF; vitamin E, TPGS; Span 60; hydrogenated soy lecithin (LIPOID SPC3); Poloxamer 188; glyceryl monosterate; polyvinyl alcohol (PVA), stearic acid, propylene glycol, and canola oil.

Formulations prepared and tested are summarized in Table 11 and Table 12. The values in the boxes of Table 11 are weight percentages of constituents of the formulations and are weights in mg per 1.2 g of formulation in Table 12. QS means in Table 12 "quantity sufficient to make 1.2 g when added to the other ingredients."

TABLE 11

Formulations prepared and tested.

| Weight % | F15 | F16 | F17 | F18 | F19 | F20 | F21 | F22 | F23 | F24 | F10 | F25 | F26 | F27 |
|---|---|---|---|---|---|---|---|---|---|---|---|---|---|---|
| LD | 50.3 | 50.3 | 50.3 | 50.3 | 50.3 | 50.3 | 50.3 | 50.3 | 50.3 | 50.3 | 50.3 | 50.3 | 50.3 | 50.3 |
| CD | 12.6 | 12.6 | 12.6 | 12.6 | 12.6 | 12.6 | 12.6 | 12.6 | 12.6 | 12.6 | 12.6 | 12.6 | 12.6 | 12.6 |
| Miglyol 812 | 32.1 | 24.3 | 32.1 | 32.1 | 32.1 | 32.1 | 32.1 | 32.1 | 32.1 | 32.1 | 37.1 |  | 24.3 |  |
| Polysorbate 60 | 5 | 5 |  |  |  |  |  |  |  |  |  | 5 | 5 | 5 |
| Vitamin E TPGS |  |  | 5 |  |  |  |  |  |  |  |  |  |  |  |
| Span 60 |  |  |  | 5 |  |  |  |  |  |  |  |  |  |  |
| Cremophor (Kolliphor) RH40 |  |  |  |  | 5 |  |  |  |  |  |  |  |  |  |
| Lecithin SPC3 |  |  |  |  |  | 5 |  |  |  |  |  |  |  |  |
| Poloxamer 188 |  |  |  |  |  |  | 5 |  |  |  |  |  |  |  |
| Glyceryl monostearate |  |  |  |  |  |  |  | 5 |  |  |  |  |  |  |
| PVA |  |  |  |  |  |  |  |  | 5 |  |  |  |  |  |
| Stearic acid |  |  |  |  |  |  |  |  |  | 5 |  |  |  |  |
| H$_2$O (DI water) |  | 7.9 |  |  |  |  |  |  |  |  |  | 7.9 |  |  |
| Canola oil |  |  |  |  |  |  |  |  |  |  |  | 24.3 |  | 24.3 |
| BHA |  |  |  |  |  |  |  |  |  |  |  | 0.1 |  |  |
| Propylene glycol |  |  |  |  |  |  |  |  |  |  |  |  | 7.9 | 7.9 |

TABLE 12

Formulations prepared and tested.

| mg/1.2 g | F15 | F16 | F17 | F18 | F19 | F20 | F21 | F22 | F23 | F24 | F10 | F25 | F26 | F27 |
|---|---|---|---|---|---|---|---|---|---|---|---|---|---|---|
| LD | 600 | 600 | 600 | 600 | 600 | 600 | 600 | 600 | 600 | 600 | 600 | 600 | 600 | 600 |
| CD | 150 | 150 | 150 | 150 | 150 | 150 | 150 | 150 | 150 | 150 | 150 | 150 | 150 | 150 |
| Polysorbate 60 | 60 | 60 |  |  |  |  |  |  |  |  |  | 60 | 60 | 60 |
| Vitamin E TPGS |  |  | 60 |  |  |  |  |  |  |  |  |  |  |  |
| Span 60 |  |  |  | 60 |  |  |  |  |  |  |  |  |  |  |
| Cremophor (Kolliphor) RH40 |  |  |  |  | 60 |  |  |  |  |  |  |  |  |  |
| Lecithin SPC3 |  |  |  |  |  | 60 |  |  |  |  |  |  |  |  |
| Poloxamer 188 |  |  |  |  |  |  | 60 |  |  |  |  |  |  |  |
| Glyceryl monosterate |  |  |  |  |  |  |  | 60 |  |  |  |  |  |  |
| PVA |  |  |  |  |  |  |  |  | 60 |  |  |  |  |  |
| Steric acid |  |  |  |  |  |  |  |  |  | 60 |  |  |  |  |
| Water |  | 94 |  |  |  |  |  |  |  |  |  | 94 |  |  |
| Miglyol 812 | QS | QS | QS | QS | QS | QS | QS | QS | QS | QS | QS | — | QS | — |
| Canola oil + BHA |  |  |  |  |  |  |  |  |  |  |  | 290 |  | 290 |
| BHA |  |  |  |  |  |  |  |  |  |  |  | 1.2 |  | 1.2 |
| Propylene glycol |  |  |  |  |  |  |  |  |  |  |  |  | 94 | 94 |

The formulations were prepared as follows: LD and CD at a 4:1 weight/weight ratio was weighed into a 50 mL Falcon tube, then mixed to uniformity by tumble mixing for 15 min. 750 mg of the 4:1 (weight/weight) mixture of LD and CD was transferred to a 1.5 mL Eppendorf vial and the weight was recorded. In a second tube 600 mg of surfactant was mixed to uniformity with 3900 mg of Miglyol 812. 450 mg of the surfactant-Miglyol mixture was added to the Eppendorf tube containing the 760 mg LD and CD and the weight was recorded, mixed to uniformity, warmed to 60° C. to complete the mixing, then the two mixing steps were repeated. Each mixing was in a BeadBeater (BB), was of 2 min duration and was repeated.

In formulation F16, 600 mg surfactant, 940 mg DI water and 2960 mg Miglyol 812 were mixed to uniformity in an empty Eppendorf tube, warmed to 60° C. to complete the mixing, using for the mixing a BeadBeater (BB), twice for 2 min.

The formulations were transferred to a new Eppendorf vials and reference vials were stored at 2-8° C., while the test-vials were stored at 60° C. After one week of storage at 60° C. the test samples were checked for color change indicating oxidation and assayed by HPLC for impurities, their impurity concentrations compared with those of the reference samples stored at 2-8° C. The results are summarized in Table 13.

Upon 1 week storage at 60° C. the hydrazine concentrations increased measurably in the water-containing formulations F16 and F25. These formulations as well as the propylene glycol comprising formulations, also changed their color, showing that water and propylene glycol enhanced the rate of air-oxidation to colored products relative to the rate in oils, suggesting that mostly or only dissolved LD and/or CD was air oxidized. In most of the formulations made with the 2 oils and 7 surfactants the impurity levels remained very low. The results also identify several surfactants potentially suitable for use in suspensions of the inventions.

TABLE 13

Impurities in drug formulations.

| ID | Impurities (% of the sum of all peak areas) at start | Impurities (% of the sum of all peak areas) after 1 week storage at 60° C. |
|---|---|---|
| F15 | <0.05 | <0.05 |
| F16 | <0.05 | <0.05 |
| F17 | <0.05 | <0.05 |
| F18 | <0.05 | 0.07 |
| F19 | <0.05 | 0.06 |
| F20 | <0.05 | 0.05 |
| F21 | <0.05 | 0.07 |
| F22 | <0.05 | 0.05 |
| F23 | <0.05 | <0.05% |
| F24 | <0.05 | <0.05% |
| F25 | <0.05 | <0.05% |
| F26 | <0.05 | <0.05% |
| F27 | <0.05 | 0.09 |

EXAMPLE 16

Showing the Discovery of Novel, Physically and Chemically Stable, Extrudable Suspensions Containing 62.5 Weight % of Drug Ingredients: The LD, CD, Miglyol 812, and water were those of Example 11; other ingredients were Polysorbate 60, NF (Spectrum, 1CK0247), canola oil (Spectrum, 1DK0517), and BHA antioxidant (Spectrum, XV3021).

The formulations, in mg per 1.5 g of prepared suspension, are listed in Table 14. The oil (Miglyol 812 or canola oil) to polysorbate weight/weight ratio was constant at 6.5:1.

TABLE 14

Suspensions prepared.

| mg/1.5 g | F29 | F30 | F16 | F31 | F32 | F33 | F34 | F35 | F36 |
|---|---|---|---|---|---|---|---|---|---|
| LD | 750 | 750 | 750 | 750 | 750 | 750 | 750 | 750 | 750 |
| CD | 187.5 | 187.5 | 187.5 | 187.5 | 187.5 | 187.5 | 187.5 | 187.5 | 187.5 |
| Miglyol 812 + Polysorbate 60 (6.5:1, w/w) | 500 | 470 | 440 | 410 | 380 | 350 | 440 | 350 | |
| Canola oil + Polysorbate 60 (6.5:1, w/w) | | | | | | | | | 440 |
| BHA | 1.5 | 1.5 | 1.5 | 1.5 | 1.5 | 1.5 | 1.5 | 1.5 | 1.5 |
| DI-H$_2$O | 60 (4%) | 90 (6%) | 120 (8%) | 150 (10%) | 180 (12%) | 210 (14%) | 0 | 210 (14%) | 120 (8%) |
| 50 mM PBS (pH 2.7) | | | | | | | 120 (8%) | | |

The suspensions were prepared as follows:

A 50 mM, pH 2.7 sodium phosphate buffer solution was prepared.

To each of a series of 1.5 mL Eppendorf vials, 750 mg of a mixture of LD and CD was added, the added mixture comprising 600 mg of LD and 150 mg CD, followed by the Miglyol 812 or canola oil containing the Polysorbate 60 of which the amounts shown in Table 14 were added. Next either DI water or 50 mM, pH 2.7 phosphate buffer was added in the amounts shown in Table 14, then the components were mixed using a BeadBeater (2×2 min). For fomulation F35, but not for the other formulations, water was vacuum evaporated, leaving 40 mg of the initial 210 mg of the water.

Next, the 1.5 g of the formulation in each Eppendorf vial was split, i.e., 750 mg was transferred to a second Eppendorf vial. One vial of each formulation was closed and stored at 60° C. and the second was centrifuged at 13,000 rpm, providing an acceleration of 16,060 G (16,060 times that of sea level gravity) for 1 hour at 25° C.

After checking for phase separation, 15 mg samples were drawn from the top layer and from the bottom layer of each of the centrifuged suspensions and transferred into 15 mL 0.01 N phosphoric acid diluent containing Falcon tubes for HPLC assays, so as to determine if the top and bottom layers of the 16,060 G centrifuged suspensions differed in their LD or CD concentrations.

The same centrifugation test and assay were then performed on each of the suspensions after storage for 1 week at 60° C.

Occulsion was observed upon attempted manual extrusion of suspension F35 from a filled 1.0 mL syringe with a 16 gauge, 26 mm long nozzle. None of the other suspensions occluded in identical tests, i.e., in each case all of the 1 mL in the syringe passed through the nozzle.

Suspensions F16 (containing 8 weight % water), F29 (containing 4 weight % water), F30 (containing 6 weight % water), and F36 (containing 8 weight % water) did not show phase separation upon centrifugation. Of these, F16, F29 and F30 were made with Miglyol 812, while F36 was made with canola oil. Suspension F34 is similar to F16, except for its pH of 2.7.

Assays of samples taken from the top and from the bottom layers of centrifuged suspensions F16, F34 and F36 after their storage for 1 week at 60° C. are provided in Table 15.

The estimated densities and drug concentratons in the suspensions that did not sediment or phase separate upon centrifugation for 1 hour at 16,060 G are as follows:

Suspension F16 with an estimated density of about 1.24 g/mL at about 25° C. contains about 621 mg/mL of LD and about 155 mg/mL CD, i.e., the respective molar concentrations of LD and CD are 3.15 M and 0.73 M.

Suspension F29 with an estimated density of about 1.24 g/mL at about 25° C. contains about 619 mg/mL of LD and about 155 mg/mL CD, i.e., the respective molar concentrations of LD and CD are 3.14 M and 0.73 M.

Suspension F30 with an estimated density of about 1.24 g/mL at about 25° C. contains about 620 mg/mL of LD and about 155 mg/mL CD, i.e., the respective molar concentrations of LD and CD are 3.15 M and 0.73 M.

Suspension F36 with an estimated density of about 1.23 g/mL at about 25° C. contains about 613 mg/mL of LD and about 153 mg/mL CD, i.e., the respective molar concentrations of LD and CD are 3.11 M and 0.72 M.

Suspension F34 is similar to F16, except for its pH of 2.7. Of the suspensions that were stored for one week at 60° C., formulations F16, F34 and F36 did not show visible phase separation after centrifugation at 16,060 G for 1 hour. Importantly, after centrifugation the top and bottom layer LD and CD concentrations of F16 and of F36 were not significantly different, making these the preferred compositions of the series. Their water content was about 8 weight %, their oil content was about 25 weight %, their surfactant content was about 4 weight %, and they contained about 62.5% by weight of the drugs. The suspensions also contained 0.1 weight % of the antioxidant.

TABLE 15

Top and Bottom Layer LD and CD Concentrations After 1 Week Storage at 60° C. and 1 Hour Centrifugation at 16,060 G.

| Sample | LD (mg/g) | CD (mg/g) |
|---|---|---|
| F16-Top | 0.52 | 0.13 |
| F16-Bottom | 0.53 | 0.14 |
| F34-Top | 0.39 | 0.10 |
| F34-Bottom | 0.51 | 0.13 |
| F36-Top | 0.50 | 0.13 |
| F36-Bottom | 0.51 | 0.13 |

EXAMPLE 17

Showing Physically and Chemically Stable Suspensions for Managing Parkinson's Disease by Continuous Oral Extrusion of LD and CD, Including their Low Rate of Hydrazine Production Ingredients: The ingredients were those of Example 11 or 15; the Cremophor (Kolliphor) RH40 USP/NF/EP was from BASF.

TABLE 16

Compositions by Weight %.

|  | F16 % (w/w) | F36 % (w/w) | F37 % (w/w) |
|---|---|---|---|
| LD | 50.0 | 50.0 | 50.0 |
| CD | 12.5 | 12.5 | 12.5 |
| Polysorbate 60 | 5 | 5 | |
| Cremophor (Kolliphor) RH40 | | | 4.2 |
| Miglyol 812 | 24.4 | | |
| Canola oil | | 24.4 | 24.4 |
| BHA | 0.1 | 0.1 | 0.1 |
| DI-H$_2$O | 8.0 | 8.0 | 8.0 |

TABLE 17

Compositions by weight in mg per 1.5 g of product.

| (mg/1.5 g) | F16 | F36 | F37 |
|---|---|---|---|
| LD | 750 | 750 | 750 |
| CD | 187.5 | 187.5 | 187.5 |
| DI-H$_2$O | 120 | 120 | 120 |
| Polysorbate 60 | 75 | 75 | — |
| Cremophor (Kolliphor) RH40 | — | — | 63 |
| Miglyol 812 | 366 | — | — |
| Canola oil | — | 366 | 378 |
| BHA | 1.5 | 1.5 | 1.5 |

For the preparations, 15.0 g LD and 3.75 g CD were mixed for 15 min to uniformity in a 50 mL Falcon tube. 75 mg polysorbate 60 or 63 mg Cremophor (Kolliphor) RH40 were mixed in an Eppendorf tube with 120 mg DI-H20, warmed to about 60° C., and mixed by vortexing; the 937.5 mg LD +CD mixture in the Falcon tube was added and the mixture was homenized with a BeadBeater twice for 2 min, then allowed stand at about 25° C. for 4 hours after which the Miglyol 812 or canola oil was added. Next 1.5 mg of BHA was added and the mixture was homogenized twice each time for 2 min using a BeadBeater. The suspensions were then divided into 3 parts, each of 0.5 g. One was kept at 25° C., the second at 40° C., and the third at 60° C. for 2 hours. All were centrifuged at 13,000 rpm (producing an acceleration of 16,060 G) for 1 hr at 25° C., and checked for phase separation and sedimentation. Next 15 mg of the top and 15 mg of the bottom of the centrifuged suspensions was transferred into 15 mL Falcon tubes for HPLC assays as described in the previous Example.

There was no visually observable phase separation in the centrifuged suspension F16 made with Miglyol 812 and Polysorbate 60 after aging at any of the three temperatures 25° C., 40° C., or 60° C. Phase separation was, however, observed in all of the centrifuged F37 suspensions made with Miglyol 812 and Cremophor (Kolliphor) RH 40. The F36 suspension made with canola oil and Polysorbate 60 did not phase separate upon its centrifugation after 24 hour aging at 60° C., but it did phase separate after its aging for 24 hours at the two lower temperatures, 25° C. and 40° C., showing that aging for 24 hours at 60° C. stabilizes suspension F36, but aging at 25° C. or 40° C. does not.

TABLE 18

Absence of Substantial Difference in the LD and CD Concentrations of Top and Bottom Layers of Centrifuged, Differently Aged F16 Suspensions (containing 50 weight % LD and 12.5 weight % CD).

|  | 24 Hour Aging Temp, ° C. | LD (mg/g) | CD (mg/g) |
|---|---|---|---|
| Fresh LD & CD | 2 to 8 | 0.54 | 0.14 |
| Centrifuged, top | 25 | 0.50 | 0.13 |
| Centrifuged, bottom | 25 | 0.49 | 0.13 |
| Centrifuged, top | 40 | 0.52 | 0.13 |
| Centrifuged, bottom | 40 | 0.50 | 0.13 |
| Centrifuged, top | 60 | 0.53 | 0.13 |
| Centrifuged, bottom | 60 | 0.51 | 0.13 |

TABLE 19

Hydrazine Concentrations in Aged F16 Suspensions.

|  | 24 Hour Aging Temperature, ° C. | Hydrazine/(LD + CD), μg/mg* |
|---|---|---|
| Fresh LD & CD (baseline) | 2 to 8 | 0.61 |
| Centrifuged, top | 25 | 0.62 |
| Centrifuged, bottom | 25 | 0.59 |
| Centrifuged, top | 40 | 0.81 |
| Centrifuged, bottom | 40 | 0.84 |
| Centrifuged, top | 60 | 0.85 |
| Centrifuged, bottom | 60 | 0.91 |

*The target hydrazine concentration is 1.6 μg per mg of combined LD and CD.

The F16 formulation has no taste, which is a desirable feature.

EXAMPLE 18

Showing that a Suspension Containing 625 mg/mL (3.17 M) LD, 156 mg/mL (0.74 M) CD, and Poloxamer 188 Surfactant is Physically Stable When Centrifuged for 1 Hour at About 16,000 G, is Chemically Stable at 60 C. for 24 Hours, that its Rate of Hydrazine Formation is Slow, and that it is Tasteless Ingredients: LD ($D_{50}$ about 75 µm, $D_{90}$ about 200 µm). CD ($D_{95}$ about 100 µm, $D_{80}$ about 45 µm); Poloxamer 188 (NF BAS WPDX-577B); Miglyol 812 (Peter Cremer, Cincinnati, Ohio); butylated hydroxyanisole (BHA) antioxidant FCC (Spectrum, XV3021); de-ionized water.

Most of the LD and most of the CD in the suspension were particulate, i.e., they were not dissolved. The suspension comprised 50.0 weight % (w/w) LD; 12.5 weight % CD; 24.4 weight % Miglyol 812; 5 weight % of Poloxamer 188; and 8.0 weight % water. It was prepared as follows: (a) the LD (5 g) and CD (1.25 g) powders were mixed for 15 min to homogeneity; (b) the Poloxamer 188 (0.5 g) was mixed with deionized water (0.8 g), the mixture was warmed to about 60° C. and homogenized by thorough mixing; (c) the LD and CD powder mixture of (a) and 10 mg of BHA were added to the Poloxamer 188 and water of (b) and mixed thoroughly. The mixture was kept at ambient temperature for 4 hours; (d) after the 4 hours, 2.44 g of Miglyol 812 containing 10 mg of BHA was added, mixed thoroughly, then the mixture was aged at ambient temperature for at least 2 hours then centrifuged. There was no visible sedimentation of the solid drug particles nor was there any visible phase separation of the oil and the water upon 1 hour centrifugation at 13,000 rpm providing an acceleration of about 16,000 G (G being the gravity at about sea level), suggestive of shelf life physical stability for about 22 months at 1 G and room temperature. The suspension also remained unchanged, i.e., homogeneous, after storage for 24 hours at about 25° C., 40° C., and 60° C.

After centrifugation of the suspension that was stored for 2 hours or more at about 25° C., the top and bottom layers were assayed for LD, CD and hydrazine. The difference in their LD and CD content was less than about 2% and was within the resolution limit of the assay. The hydrazine concentration was only slightly higher than in the 0.52 µg/mg of the combined weights of LD and CD in the freshly made suspension. The hydrazine concentrations increased in the top and bottom layers respectively only to 0.56 µg/mg and 0.61 µg/mg, well below the targeted upper limit of 1.6 µg/mg. The composition was tasteless.

EXAMPLE 19

Showing that a Suspension Containing 625 mg/mL (3.17 M) LD, 156 mg/mL (0.74 M) CD, and Cremophor RH40 Surfactant is Physically Stable When Centrifuged for 1 Hour at About 16,000 G, Physically Stable at 60° C. for 24 Hours, Chemically Stable at 60° C. for a Week, and that the Rate of Hydrazine Formation is Slow Even at 60° C. in the Air-exposed Suspension Ingredients: LD ($D_{50}$ about 75 µm, $D_{90}$ about 200 µm). CD ($D_{95}$ about 100 µm, $D_{80}$ about 45 µm); Cremophor RH40 (USP/NF/EP; BASF; 78105416K0); Miglyol 812 (Peter Cremer, Cincinnati, Ohio); butylated hydroxyanisole (BHA) antioxidant FCC (Spectrum, XV3021); de-ionized water.

Most of the LD and most of the CD in the suspension were particulate, i.e., they were not dissolved. The composition comprised 50.0 weight % (w/w) LD; 12.5 weight % CD; 24.4 weight % Miglyol 812; 5 weight % of Cremophor RH40; and 8.0 weight % water. It was prepared as follows: (a) the LD (5 g) and CD (1.25 g) powders were mixed for 15 min to homogeneity; (b) the Cremophor RH40 (0.5 g) was mixed with deionized water (0.8 g), the mixture was warmed to about 60° C. and homogenized by thorough mixing; (c) the LD and CD powder mixture of (a) and 10 mg of BHA were added to the Cremophor RH40 and water of (b) and mixed thoroughly. The mixture was kept at ambient temperature for 4 hours; (d) after the 4 hours, 2.44 g of Miglyol 812 containing 10 mg of BHA was added, mixed thoroughly, then the mixture was aged at ambient temperature for at least 2 hours and centrifuged at 13,000 rpm providing an acceleration of about 16,000 G. There was no visible indication of sedimentation of the solid drug particles nor was there any visible indication of phase separation of the oil and the water upon 1 hour centrifugation at about 16,000 G (G being the gravity at about sea level), suggestive of shelf life physical stability for about 22 months at 1 G and room temperature. The suspension also remained unchanged, i.e., homogeneous, after storage for 24 hours at about 25° C., 40° C., and 60° C. After the centrifugation of the composition that was stored for 2 hours at about 25° C. the top and bottom layers were assayed for LD, CD and hydrazine. The difference in their LD and CD content was less than about 2%, within the resolution limit of the assay. The hydrazine concentrations were only slightly higher than the initial 0.52 µg/mg of the combined weights of LD and CD: the respective hydrazine concentrations in the top and bottom layers of the centrifuged composition were only 0.67 µg/mg and 0.60 µg/mg of the combined weights of LD and CD, well below the targeted upper limit of 1.6 µg/mg. After a week of storage at 60° C. the hydrazine concentration was still only 0.76 µg/mg of the combined weights of LD and CD. Furthermore, the concentration of all other impurities as measured by their percentage of the HPLC peaks was less than 0.05% after 1 week of storage at 60° C. The formulation has an acceptable, slightly bitter taste.

EXAMPLE 20

An 80 mg/mL Baclofen-comprising Orally Extrudable Paste for Managing Spastic Conditions in Multiple Sclerosis and Cerebral Palsy 0.8 g Poloxamer 188 can be mixed to homogeneity with 1.5 g water by warming to 60° C. 1.32 g of Baclofen and 12 g of L-tyrosine can be added and the mixture can be homogenized, then allowed to age for 10 hours with periodic mixing. Next 4.75 g of the medium chain triglyceride Miglyol 812 can be the Baclofen-L-tyrosine -Poloxamer 188-water paste, homogenized and allowed to age for 3 hours with periodic mixing. The resulting paste can be physically stable upon centrifugation at 3000 G and it can be centrifuged to remove trapped air. Its expected density at 23±2° C. is 1.25 g/mL±0.05 g/mL. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.04 mL/hour, 0.64 mL of the paste, containing about 51.2 mg of Baclofen, would be extruded over 16 awake hours into the mouth.

EXAMPLE 21

An 80 mg/mL Baclofen-comprising Orally Pumpable Suspension for Managing Spastic Conditions in Multiple Sclerosis and Cerebral Palsy Cocoa butter, an edible oil extracted from cocoa beans, has a typical melting range of about 34° C.-36.5° C., so that it is a solid at room temperature but becomes liquid at body temperature. An 80 mg/mL suspension of Baclofen can be prepared by homogenizing 1.9 g Baclofen with 20 g of cocoa butter. The volume of the suspension at 37±2° C. is expected to be about 23.7 mL and the Baclofen concentration is expected to be at 37±2° C. near 80 mg/mL. At 0.04 mL/hour flow rate about 0.64 mL of the solution containing about 0.51 mg of Baclofen could be pumped into the mouth in 16 awake hours.

EXAMPLE 22

A 50 mg/mL Treprostinil-comprising Orally Extrudable Paste for Pulmonary Arterial Hypertension Management Ingredients: Treprostinil (Bio-Techne Minneapolis, Minn.); L-tyrosine, nominal particle size 20 μm; Poloxamer 188; Miglyol 812 (Peter Cremer, Cincinnati, Ohio); de-ionized water.

0.8 g Poloxamer 188 can be mixed to homogeneity with 1.5 g water by warming to 60° C. 12 g of L-tyrosine can be added and the mixture can be homogenized, then allowed to age for 10 hours with periodic mixing. 0.8 g of treprostinil can be dissolved in 4.75 g of the medium chain triglyceride Miglyol 812. The treprostinil solution in Miglyol 812 can be mixed with the L-tyrosine -Poloxamer 188-water paste, homogenized and allowed to age for 3 hours with periodic mixing. The resulting paste can be physically stable upon centrifugation at 3000 G and it can be centrifuged to remove trapped air. Its expected density at 23±2° C. is 1.25 g/mL±0.05 g/mL. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.02 mL/hour, 0.32 mL of the paste, containing about 16 mg of treprostinil, would be extruded over 16 awake hours into the mouth.

EXAMPLE 23

An 80 mg/mL Midoridine-comprising Orally Extrudable Paste for Managing Spastic Conditions in Multiple Sclerosis and Cerebral Palsy 0.8 g Poloxamer 188 can be mixed to homogeneity with 1.5 g water by warming to 60° C. 1.32 g of Midoridine and 12 g of L-tyrosine can be added and the mixture can be homogenized, then allowed to age for 10 hours with periodic mixing. Next 4.75 g of the medium chain triglyceride Miglyol 812 can be the Baclofen-L-tyrosine -Poloxamer 188-water paste, homogenized and allowed to age for 3 hours with periodic mixing. The resulting paste can be physically stable upon centrifugation at 3000 G and it can be centrifuged to remove trapped air. Its expected density at 23±2° C. is 1.25 g/mL±0.05 g/mL. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.04 mL/hour, 0.64 mL of the paste, containing about 51.2 mg of Midoridine, would be extruded over 16 awake hours into the mouth.

EXAMPLE 24

A 0.5 mg/mL Iloprost-comprising Orally Extrudable Paste for Management of Pulmonary Arterial Hypertension Ingredients: 0.5 g Poloxamer 188 can be mixed to homogeneity with 0.8 g deionized water by warming to about 60° C., and then homogenized with 6.25 g of L-tyrosine (D50 about 20 μm particle size) powder by thorough mixing, aging the mixture at ambient temperature for about 24 hours, and thorough re-mixing. 4 mg of iloprost and 10 mg of BHA (butylated hydroxyanisole) can be dissolved in 2.44 g of Miglyol 812 and the solution can be mixed thoroughly with the L-tyrosine-Poloxamer-water mixture, aging the mixture at ambient temperature for at least 24 hours, then thoroughly re-mixing and again aging for about 24 hours. Next the mixture can be centrifuged for 1 hour at 16,000 G to remove any trapped air. The resulting mixture can be physically stable, i.e. may not phase separate under the centrifugation suggestive of shelf life physical stability for more than 22 months at normal gravity at 23±2° C. Its density can be 1.25±0.05 g/mL at about 25° C. It can be non-pourable at 23±2° C. but can be extruded at 37±2° C. At a continuous extrusion rate of 0.02 mL/hour, 0.36 mL of the paste, containing 0.18 mg of iloprost would be extruded daily into the mouth over 16 awake hours.

EXAMPLE 25

A Temperature Sensitive 0.5 mg/mL Iloprost Solution in Cocoa Butter for Management of Pulmonary Arterial Hypertension Cocoa butter, an edible oil extracted from cocoa beans, has a typical melting range of about 34° C.-36.5° C., so that it is a solid at room temperature but becomes liquid at body temperature. A solution of iloprost can be prepared by melting about 50 g of cocoa butter at about 40° C. and then stirring in 28 mg iloprost. The paste can then be put into the reservoir and upon cooling will solidify. The volume of the cocoa butter at 37±2° C. is expected to be about 56 mL and the iloprost concentration is expected to be at 37±2° C. 0.5 mg/mL. At 0.02 mL/hour flow rate about 0.32 mL of the solution containing about 0.16 mg of iloprost could be pumped into the cheek pocket proximally to the buccal mucosa in 16 awake hours.

EXAMPLE 26

A Temperature Sensitive 50 mg/mL Treprostinil Solution in Butter for Management of Pulmonary Arterial Hypertension An emulsion can be prepared by melting at about 40° C. 10 mL of butter (a water-in-oil emulsion remaining solid when refrigerated, melting between about 32° C. and about 35° C.), then stirring in 500 mg of treprostinil. The emulsion can then be put into the reservoir and upon cooling will solidify. The reservoir containing the emulsion could solidify and stored as a solid in a refrigerator at 8±3° C. At 37±2° C. and at a continuous extrusion rate of 0.02 mL/hour, 0.36 mL of the paste about 18 mg of treprostinil would be pumped daily into the cheek pocket near the buccal mucosa over 16 awake hours.

EXAMPLE 27

A 1 mg/mL Ciclosenide Solution for COPD or PAH Management

A solution of 1 mg/mL Ciclesonide in glycerol could be prepared by dissolving 100 mg Ciclesonide in 100 mL glycerol. The solution would be continuously pumped at 10 μL/hour flow rate. Daily 0.24 mL containing 0.24 mg of Ciclesonide would be pumped into the mouth near the buccal mucosa.

EXAMPLE 28

A 1 mg/mL Vilanterol Solution for COPD Management

A solution of 1 mg/mL Vilanterol could be prepared by dissolving 100 mg Vilanterol in 100 mL glycerol. The solution would be continuously pumped at 10 μL/hour flow rate into the mouth. Daily 0.24 mL containing 0.24 mg of Vilanterol would be pumped into the mouth near the buccal mucosa.

EXAMPLE 29

A 0.2 mg/mL Glycopyrronium Bromide Solution for COPD Management

A solution of 0.2 mg/mL Glycopyrronium bromide could be prepared by dissolving 20 mg Glycopyrronium bromide in 100 mL water. The solution would be continuously pumped at 10 μL/hour flow rate into the mouth. Daily 0.24 mL containing 0.048 mg of Glycopyrronium bromide would be pumped into the mouth near the buccal mucosa.

EXAMPLE 30

A 1.44 mg/mL Ipratropium Bromide Solution for COPD Management

A solution of 1.44 mg/mL Ipratropium bromide could be prepared by dissolving 144 mg Ipratropium bromide in 100 mL water. The solution would be continuously pumped at 20 μL/hour flow rate into the mouth. In 24 hours 0.48 mL containing 0.69 mg Ipratropium bromide would be pumped into the mouth near the buccal mucosa.

EXAMPLE 31

An 833 mg/mL Carbocisteine Paste for COPD Management

Ingredients: Carbocisteine, about 20 μm nominal particle size; Poloxamer 188; Miglyol 812 (Peter Cremer, Cincinnati, Ohio); de-ionized water.

0.8 g Poloxamer 188 can be dissolved in 1.5 g water then homogenized with 10 g of carbocisteine. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.075 mL/hour, 0.72 mL of the paste containing 1.43 g of carbocisteine would be extruded over 24 hours into the mouth.

EXAMPLE 32

A 5 mg/mL Hexoprenaline Sulfate Solution for Reducing the Incidence of Asthma Attacks A solution of 5 mg/mL Hexoprenaline sulfate could be prepared by dissolving 0.5 g of Hexoprenaline sulfate in 100 mL water. The solution would be continuously pumped at 10 μL/hour flow rate into the mouth. In 24 hours 0.24 mL containing 1.2 mg Hexoprenaline sulfate would be pumped into the mouth near the buccal mucosa.

EXAMPLE 33

An 800 mg/mL Erythromycin-comprising Orally Extrudable Paste for COPD Management Ingredients: Erythromycin, about 20 μm nominal particle size; Poloxamer 188; Miglyol 812 (Peter Cremer, Cincinnati, Ohio); de-ionized water.

0.8 g Poloxamer 188 can be dissolved in 1.5 g water then homogenized with 10 g of erythromycin. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.03 mL/hour, 0.72 mL of the paste containing 576 mg of erythromycin would be extruded over 24 hours into the mouth.

EXAMPLE 34

An 800 mg/mL Erythromycin-comprising Orally Extrudable Paste for Management of Gastroparesis, e.g. Diabetic Gastroparesis Ingredients: Erythromycin, about 20 μm nominal particle size; Poloxamer 188; Miglyol 812 (Peter Cremer, Cincinnati, Ohio); de-ionized water.

0.8 g Poloxamer 188 can be dissolved in 1.5 g water then homogenized with 10 g of erythromycin. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.01 mL/hour, 0.24 mL of the paste containing 192 mg of erythromycin would be extruded over 24 hours into the mouth.

EXAMPLE 35

An 30 mg/mL Tizanidine-comprising Orally Extrudable Paste for Managing Spastic Conditions in Multiple Sclerosis and Cerebral Palsy 0.8 g Poloxamer 188 can be mixed to homogeneity with 1.5 g water by warming to 60° C. 0.5 g of Tizanidine and 12 g of L-tyrosine can be added and the mixture can be homogenized, then allowed to age for 10 hours with periodic mixing. Next 4.75 g of the medium chain triglyceride Miglyol 812 can be the Baclofen-L-tyrosine -Poloxamer 188-water paste, homogenized and allowed to age for 3 hours with periodic mixing. The resulting paste can be physically stable upon centrifugation at 3000 G and it can be centrifuged to remove trapped air. Its expected density at 23±2° C. is 1.25 g/mL±0.05 g/mL. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.04 mL/hour, 0.64 mL of the paste, containing about 20 mg of Tizadinide, would be extruded over 16 awake hours into the mouth.

EXAMPLE 36

An 800 mg/mL Flavoxate-comprising Orally Extrudable Paste for Urinary Urge and Incontinence ("Overactive Bladder") Management Ingredients: Flavoxate, about 20 µm nominal particle size; Poloxamer 188; Miglyol 812 (Peter Cremer, Cincinnati, Ohio); de-ionized water.

0.8 g Poloxamer 188 can be dissolved in 1.5 g water then homogenized with 10 g of flavoxate. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.04 mL/hour, 0.96 mL of the paste containing 768 mg of flavoxate would be extruded over 24 hours into the mouth.

EXAMPLE 37

A 1.14 g/mL Magnesium Carbonate Comprising Orally Extrudable Paste e.g. for Managing a Neurological Disorder Like Alzheimer's Disease or Parkinson's Disease Ingredients: Magnesium carbonate, about 20 µm nominal particle size; Poloxamer 188; Miglyol 812 (Peter Cremer, Cincinnati, Ohio); de-ionized water.

0.8 g Poloxamer 188 can be dissolved in 5 g water then homogenized with 20 g of magnesium carbonate. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.2 mL/hour, optionally from 1.2 mL paste containing reservoirs replaced every 6 hours, 4.8 mL of the paste containing 5.6 g or about 0.067 moles of magnesium carbonate would be extruded over 24 hours into the mouth. With a pair of bilateral devices 11.2 g or about 0.132 moles of magnesium carbonate would be extruded daily into the mouth.

EXAMPLE 38

A 1.4 g/mL Magnesium Oxide Comprising Orally Extrudable Paste e.g. for Managing a Neurological Disorder Like Alzheimer's Disease or Parkinson's Disease Ingredients: Magnesium oxide, about 20 µm nominal particle size; Poloxamer 188; Miglyol 812 (Peter Cremer, Cincinnati, Ohio); de-ionized water.

0.8 g Poloxamer 188 can be dissolved in 5 g water then homogenized with 24 g of magnesium oxide. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.075 mL/hour, 1.8 mL of the paste containing 2.5 g or about 0.064 moles of magnesium oxide would be extruded over 24 hours into the mouth. With a pair of bilateral devices 5 g or about 0.13 moles of magnesium oxide would be extruded daily into the mouth.

EXAMPLE 39

An 800 mg/mL Trimebutine-comprising Orally Extrudable Paste for Irritable Bowel Syndrome Management Ingredients: Trimebutine, about 20 µm nominal particle size; Poloxamer 188; Miglyol 812 (Peter Cremer, Cincinnati, Ohio); de-ionized water.

0.8 g Poloxamer 188 can be dissolved in 1.5 g water then homogenized with 10 g of trimebutine. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.03 mL/hour, 0.72 mL of the paste containing 576 mg of trimebutine would be extruded over 24 hours into the mouth.

EXAMPLE 40

An 800 mg/mL Curcumin-comprising Orally Extrudable Paste for Cancer Therapy

Ingredients: Curcumin, about 20 µm nominal particle size; Poloxamer 188; Miglyol 812 (Peter Cremer, Cincinnati, Ohio); de-ionized water.

0.8 g Poloxamer 188 can be dissolved in 1.5 g water then homogenized with 10 g of curcumin. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.1 mL/hour, 2.4 mL of the paste containing 1.92 g of curcumin would be extruded over 24 hours into the mouth.

EXAMPLE 41

An 800 mg/mL Curcumin-analog EF31-comprising Orally Extrudable Paste for Cancer Therapy Ingredients: Curcumin-analog EF31, about 20 µm nominal particle size; Poloxamer 188; Miglyol 812 (Peter Cremer, Cincinnati, Ohio); de-ionized water.

0.8 g Poloxamer 188 can be dissolved in 1.5 g water then homogenized with 10 g of Curcumin-analog EF31. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.1 mL/hour, 2.4 mL of the paste containing 1.92 g of curcumin-analog EF31 would be extruded over 24 hours into the mouth.

EXAMPLE 42

An 800 mg/mL Curcumin-analog UBS109-comprising Orally Extrudable Paste for Cancer Therapy Ingredients: Curcumin-analog UBS109, about 20 µm nominal particle size; Poloxamer 188; Miglyol 812 (Peter Cremer, Cincinnati, Ohio); de-ionized water.

0.8 g Poloxamer 188 can be dissolved in 1.5 g water then homogenized with 10 g of curcumin-analog UBS109. The mixture can be allowed to age for 10 hours at 23±2° C. with periodic mixing, and then homogenized by thorough mixing with 4.75 g of the medium chain triglyceride Miglyol 812. The mixture can be allowed to age for at least 12 hours with periodic mixing. The resulting paste can be physically stable upon centrifugation at 3000 G and it can be centrifuged to remove trapped air. The paste is expected to be soft, compliant, and easy to mechanically deform and to retain at 23±2° C. its shape after deformation. The paste is not expected to be pourable at 23±2° C., but at 37±2° C. it could be extruded. At a continuous extrusion rate of 0.1 mL/hour, 2.4 mL of the paste containing 1.92 g of curcumin-analog UBS109 would be extruded over 24 hours into the mouth.

EXAMPLE 43

Showing the Shape and Dimensions of an Exemplary Model of the Oral Drug Pump

Testing for comfort of various pump models in volunteers that can comprise about 0.8 mL of the LD/CD paste pharmaceutical composition showed that for comfort of wear the surfaces must not have corners or edges that are sharp, i.e., that the edges and corners should be about rounded; furthermore the surfaces, particularly those contacting buccal surfaces should be smooth. Pump models of obround shape and 0.81 mL LD/CD paste pharmaceutical composition volume were particularly comfortable to wear and did not substantially alter the appearance of the face. The width of the pumps (their dimension from the vestibular surface of the teeth outward) was most important for comfort, followed by their length. When pumps span a third tooth (i.e. more than two teeth) and the teeth were even slightly misaligned there were visible changes in the appearance of the face of the wearer. Tests in four people showed that tooth attached obround pumps that were 0.27" wide, 0.50" high, and 0.95" long were particularly comfortable, did not interfere with speech, did not interfere with swallowing food or drink, and did not substantially alter the appearance of the face of the wearer.

EXAMPLE 44

Figure 27:
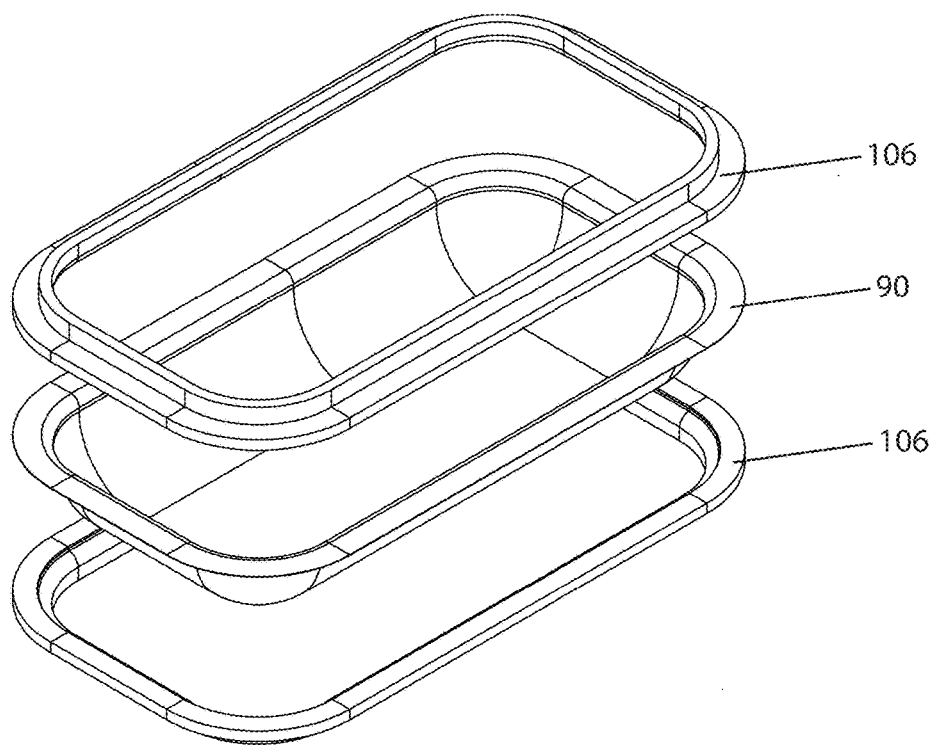
FIG. 27 illustrates titanium coupons that were resistance welded, (i.e., brazed) to silver diaphragms by applying an electrical current pulse or pulses.

Describing the Welding of a Silver Diaphragm to a Titanium Housing to Form Hermetically Sealed Chambers with Ports Hermetically sealed obround-shaped test units were made. The obround hermetically sealed units were 0.27" wide, 0.50" high, and 0.95" long. Their housing was Grade 2 titanium and their 0.50"×0.95", 0.03 mm thick diaphragms were commercially pure, fully annealed silver foils. As shown in FIG. 27, hermetically sealed chambers can be formed by resistance welding of Ti—Ag—Ti (in ambient air and without using a flux) where the rim (i.e. the flange) of the silver foil diaphragm was welded. Resistance brazing coupons 106 were welded to silver diaphragm 90. For the resistance welding a sequence of unequal duration pulses of unequal currents were passed through the Ti—Ag—Ti structure while its parts were pressed together. Only the shortest and largest current pulse melted part or most of the silver diaphragm rim; it did not melt most of the silver diaphragm nor did it melt the titanium housing.

EXAMPLE 45

Describing the Shape, Method of Forming and Material of an Exemplary Diaphragm

Figure 28:
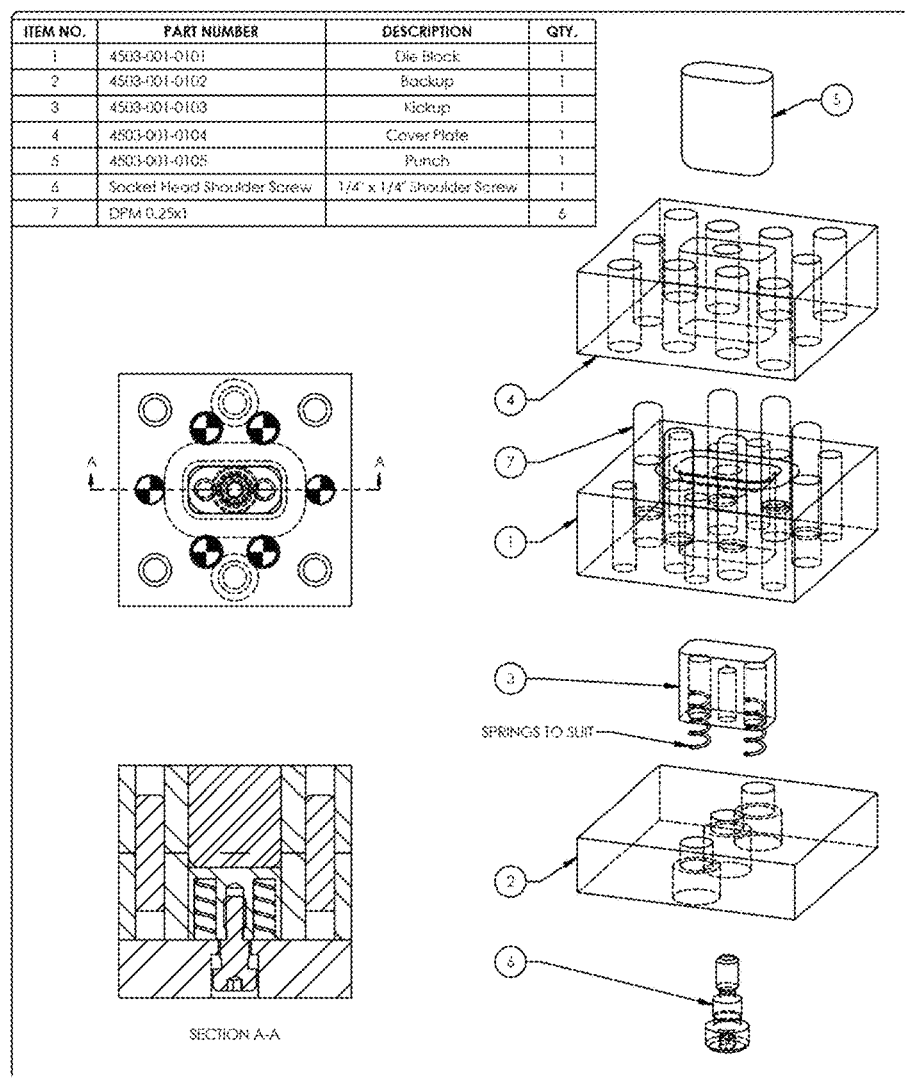
FIG. 28 is a schematic drawing of a stamp die block, cover plate, and punch designed to form flexible and/or deformable metal diaphragms.

To assess the formability of the diaphragm, pure silver sheet of 0.025 and 0.03 mm thickness were procured and a stamp die block, cover plate, and punch were designed to form diaphragms per the schematic drawing of FIG. 28.

Figure 29:
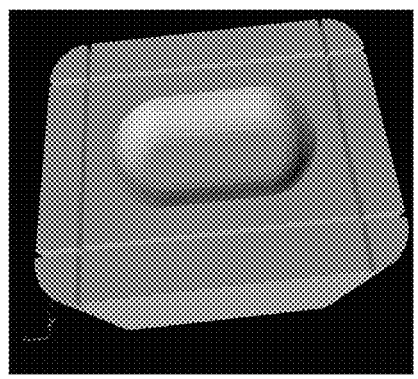
FIG. 29 shows a tool used to make flexible and/or deformable metal diaphragms.
Figure 30:
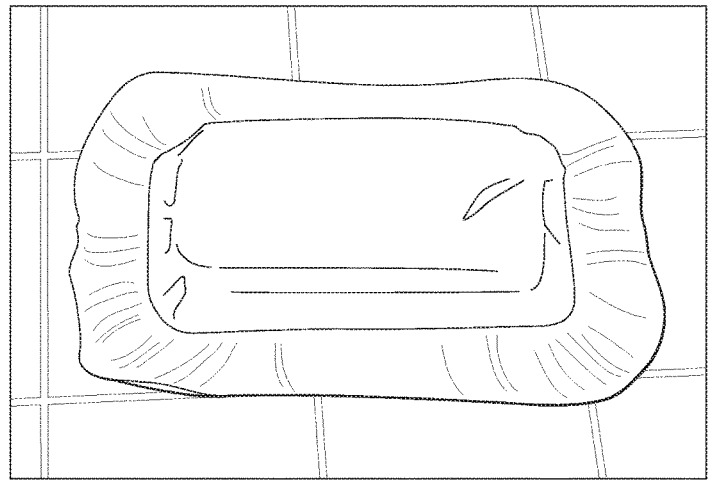
FIG. 30 shows a flexible and/or deformable metal diaphragm.

Diaphragms were also made using the tool shown in FIG. 29. The diaphragms were slightly oversized to allow for spring-back. They were also made of a sheet of 0.03 mm thick commercially pure, fully annealed, silver foil. The silver foil sheet was cut to the approximate size of the surface of the tool, placed on the surface of the tool and forced into the cavity by pressing on the flat surface of the tool. By pressing on the tool while the worked piece was rotated the silver foil was made to conform to the bottom of the tool. After stamping, some diaphragms were wrinkled at their rims (i.e. at their flanges) as seen in the photograph of FIG. 30. To straighten the wrinkles (i.e. to reduce their heights) the rims were flattened by coining. The diaphragms were then tested for absence of light passing through pinholes or tears, then trimmed with a blade along the grooves of the tool shown in FIG. 29.

EXAMPLE 46

Figure 31:
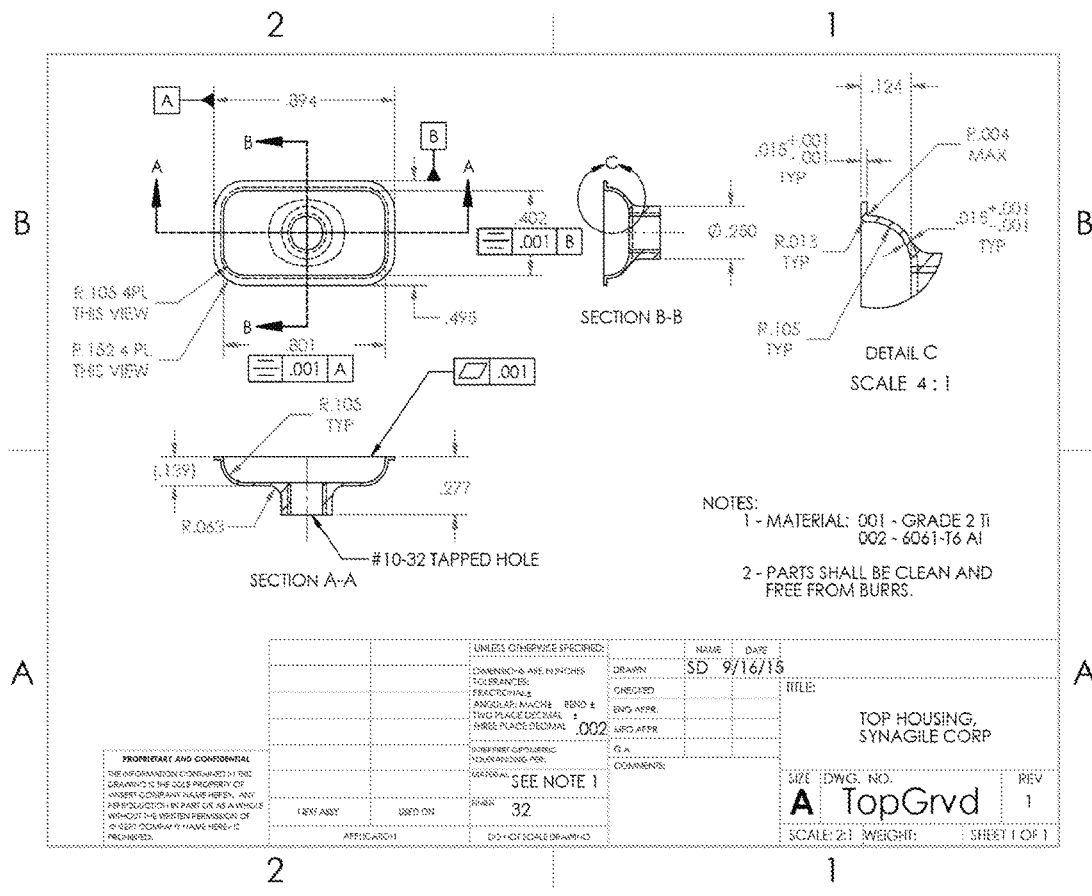
FIG. 31 shows schematics for a titanium test housing including fittings that allowed for testing for hermeticity. The test housing is welded to a silver diaphragm.

Showing the Welding of Titanium Housing Parts and Titanium Foil to Form Hermetically Sealed Chambers Test housings were machined from Grade 2 titanium and diaphragms were made of a 0.05 mm thick commercially pure, fully annealed silver foil sheet. The test housings contained fittings that allowed testing for hermeticity, as shown in FIG. 31.

A benchtop medium-frequency inverter Amada Miyachi resistance welder was used. A pre-weld current pulse was passed prior to application of the welding current pulse. The pre-weld current pulse was of a duration 40 times longer and a current that was 45% of the welding current pulse. After application of the brief welding current pulse, the now joined parts were annealed in an oven for 30 min at 600° C. then allowed to cool to room temperature over 45 minutes or more. To test chambers for the hermeticity of their welds, each chamber was connected through its port to a helium leak tester known as "sniffer" according to the US Military's standard MIL-STD-750E hermetic seal test, i.e., leak test. Each of five units passed tests showing hermeticity of the seals and the diaphragms for the specification "time to exchange 50% atmosphere of >>17.6 years", i.e., there were no detectable leaks through either the diaphragms or through the titanium/silver joints (i.e., welds).

EXAMPLE 47

Figure 32:
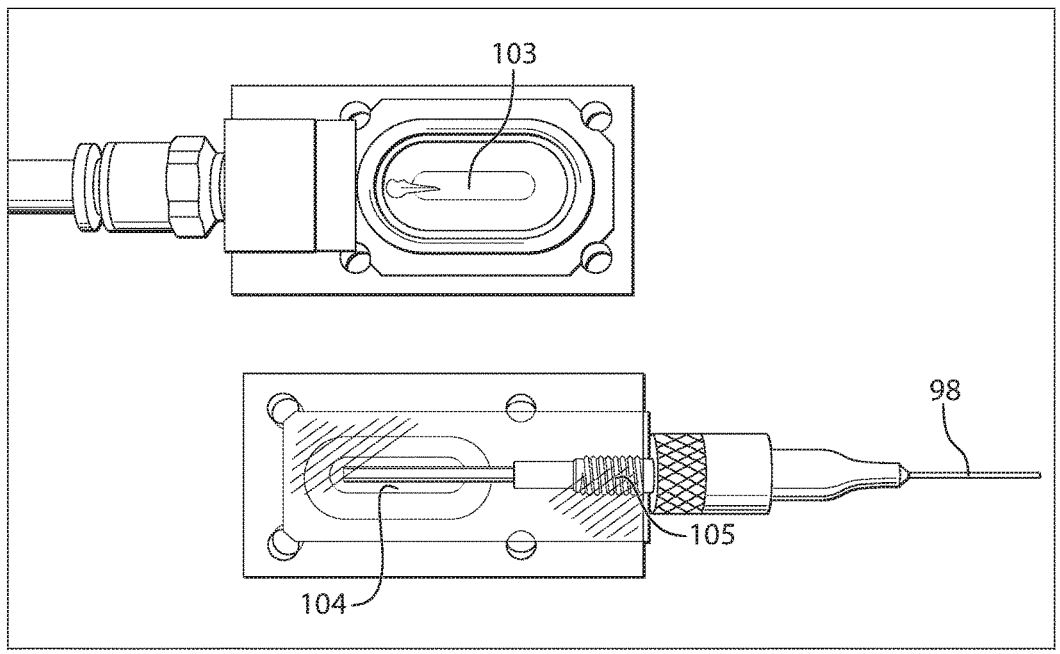
FIG. 32 shows a test housing for a propellant-driven pump.

Showing Incomplete Delivery and Variation in Extrusion Rate by a Pump without a Grooved Drug Chamber Wall A re-usable testing tool referred to as "test bed" was machined, as shown in FIG. 32. It simulated the pump and measured the flow rate of different LD/CD pharmaceutical composition formulations, at different gas pressures, with flow-controlling nozzles of different internal diameter and length. The test bed comprised two blocks machined to the dimensions of the obround pump geometry, separated by a diaphragm, the blocks and the diaphragm pressed together to prevent leakage of the LD/CD paste pharmaceutical composition and of the gas. The blocks of the test bed comprised two identical cavities in the housings of the propellant chamber 103 and the drug chamber 104, one cavity 103 having a port for pressurizing with a gas (typically $CO_2$) to simulate the pressure from a propellant, and the other 104 containing a port 105 and nozzle 98 for the outlet of the drug formulation.

The two cavities sandwiched a 0.030 mm thick pinhole-free silver diaphragm. The silver diaphragm was prepared by manually pressing a sheet of 0.030 mm silver into a mold that simulates the drug cavity side of the pump. The diaphragm was placed into drug the cavity, the drug was then injected beneath it until the cavity was filled, then the flow controlling nozzle was attached.

Figure 33:
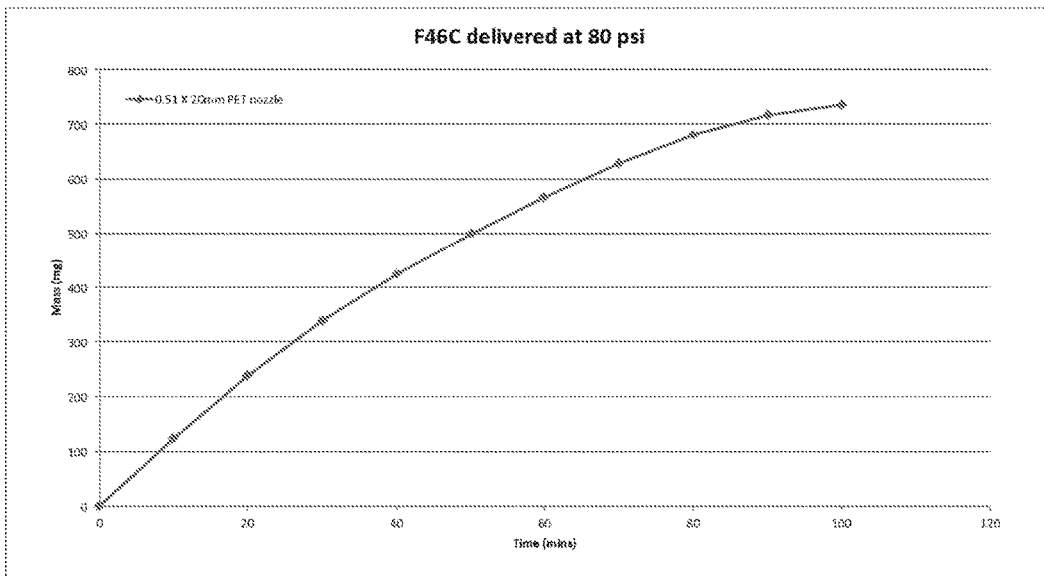
FIG. 33 is a graph showing the time dependence of the mass of the delivered pharmaceutical composition for the device of FIG. 32. The graph shows that the slope, i.e., the rate of delivery, was not constant over the 100 min extrusion period.
Figure 34:
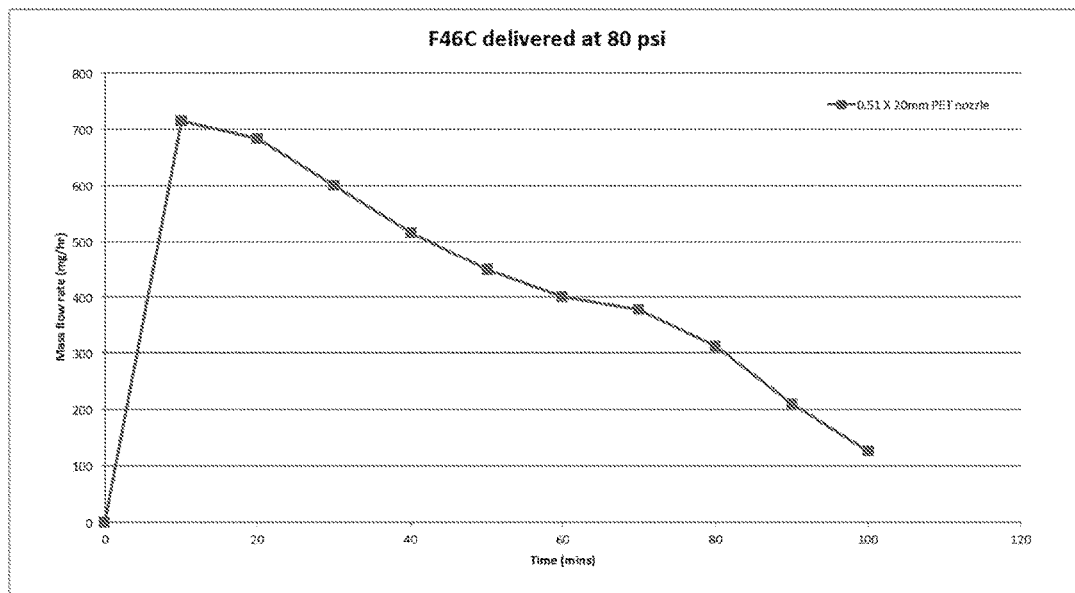
FIG. 34 is a graph showing the time dependence of rate of delivery, i.e., rate of extrusion, of the pharmaceutical composition for the device of FIG. 33. The graph shows that the rate was not constant over the 100 min extrusion period.

The weight of the extruded LD/CD paste pharmaceutical composition was monitored with an analytical balance. The figure below shows the typical time dependence of the extruded mass. In the particular experiment described the pressure of the propelling $CO_2$ was kept constant at 80 psi and a 20 mm long 0.51 mm internal diameter polyethylene terephthalate nozzle was attached. FIG. 33 is a graph of the amount of the pharmaceutical composition delivered versus time and shows that the slope was not constant over the 100 min extrusion, i.e., that the rate of extrusion was not constant. The non-constant flow rate in the same experiment is shown also in the FIG. 34, where the time dependence of the flow rate is plotted.

Figure 35:
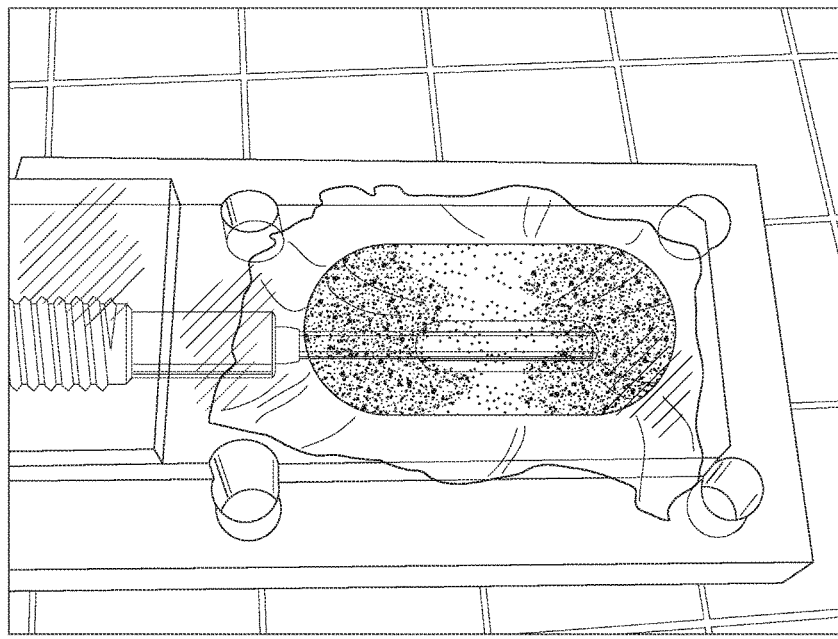
FIG. 35 shows incomplete emptying of the pharmaceutical composition from the device of FIG. 32.

The drug was not only delivered non-linearly, but was also not completely delivered from the drug reservoir. FIG. 35 shows the drug remaining in the drug chamber after the drug had ceased to flow from the pump.

EXAMPLE 48

Figure 36:
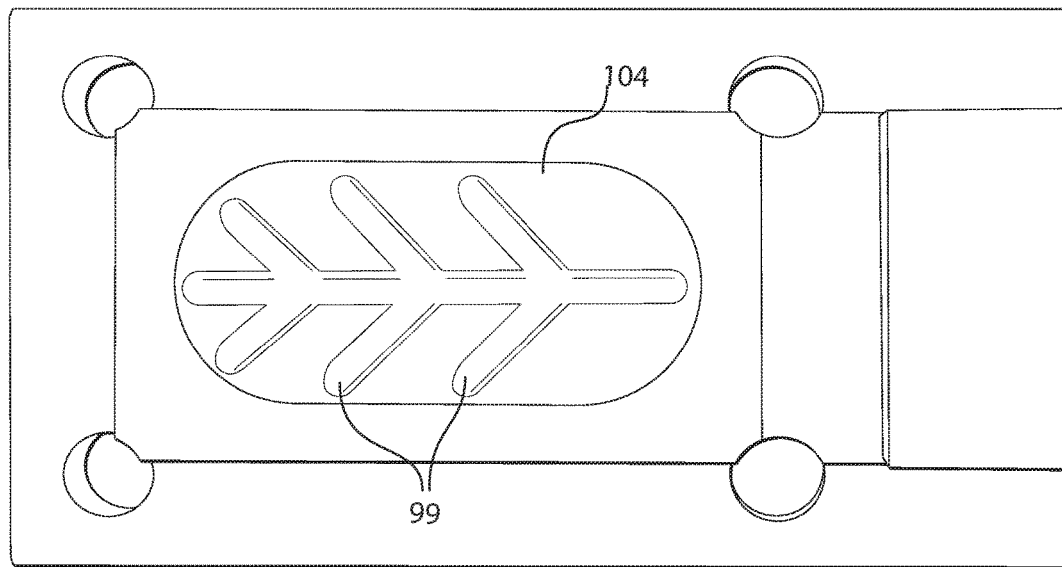
FIG. 36 shows flow-enhancing grooves in the interior housing wall of the drug-containing chamber for a propellant-driven pump.
Figure 37:
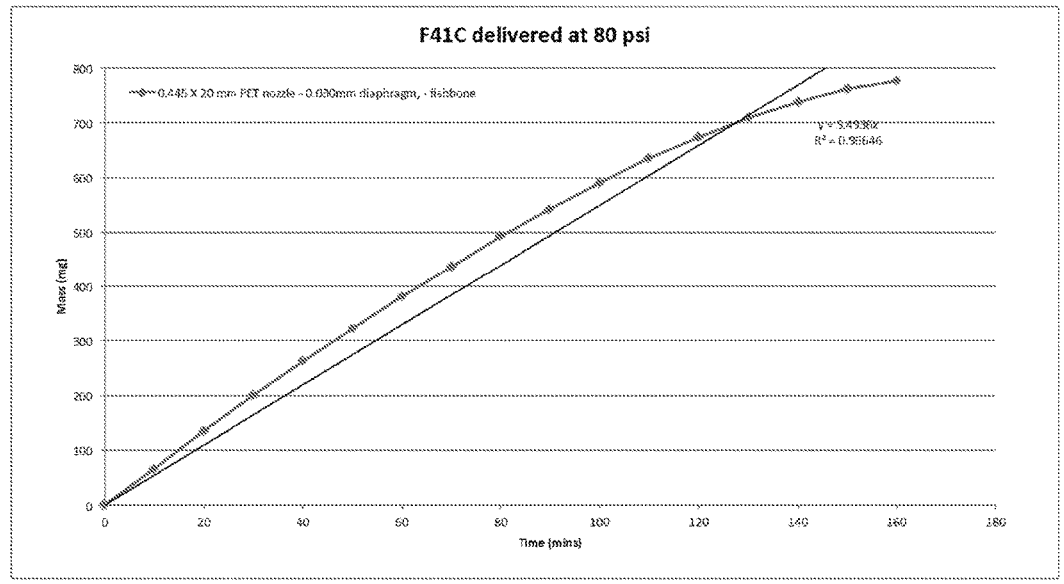
FIG. 37 is a graph showing the time dependence of the mass of the delivered, i.e., extruded, pharmaceutical composition for the device of FIG. 36.
Figure 38:
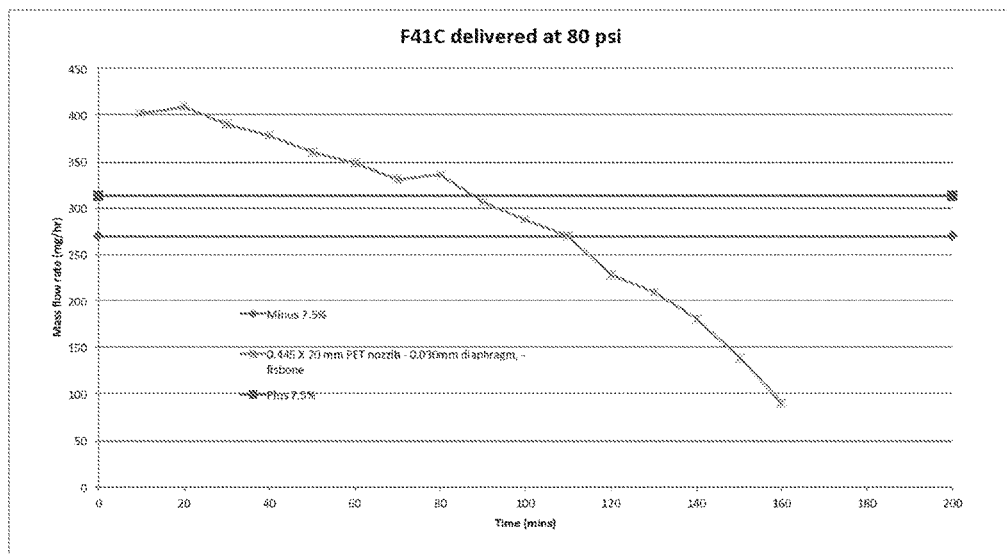
FIG. 38 is a graph of showing the time dependence of the rate of delivery, i.e., extrusion, of the pharmaceutical composition for the device of FIG. 36.

Showing Lesser Variability in Flow Rate and Delivery of a Larger Fraction of the Drug When the Drug Chamber Wall is Grooved The experiment of Example 47 was repeated but with flow channel-forming grooves in the housing wall of the LD/CD drug-containing chamber. The channels were designed to provide a path for the drug to flow when the diaphragm collapses into the drug-containing chamber. As the drug empties the diaphragm typically makes contact with the bottom of the housing, thereby preventing or slowing the flow of the drug-comprising fluid from part of the chamber, i.e., trapping the drug-comprising fluid between the collapsed diaphragm and the chamber's wall. The photograph of FIG. 36 shows the grooves 99 in the housing wall of the drug-containing chamber 104 of the test bed. As seen in FIG. 37 the grooves improved the constancy of the flow rate of a LD/CD comprising paste, but did not make it actually constant. As seen in FIG. 38, where the time dependence of the flow rate is plotted, the flow rate continued to decline throughout the 160 min run.

EXAMPLE 49

Figure 39:
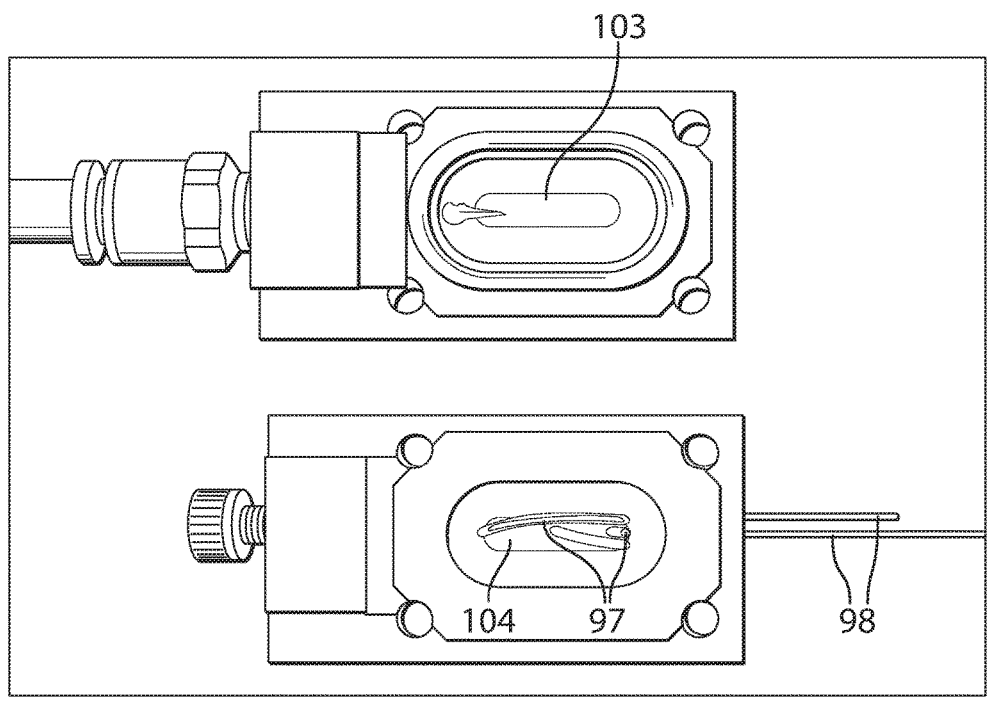
FIG. 39 shows the housing of a propellant-driven pump including two tubes that include flow channels for the drug-including pharmaceutical composition.
Figure 40:
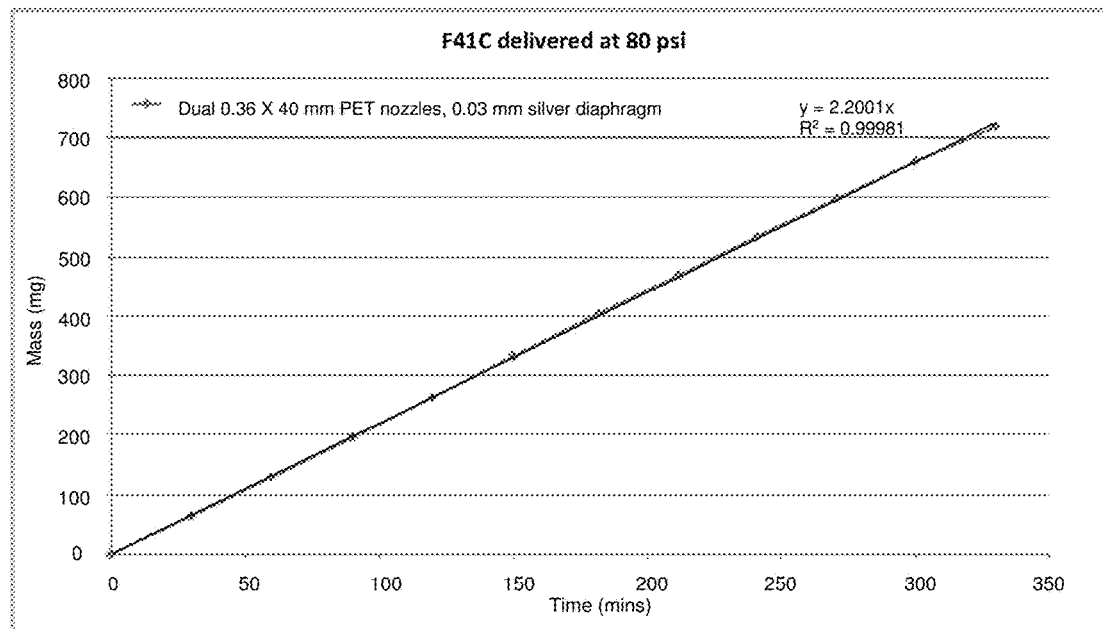
FIG. 40 is a graph showing that the time dependence of the mass of the pharmaceutical composition delivered for the device of FIG. 39 is linear, i.e., that the rate of delivery of the drug-including fluid is constant.
Figure 41:
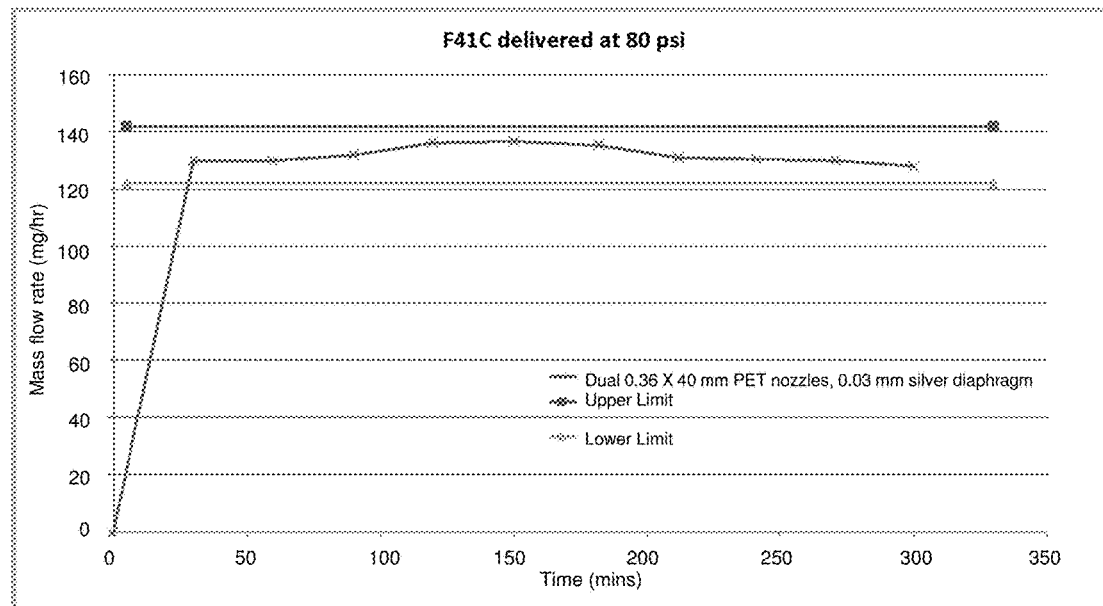
FIG. 41 is a graph showing the time dependence of the rate of delivery, i.e., the rate of extrusion of the pharmaceutical composition for the device of FIG. 39. The rate of delivery, i.e., extrusion, is about constant.

Showing the About Constant Rate Delivery of a Drug Comprising Composition and near Complete Delivery of the Drug in the Chamber When the Flow Channels are Flow-controlling Tubes in the Chamber The testing tool (test bed) was similar to that of Examples 47, but now comprised two tubular flow channels 98 as shown in FIG. 39. The tubes also served as flow-rate controlling nozzles. Their internal diameter was about 0.36 mm and their length was about 40 mm. The tubes were positioned in grooves 97 cut in the housings of the propellant chamber 103 and the drug chamber 104 and extended outside of the housing. The flow rate, controlled by the tubes or nozzles, now maintained a constant flow rate of approximately 2.2 mg/min. FIG. 40 shows a typical mass vs. time run over a period of 5.5 hrs. The time dependence of the flow rate shown in FIG. 41 confirmed that the flow rate was now constant within better than ±7.5%.

EXAMPLE 50

Showing that the Rate of Galvanic Corrosion in Titanium-silver Joints is Slow

In the absence of air or oxygen metals can corrode by reacting with water. The corrosion requires an oxidation reaction whereby the metal is oxidized to its oxide or its hydroxide and a reduction reaction whereby water is reduced to molecular hydrogen or to a metal hydride. Because the currents associated with the two rates are equal, the corrosion rate of a particular metal can be slow either if the oxidation or the hydrogen evolution is slow. If two different metals are contacted, the less noble metal is oxidized while the more noble metal is reduced to its hydride or evolves $H_2$. The rate of oxidation of the less noble metal can depend on its passivating oxide or hydroxide layer that can slow or prevent mass transport between the solution and the metal. The corrosion rate depends on the pH of the composition, typically 4±1 for the extruded the LD/CD paste pharmaceutical compositions. To assess the rates of corrosion, the currents flowing between shorted electrode pairs of about 2 cm$^2$ solution-contacting area in a 0.1 M citrate buffer pH 4 solution (made with trisodium citrate and citric acid) were measured under air and under nitrogen at about 23±3° C. after about 24 hour aging (while shorted) in the buffer solution, both without adding carbidopa and with enough carbidopa added to saturate the solution. The results are summarized in the Table 20.

TABLE 20

Corrosion Currents.

| Anode | Cathode | Air or $N_2$ | Carbidopa added | Corrosion Current, µA |
|---|---|---|---|---|
| Titanium | Tin | $N_2$ | no | 60 |
| Titanium | Tin | $N_2$ | no | 40 |
| Titanium | Silver | Air | no | 0.15 |
| Titanium | Silver | $N_2$ | no | 0.1 |
| Titanium | Silver | $N_2$ | yes | 0.2 |
| 316 stainless steel | Tin | $N_2$ | yes | 30 |
| 316 stainless steel | Tin | $N_2$ | yes | 30 |
| 316 stainless steel | Silver | $N_2$ | no | 0.5 |
| 316 stainless steel | Silver | $N_2$ | no | 1 |
| 316 stainless steel | Silver | Air | Yes | 1.5 |

The surface of the tin was visibly roughened, possibly because of reduction to tin hydride. The surfaces of the titanium, the silver, and the 316 stainless steel appeared unchanged to the eye. The data show much more rapid corrosion of the couples with tin than with silver. The data show possibly acceptable corrosion for the 316 stainless steel-silver couple. The least corroding couple is, however, the titanium/silver couple, indicating the absence of substantial corrosion of joints formed of the two metals, for example of titanium welded with silver.

EXAMPLE 51

Showing that a pH 2.7-pH 3.3 Suspension Comprising an Antimicrobial Excipient, a Transition Metal Complexing Agent, 625 mg/mL (3.17 M) LD, 156 mg/mL (0.74 M) CD, and Poloxamer 188 Surfactant is Physically Stable When Centrifuged for 1 Hour at About 16,000 G Most of the LD and most of the CD in the suspension is particulate, i.e., the solid drugs are not dissolved. The suspension comprises 50.0 weight % (w/w) LD; 12.5 weight % CD; 24.1 weight % Miglyol 812; 5.0 weight % of Poloxamer 188; 7.9 weight % water; 0.3 weight % benzoic acid; 0.05 weight % EDTA (free acid form); 0.05 weight % EDTA disodium salt; and 0.1 weight % BHA. It is prepared as follows: (a) the LD (5 g) and CD (1.25 g) powders are mixed for 15 min to homogeneity; (b) the Poloxamer 188 (0.5 g) is mixed with deionized water (0.79 g) in which 5 mg of EDTA (free acid) and 5 mg disodium EDTA are dissolved. The mixture is warmed to about 60° C. and homogenized by thorough mixing; (c) the LD and CD powder mixture of (a) and 10 mg of BHA is added to the Poloxamer 188 and water of (b) and mixed thoroughly. The mixture is kept at ambient temperature for 24 hours; (d) after the 24 hours, 2.41 g of Miglyol 812 containing 30 mg of benzoic acid and 10 mg of BHA are added, mixed thoroughly, then the mixture is aged at ambient temperature for at least 6 hours, remixed, then centrifuged. There is no visible sedimentation of the solid drug particles nor is there any visible phase separation of the oil and the water upon 1 hour centrifugation at 13,000 rpm providing an acceleration of about 16,000 G (G being the gravity at about sea level), suggestive of shelf life physical stability for about 22 months at 1 G and room temperature. The pH of the mixture as measured with a pH glass electrode at about 23±3° C. is between about 2.7 and about 3.3. The suspension remains unchanged, i.e., homogeneous, after storage for 24 hours at about 25° C., 40° C., and 60° C.

EXAMPLE 52

Showing that a Thiol-containing Suspension Containing 625 mg/mL (3.17 M) LD, 156 mg/mL (0.74 M) CD, and Poloxamer 188 Surfactant may be Physically Stable When Centrifuged for 1 Hour at About 16,000 G and may Generate Little or no Hydrazine When Stored under Nitrogen at About 30 C.

Most of the LD and most of the CD in the suspension is particulate, i.e., the solid drugs are not dissolved. The suspension comprises 49.9 weight % (w/w) LD; 12.4 weight % CD; 0.2 weight % cysteine; 24.4 weight % Miglyol 812; 5.0 weight % of Poloxamer 188; 7.9 weight % water in which 0.05 weight % of EDTA (free acid) and 0.05 weight % disodium EDTA are dissolved; and 0.1 weight % BHA. It is prepared as follows: (a) the LD (4.99 g) and CD (1.24 g) and cysteine (0.2 g) powders are mixed for 15 min to homogeneity; (b) the Poloxamer 188 (0.5 g) is mixed with deionized water (0.79 g) in which 5 mg of EDTA (free acid) and 5 mg disodium EDTA are dissolved. The mixture is warmed to about 60° C. and homogenized by thorough mixing; (c) the LD and CD powder mixture of (a) and 10 mg of BHA are added to the Poloxamer 188 and water of (b) and mixed thoroughly. The mixture is kept at ambient temperature for 24 hours; (d) after the 24 hours, 2.44 g of Miglyol 812 containing 30 mg of benzoic acid and 10 mg of BHA are added, mixed thoroughly, then the mixture is aged at ambient temperature for at least 6 hours, remixed then centrifuged. There is no visible sedimentation of the solid drug particles nor is there any visible phase separation of the oil and the water upon 1 hour centrifugation at 13,000 rpm, providing an acceleration of about 16,000 G (G being the gravity at about sea level), suggestive of shelf life physical stability for about 22 months at 1 G and room temperature. The suspension remains unchanged, i.e., homogeneous, after storage for 24 hours at about 25° C., 30° C., 40° C., and 60° C. The concentration of hydrazine increases by less than 0.5 µg/mg when the mixture is stored under nitrogen for 1 month at about 30° C.

EXAMPLE 53

Clinical Trial of Frequent Intermittent Delivery of a LD/CD Suspension to Patients with Advanced Parkinson's Disease The clinical trial was an open-label, single-center study of 18 Parkinson's disease patients who experienced ≥2 hours of OFF time per day while on their regular anti-PD medications. Standard intermittent oral LC/CD Sinemet tablets were compared with the same total doses of LD/CD suspension delivered into the mouth every 5-10 minutes using an oral syringe. The LD/CD suspensions were prepared by dispersing the Sinemet tablets in a small amount of water. Patients were admitted to the clinic on Day 1 for baseline evaluations. On Day 2 (the "Control Day"), LD/CD was administered as commercially available LD/CD tablets at each patient's pre-baseline dosing regimen. Plasma levels of levodopa as well as ON and OFF time were measured repeatedly over the course of 8 hours. On Day 3 (the "PK Day"), a suspension of LD/CD was administered intraorally every 5-10 minutes over a period of 8 hours at a dose equal to the total dose of standard oral LD/CD that the patient consumed over the same 8-hour period on the Control Day, and plasma levels of levodopa were obtained. On Day 4 (the "Efficacy Day"), each patient received his or her first LD/CD morning dose as an oral tablet at the same dosage as the first morning dose on the Control Day. They then received the balance of the total 8-hour dose that they took on the Control Day by way of intraoral administration of a suspension of LD/CD every 5-10 minutes over a period of 8 hours. ON and OFF time were assessed as on Day 2. Patients were then discharged from the clinic on their standard medication and returned on Day 18 for a safety evaluation.

The primary endpoint was defined as the variability of the levodopa concentrations; standard intermittent oral and semi-continuous intraoral administration were compared. Pharmacokinetic endpoints included deviation from linearity and the mean levodopa fluctuation index (($C_{max}-C_{min}$)/$C_{average}$). Efficacy was measured by neurologist-based assessment of motor state and dyskinesia at 30-minute intervals over the 8 hours and by UPDRS Part III, assessed at 0,2,4, and 8 hours on the Control Day (Day 2) and the Efficacy Day (Day 4).

Safety parameters measured included physical examinations, neurological examinations, ECGs, vital signs, blood and urine laboratory assessments, and oral site assessments by both the neurologist and the patient.

Patient baseline characteristics are shown in Table 21.

TABLE 21

Patient Demographic and Baseline Characteristics.

|  | Mean (SD) or N(%) | Range |
| --- | --- | --- |
| Age (years) | 68.0 (8.9) | 44-81 |
| Gender (male) | 11 (61.1%) |  |
| Race (white) | 18 (100%) |  |
| Weight (kg) | 73.4 (14.8) | 45-98 |
| Height (cm) | 170.9 (11.4) | 144-190 |
| BMI (kg/m$^2$) | 24.1 (3.8) | 19-32 |
| Total daily dose of LD (mg) | 781 (228) | 350-1075 |
| Dosing frequency (number of doses per day) |  |  |
| Time since PD diagnosis (years) | 13.8 (6.5) | 6-35 |

Concomittant anti-PD medications taken by the study participants are shown in Table 22.

TABLE 22

Other Anti-PD Medication.

|  | N | % |
| --- | --- | --- |
| At least one anti-PD medication other than LD | 17 | 94.4 |
| Amantadine | 6 | 33.3 |
| Dopamine agonists | 6 | 33.3 |
| Pramipexole | 1 | 5.6 |
| Ropinirole | 4 | 22.2 |
| Rotigotine | 1 | 5.6 |
| MAO-B inhibitors | 14 | 77.8 |
| Rasagiline | 13 | 72.8 |
| Selegiline | 1 | 5.6 |
| COMT inhibitors | 9 | 50 |
| Entacapone | 7 | 38.9 |
| Tolcapone | 2 | 11.1 |

Figure 42:
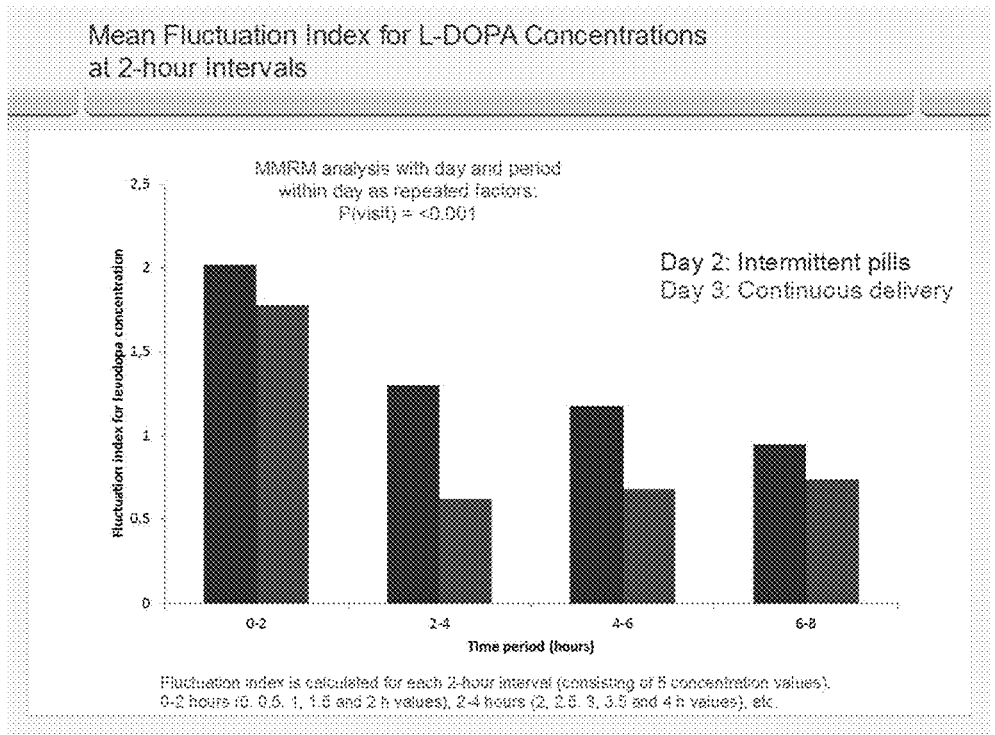
FIG. 42 is a bar chart showing the fluctuation index for each two hour interval during on Day 2 and on Day 3 during the clinical trial described of Example 53.

For the primary endpoint, statistically significant improvements were observed for variability in plasma levodopa concentration (as determined by linearity) and for reduction in 1-hour and 2-hour fluctuation indexes (p<0.001 for each). FIG. 42 shows the reduction in the fluctuation index for each 2-hour window during the study.

Figure 43:
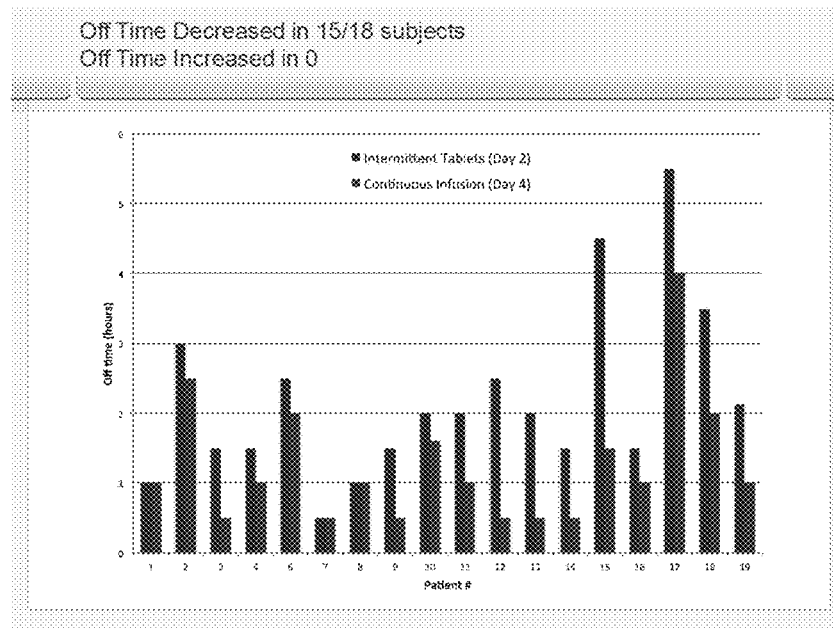
FIG. 43 is a bar chart showing the OFF time of each patient on Day 2 and on Day 4 during the clinical trial described of Example 53.
Figure 44:
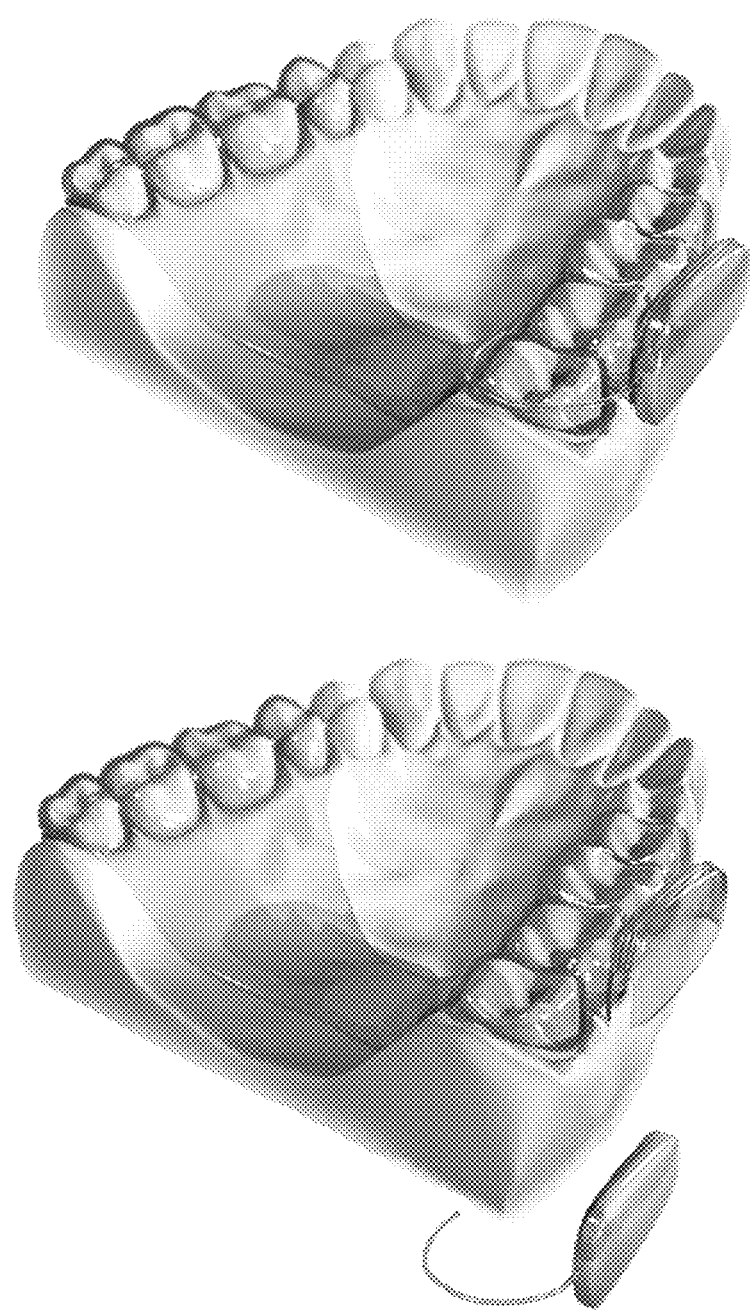
FIG. 44 illustrates the drug delivery device configured to be removably inserted in a patient's mouth and for continuous or semi-continuous intraoral administration a drug.

As shown in Table 23, OFF time was reduced by 43% (p<0.001). The UPDRS Part III motor score improved (p=0.010), confirming reduce motor impairment in the patients. As shown in FIG. 43, OFF time was reduced in 15 out of 18 patients, was unchanged in 3 patients, and increased in 0 patients.

TABLE 23

Motor State.

| State | Intermittent Tablets (Day 2) Mean (SEM) | Continuous Delivery (Day 4) Mean (SEM) |
| --- | --- | --- |
| OFF | 2.20 (0.30) | 1.26 (0.22) |
| Troublesome dyskinesia | 0.00 (0.00) | 0.39 (0.33) |
| ON without troublesome dyskinesia | 5.79 (0.45) | 6.35 (0.47) |

SEM = Standard error of measurement

No clinical study related adverse events were observed. In particular, local tolerability appeared good: no gum or mucosal irritation, redness, or ulceration was observed by physician inspection in any patient at any observation. Furthermore, no patient reported any complaint about his/her mouth at any time.

EXAMPLE 54

Chemical Instability of Dilute, Commercially Available, Duodopa LD/CD Gel for Intestinal Infusion In animal studies, hydrazine shows notable systemic toxicity, particularly upon inhalation. Hydrazine is also hepatotoxic, has CNS toxicities (although not described after oral treatment), and is genotoxic as well as carcinogenic. Consequently, it is important to minimize hydrazine formation during storage of CD or LD/CD formulations.

Duodopa™ (sold as Duopa in the United States), a LD/CD suspension for continuous intraduodenal infusion, degrades during storage and produces hydrazine. The average recommended daily dose of Duodopa is 100 mL, containing 2 g levodopa and 0.5 g CD. The maximum recommended daily dose is 200 mL. According to the labeling, this includes hydrazine at up to an average exposure of 4 mg/day, with a maximum of 8 mg/day. In order to meet these exposure limits, Duodopa's labeling in the United States requires frozen storage and its labeled shelf life is 12 weeks refrigerated (after thawing). The concentrations of LD and CD in Duodopa are 20 mg/mL and 5 mg/mL, respectively.

Six sealed 100 mL packages of commercial Duodopa were purchased and stored according to the storage instructions in the labeling. Hydrazine concentrations of three packages were measured by HPLC immediately upon thawing (t=0) and provided concentrations of 547, 676, and 662 µg of hydrazine per gram of LD+CD (average=629 pg hydrazine / g LD+CD). The hydrazine concentrations of the three remaining packages were measured after 12 weeks refrigerated storage at 2-8° C. and provided concentrations of 3,653, 3,725, and 3,729 pg of hydrazine per gram of LD+CD (average=3,702 µg hydrazine/g LD+CD).

EXAMPLE 55

Superior Stability of Concentrated LD/CD Suspensions in Emulsions of the Invention Three LD/CD suspensions of the invention (labeled F16C, F41 C, and F46C) were prepared according to the compositions of Table 24, packaged into glass vials, and placed on stability at five storage temperatures: −20, 2-8, 25, 30, and 40° C. Vials were prepared with the formulations stored under air as well as nitrogen blanketed. The samples were evaluated for physical and chemical stability at t=0, 1, 2, 3, and 6 months.

TABLE 24

| Compositions of F16C, F41C, and F46C for stability study (%) | | | |
|---|---|---|---|
| | F16C | F41C | F46C |
| LD (micronized) | 50 | 50 | 50 |
| CD (micronized) | 12.5 | 12.5 | 12.5 |
| Polysorbate 60 | 5 | — | — |
| Poloxamer 188 | — | 5 | — |
| Cremophor RH40 | — | — | 5 |
| Miglyol 812 | 24.4 | 24.4 | 23.9 |
| BHA | 0.1 | 0.1 | 0.1 |
| DI-$H_2O$ | 8.0 | 8.0 | 8.0 |
| Sucralose (Spectrum, NF grade) | — | — | 0.5 |

Physical stability was assessed by one hour centrifugation at about 16,000 G (G being the gravity at about sea level), which would be suggestive of shelf life physical stability for about 22 months at 1 G. Samples passed the test if there was no visible sedimentation of the solid drug particles nor was there any visible phase separation of the oil and the water. Results of the centrifugation test are shown in Table 25. F16C and F46C were physically stable when stored refrigerated for 6 months. F41C was physically stable when stored at 2-8, 25, 30, and 40° C. for 6 months.

TABLE 25

Physical stability during 6 month real time stability study
Centrifugation test comparison (1 M, 2 M, 3 M & 6 M)

| Storage temp. (° C.) | Centrifugation Test | | | | | | | | | | | | | | | | | |
|---|---|---|---|---|---|---|---|---|---|---|---|---|---|---|---|---|---|---|
| | F16C | | | | | | F41C | | | | | | F46C | | | | | |
| | $T_0$ | 1 M | 2 M | 3 M | 6 M | 6 M @ $N_2$ | $T_0$ | 1 M | 2 M | 3 M | 6 M | 6 M @ $N_2$ | $T_0$ | 1 M | 2 M | 3 M | 6 M | 6 M @ $N_2$ |
| −20 | P | F | F | F | F | F | P | F | F | F | F | F | P | P | P | P | F | F |
| 2 to 8 | | P | P | P | P | P | | P | P | P | P | P | | P | P | P | P | P |
| 25 | | F | F | F | F | F | | P | P | P | P | P | | P | P | F | F | F |
| 30 | | F | F | F | F | F | | P | P | P | P | P | | P | F | F | F | F |
| 40 | | F | F | F | F | F | | P | P | P | P | P | | F | F | F | F | F |

M = months,
F = fail,
P = pass

Chemical stability was assessed by the amount of hydrazine in the samples as measured by HPLC. Table 26 provides the measured hydrazine amounts, expressed as pg hydrazine per gram of LD+CD. Hydrazine at 6 months for F16C, F41C, and F46C were 89, 391, and 142 µg hydrazine per gram of LD+CD, respectively, for the samples stored in vials with nitrogen blanketing. In contrast to the average of 3,702 pg hydrazine per gram of LD+CD found in Duodopa after storage for 12 weeks, only 7 and 9 µg hydrazine per gram of LD+CD were found in the F41 C and F46C, respectively, after storage for 3 months at 2-8° C. with nitrogen blanketing.

Comparing these results to those of Example 53, after storage under identical conditions the inventive formulations contain a factor of 400× less hydrazine than the commercially available Duodopa product.

TABLE 26

Chemical stability during 6 month real time stability study
Hydrazine level comparison (1 M, 2 M, 3 M, and 6 M)

Hydrazine (μg per g of LD + CD)

| Storage temp. (°C.) | F16C | | | | | F41C | | | | | | Under $N_2$ | | F46C | | | | | Under $N_2$ | |
|---|---|---|---|---|---|---|---|---|---|---|---|---|---|---|---|---|---|---|---|---|---|
| | $T_0$ | 1 M | 2 M | 6 M | 6 M @ $N_2$ | $T_0$ | 1 M | 2 M | 3 M | 6 M | 3 M | 6 M | $T_0$ | 1 M | 2 M | 3 M | 6 M | 3 M | 6 M |
| −20 | 4.5 | 5.6 | 5.3 | 8.9 | 8.3 | 3.4 | 1.9 | 3.5 | 5.5 | 11.3 | N/D | 10.4 | 3.9 | 2.5 | 4.7 | 7.4 | 5.2 | 6.8 | 6.5 |
| 2 to 8 | | 6.0 | 6.8 | 18.1 | 19.5 | | 2.6 | 6.6 | 9.9 | 37.9 | 6.8 | 48.6 | | 3.5 | 9.6 | 9.6 | 11.4 | 9 | 11.1 |
| 25 | | 9.9 | 27.5 | 34.4 | 30.5 | | 13.5 | 12.7 | 30.2 | 92.7 | 30.4 | 57.4 | | 19.1 | 51.9 | 25.1* | 56.3 | N/D | 16 |
| 30 | | 75.8 | 185.8 | 182.6 | 68.1 | | 55.4 | 176.5 | 166.6 | 785.1 | 46.3 | 395.7 | | 48.2 | 139.4 | 150.2 | 48.2 | N/D | 36.4 |
| 40 | | 156.2 | 205.1 | 205.9 | 89.4 | | 122.8 | 180.1 | 161.4 | 791.2 | 64.4 | 390.6 | | 113.8 | 171.4 | 176.9 | 146.2 | N/D | 142.2 |

M = months

Table 27 provides the apparent pH of the formulations during the stability studies at t=0, 1, 2, and 3 months. As can be seen from the data, the pH is less than pH 5 and remains less than pH 5 after 3 months storage at 25° C.

TABLE 27 pH during 3 month real time stability study pH at different storage conditions for 1 M, 2 M and 3 M

| Sample ID | pH @ −20° C. | pH @ −2-8° C. | pH @ 25° C. | pH @ 30° C. | pH @ 40° C. |
|---|---|---|---|---|---|
| F16C_1 M | 3.8 | 3.7 | 3.4 | 4.4 | 4.2 |
| F16C_2 M | 3.8 | 3.8 | 3.7 | 4.8 | 4.6 |
| F16C_3 M | 4.1 | 4.5 | 4.8 | 4.5 | 4.9 |
| F16C_3 M_$N_2$ | 3.9 | 4.0 | 4.5 | 4.3 | 4.7 |
| F41C_1 M | 3.5 | 3.5 | 3.8 | 4.5 | 4.5 |
| F41C_2 M | 4.1 | 4.5 | 4.8 | 4.5 | 4.9 |
| F41C_3 M | 4.0 | 4.4 | 4.0 | 4.4 | 5.1 |
| F41C_3 M_$N_2$ | 4.1 | 4.1 | 4.0 | 4.3 | 4.8 |
| F46C_1 M | 4.0 | 4.0 | 4.1 | 4.3 | 4.3 |
| F46C_2 M | 5.3 | 4.7 | 4.9 | 4.7 | 4.8 |
| F46C_3 M | 4.8 | 4.7 | 4.1 | 4.7 | 4.7 |
| F46C_3 M_$N_2$ | 4.8 | 4.4 | 4.2 | 4.6 | 4.9 |

In this experiment it was discovered that the stabilities of similarly made drug-comprising pastes for continuous extrusion into the mouth depend on their surfactants.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A pharmaceutical composition comprising a suspension comprising (i) from about 35% to 70% (w/w) drug particles, (ii) from 19% to 30% (w/w) of one or more water-immiscible compounds, (iii) from 2% to 16% (w/w) water, and (iv) from 1% to 8% (w/w) surfactant, wherein the pharmaceutical composition is physically stable.

2. A pharmaceutical composition comprising a suspension comprising (i) from about 20% to about 80% (w/w) solid excipients; (ii) from about 5% to 60% (w/w) drug particles, (iii) from 19% to 30% (w/w) of one or more water-immiscible compounds, (iv) from 2% to 25% (w/w) water, and (v) from 1% to 10% (w/w) surfactant, wherein the pharmaceutical composition is physically stable.

3. A pharmaceutical composition comprising a suspension comprising (i) an oil, and (ii) from about 35% to 70% (w/w) solid drug particles comprising levodopa or a levodopa prodrug and/or carbidopa or a carbidopa prodrug, wherein the pharmaceutical composition has a dynamic viscosity of at least 100 cP at 37° C.

4. The pharmaceutical composition of claim 3, wherein said suspension comprises less than or equal to about 30% (w/w) of said oil.

5. The pharmaceutical composition of claim 4, wherein said suspension comprises greater than or equal to about 19% (w/w) of said oil.

6. The pharmaceutical composition of claim 4, wherein said suspension comprises water and a surfactant.

7. The pharmaceutical composition of claim 1, wherein said suspension has a dynamic viscosity of at least 100 cP at 37° C.

8. The pharmaceutical composition of claim 7, wherein the $D_{50}$ of the drug particles is greater than or equal to 1 μm and less than or equal to 500 μm.

9. The pharmaceutical composition of claim 8, wherein said suspension does not cream or sediment when centrifuged for 1 hour at an acceleration of about 5,000 G at 25±3° C.

10. The pharmaceutical composition of claim 9, wherein after said centrifugation for 1 hour at an acceleration of about 5,000 G at 25±3° C. the concentrations of drug in the layer containing the top 20 volume % and the layer containing the bottom 20 volume % of the composition differ by less than 6%.

11. The pharmaceutical composition of claim 8, wherein the shelf life of said pharmaceutical composition is 6 months or longer at 5±3° C. and said pharmaceutical composition does not substantially cream or sediment when stored for 6 months at 5±3° C.

12. The pharmaceutical composition of claim 9, wherein said suspension comprises less than or equal to about 12% (w/w) water.

13. The pharmaceutical composition of claim 12, wherein said suspension comprises 8±2% (w/w) water.

14. The pharmaceutical composition of claim 7, comprising an edible oil.

15. The pharmaceutical composition of claim 14, wherein said oil comprises a saturated fatty acid triglyceride, an unsaturated fatty acid triglyceride, a mixed saturated and unsaturated fatty acid triglyceride, a medium-chain fatty acid triglyceride, canola oil, coconut oil, palm oil, olive oil, soybean oil, sesame oil, corn oil, or mineral oil.

16. The pharmaceutical composition of claim 15, wherein said oil comprises a medium-chain fatty acid triglyceride.

17. The pharmaceutical composition of claim 14, wherein said pharmaceutical composition comprises a non-ionic surfactant.

18. The pharmaceutical composition of claim 17, wherein said non-ionic surfactant comprises a polyglycolized glyceride, an alkyl saccharide, an ester saccharide, or a polysorbate surfactant.

19. The pharmaceutical composition of claim 17, wherein said pharmaceutical composition comprises about 5±2% (w/w) of said surfactant.

20. The pharmaceutical composition of claim 7, wherein said pharmaceutical composition comprises an emulsion.

21. The pharmaceutical composition of claim 7, wherein said drug particles comprise baclofen.

22. The pharmaceutical composition of claim 7, wherein said drug particles comprise levodopa or a levodopa prodrug and/or carbidopa or a carbidopa prodrug.

23. The pharmaceutical composition of claim 22, wherein said drug particles comprise carbidopa, and further comprising less than 8 µg of hydrazine per mg of carbidopa after 12 months storage at 5±3° C.

24. The pharmaceutical composition of claim 23, wherein said composition comprises less than 1 µg of hydrazine per mg of carbidopa after said 12 month storage.

25. The pharmaceutical composition of claim 22, wherein said drug particles comprise carbidopa, and further comprising less than 8 µg of hydrazine per mg of carbidopa after 12 months storage at 25±3° C.

26. The pharmaceutical composition of claim 25, wherein said composition comprises less than 1 µg of hydrazine per mg of carbidopa after said 12 month storage.

27. The pharmaceutical composition of claim 7, wherein said suspension comprises a paste.

28. The pharmaceutical composition of claim 7, wherein said suspension comprises benzoic acid or a benzoate salt.

29. A method of treating Parkinson's disease comprising administering the pharmaceutical composition of claim 22 to a patient.

30. A method for treating Parkinson's disease in a patient, said method comprising:
(a) inserting a drug delivery device comprising the pharmaceutical composition of claim 22 into said patient's mouth, said pharmaceutical composition comprising levodopa or levodopa prodrug;
(b) administering into said patient's mouth said levodopa or levodopa prodrug for a period of at least 4 hours at an hourly rate in the range of 30 mg/hour to 150 mg/hour, such that a circulating plasma levodopa concentration greater than 1,200 ng/mL and less than 2,500 ng/mL is continuously maintained for a period of at least 4 hours during said administration; and
(c) removing said drug delivery device from the mouth.

31. The pharmaceutical composition of claim 2, wherein said suspension has a dynamic viscosity of at least 100 cP at 37° C.

32. The pharmaceutical composition of claim 1, wherein said suspension has a dynamic viscosity of at least 1,000 cP at 37° C.

33. The pharmaceutical composition of claim 1, wherein said suspension has a dynamic viscosity of at least 10,000 cP at 37° C.

34. The pharmaceutical composition of claim 2, wherein said suspension has a dynamic viscosity of at least 10,000 cP at 37° C.

35. The pharmaceutical composition of claim 3, wherein said suspension has a dynamic viscosity of at least 10,000 cP at 37° C.

36. The pharmaceutical composition of claim 1, wherein said suspension has a dynamic viscosity of at least 100,000 cP at 37° C.

37. The pharmaceutical composition of claim 7, wherein the $D_{50}$ of the drug particles is less than or equal to 100 µm.

38. The pharmaceutical composition of claim 2, wherein the $D_{50}$ of the solid drug particles is less than or equal to 100 µm.

39. The pharmaceutical composition of claim 3, wherein the $D_{50}$ of the solid drug particles is less than or equal to 100 µm.

40. The pharmaceutical composition of claim 7, wherein the $D_{50}$ of the drug particles is less than or equal to 25 µm.

41. The pharmaceutical composition of claim 17, wherein said non-ionic surfactant comprises a poloxamer.

42. The pharmaceutical composition of claim 2, wherein said pharmaceutical composition comprises a non-ionic surfactant.

43. The pharmaceutical composition of claim 3, wherein said pharmaceutical composition comprises a non-ionic surfactant.

44. The pharmaceutical composition of claim 2, wherein the shelf life of said pharmaceutical composition is 6 months or longer at 5±3° C. and said pharmaceutical composition does not substantially cream or sediment when stored for 6 months at 5±3° C.

45. The pharmaceutical composition of claim 3, wherein the shelf life of said pharmaceutical composition is 6 months or longer at 5±3° C. and said pharmaceutical composition does not substantially cream or sediment when stored for 6 months at 5±3° C.

46. The pharmaceutical composition of claim 2, wherein said suspension comprises less than or equal to about 12% (w/w) water.

47. The pharmaceutical composition of claim 3, wherein said suspension comprises less than or equal to about 12% (w/w) water.

48. The pharmaceutical composition of claim 2, comprising an edible oil.

49. The pharmaceutical composition of claim 3, comprising an edible oil.

50. The pharmaceutical composition of claim 2, wherein said pharmaceutical composition comprises an emulsion.

51. The pharmaceutical composition of claim 3, wherein said pharmaceutical composition comprises an emulsion.

52. The pharmaceutical composition of claim 2, wherein said suspension comprises a paste.

53. The pharmaceutical composition of claim 3, wherein said suspension comprises a paste.

54. The pharmaceutical composition of claim 3, wherein said drug particles comprise carbidopa, and further comprising less than 8 µg of hydrazine per mg of carbidopa after 12 months storage at 5±3° C.

55. The pharmaceutical composition of claim 54, wherein said composition comprises less than 1 µg of hydrazine per mg of carbidopa after said 12 month storage.

56. A method of treating Parkinson's disease comprising administering the pharmaceutical composition of claim 3 to a patient.

\* \* \* \* \*